(12) United States Patent
Li et al.

(10) Patent No.: US 9,434,748 B2
(45) Date of Patent: *Sep. 6, 2016

(54) CYTOTOXIC BENZODIAZEPINE DERIVATIVES

(71) Applicant: ImmunoGen, Inc., Waltham, MA (US)

(72) Inventors: Wei Li, Acton, MA (US); Michael Louis Miller, Framingham, MA (US); Nathan Elliott Fishkin, Weymouth, MA (US); Ravi V. J. Chari, Newton, MA (US)

(73) Assignee: ImmunoGen, Inc., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/849,270

(22) Filed: Sep. 9, 2015

(65) Prior Publication Data

US 2016/0108129 A1 Apr. 21, 2016

Related U.S. Application Data

(63) Continuation of application No. 14/512,059, filed on Oct. 10, 2014, now Pat. No. 9,169,272, which is a continuation of application No. 13/827,355, filed on Mar. 14, 2013, now Pat. No. 8,889,669, which is a continuation of application No. 13/397,195, filed on Feb. 15, 2012, now Pat. No. 8,765,740.

(60) Provisional application No. 61/483,499, filed on May 6, 2011, provisional application No. 61/443,062, filed on Feb. 15, 2011, provisional application No. 61/443,092, filed on Feb. 15, 2011.

(51) Int. Cl.

| *A61K 31/5517* | (2006.01) |
|---|---|
| *A61K 31/55* | (2006.01) |
| *C07D 519/00* | (2006.01) |
| *A61K 47/48* | (2006.01) |
| *C07D 487/04* | (2006.01) |
| *A61K 45/06* | (2006.01) |
| *C07K 16/30* | (2006.01) |
| *A61K 39/00* | (2006.01) |

(52) U.S. Cl.
CPC ......... *C07D 519/00* (2013.01); *A61K 31/5517* (2013.01); *A61K 45/06* (2013.01); *A61K 47/48215* (2013.01); *A61K 47/48276* (2013.01); *A61K 47/48384* (2013.01); *A61K 47/48561* (2013.01); *A61K 47/48569* (2013.01); *C07D 487/04* (2013.01); *C07K 16/30* (2013.01); *A61K 2039/505* (2013.01); *C07K 2317/24* (2013.01); *C07K 2317/92* (2013.01)

(58) Field of Classification Search
CPC .......................... A61K 31/5517; A61K 31/55
See application file for complete search history.

(56) References Cited

U.S. PATENT DOCUMENTS

| 3,763,183 | A | 10/1973 | Carabateas |
|---|---|---|---|
| 3,860,600 | A | 1/1975 | Carabateas |
| 8,426,402 | B2 | 4/2013 | Li et al. |
| 8,765,740 | B2 | 7/2014 | Li et al. |
| 8,802,667 | B2 | 8/2014 | Li et al. |
| 8,809,320 | B2 | 8/2014 | Li et al. |
| 8,889,669 | B2 | 11/2014 | Li et al. |
| 2009/0036431 | A1 | 2/2009 | Gauzy et al. |
| 2010/0316656 | A1 | 12/2010 | Bouchard et al. |
| 2011/0256157 | A1 | 10/2011 | Howard et al. |
| 2012/0238731 | A1 | 9/2012 | Fishkin et al. |
| 2013/0302359 | A1 | 11/2013 | Li et al. |

FOREIGN PATENT DOCUMENTS

| EP | 0219292 A2 | 4/1987 |
|---|---|---|
| EP | 2019104 A1 | 1/2009 |
| JP | 57131791 | 8/1982 |
| RU | 2005133443 A | 4/2006 |
| RU | 2005133442 A | 5/2006 |
| WO | WO-93/18045 A1 | 9/1993 |
| WO | WO-00/12507 A2 | 3/2000 |
| WO | WO-00/12508 A2 | 3/2000 |
| WO | WO-2004/087716 A1 | 10/2004 |
| WO | WO-2004/087717 A1 | 10/2004 |
| WO | WO-2005/040170 A2 | 5/2005 |
| WO | WO-2005/085250 A1 | 9/2005 |
| WO | WO-2005/110423 A2 | 11/2005 |
| WO | WO-2007/039752 A1 | 4/2007 |
| WO | WO-2009/016647 A1 | 2/2009 |
| WO | WO-2010/043880 A1 | 4/2010 |
| WO | WO-2010/091150 A1 | 8/2010 |
| WO | WO-2011/106528 A1 | 9/2011 |

(Continued)

OTHER PUBLICATIONS

English abstract of JP 57 131791 (1982).
International Search Report and Written Opinion dated Mar. 31, 2010, as issued in International Application No. PCT/US10/23150.
Li et al., "Design, Synthesis and Evaluation of a Novel DNA-Interactive Agent: A Promising New Class of Cytotoxic Molecules for Use in Antibody-Drug Conjugates," 239th ACS National Meeting, San Francisco, CA 2010 [MEDI 251].
Miller et al., "Potent antigen-specific anti-tumor activity observed with antibody-drug conjugates (ADCs) made using a new class of DNA-crosslinking agents," poster presentation AACR-NCI-EORTC, Abstract B126 (Nov. 2009).
Miller et al., "Abstract B126: Potent antigen-specific anti-tumor activity observed with antibody-drug conjugates (ADCs) made using a new class of DNA-crosslinking agents," *Mol. Cancer Ther.*, 8(12) Suppl 1 (2009).

(Continued)

*Primary Examiner* — Bruck Kifle
(74) *Attorney, Agent, or Firm* — McCarter & English, LLP; Steven G. Davis; Yu Lu

(57) ABSTRACT

The invention relates to novel benzodiazepine derivatives with antiproliferative activity and more specifically to novel benzodiazepine compounds of formula (I)-(VII). The invention also provides conjugates of the benzodiazepine compounds linked to a cell-binding agent. The invention further provides compositions and methods useful for inhibiting abnormal cell growth or treating a proliferative disorder in a mammal using the compounds or conjugates of the invention.

25 Claims, 52 Drawing Sheets

(56) References Cited

FOREIGN PATENT DOCUMENTS

| WO | WO-2011/130613 A1 | 10/2011 |
|---|---|---|
| WO | WO-2011/130616 A1 | 10/2011 |
| WO | WO-2012/112687 A1 | 8/2012 |
| WO | WO-2014/031566 A1 | 2/2014 |

OTHER PUBLICATIONS

Thurston et al., "Synthesis and reactivity of a novel oxazolo[2,3-c][1,4]benziodiazepine ring system with DNA recognition potential: a new class of anthramycins," J. Chem. Soc., No. 12, p. 874 (1990).

Tozuka et al., "Studies on tomaymycin. III. Syntheses and antitumor activity of tomaymycin analogs," J. Antibiot., 36(12):1699-1708 (1983).

International Preliminary Report on Patentability issued on the International Application PCT/US2010/023150, dated Aug. 9, 2011.

International Preliminary Report on Patentability issued on the International Application PCT/US2012/025252 dated Jun. 14, 2013.

International Preliminary Report on Patentability issued on the International Application PCT/US2012/025257, dated Aug. 21, 2013.

International Preliminary Report on Patentability issued on the International Application PCT/US2012/025292, dated Aug. 21, 2013.

International Search Report and Written Opinion issued in International Application PCT/US2012/025252, dated Jun. 26, 2012.

International Search Report and Written Opinion issued in International Application PCT/US2012/025257, dated Jun. 29, 2012.

Kamal et al.; "Design, synthesis, and evaluation of mixed imine-amine pyrrolobenzodiazepine dimers with efficient DNA binding affinity and potent cytotoxicity;" Bioorg. Med. Chem.; 12:5427-5436 (2004).

Kamal et al.; "Development of Pyrrolo[2,1-c][1,4]benzodiazepine β-Galactoside Prodrugs for Selective Therapy of Cancer by ADEPT and PMT;" ChemMedChem; 3:794-802 (2008).

Masterson et al.; "Synthesis and biolgoical evaluation of novel pyrrolo[2,1-c][1,4]benzodiazepine prodrugs for use in antibody-directed enzyme prodrug therapy;" Bioorg. Med. Chem. Lett.; 16:252-256 (2006).

Guo et al.; "Synthesis and Evaluation of a Cyclic Imine Derivative Conjugated to a Fluorescent Molecule for Labeling Proteins;" Bioorg. Med. Chem. Letters; 19(4):1210-1213 (2009).

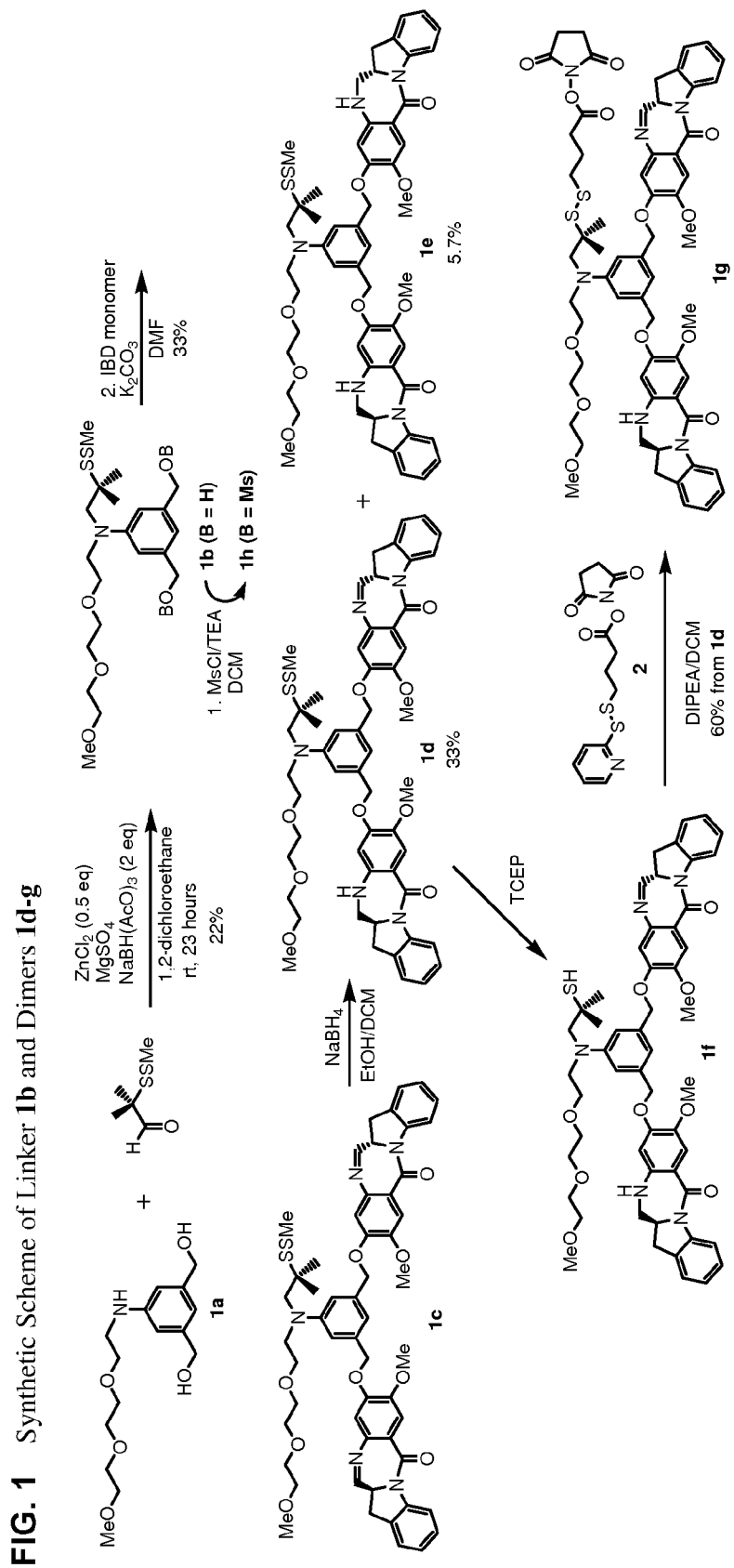
FIG. 1  Synthetic Scheme of Linker 1b and Dimers 1d-g

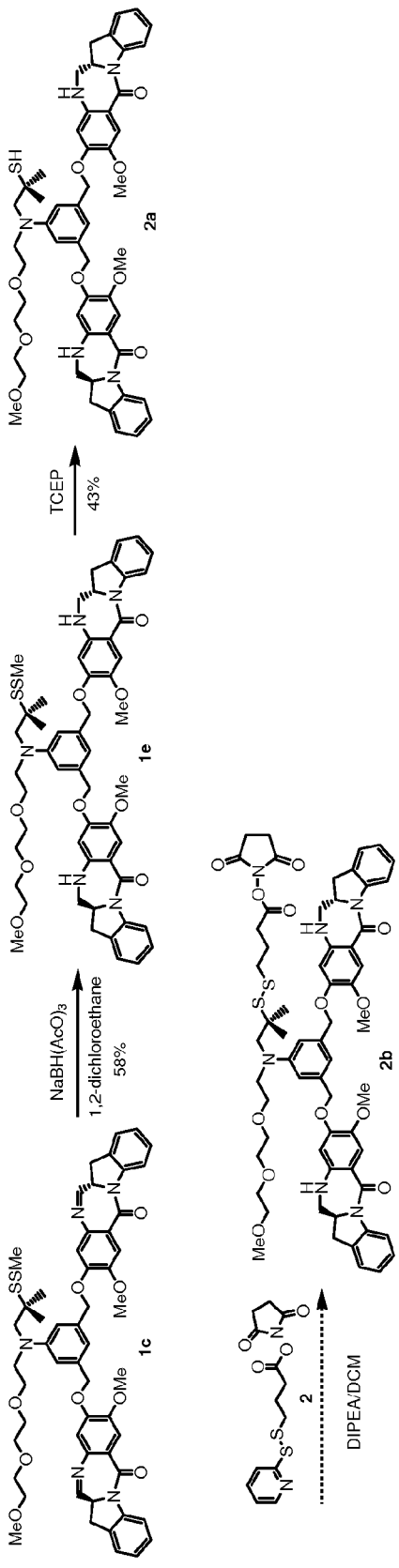
FIG. 2 Synthetic Scheme of Dimers 2a-b
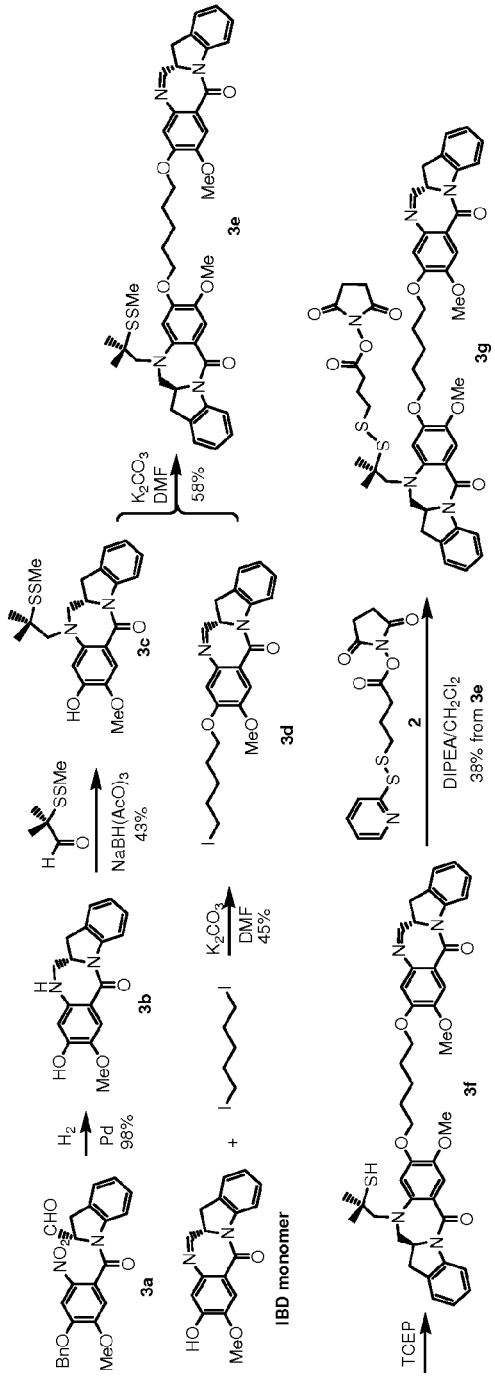
FIG. 3 Synthetic Scheme of Dimers 3e-g

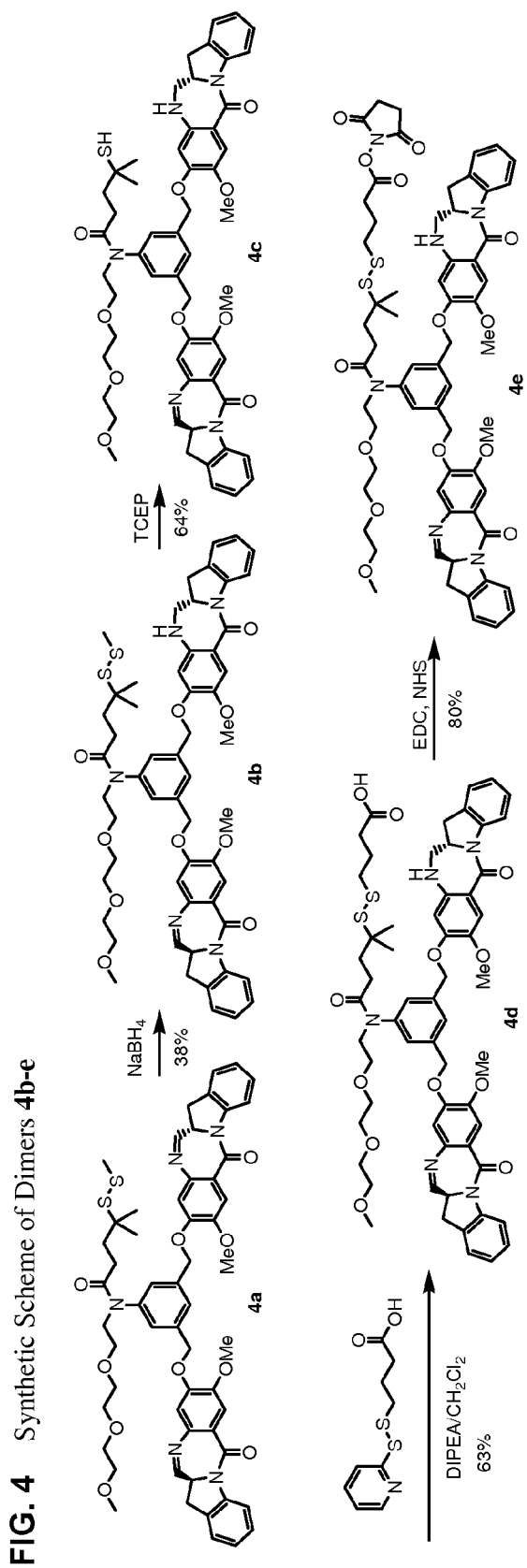
FIG. 4 Synthetic Scheme of Dimers 4b-e

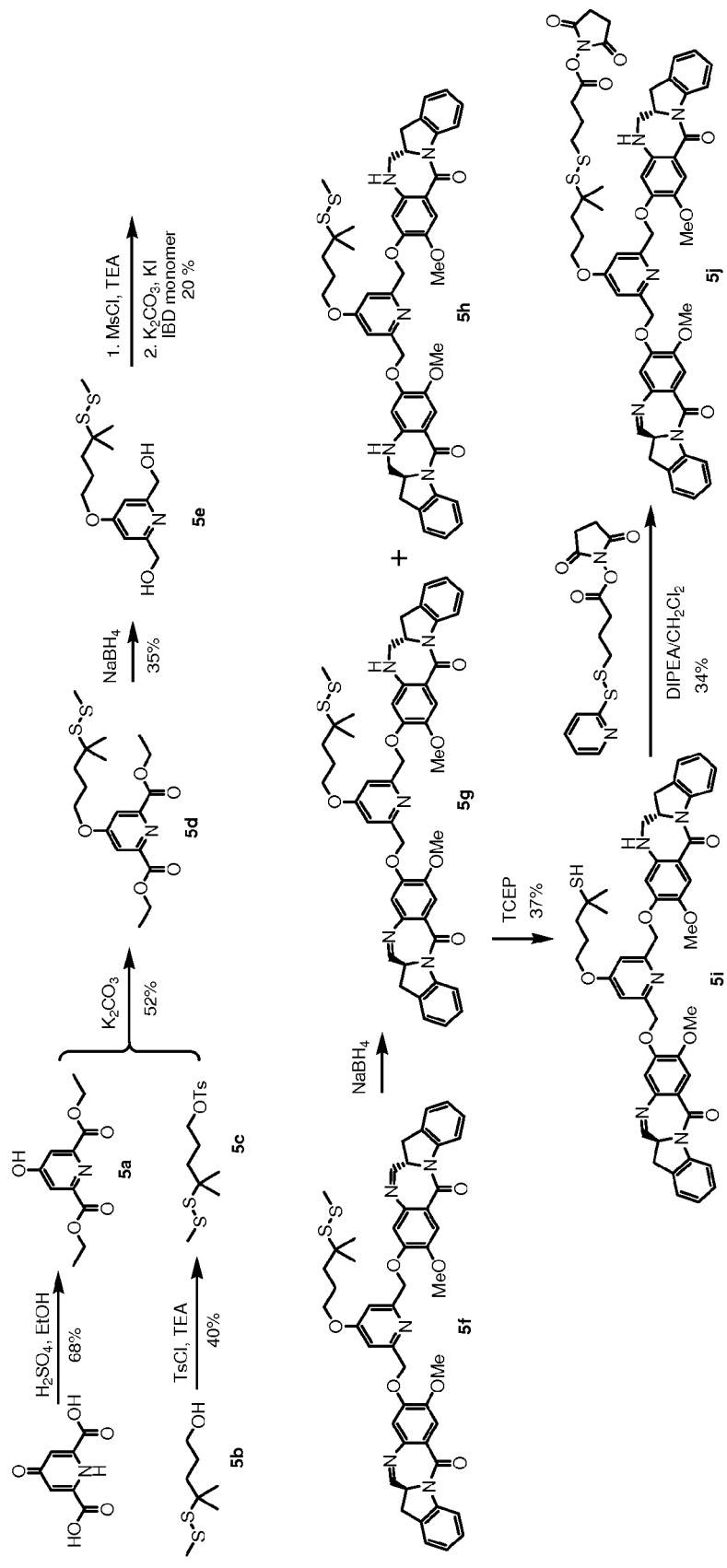
FIG. 5  Synthetic Scheme of Linker 5e and Dimers 5g-j

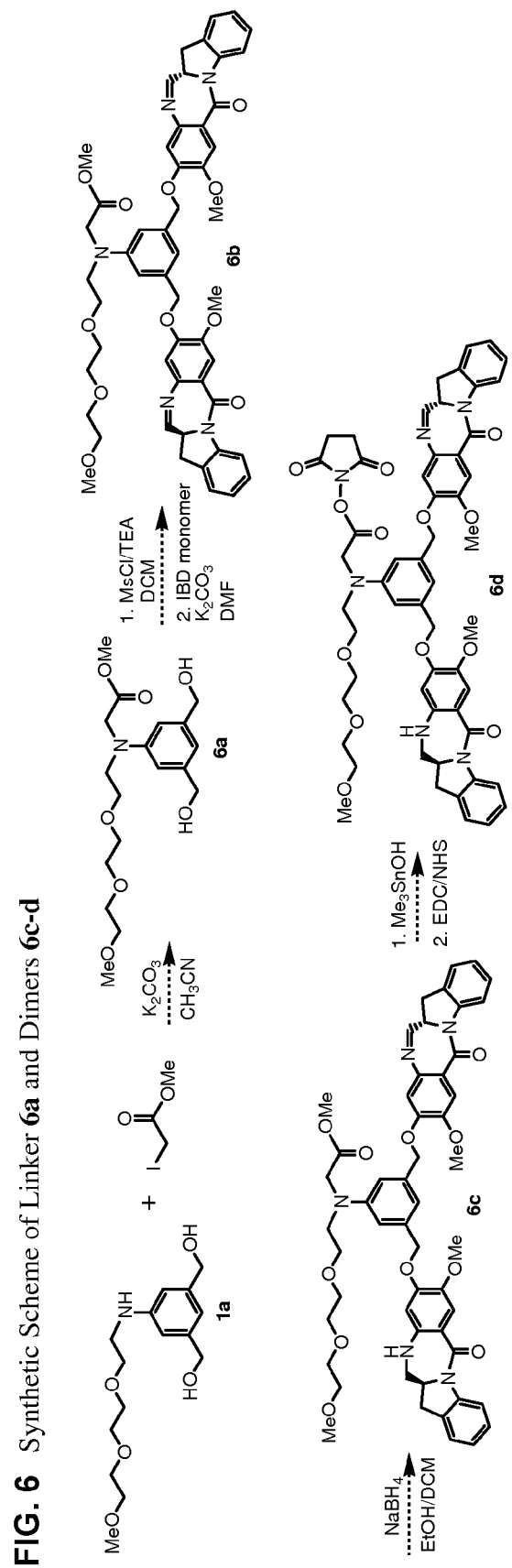
FIG. 6 Synthetic Scheme of Linker 6a and Dimers 6c-d

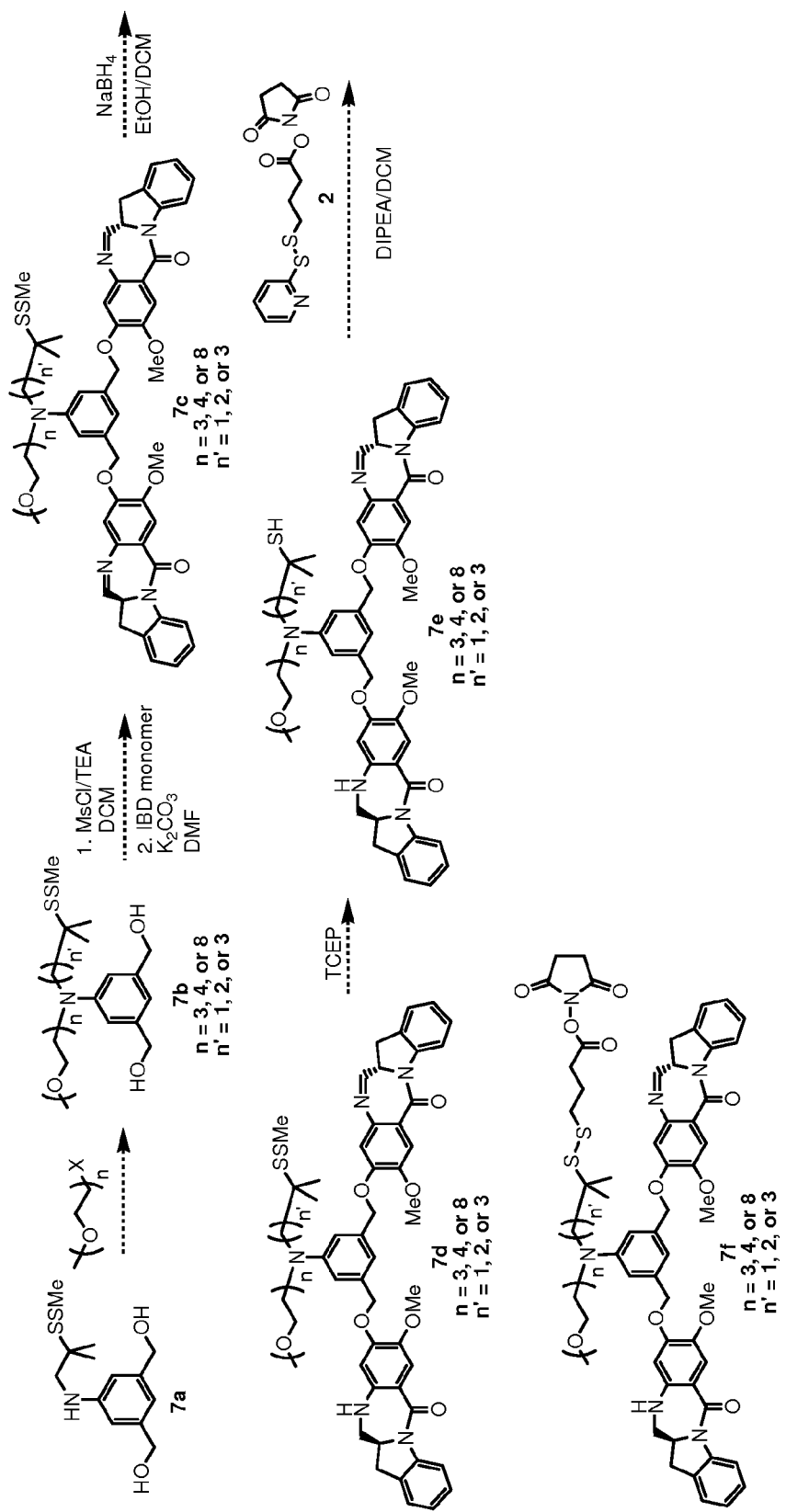
FIG. 7 Synthetic Scheme of PEG Modified Linkers 7b and Dimers 7d-f

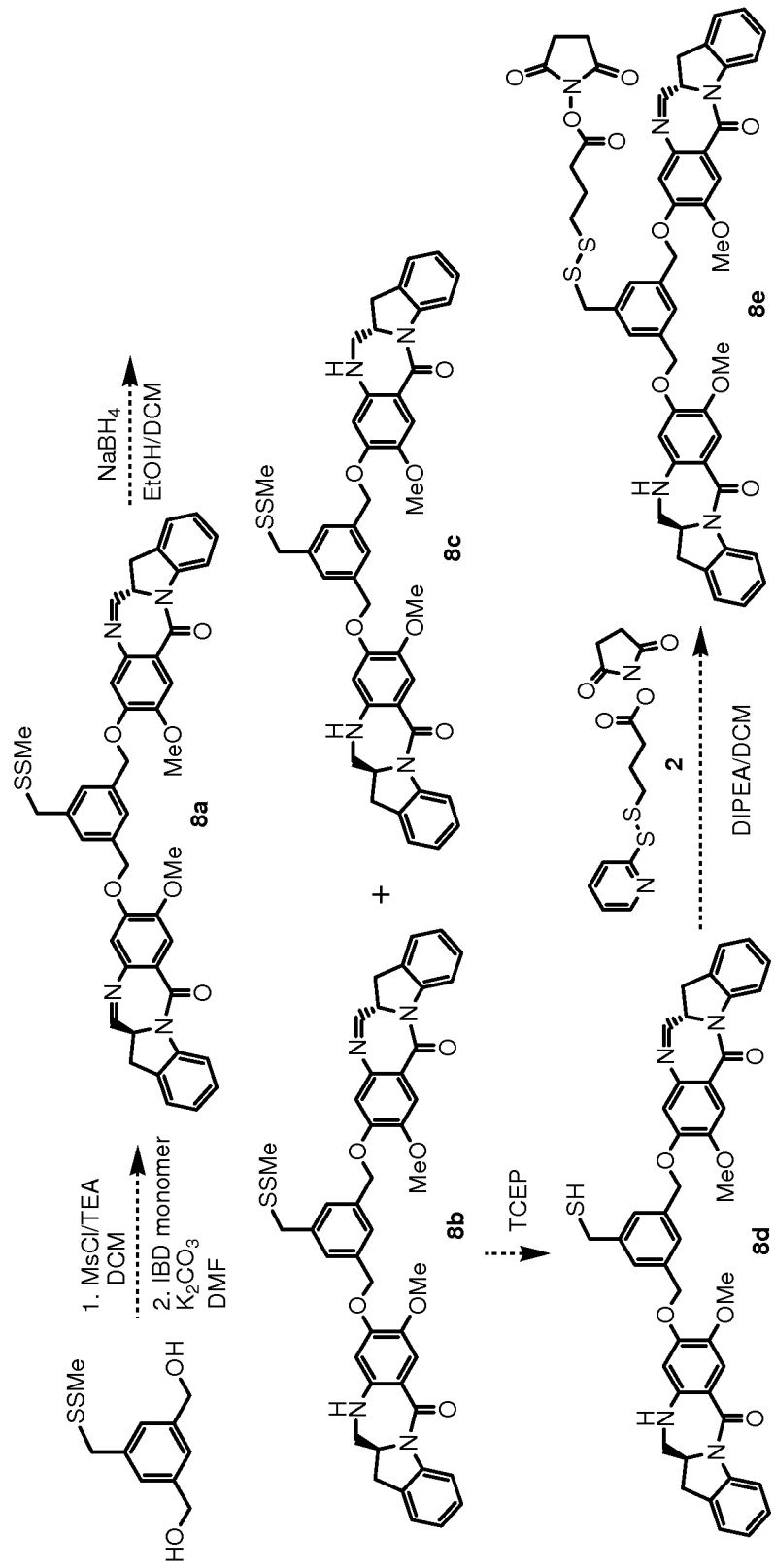
FIG. 8 Synthetic Scheme of Thiol-containing Dimers 8b-e

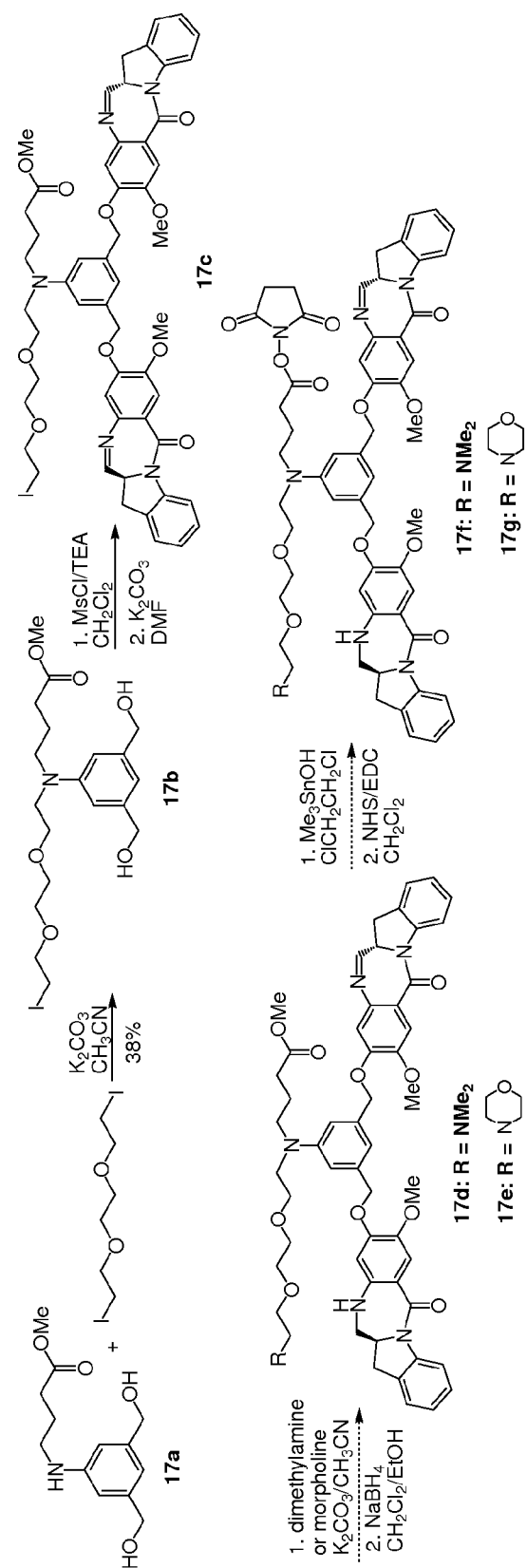
FIG. 9 Synthetic Scheme of Dimers 17d-g Containing a Tertiary Amine

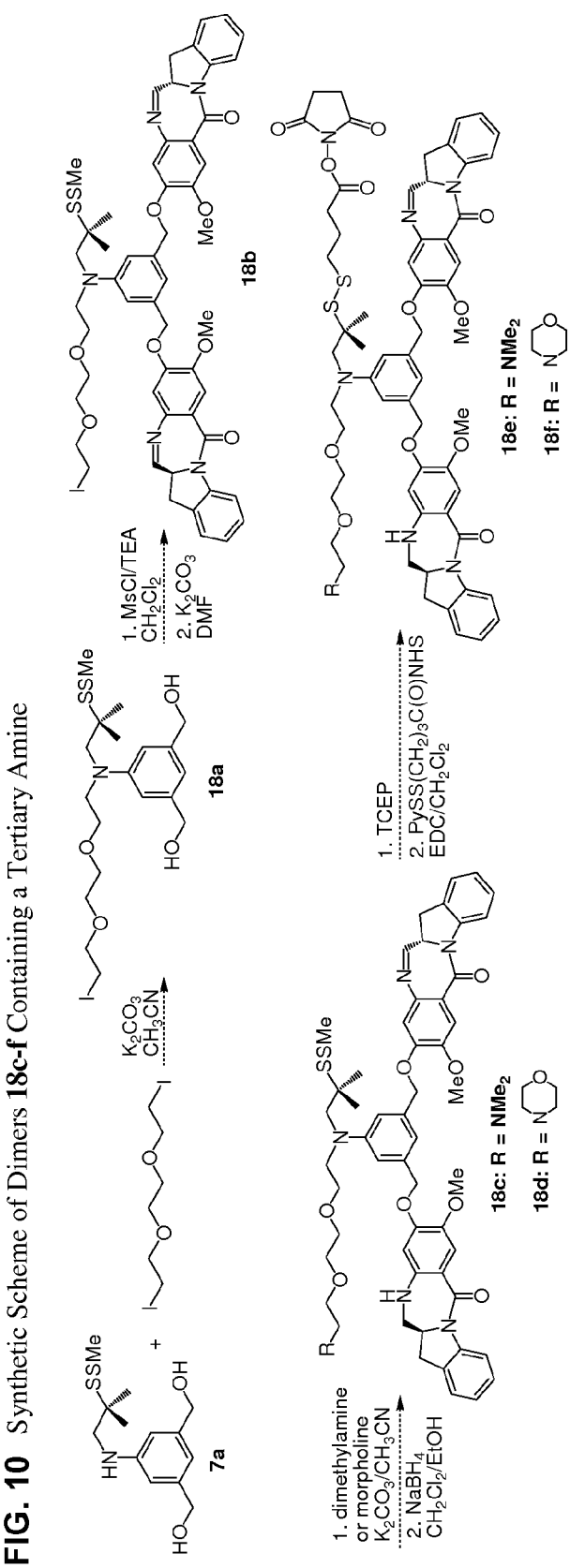
FIG. 10 Synthetic Scheme of Dimers 18c-f Containing a Tertiary Amine

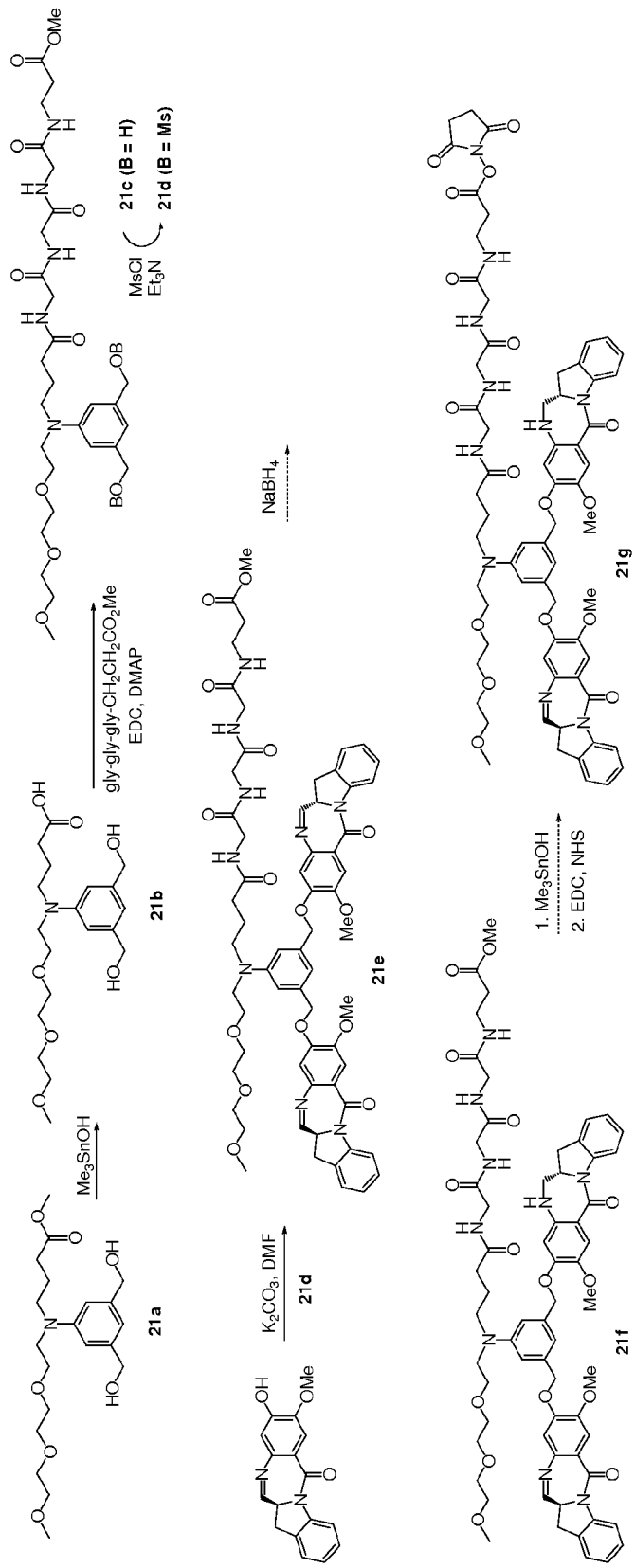
FIG. 11 Synthetic Scheme of Dimers 21f-g Containing a Peptide Linker

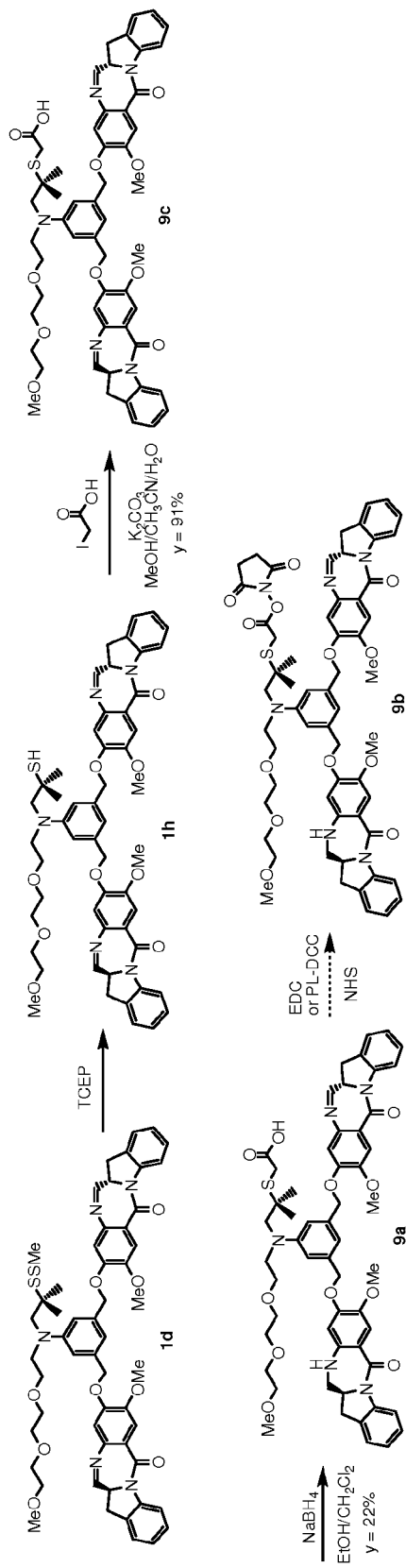
FIG. 12A Synthetic Scheme of the One-step Thioacetyl Linkable Dimers 9a-b

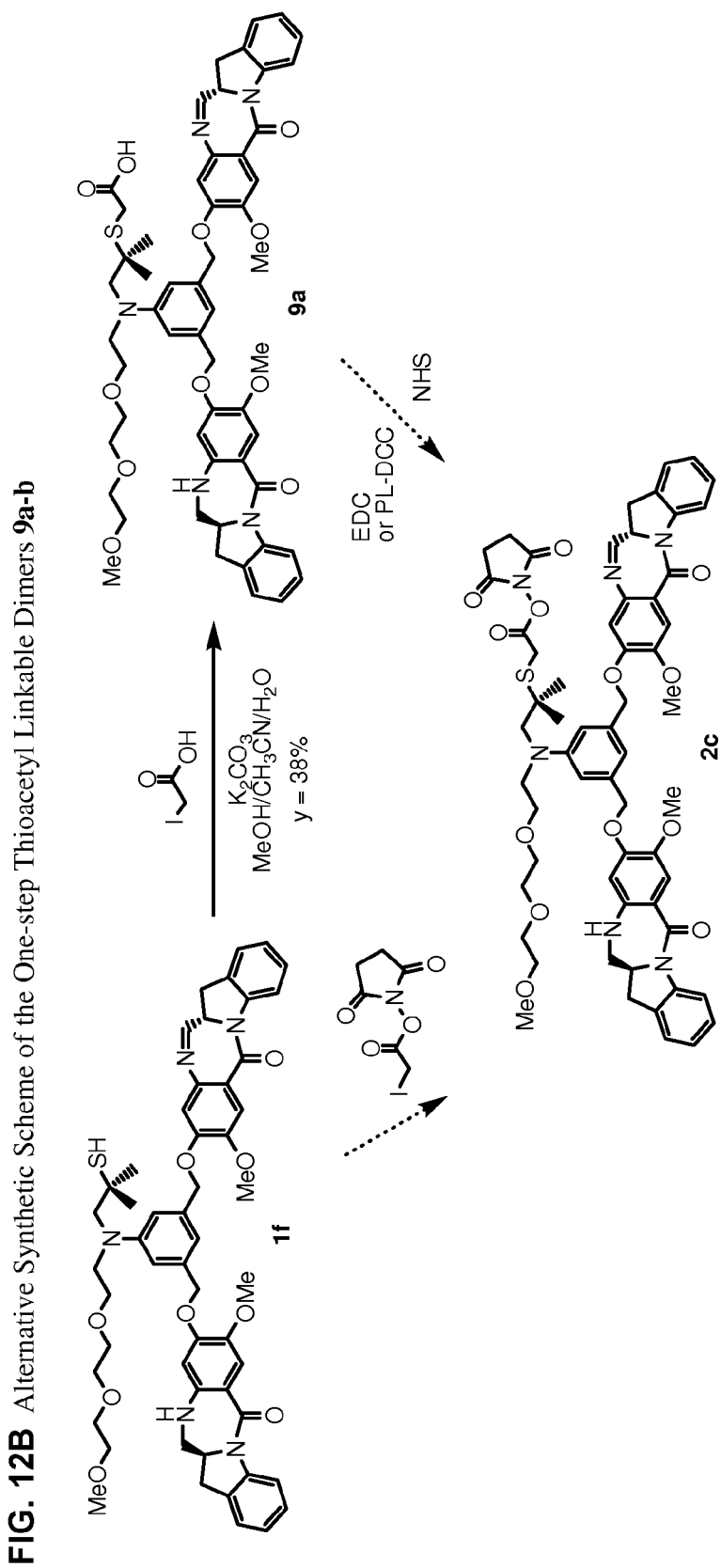
FIG. 12B Alternative Synthetic Scheme of the One-step Thioacetyl Linkable Dimers 9a-b

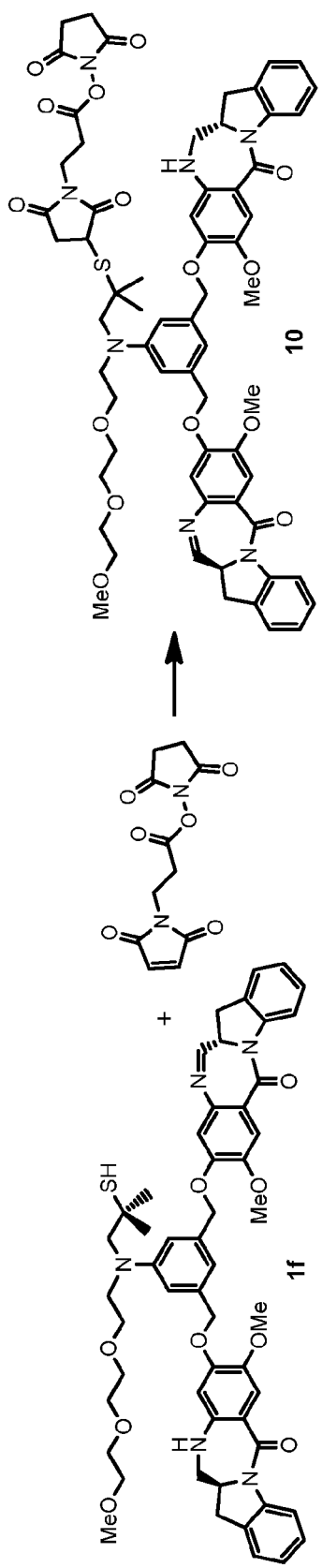
FIG. 13 Synthetic Scheme of the One-step BMPS Linkable Dimer 10
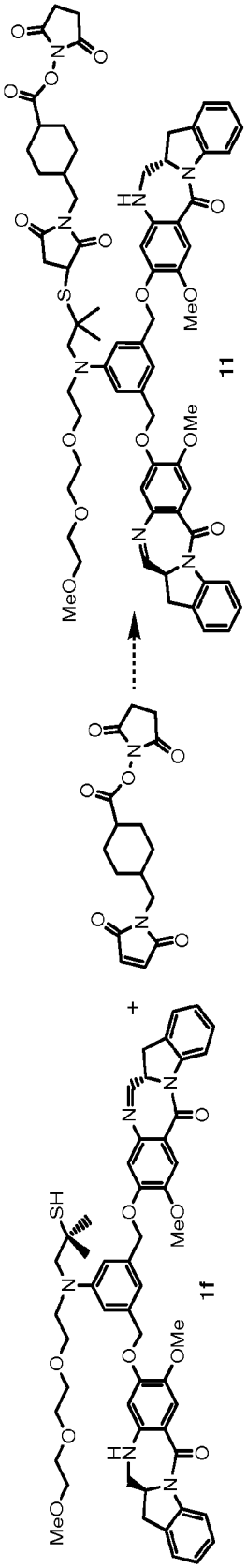
FIG. 14 Synthetic Scheme of the One-step SMCC Linkable Dimer 11

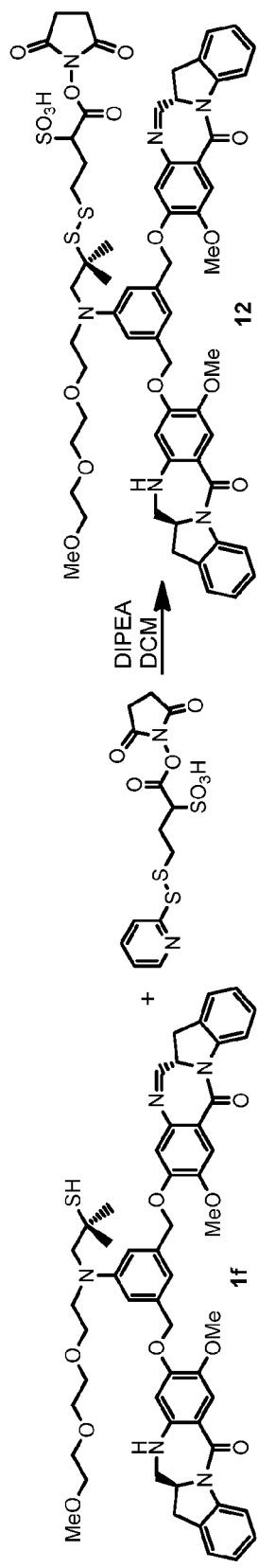
FIG. 15 Synthetic Scheme of the One-step Sulfo-SPDB Linkable Dimer 12
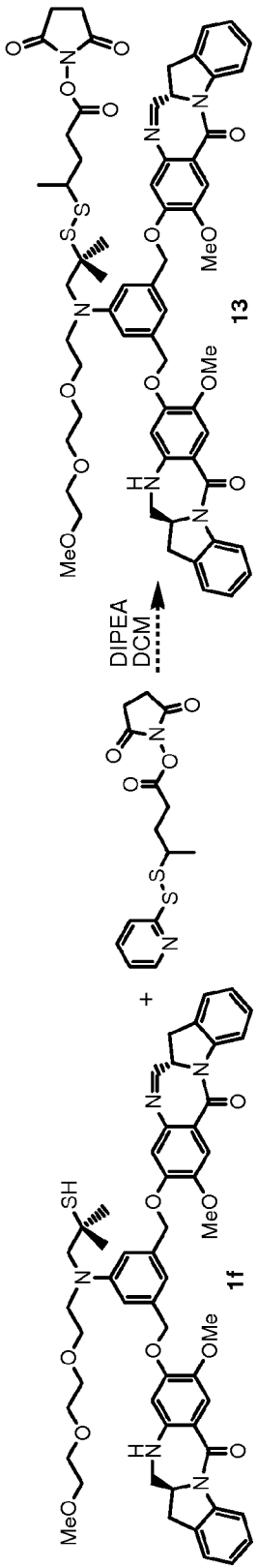
FIG. 16 Synthetic Scheme of the One-step SPP Linkable Dimer 13

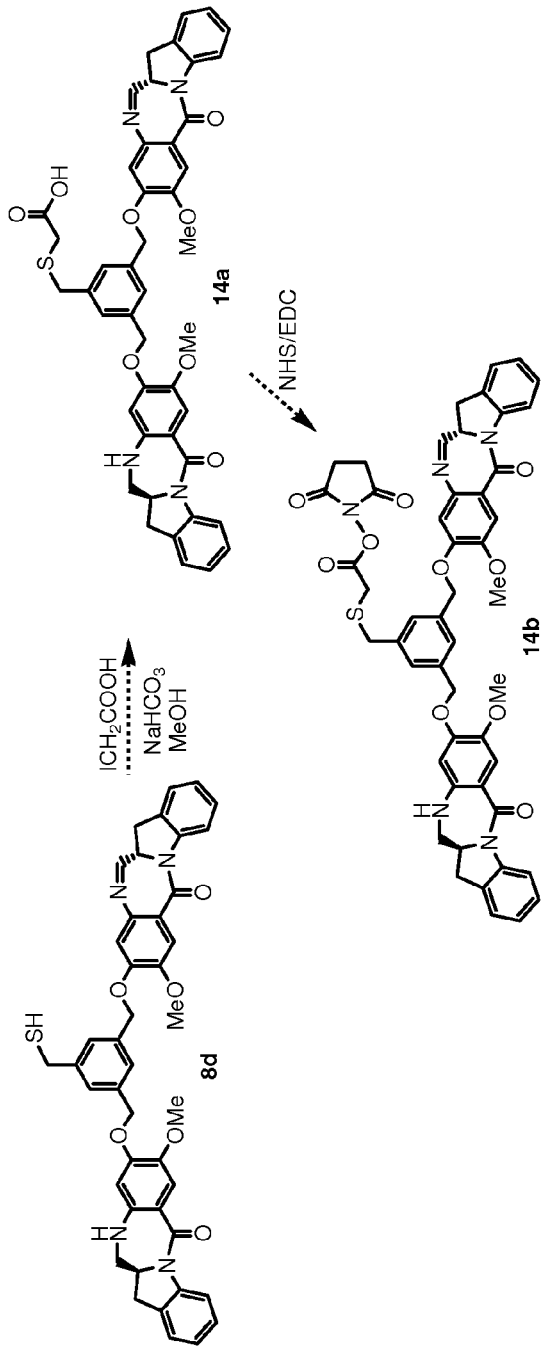
FIG. 17 Synthetic Scheme of the One-step Thioacetyl Linkable Dimers 14a-b
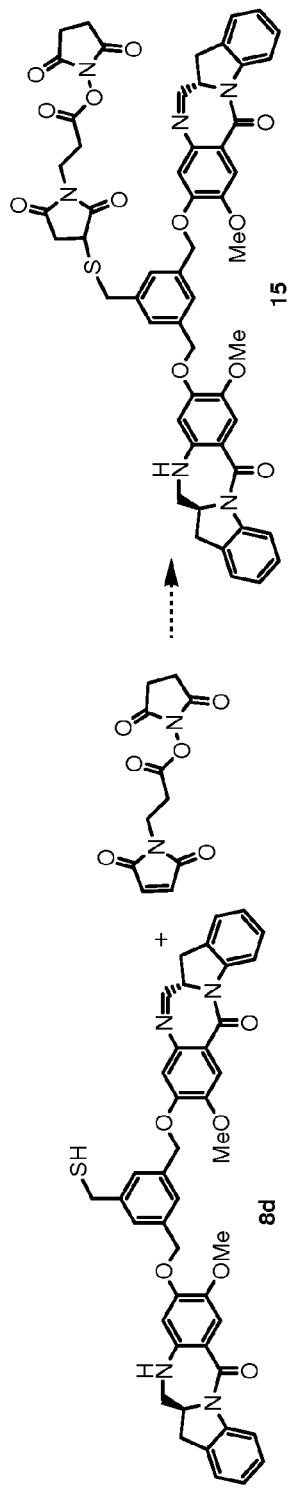
FIG. 18 Synthetic Scheme of the One-step BMPS Linkable Dimer 15

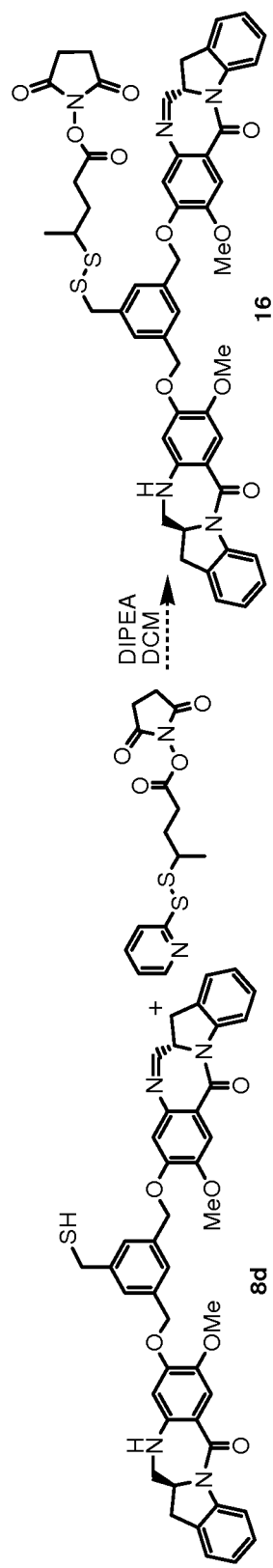
FIG. 19 Synthetic Scheme of the One-step SPP Linkable Dimer 16

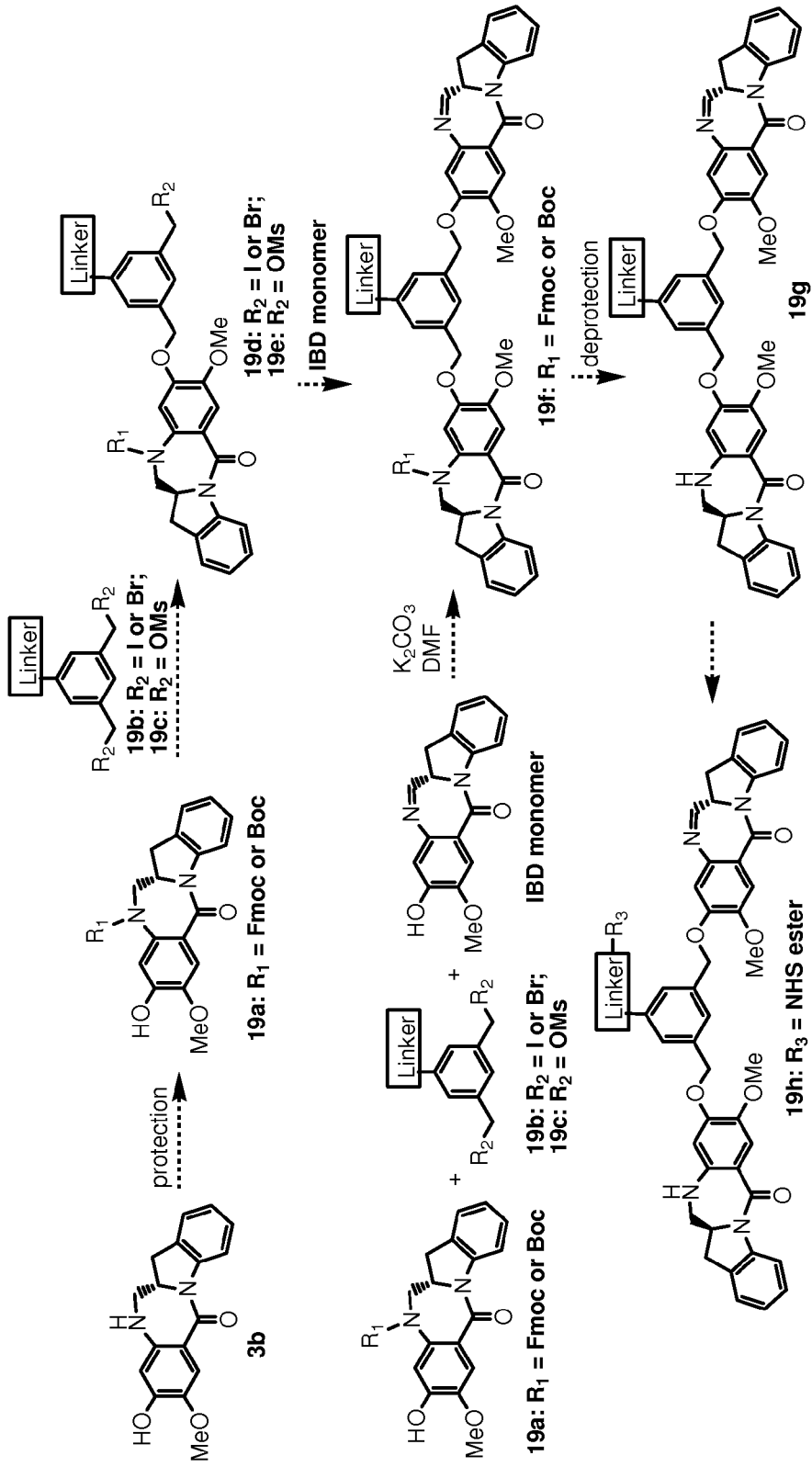
FIG. 20 Synthetic Scheme for a Two-step Mono-imine Dimer Synthesis

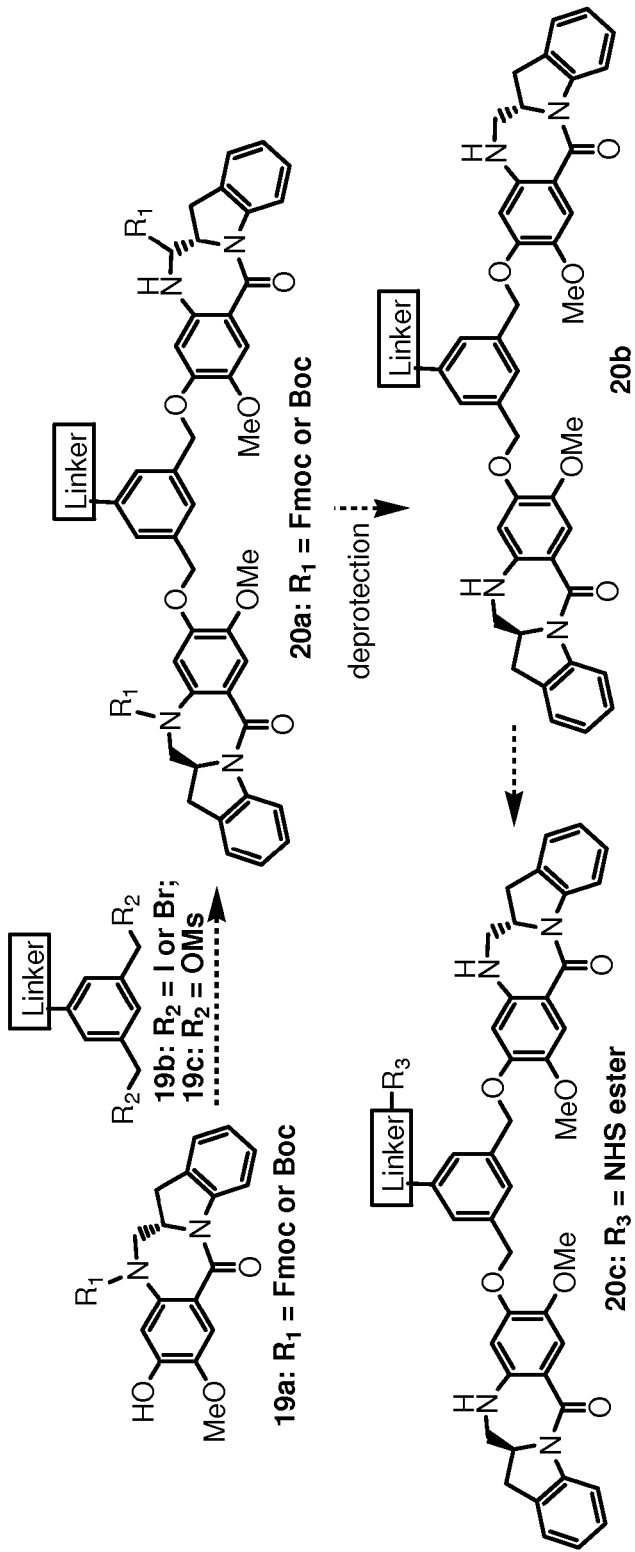
FIG. 21 Synthetic Scheme for a Two-step Di-reduced Dimer Synthesis

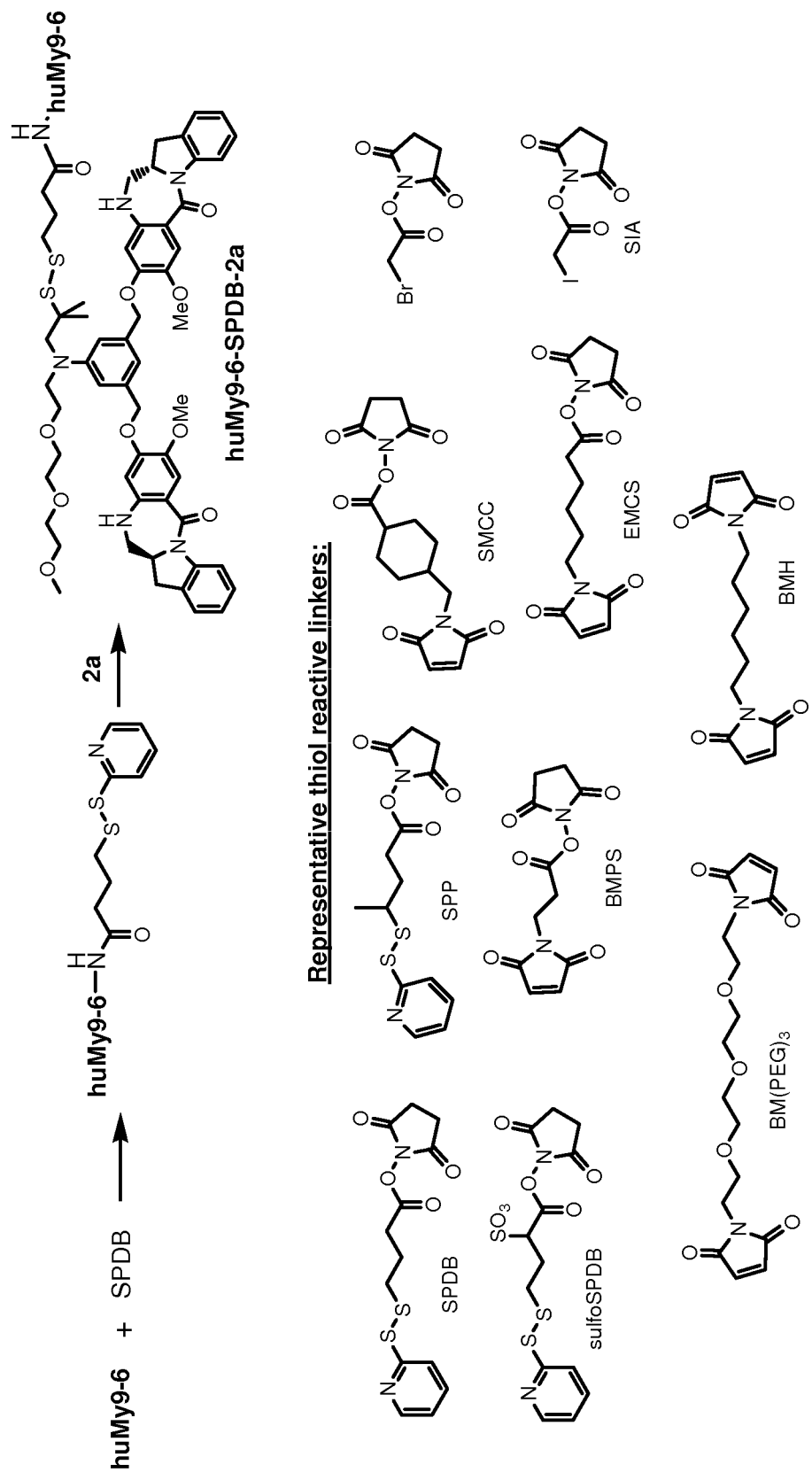
FIG. 23 Two-step Conjugation Scheme

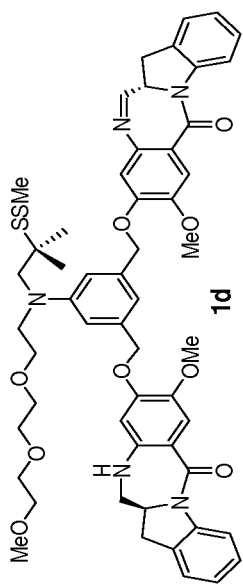
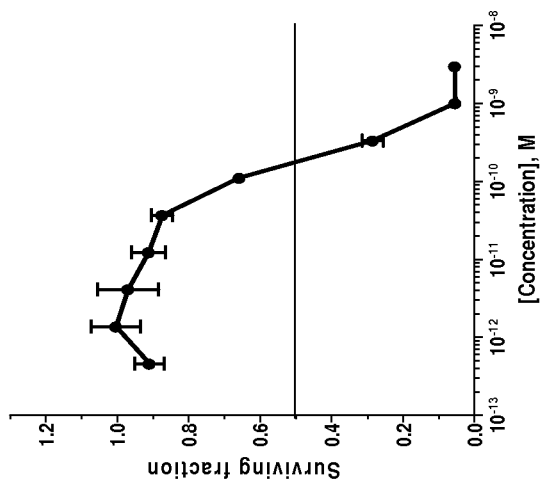
FIG. 24C
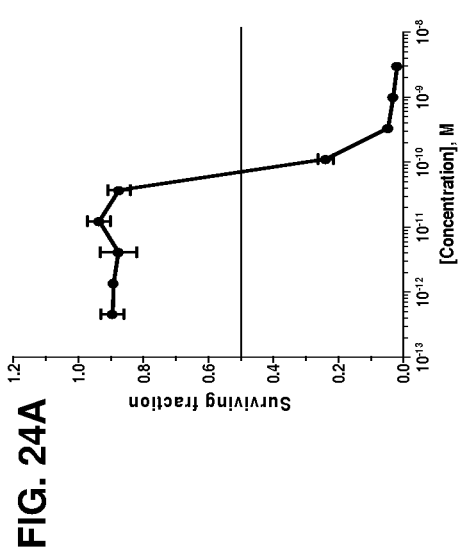
FIG. 24A
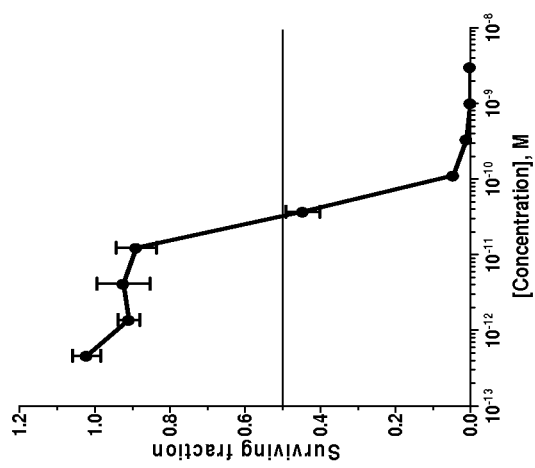
FIG. 24B

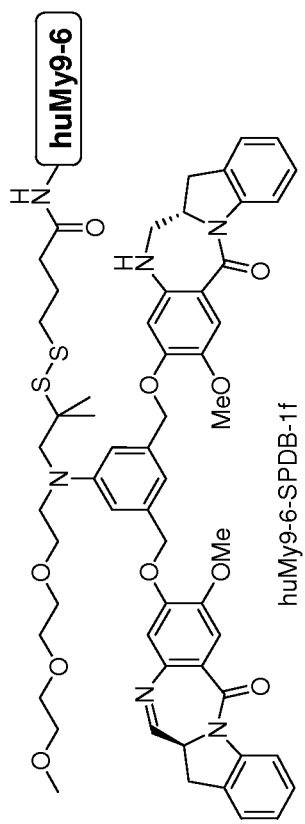
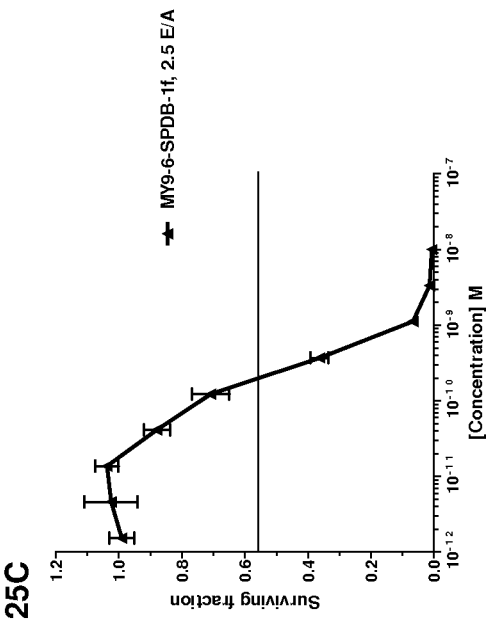
FIG. 25C
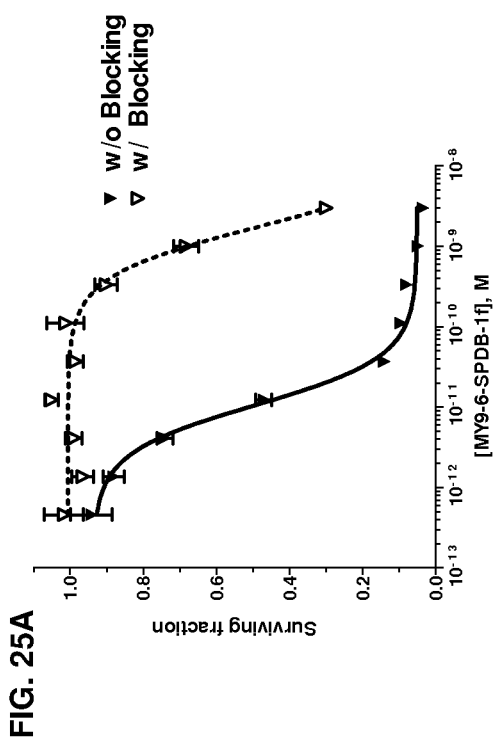
FIG. 25A
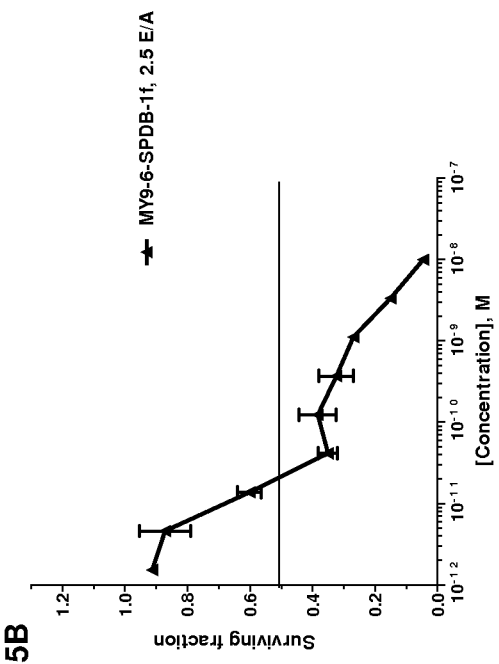
FIG. 25B

FIG. 26 Antiproliferative Activity of huFOLR1-SPDB-1f against KB (Ag⁺) cells with and without blocking of antigen binding sites
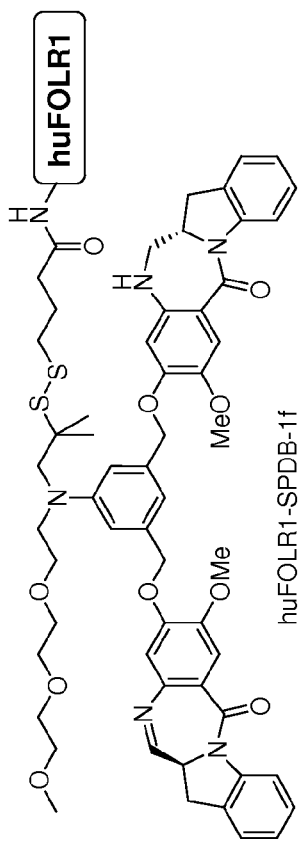
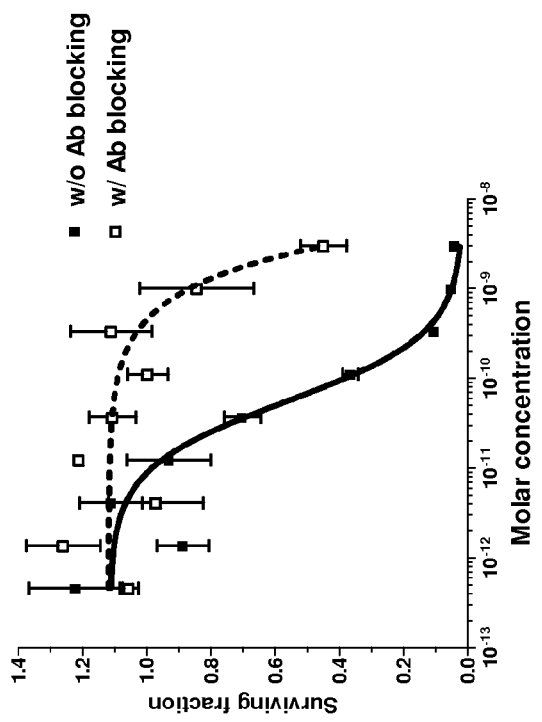

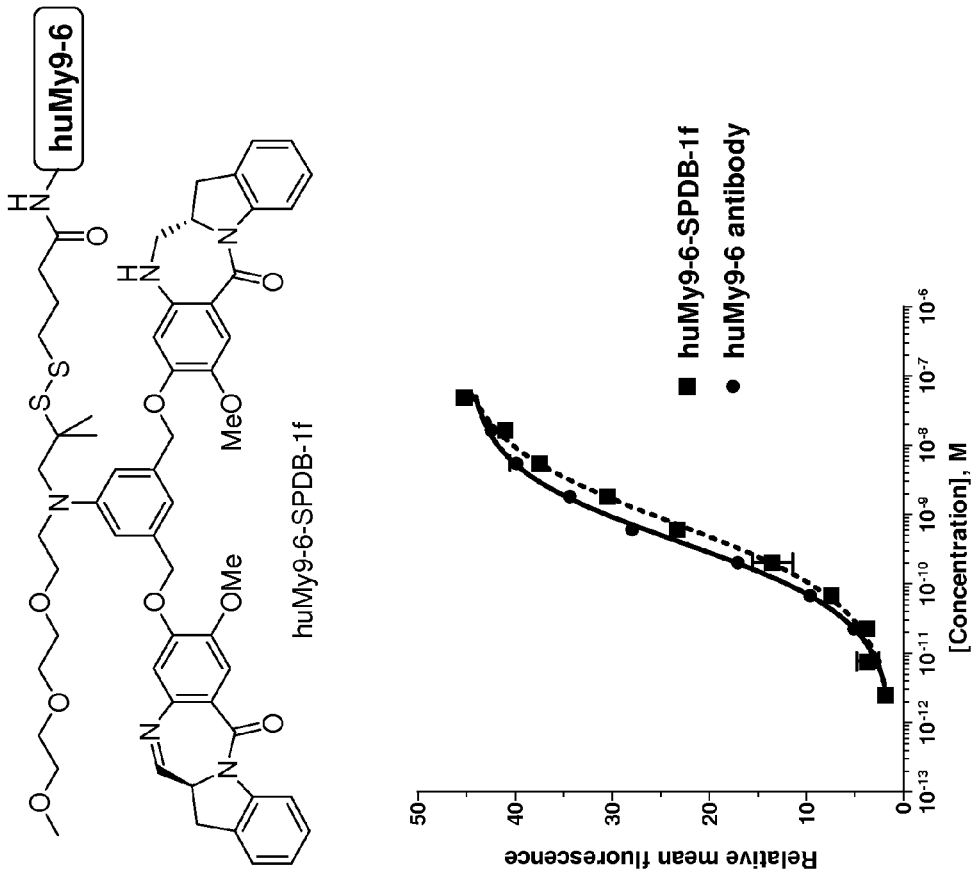
FIG. 27 Binding Affinity of huMY9-6-SPDB-1f (FACS analysis)

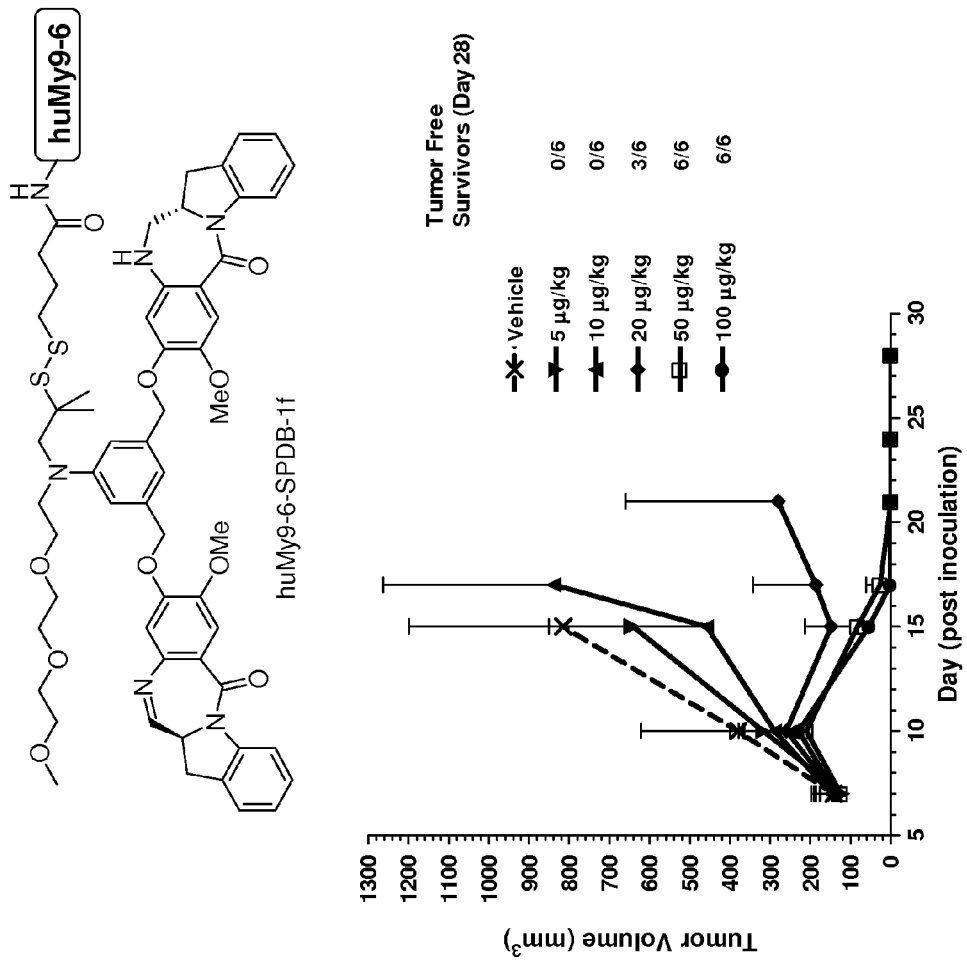
FIG. 28 *In vivo* Efficacy of huMy9-6-SPDB-1f in HL60/QC Tumor Bearing Nude Mice

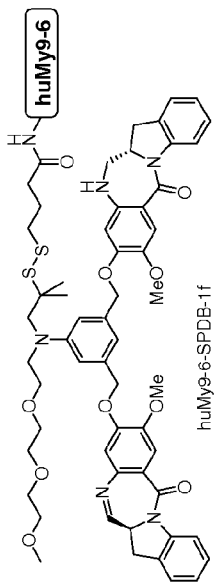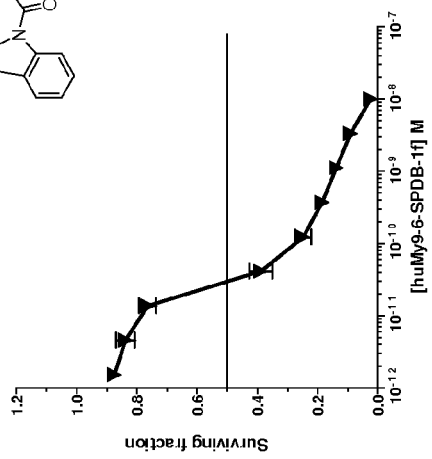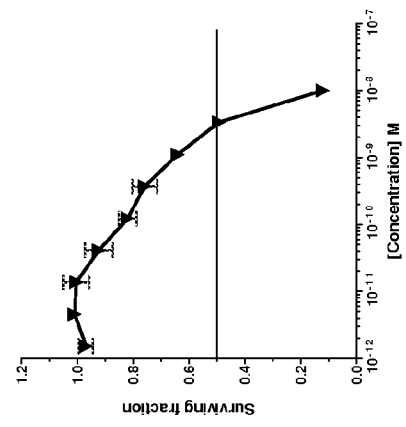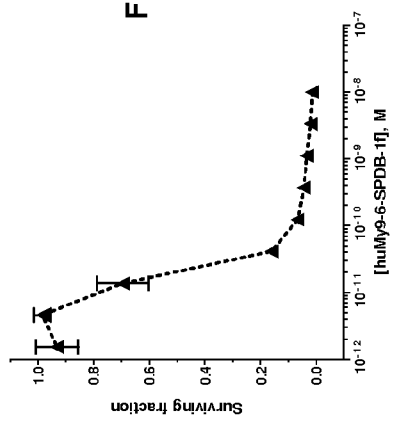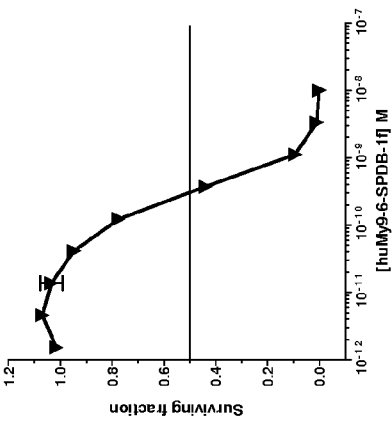
FIG. 29A  FIG. 29B  FIG. 29C  FIG. 29D

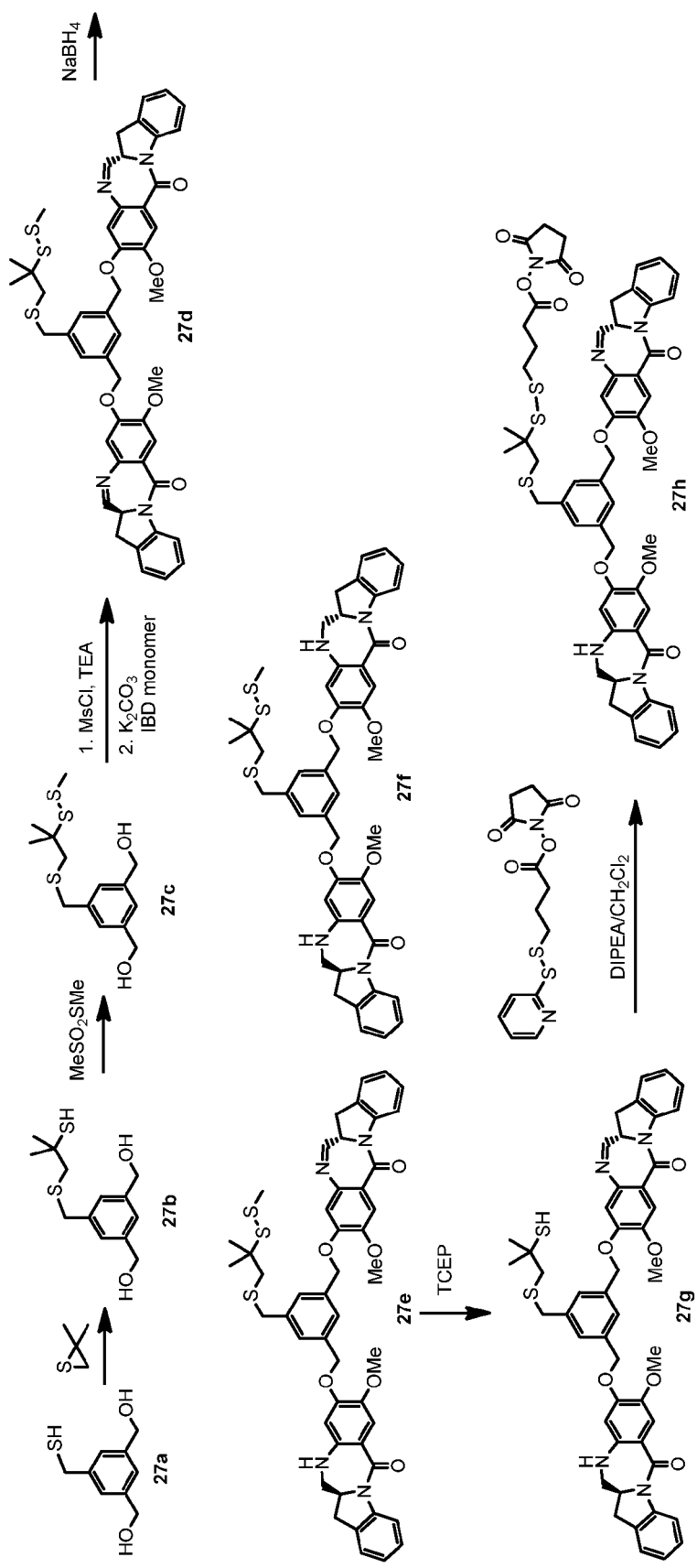
FIG. 30 Synthetic Scheme for Thioether-containing Linker Disulfides 27e-h.

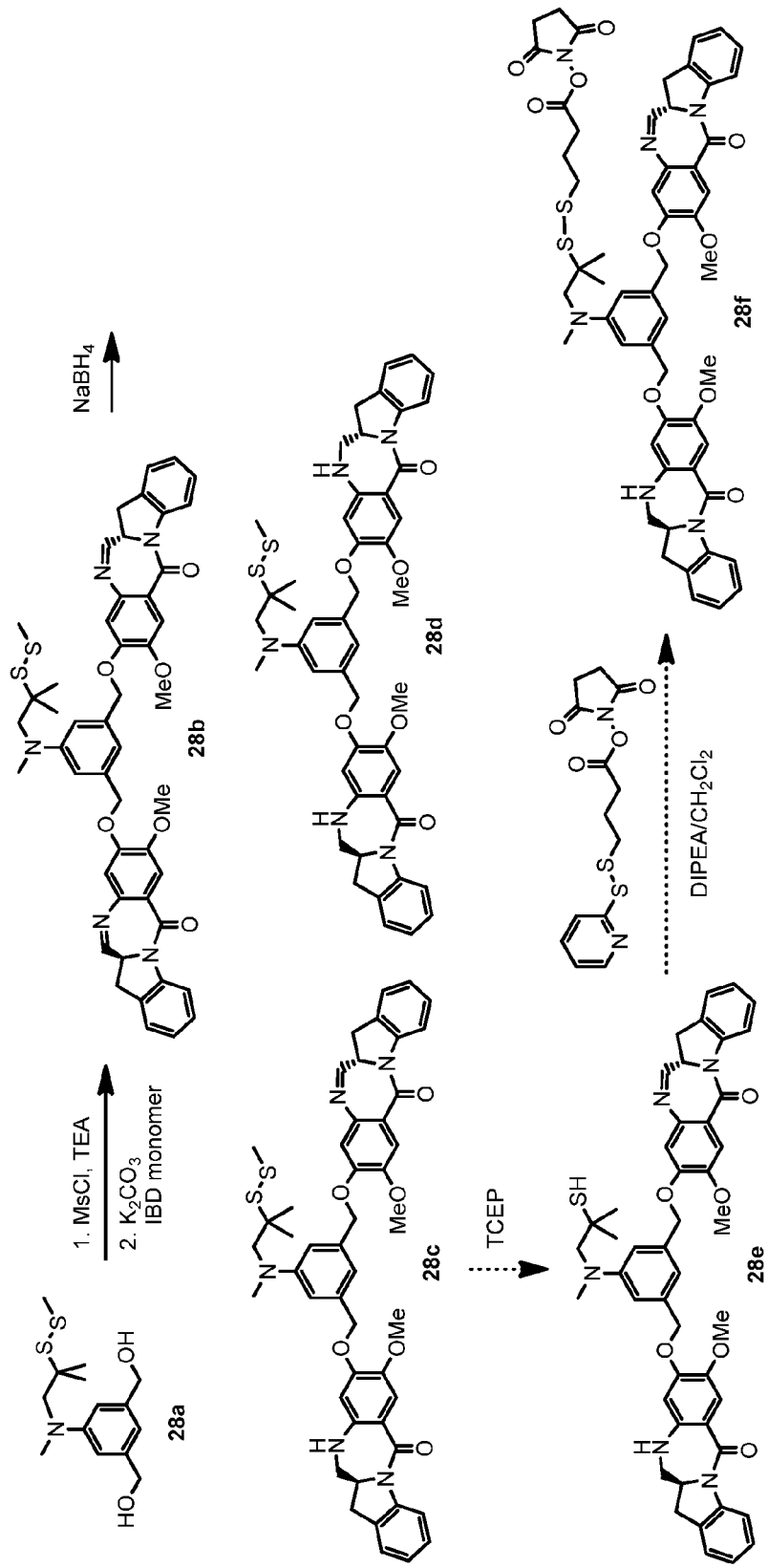
FIG. 31 Synthetic Scheme of Dimers 28c-f

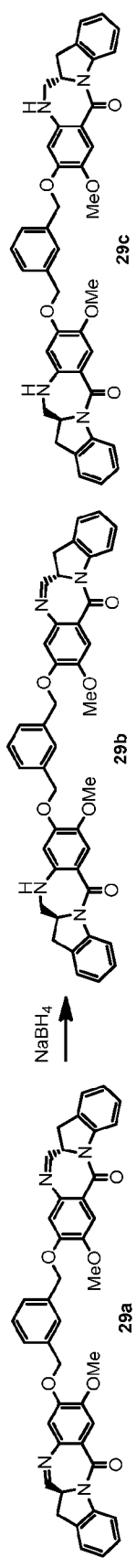
FIG. 32 Synthetic Scheme for Phenyl Linked Dimers 29b-c
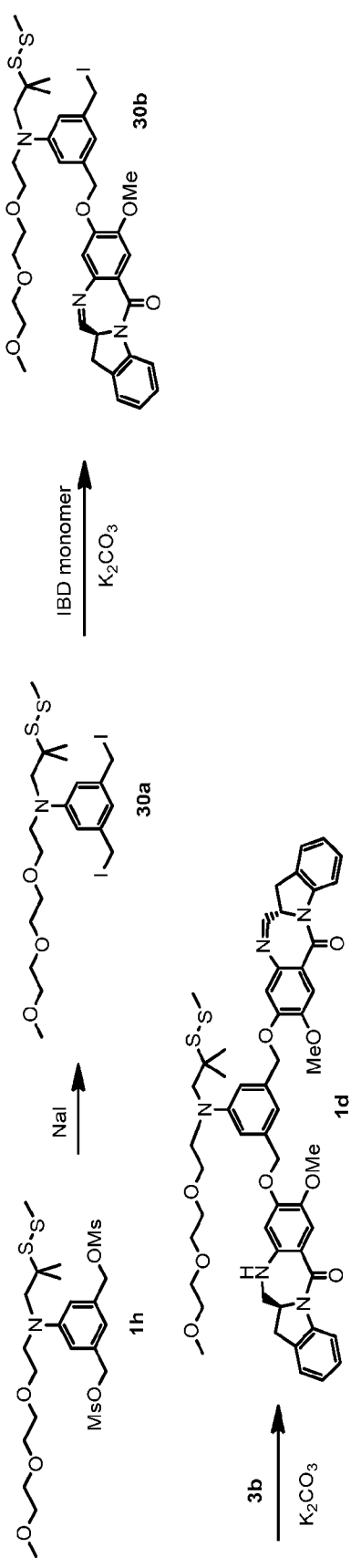
FIG. 33 Alternate Two-step Mono-imine Dimer Synthesis

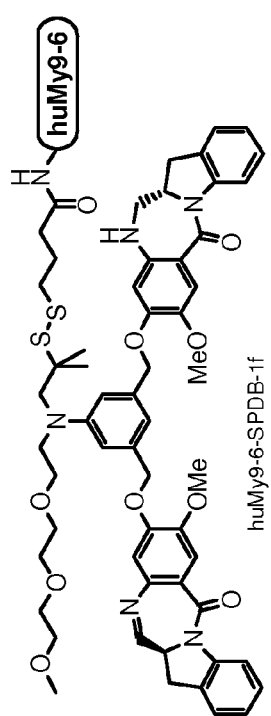
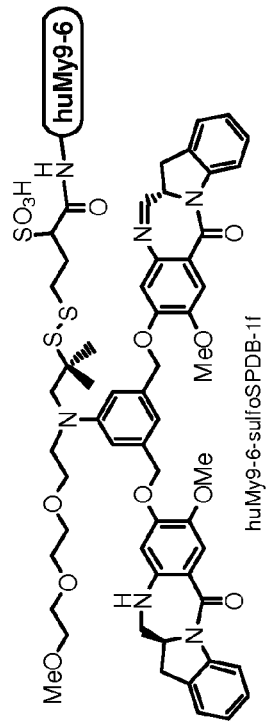
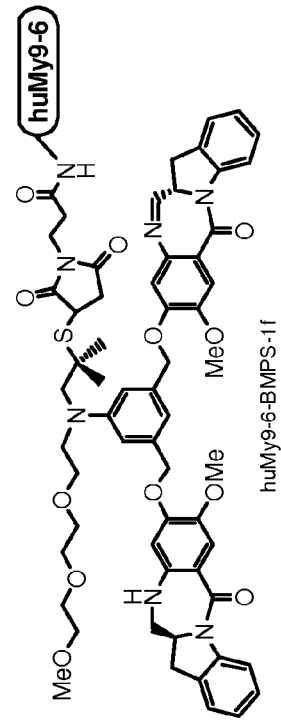
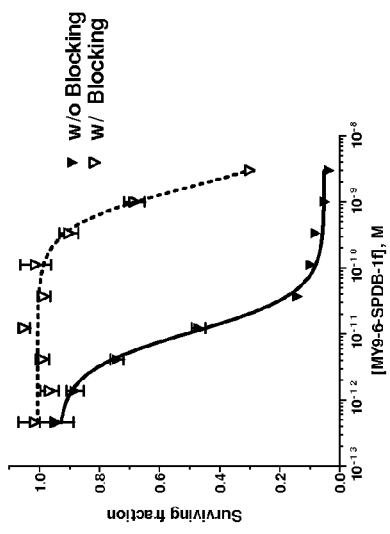
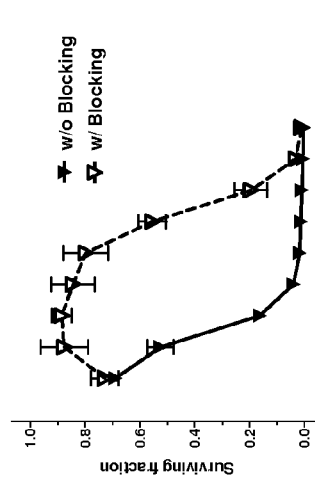
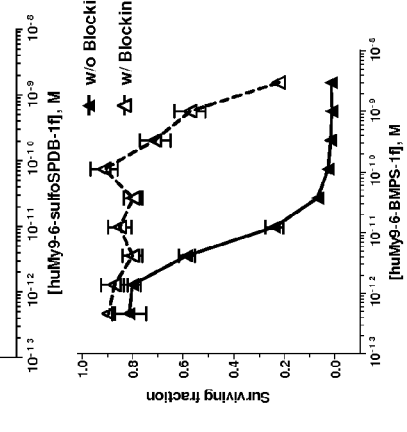
FIG. 34A
FIG. 34B
FIG. 34C

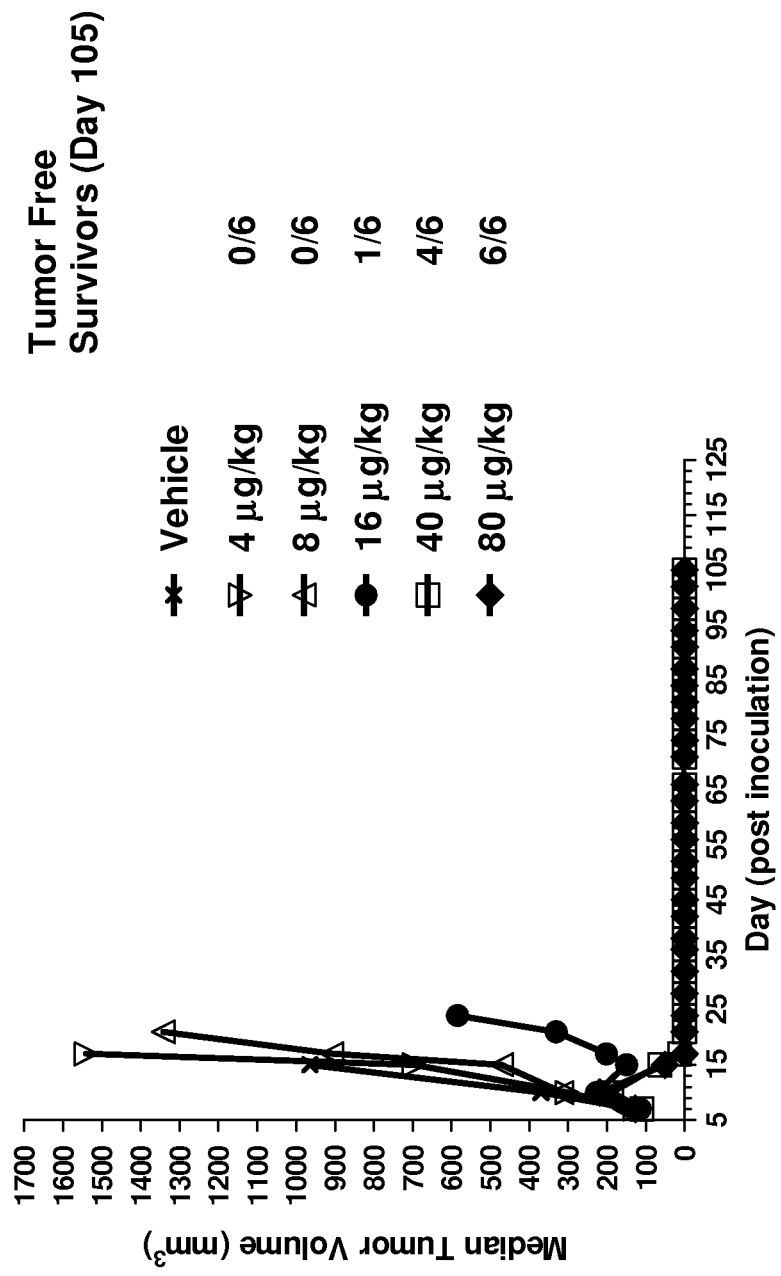
FIG. 36 *In vivo* Efficacy of huMy9-6-SPDB-1f in HL60/QC Tumor Bearing Mice

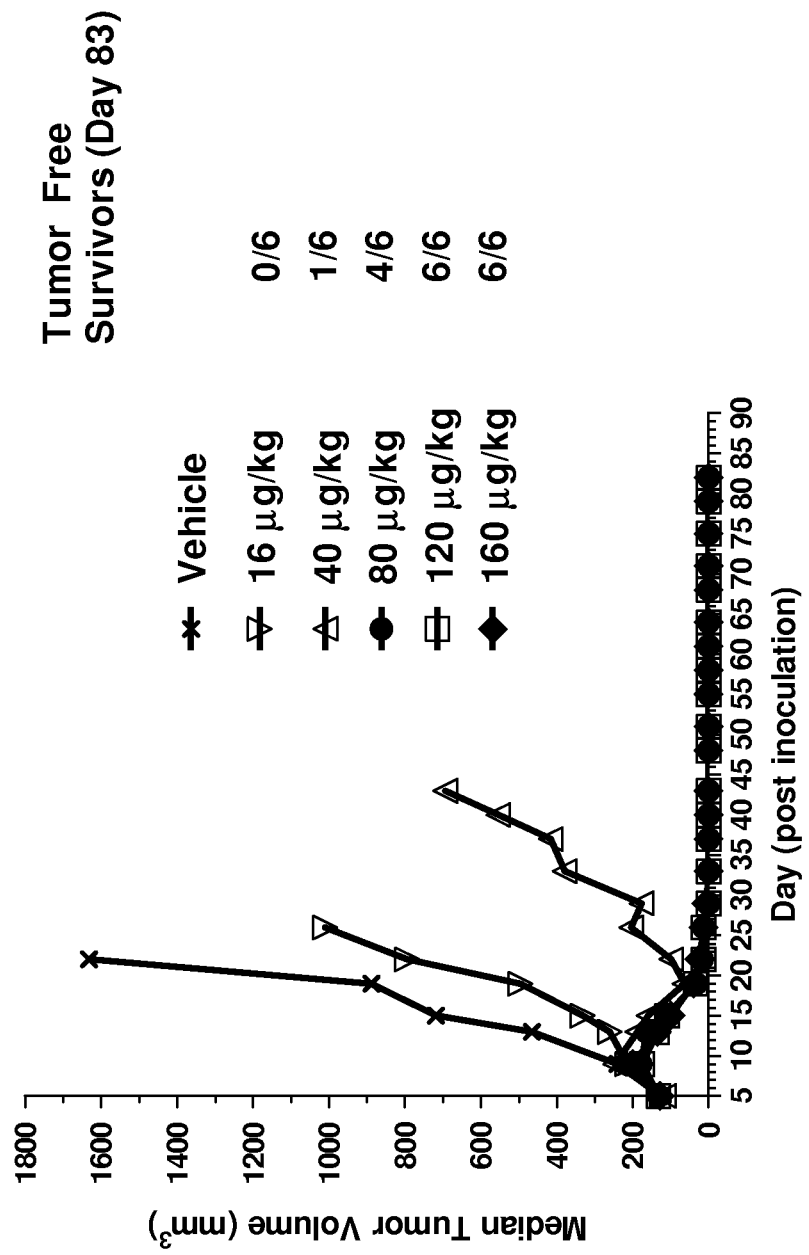
FIG. 37  *In vivo* Efficacy of huFOLR1-SPDB-1f in KB Tumor Bearing Mice

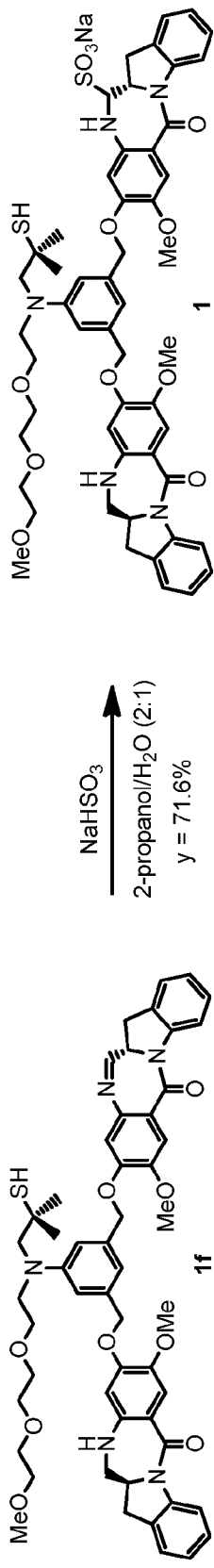
FIG. 38 Synthetic Scheme of Compound 1
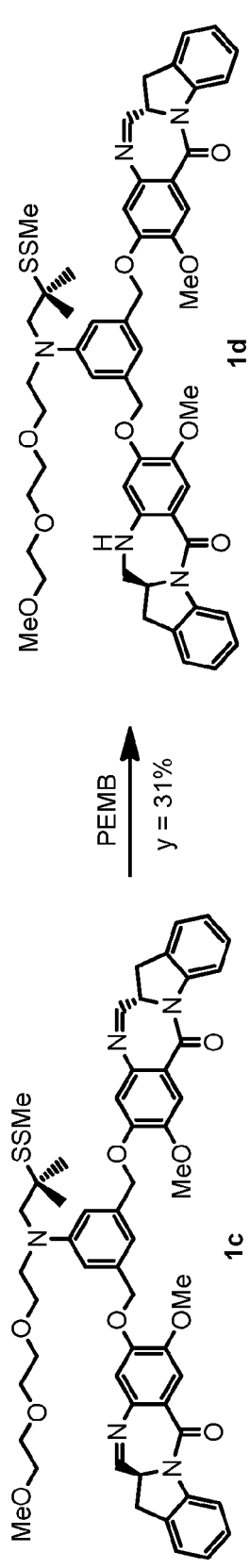
FIG. 39 Synthetic Scheme of Compound 1d with 5-ethyl-2-methylpyridine borane (PEMB)
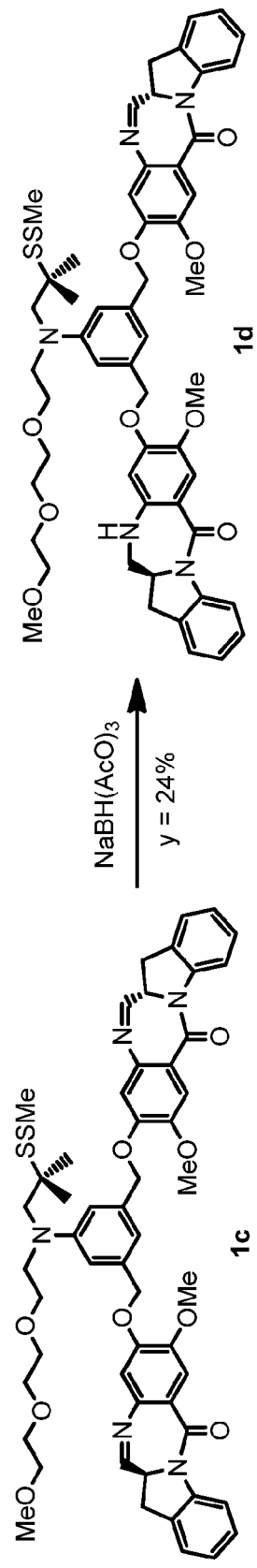
FIG. 40 Synthetic Scheme of Compound 1d with sodium triacetoxyborohydride (STAB)

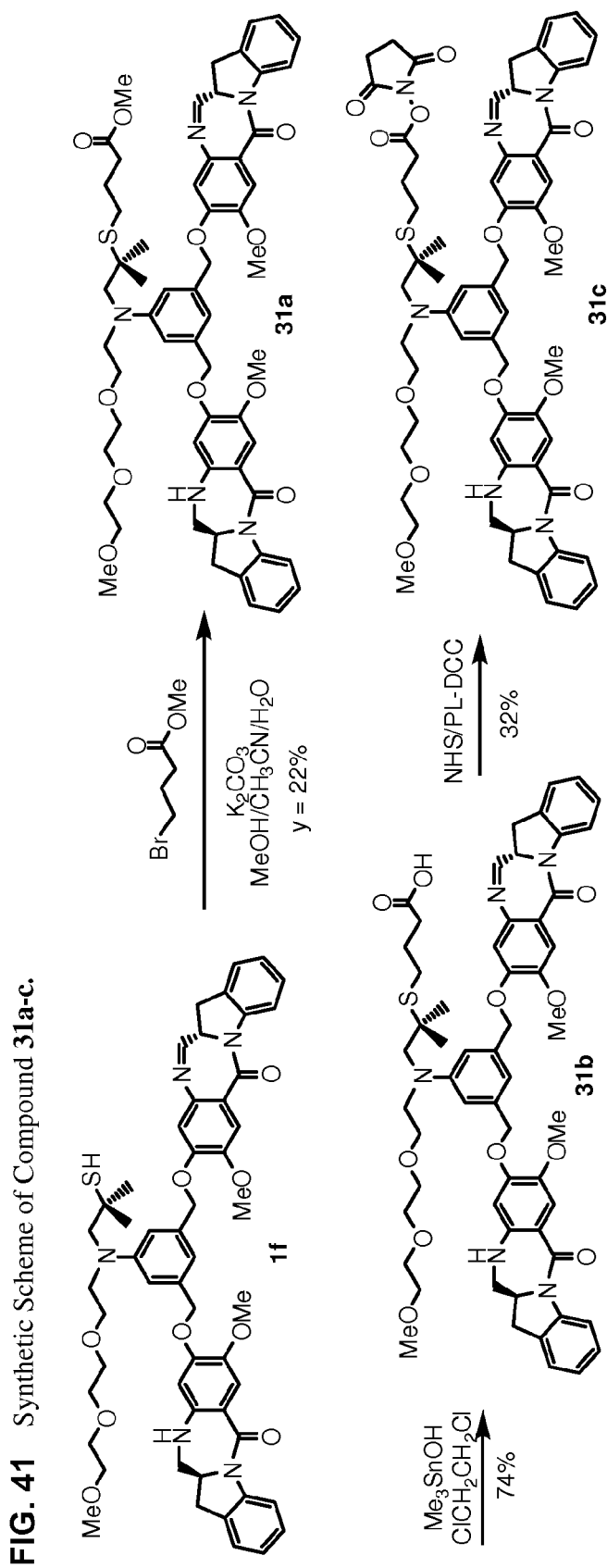
FIG. 41 Synthetic Scheme of Compound 31a-c.

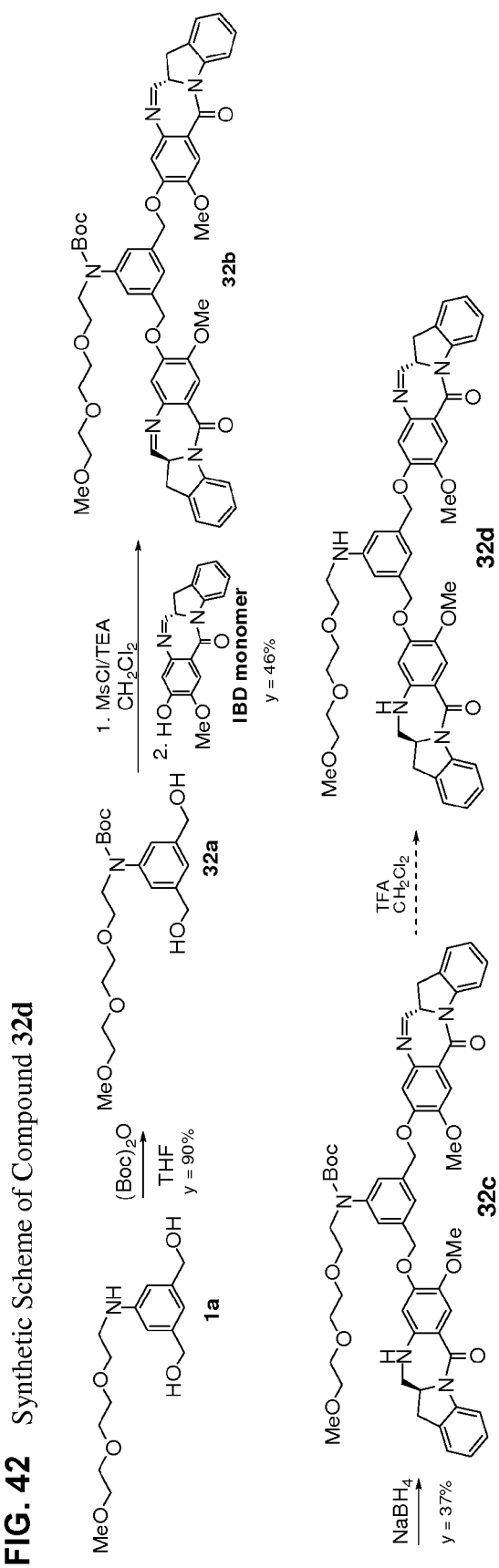
FIG. 42 Synthetic Scheme of Compound 32d

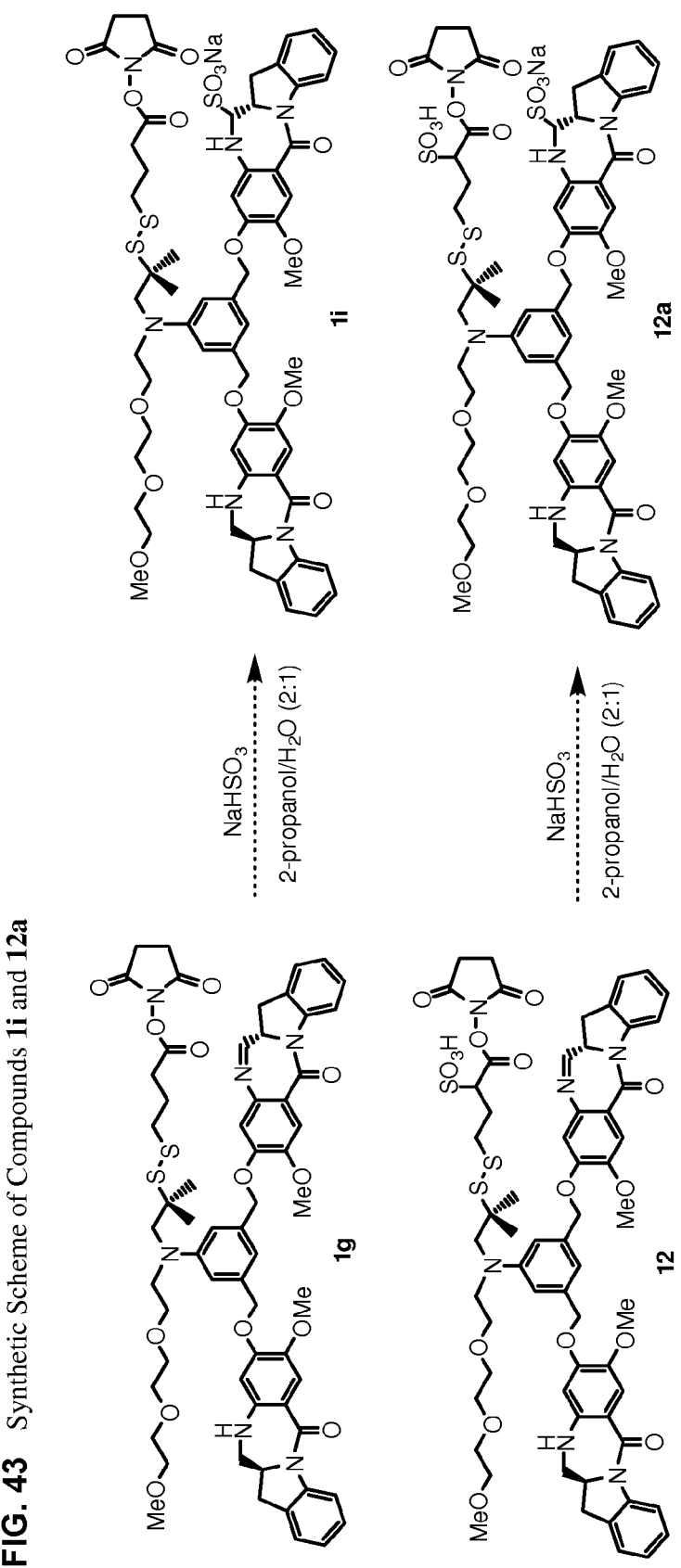
FIG. 43 Synthetic Scheme of Compounds 1i and 12a

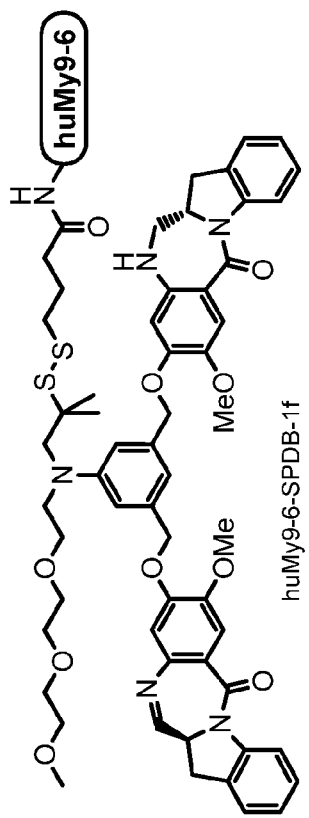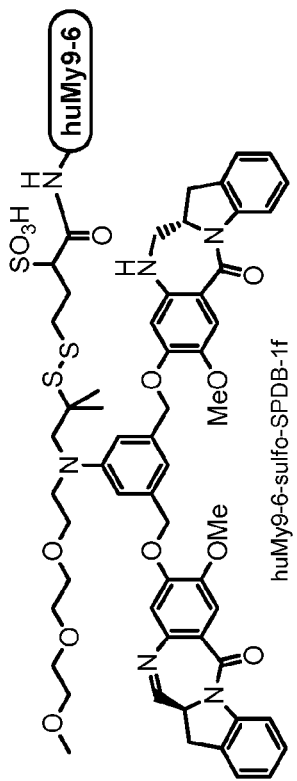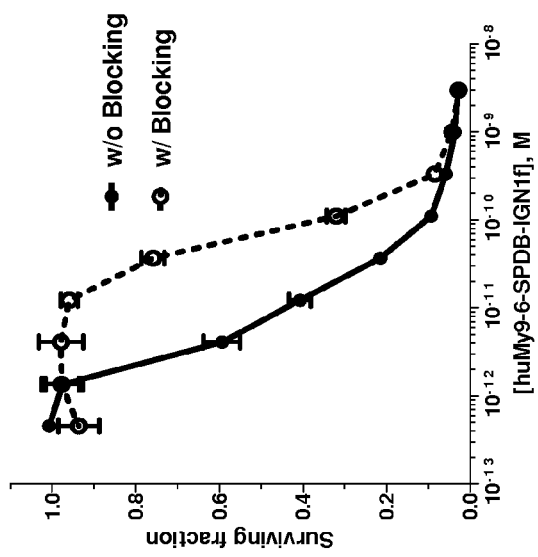
FIG. 44A
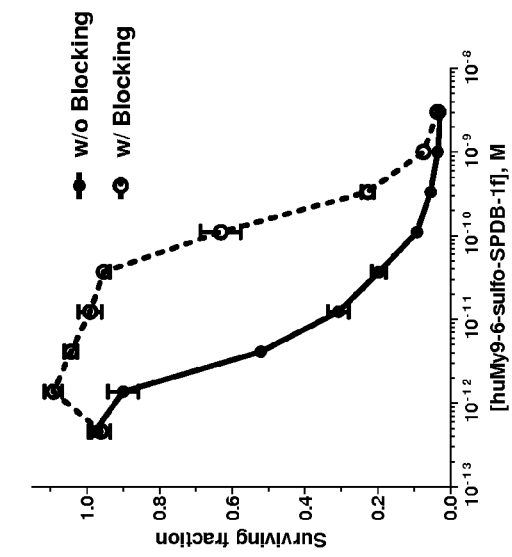
FIG. 44B

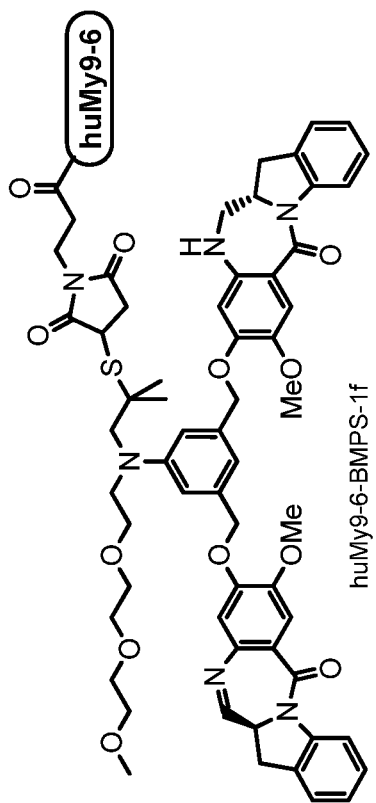
FIG. 44C
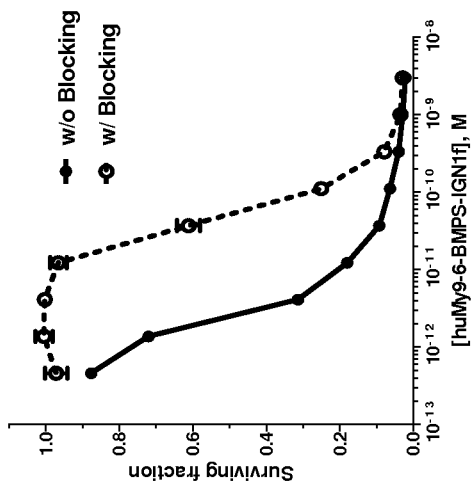
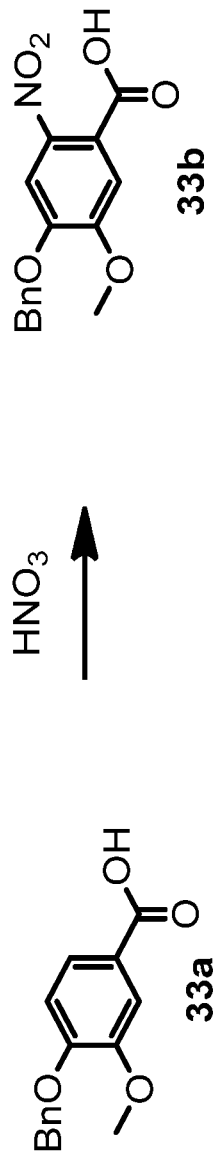
FIG. 45 Synthsis of 4-(benzyloxy)-5-methoxy-2-nitrobenzoic acid used in the Preperation of IBD Monomer

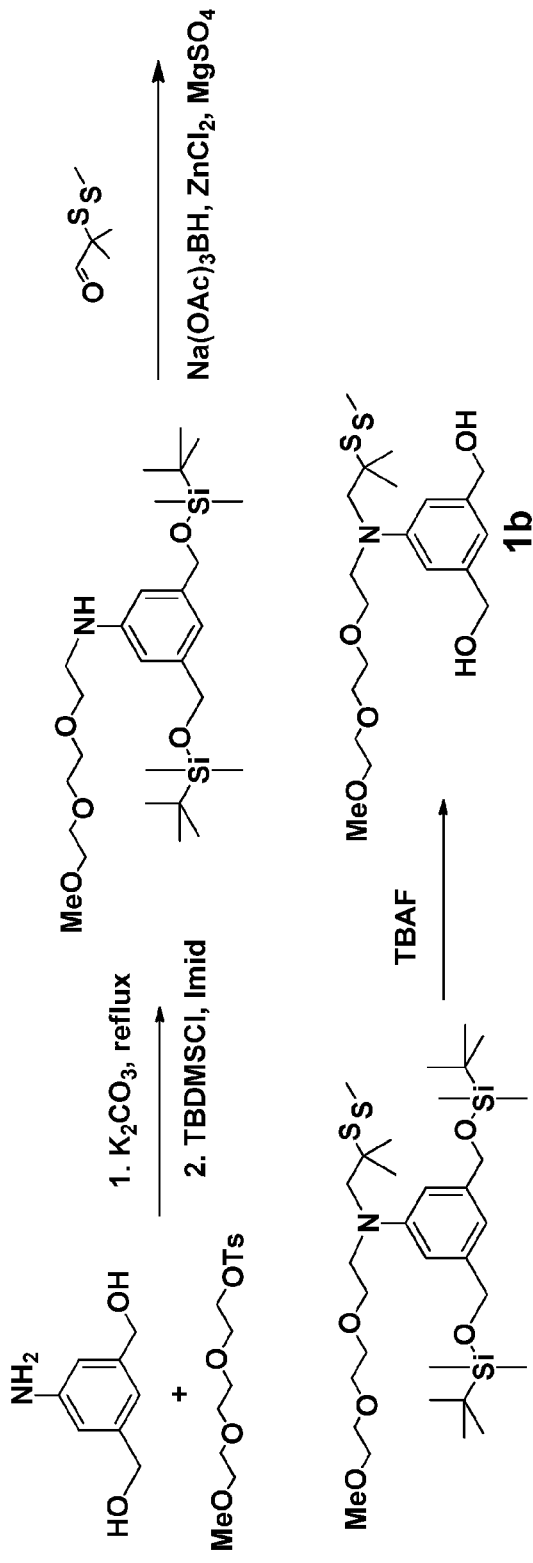
FIG. 46 Alternate Synthesis of (5-((2-(2-(2-(2-methoxyethoxy)ethoxy)ethyl)(2-methyl-2-(methyldisulfanyl)propyl)amino)-1,3-phenylene)dimethanol (1b)
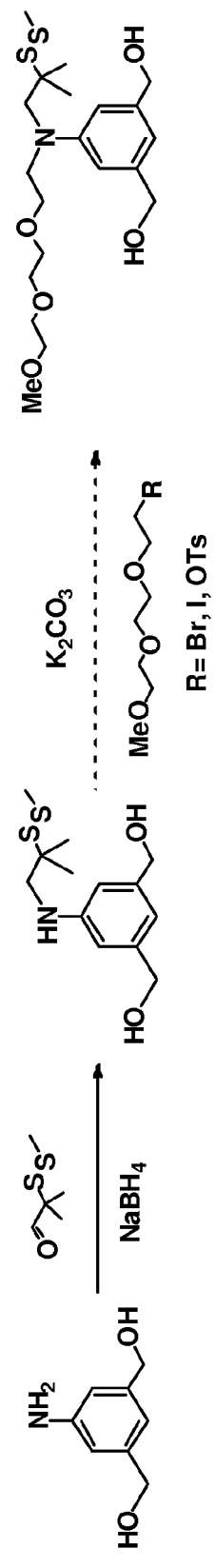
FIG. 47 Alternate Synthesis of (5-((2-(2-(2-(2-methoxyethoxy)ethoxy)ethyl)(2-methyl-2-(methyldisulfanyl)propyl)amino)-1,3-phenylene)dimethanol (1b)

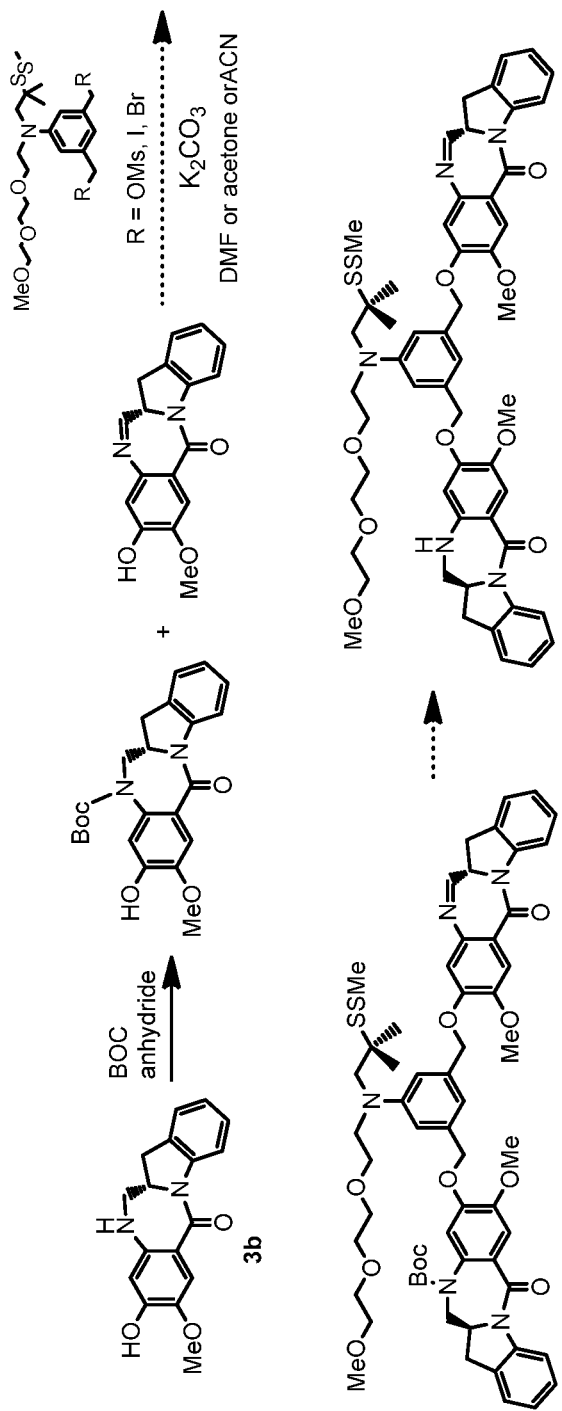
FIG. 48  Alternate Synthetic Scheme for a Two-step Mono-imine Dimer Synthesis
FIG. 49  Potency of Conjugates against Various Cell Lines Measured by IC$_{50}$ values (nM)
| conjugate | HL60/QC | MOLM-13 | NB4 | HEL92.1.7 | OCI-AML3 |
|---|---|---|---|---|---|
| huMy9-6-SPDB-1f | 0.005 | 0.003 | 0.3 | 0.5 | 0.01 |
| huMy9-6-sulfo-SPDB-1f | 0.006 | 0.002 | 0.4 | 0.05 | 0.008 |
| huMy9-6-BMPS-1f | 0.003 | 0.001 | 0.04 | 0.04 | 0.003 |

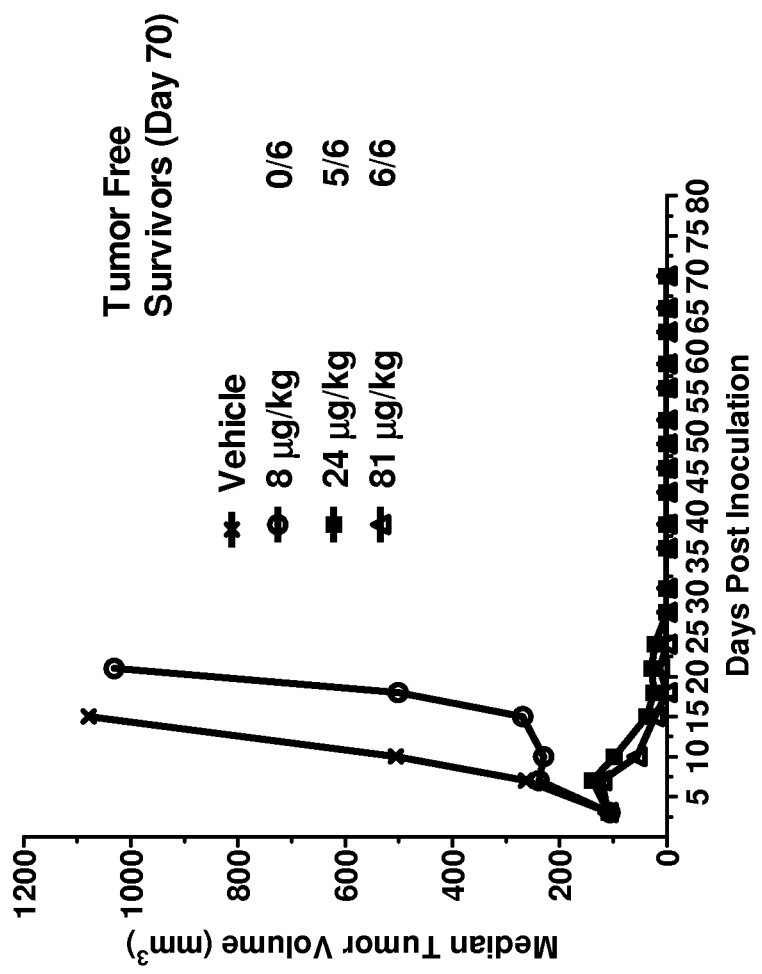
FIG. 50  *In Vivo* Efficacy of huMy9-6-sulfo-SPDB-1f in MOLM-13 Tumor Bearing Mice

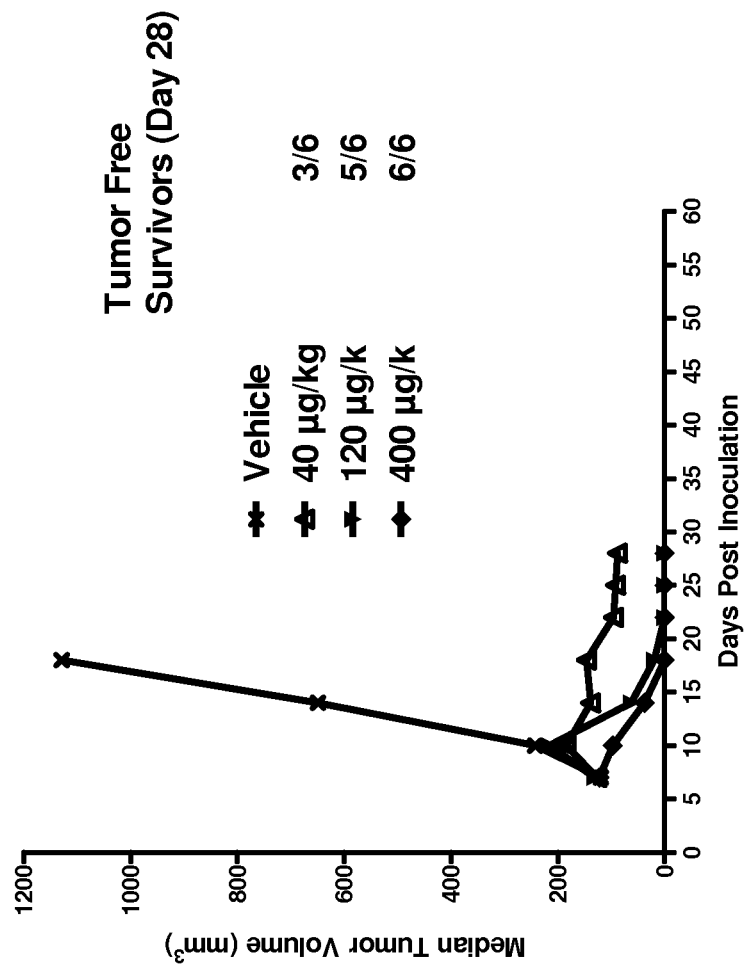
FIG. 51  *In Vivo* Efficacy of huMy9-6-sulfo-SPDB-1f in NB4 Tumor Bearing Mice

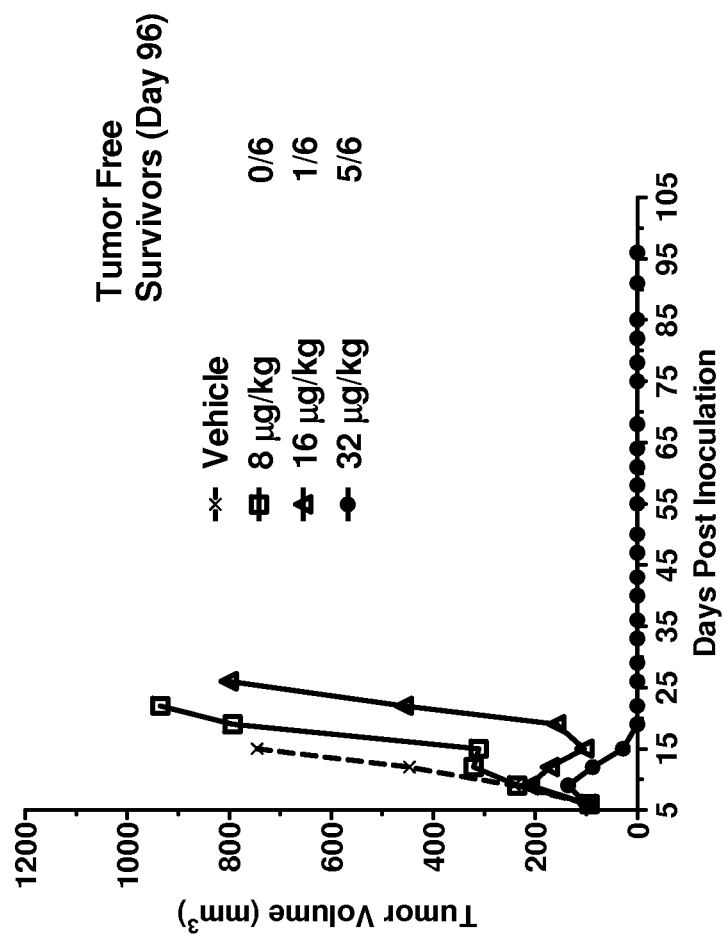
FIG. 52  *In Vivo* Efficacy of huMy9-6-BMPS-1f in HL60/QC Tumor Bearing Mice

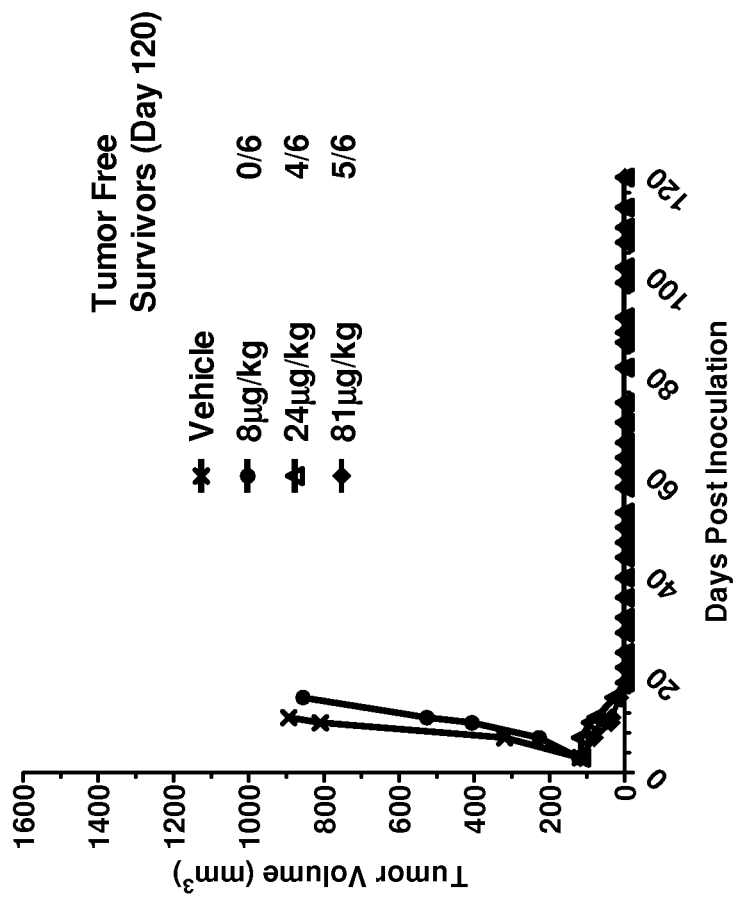
FIG. 53  *In vivo* Efficacy of huMy9-6-BMPS-1f in MOLM-13 Tumor Bearing Mice

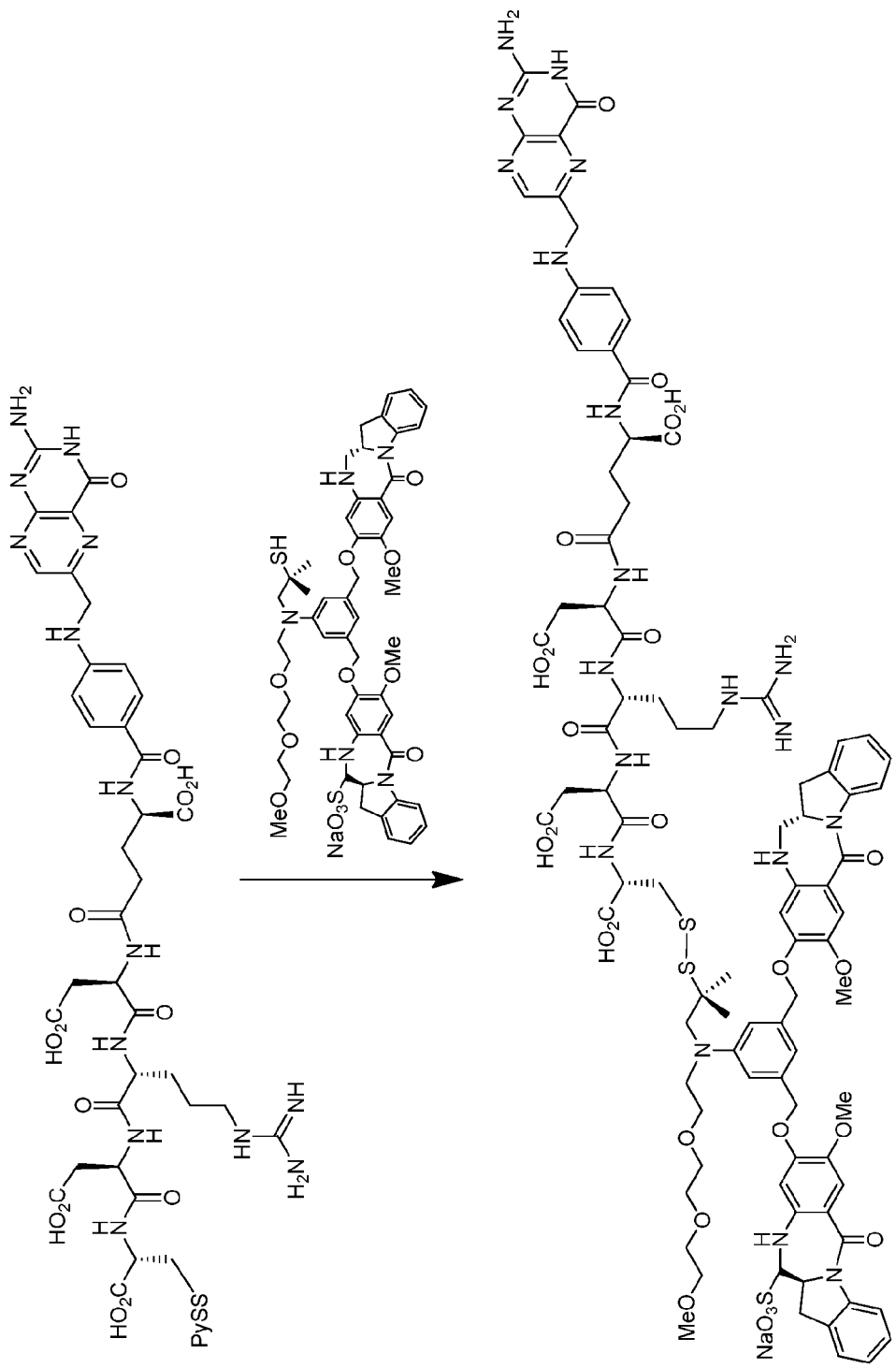
FIG. 54  Representative Synthesis Scheme for a Sulfonated Folate / Cytotoxic Compound Conjugate

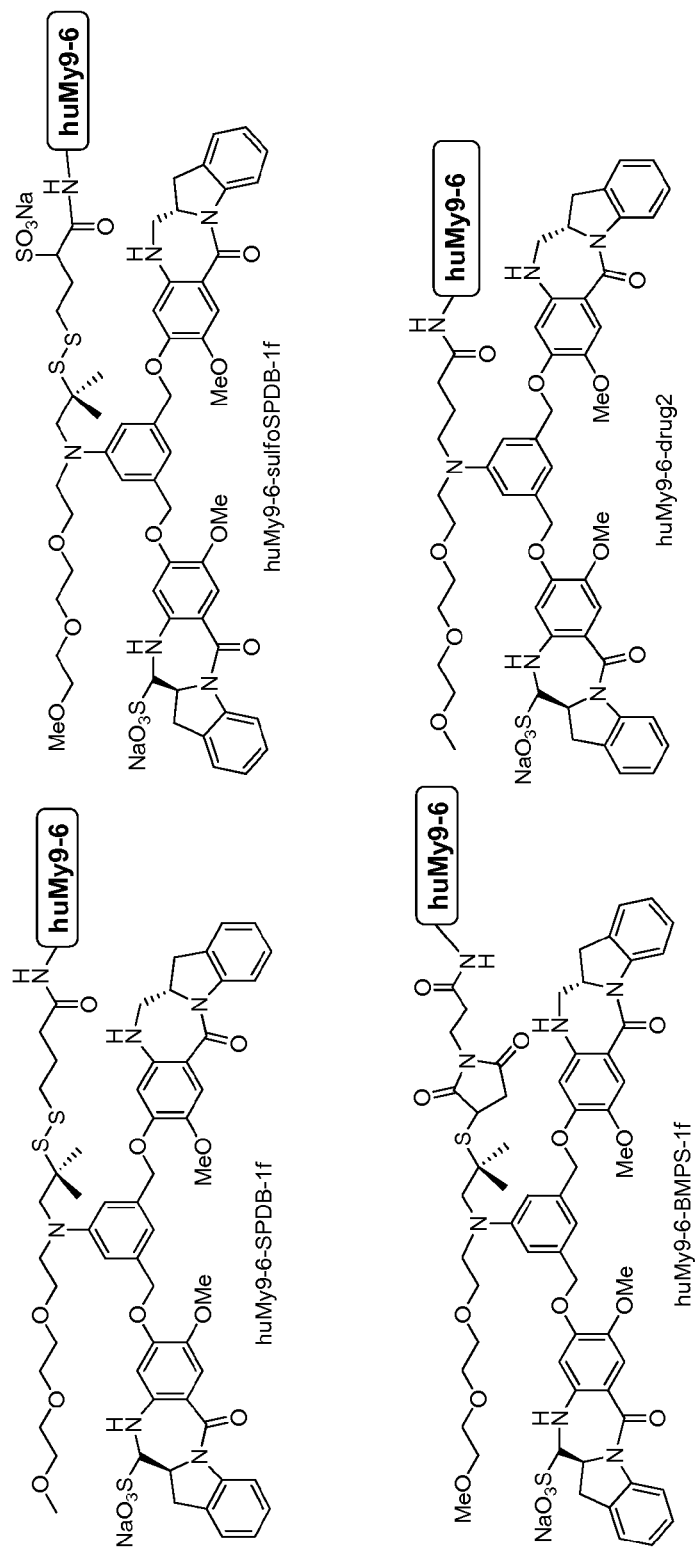
FIG. 55  Structures of Several Sulfonated Drug-Antibody (huMy9-6) Conjugates

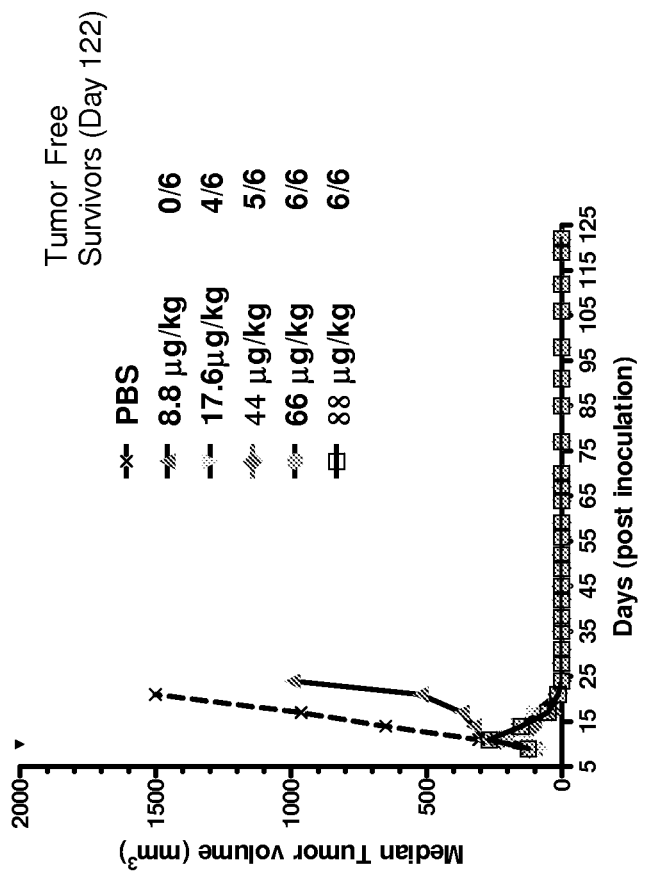
FIG. 56  *In vivo* Efficacy of huMy9-6-drug2 in HL60/QC Tumor Bearing Mice

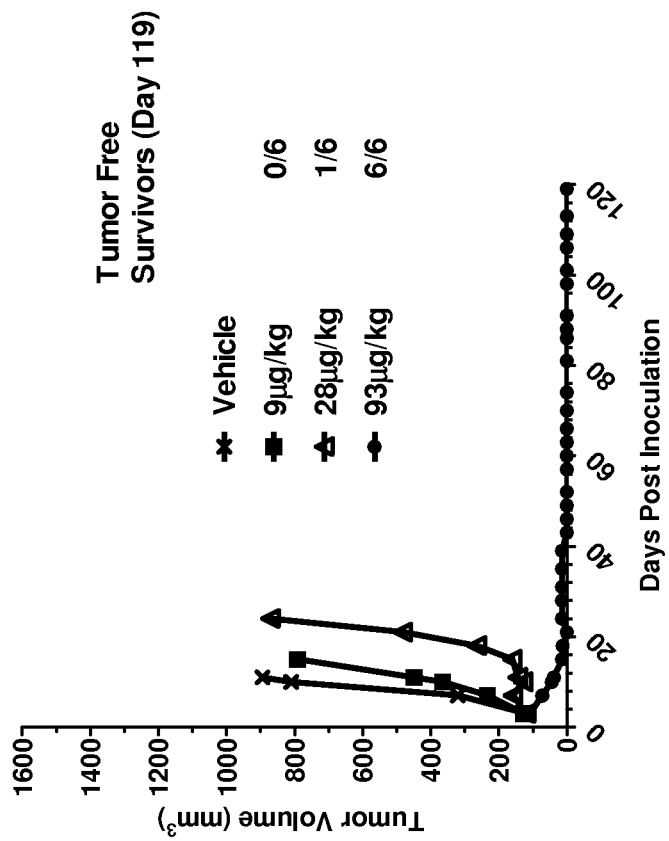
FIG. 57 *In vivo* Efficacy of huMy9-6-drug2 in MOLM-13 Tumor Bearing Mice HuMy9-6-2 conjugates prepared without and with sodium bisulfite show similar *in vitro* cytotoxicity toward CD33-antigen expressing HL60 cells Anti-CD22 Ab-2 conjugates prepared without and with sodium bisulfite show similar *in vitro* cytotoxicity toward CD22-antigen expressing BJAB cells.

SEQUENCE LISTING

```
<160> NUMBER OF SEQ ID NOS: 14

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Tyr Phe Met Asn
1               5

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Lys, Gln, His or Arg
<220> FEATURE:
<221> NAME/KEY: MOD_RES
<222> LOCATION: (16)..(16)
<223> OTHER INFORMATION: Gln, His, Asn or Arg
<220> FEATURE:
<221> NAME/KEY: MOD_RES
<222> LOCATION: (17)..(17)
<223> OTHER INFORMATION: Gly, Glu, Thr, Ser, Ala or Val

<400> SEQUENCE: 2
```

Arg Ile His Pro Tyr Asp Gly Asp Thr Phe Tyr Asn Gln Xaa Phe Xaa
1               5                   10                  15

Xaa

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Tyr Asp Gly Ser Arg Ala Met Asp Tyr
1               5

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Lys Ala Ser Gln Ser Val Ser Phe Ala Gly Thr Ser Leu Met His
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Ala Ser Asn Leu Glu Ala
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gln Gln Ser Arg Glu Tyr Pro Tyr Thr
1               5

<210> SEQ ID NO 7
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Ile His Pro Tyr Asp Gly Asp Thr Phe Tyr Asn Gln Lys Phe Gln
1               5                   10                  15

Gly

```
<210> SEQ ID NO 8
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
                20                  25                  30

Phe Met Asn Trp Val Lys Gln Ser Pro Gly Gln Ser Leu Glu Trp Ile
            35                  40                  45

Gly Arg Ile His Pro Tyr Asp Gly Asp Thr Phe Tyr Asn Gln Lys Phe
        50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365
```

```
Leu Val Lys Gly Phe Tyr Pro Ser Asp Ile Ala Val Glu Trp Glu Ser
    370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
                420                 425                 430
Leu His Asn His Tyr Thr Gln Lys Ser Leu Ser Leu Ser Pro Gly Lys
                435                 440                 445
```

<210> SEQ ID NO 9
<211> LENGTH: 218
<212> TYPE: PRT
<213> ORGANISM: Artificial Sequence
<220> FEATURE:
<223> OTHER INFORMATION: Description of Artificial Sequence: Synthetic
       polypeptide

<400> SEQUENCE: 9

```
Asp Ile Val Leu Thr Gln Ser Pro Leu Ser Leu Ala Val Ser Leu Gly
1               5                   10                  15
Gln Pro Ala Ile Ile Ser Cys Lys Ala Ser Gln Ser Val Ser Phe Ala
                20                  25                  30
Gly Thr Ser Leu Met His Trp Tyr His Gln Lys Pro Gly Gln Gln Pro
            35                  40                  45
Arg Leu Leu Ile Tyr Arg Ala Ser Asn Leu Glu Ala Gly Val Pro Asp
        50                  55                  60
Arg Phe Ser Gly Ser Gly Ser Lys Thr Asp Phe Thr Leu Asn Ile Ser
65                  70                  75                  80
Pro Val Glu Ala Glu Asp Ala Ala Thr Tyr Tyr Cys Gln Gln Ser Arg
                85                  90                  95
Glu Tyr Pro Tyr Thr Phe Gly Gly Gly Thr Lys Leu Glu Ile Lys Arg
                100                 105                 110
Thr Val Ala Ala Pro Ser Val Phe Ile Phe Pro Pro Ser Asp Glu Gln
            115                 120                 125
Leu Lys Ser Gly Thr Ala Ser Val Val Cys Leu Leu Asn Asn Phe Tyr
        130                 135                 140
Pro Arg Glu Ala Lys Val Gln Trp Lys Val Asp Asn Ala Leu Gln Ser
145                 150                 155                 160
Gly Asn Ser Gln Glu Ser Val Thr Glu Gln Asp Ser Lys Asp Ser Thr
                165                 170                 175
Tyr Ser Leu Ser Ser Thr Leu Thr Leu Ser Lys Ala Asp Tyr Glu Lys
                180                 185                 190
His Lys Val Tyr Ala Cys Glu Val Thr His Gln Gly Leu Ser Ser Pro
            195                 200                 205
Val Thr Lys Ser Phe Asn Arg Gly Glu Cys
        210                 215
```

<210> SEQ ID NO 10
<211> LENGTH: 218
<212> TYPE: PRT
<213> ORGANISM: Artificial Sequence
<220> FEATURE:
<223> OTHER INFORMATION: Description of Artificial Sequence: Synthetic
       polypeptide

<400> SEQUENCE: 10

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Thr Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Thr Lys Leu Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 11
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
            20                  25                  30

Phe Met Asn Trp Val Lys Gln Ser Pro Gly Gln Ser Leu Glu Trp Ile
        35                  40                  45

Gly Arg Ile His Pro Tyr Asp Gly Asp Thr Phe Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser
        115

<210> SEQ ID NO 12

```
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Asn Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys Arg
            100                 105                 110

<210> SEQ ID NO 13
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Thr Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys Arg
            100                 105                 110

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ala Leu Ala Leu
1
```

CYTOTOXIC BENZODIAZEPINE DERIVATIVES

REFERENCE TO RELATED APPLICATIONS

This application is a continuation application of U.S. patent application Ser. No. 14/512,059, filed Oct. 10, 2014, which is a continuation application of Ser. No. 13/827,355, filed Mar. 14, 2013, now issued as U.S. Pat. No. 8,889,669 on Nov. 18, 2014, which is a continuation application of Ser. No. 13/397,195, filed Feb. 15, 2012, now issued as U.S. Pat. No. 8,765,740 on Jul. 1, 2014, which claims the benefit of the filing date under 35 U.S.C. §119(e), of U.S. Provisional Application No. 61/443,062, filed on Feb. 15, 2011, and U.S. Provisional Application No. 61/483,499, filed on May 6, 2011, and U.S. Provisional Application No. 61/443,092, filed on Feb. 15, 2011. The entire contents of each of the above-referenced applications, including all drawings, formulae, sequence listings, specifications, and claims, are incorporated herein by reference.

FIELD OF THE INVENTION

The present invention relates to novel cytotoxic compounds, and cytotoxic conjugates comprising these cytotoxic compounds and cell-binding agents. More specifically, this invention relates to novel benzodiazepine compounds derivatives thereof, intermediates thereof, conjugates thereof, and pharmaceutically acceptable salts thereof, which are useful as medicaments, in particular as antiproliferative agents.

BACKGROUND OF THE INVENTION

Benzodiazepine derivatives are useful compounds for treating various disorders, and include medicaments such as, antiepileptics (imidazo[2,1-b][1,3,5]benzothiadiazepines, U.S. Pat. No. 4,444,688; U.S. Pat. No. 4,062,852), antibacterials (pyrimido[1,2-c][1,3,5]benzothiadiazepines, GB 1476684), diuretics and hypotensives (pyrrolo(1,2-b)[1,2,5] benzothiadiazepine 5,5 dioxide, U.S. Pat. No. 3,506,646), hypolipidemics (WO 03091232), anti-depressants (U.S. Pat. No. 3,453,266); osteoporosis (JP 2138272).

Recently, it has been shown in animal tumor models that benzodiazepine derivatives, such as pyrrolobenzodiazepines (PBDs), act as anti-tumor agents (N-2-imidazolyl alkyl substituted 1,2,5-benzothiadiazepine-1,1-dioxide, U.S. Pat. No. 6,156,746), benzo-pyrido or dipyrido thiadiazepine (WO 2004/069843), pyrrolo[1,2-b]benzothiadiazepines and pyrrolo[1,2-b][1,2,5]benzodiazepine derivatives (WO2007/015280), tomaymycin derivatives (e.g., pyrrolo[1,4]benzodiazepines), such as those described in WO 00/12508, WO2005/085260, WO2007/085930, and EP 2019104. Benzodiazepines are also known to affect cell growth and differentiation (Kamal A., et al., Bioorg Med Chem. 2008 Aug. 15; 16(16):7804-10 (and references cited therein); Kumar R, Mini Rev Med Chem. 2003 June; 3(4):323-39 (and references cited therein); Bednarski J J, et al., 2004; Sutter A. P, et al., 2002; Blatt N B, et al., 2002), Kamal A. et al., Current Med. Chem., 2002; 2; 215-254, Wang J-J., J. Med. Chem., 2206; 49:1442-1449, Alley M. C. et al., Cancer Res. 2004; 64:6700-6706, Pepper C. J., Cancer Res 2004; 74:6750-6755, Thurston D. E. and Bose D. S., Chem Rev 1994; 94:433-465; and Tozuka, Z., et al., Journal of Antibiotics, (1983) 36; 1699-1708. General structure of PBDs is described in US Publication Number 20070072846. The PBDs differ in the number, type and position of substituents, in both their aromatic A rings and pyrrolo C rings, and in the degree of saturation of the C ring. Their ability to form an adduct in the minor groove and crosslink DNA enables them to interfere with DNA processing, hence their potential for use as antiproliferative agents.

The first pyrrolobenzodiazepine to enter the clinic, SJG-136 (NSC 694501) is a potent cytotoxic agent that causes DNA inter-strand crosslinks (S. G Gregson et al., 2001, J. Med. Chem., 44: 737-748; M. C. Alley et al., 2004, Cancer Res., 64: 6700-6706; J. A. Hartley et al., 2004, Cancer Res., 64: 6693-6699; C. Martin et al., 2005, Biochemistry., 44: 4135-4147; S. Arnould et al., 2006, Mol. Cancer Ther., 5: 1602-1509). Results from a Phase I clinical evaluation of SJG-136 revealed that this drug was toxic at extremely low doses (maximum tolerated dose of 45 µg/m$^2$, and several adverse effects were noted, including vascular leak syndrome, peripheral edema, liver toxicity and fatigue. DNA damage was noted at all doses in circulating lymphocytes (D. Hochhauser et al., 2009, Clin. Cancer Res., 15: 2140-2147). Thus, there exists a need for improved benzodiazepine derivatives that are less toxic and still therapeutically active for treating a variety of proliferative disease states, such as cancer.

SUMMARY OF THE INVENTION

Cytotoxic benzodiazepine dimers disclosed in the art possess two imine functionalities in their free form or reversibly protected form, such as a hydrate, alkoxylate or sulfonate. The presence of these two imine functionalities results in crosslinking of DNA (S. G. Gregson et al., 2001, J. Med. Chem., 44: 737-748). The present invention is partly based on the unexpected finding that cell binding agent conjugates of new cytotoxic benzodiazepine derivatives, such as indolinobenzodiazapene dimers that are devoid of two imine functionalities (e.g., one imine functionality and one amine functionality), and thus incapable of crosslinking DNA, display a much higher therapeutic index (ratio of maximum tolerated dose to minimum effective dose) in vivo compared to benzodiazepine derivatives that can crosslink DNA that are previously disclosed in the art.

Thus one object of the invention is to provide cytotoxic compound comprising a linking group with a reactive group bonded thereto capable of covalently linking the cytotoxic compound to a cell binding agent (CBA, see below), wherein the cytotoxic compound is represented by any one of the following formulas:

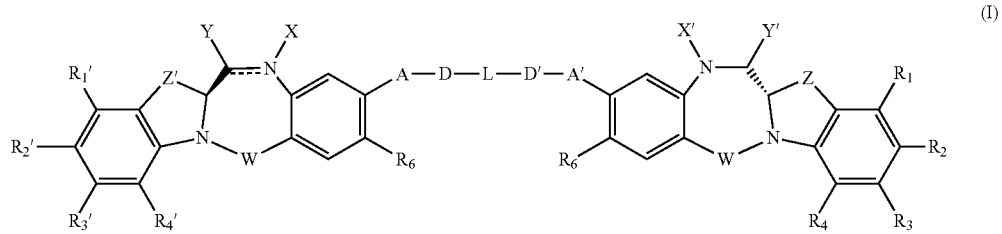

(I)

-continued

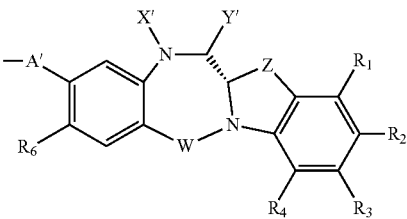

(II)

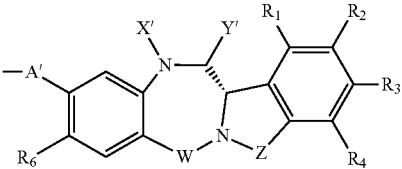

(III)

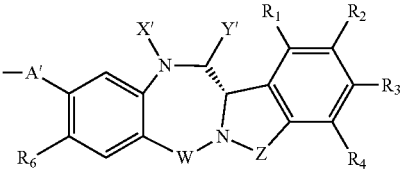

(IV)

or a pharmaceutically acceptable salt thereof, wherein:

the double line ═ between N and C represents a single bond or a double bond, provided that when it is a double bond X is absent and Y is —H, or a linear or branched alkyl having 1 to 4 carbon atoms, and when it is a single bond, X is —H, the linking group with the reactive group bonded thereto, or an amine protecting moiety;

Y is —H or a leaving group selected from —OR, —OCOR', —OCOOR', —OCONR'R", —NR'R", —NR'COR", —NR'NR'R", an optionally substituted 5 or 6-membered nitrogen-containing heterocycle (e.g., piperidine, tetrahydropyrrole, pyrazole, morpholine, etc.), a guanidinum represented by —NR'(C═NH)NR'R", an amino acid, or a peptide represented by —NRCOP', wherein P' is an amino acid or a polypeptide containing between 2 to 20 amino acid units, —SR, —SOR', —SO$_2$M, —SO$_3$M, —OSO$_3$M, halogen, cyano and an azido; or, Y is a sulfite (HSO$_3$, HSO$_2$ or a salt of HSO$_3^-$, SO$_3^{2-}$ or HSO$_2^-$ formed with a cation), metabisulfite (H$_2$S$_2$O$_5$ or a salt of S$_2$O$_5^{2-}$ formed with a cation), mono-, di-, tri-, and tetra-thiophosphate (PO$_3$SH$_3$, PO$_2$S$_2$H$_2$, POS$_3$H$_2$, PS$_4$H$_2$ or a salt of PO$_3$S$^{3-}$, PO$_2$S$_2^{3-}$, POS$_3^{3-}$ or PS$_4^{3-}$ formed with a cation), thio phosphate ester (R$^i$O)$_2$PS(OR$^i$), R$^i$S—, R$^i$SO, R$^i$SO$_2$, R$^i$SO$_3$, thiosulfate (HS$_2$O$_3$ or a salt of S$_2$O$_3^{2-}$ formed with a cation), dithionite (HS$_2$O$_4$ or a salt of S$_2$O$_4^{2-}$ formed with a cation), phosphorodithioate (P(═S)(OR$^{k'}$)(S)(OH) or a salt thereof formed with a cation), hydroxamic acid (R$^{k'}$C(═O)NOH or a salt formed with a cation), aldehyde sulfoxylate (HOCH$_2$SO$_2^-$ or a salt of HOCH$_2$SO$_2^-$ formed with a cation, such as HOCH$_2$SO$_2^-$Na$^+$) or a mixture thereof, wherein R' is a linear or branched alkyl having 1 to 10 carbon atoms and is substituted with at least one substituent selected from —N(R$^j$)$_2$, —CO$_2$H, —SO$_3$H, and —PO$_3$H; R$^i$ can be further optionally substituted with a substituent for an alkyl described herein; R$^j$ is a linear or branched alkyl having 1 to 6 carbon atoms; R$^{k'}$ is a linear, branched or cyclic alkyl, alkenyl or alkynyl having 1 to 10 carbon atoms, aryl, heterocyclyl or heteroaryl; preferably, Y is an adduct of a bisulfite, a hydrosulfite, or a metabisulfite, or salts thereof (such as sodium salt);

M is —H or a cation;

R, for each occurrence, is independently selected from the group consisting of —H, an optionally substituted linear, branched or cyclic alkyl, alkenyl or alkynyl having from 1 to 10 carbon atoms, a polyethylene glycol unit —(CH$_2$CH$_2$O)$_n$—R$^c$, an optionally substituted aryl having 6 to 18 carbon atoms, an optionally substituted 5- to 18-membered heteroaryl ring containing one or more heteroatoms independently selected from nitrogen, oxygen, and sulfur, or an optionally substituted 3- to 18-membered heterocyclic ring containing 1 to 6 heteroatoms independently selected from O, S, N and P;

R' and R" are each independently selected from —H, —OH, —OR, —NHR, —NR$_2$, —COR, an optionally substituted linear, branched or cyclic alkyl, alkenyl or alkynyl having from 1 to 10 carbon atoms, a polyethylene glycol unit —(CH$_2$CH$_2$O)$_n$—R$^c$, and an optionally substituted 3- to 18-membered heterocyclic ring having 1 to 6 heteroatoms independently selected from O, S, N and P;

R$^c$ is —H or a substituted or unsubstituted linear or branched alkyl having 1 to 4 carbon atoms, or the linking group with the reactive group bonded thereto;

n is an integer from 1 to 24;

W is selected from C═O, C═S, CH$_2$, BH, SO and SO$_2$;

X' is selected from —H, an amine-protecting group, the linking group with the reactive group bonded thereto, an optionally substituted linear, branched or cyclic alkyl, alkenyl or alkynyl having from 1 to 10 carbon atoms, a polyethylene glycol unit —(CH$_2$CH$_2$O)$_n$—R$^c$, an optionally substituted aryl having 6 to 18 carbon atoms, an optionally substituted 5- to 18-membered heteroaryl ring containing one or more heteroatoms independently selected from nitrogen, oxygen, and sulfur, and an optionally substituted 3- to 18-membered heterocyclic ring containing 1 to 6 heteroatoms independently selected from O, S, N and P;

Y' is selected from —H, an oxo group, the linking group with the reactive group bonded thereto, an optionally substituted linear, branched or cyclic alkyl, alkenyl or alkynyl having from 1 to 10 carbon atoms, an optionally substituted 6- to 18-membered aryl, an optionally substituted 5- to 18-membered heteroaryl ring containing one or more heteroatoms independently selected from nitrogen, oxygen, and sulfur, an optionally substituted 3 to 18-membered heterocyclic ring having 1 to 6 heteroatoms;

$R_1$, $R_2$, $R_3$, $R_4$, $R_1'$, $R_2'$, $R_3'$ and $R_4'$ are each independently selected from the group consisting of —H, an optionally substituted linear, branched or cyclic alkyl, alkenyl or alkynyl having from 1 to 10 carbon atoms, a polyethylene glycol unit —(OCH$_2$CH$_2$)$_n$—R$^c$, halogen, guanidinium [—NH(C=NH)NH$_2$], —OR, —NR'R", —NO$_2$, —NCO, —NR'COR", —SR, a sulfoxide represented by —SOR', a sulfone represented by —SO$_2$R', a sulfonate —SO$_3^-$M$^+$, a sulfate —OSO$_3^-$M$^+$, a sulfonamide represented by —SO$_2$NR'R", cyano, an azido, —COR', —OCOR', —OCONR'R" and the linking group with the reactive group bonded thereto;

$R_6$ is —H, —R, —OR, —SR, —NR'R", —NO$_2$, halogen or the linking group with the reactive group bonded thereto;

Z and Z' are independently selected from —(CH$_2$)$_{n'}$—, —(CH$_2$)$_{n'}$—CR$_7$R$_8$—(CH$_2$)$_{na'}$—, —(CH$_2$)$_{n'}$—NR$_9$—(CH$_2$)$_{na'}$—, —(CH$_2$)$_{n'}$—O—(CH$_2$)$_{na'}$— and —(CH$_2$)$_{n'}$—S—(CH$_2$)$_{na'}$—;

n' and na' are the same or different, and are selected from 0, 1, 2 and 3;

$R_7$ and $R_8$ are the same or different, and are each independently selected from —H, —OH, —SH, —COOH, —NHR', a polyethylene glycol unit —(OCH$_2$CH$_2$)$_n$—, an amino acid, a peptide unit bearing 2 to 6 amino acids, an optionally substituted linear, branched or cyclic alkyl having from 1 to 10 carbon atoms;

$R_9$ is independently selected from —H, an optionally substituted linear, branched or cyclic alkyl having from 1 to 10 carbon atoms, a polyethylene glycol unit —(OCH$_2$CH$_2$)$_n$—;

A and A' are the same or different, and are independently selected from —O—, oxo (—C(=O)—), —CRR'O—, —CRR'—, —S—, —CRR'S—, —NR$_5$ and —CRR'N(R$_5$)—;

R$_5$ for each occurrence is independently —H or an optionally substituted linear or branched alkyl having 1 to 10 carbon atoms;

D and D' are the same or different, and are independently absent or selected from the group consisting of an optionally substituted linear, branched or cyclic alkyl, alkenyl or alkynyl having 1 to 10 carbon atoms, an amino acid, a peptide bearing 2 to 6 amino acids, and a polyethylene glycol unit (—OCH$_2$CH$_2$)$_n$—;

L is absent, the linking group with the reactive group bonded thereto, a polyethylene glycol unit (—OCH$_2$CH$_2$)$_n$—, a linear, branched or cyclic alkyl or alkenyl having 1 to 10 carbon atoms, a phenyl group, a 3 to 18-membered heterocyclic ring or a 5- to 18-membered heteroaryl ring having 1 to 6 heteroatoms independently selected from O, S, N and P, wherein the alkyl or alkenyl is optionally substituted with the linking group with the reactive group bonded thereto; phenyl or heterocyclic or heteroaryl ring can be optionally substituted, wherein the substituent can be the linking group with the reactive group bonded thereto.

In certain embodiments, X is not the linking group with the reactive group bonded thereto. In certain embodiments, the double line == between N and C represents a single bond, Y is not —H.

In certain embodiments, the compound is not any one of the following compounds:

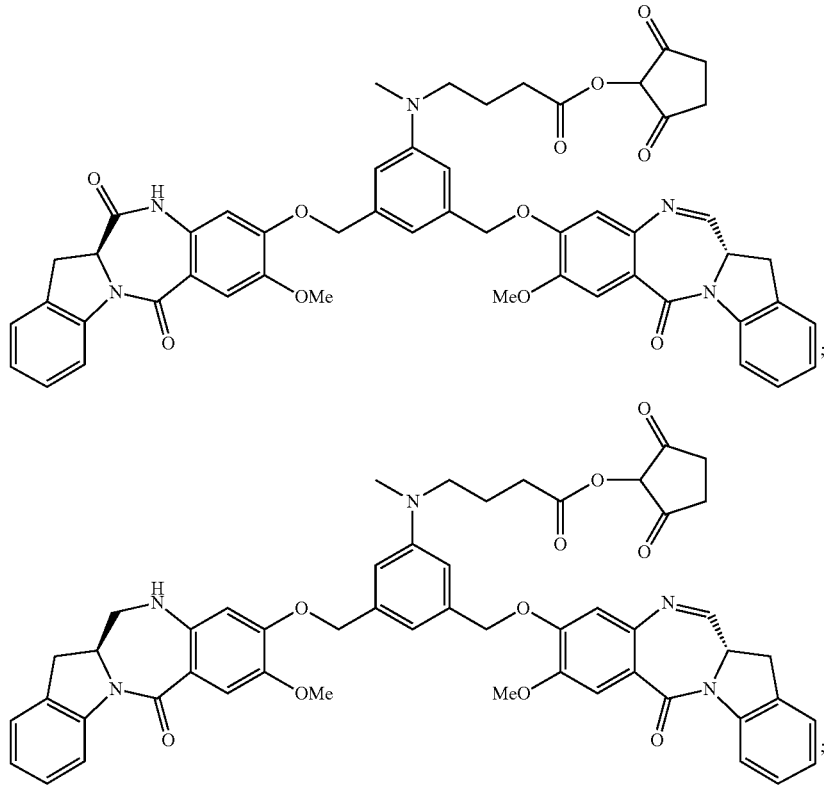

-continued
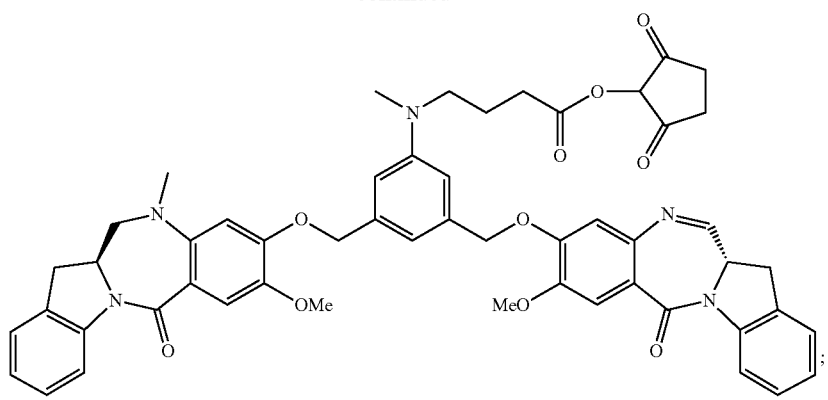
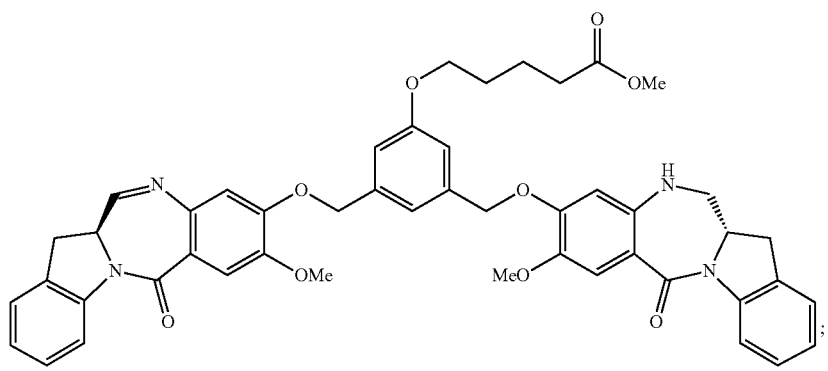
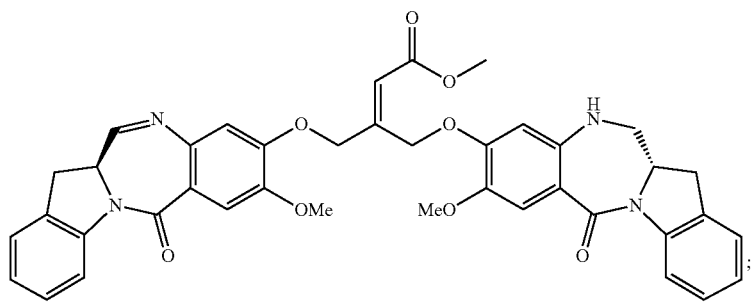
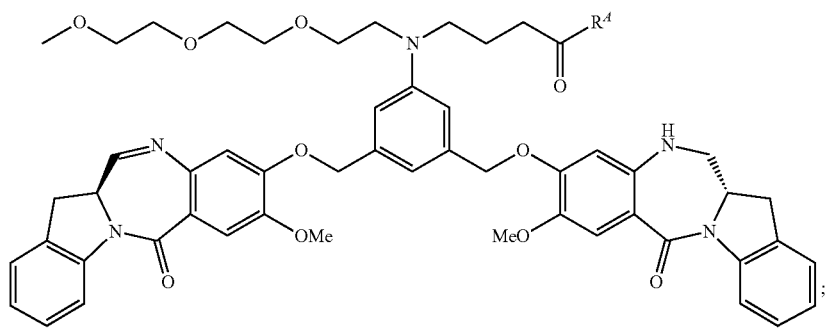
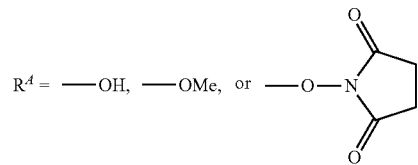

-continued
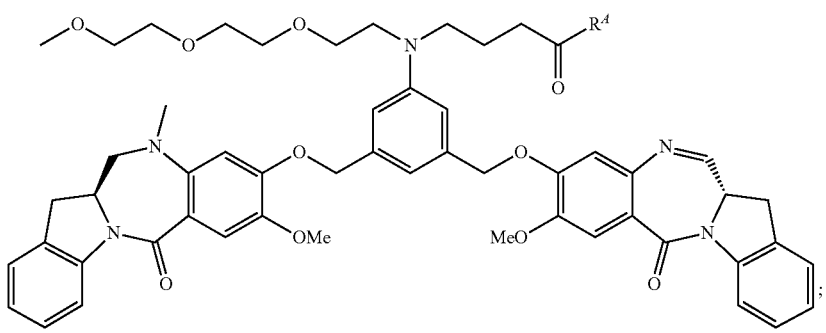
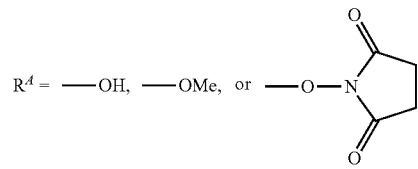
R$^A$ = —OH, —OMe, or —O—N(succinimidyl)
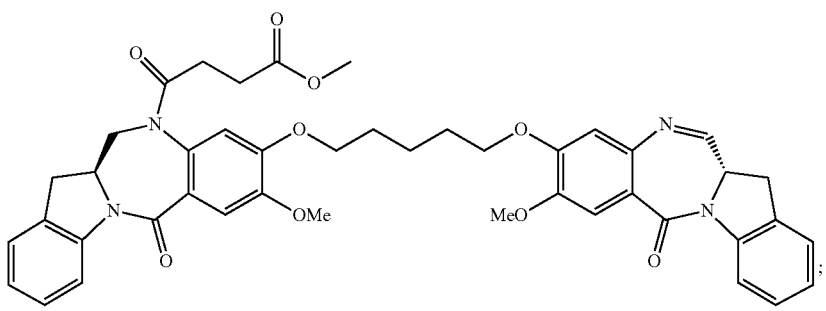
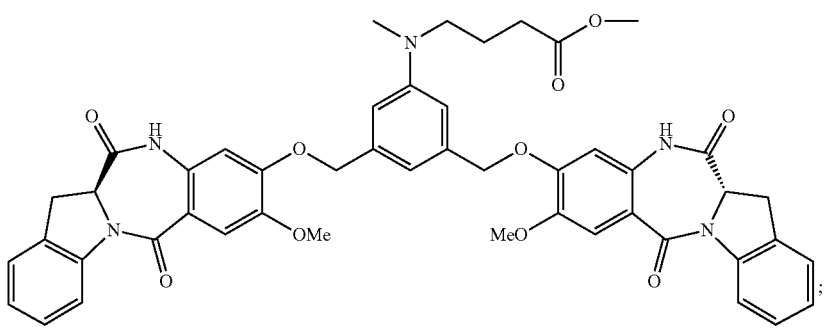
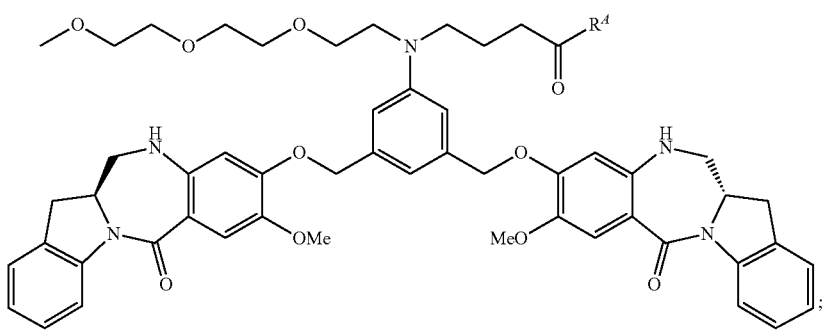
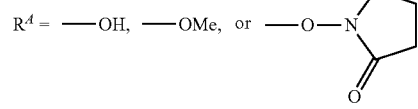
R$^A$ = —OH, —OMe, or —O—N(succinimidyl)

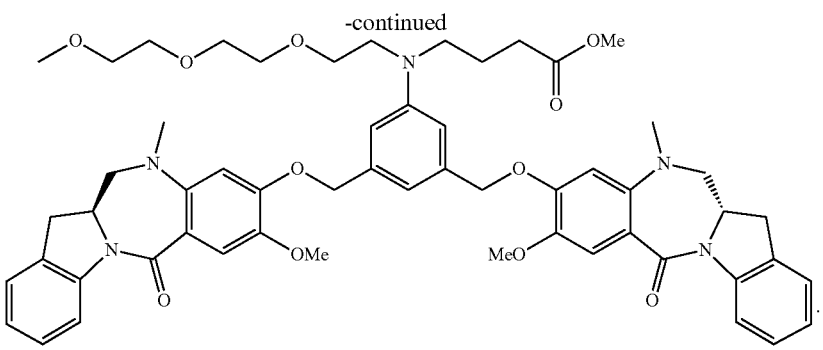

In certain embodiments, Y is a leaving group selected from —OR, —OCOR', —OCOOR', —OCONR'R", —NR'R", —NR'COR", —NR'NR'R", an optionally substituted 5- or 6-membered nitrogen-containing heterocycle (e.g., piperidine, tetrahydropyrrole, pyrazole, morpholine, etc.), a guanidinum represented by —NR'(C=NH)NR'R", an amino acid, or a peptide represented by —NRCOP', wherein P' is an amino acid or a polypeptide containing between 2 to 20 amino acid units, —SR, —SOR', —SO$_2$M, —SO$_3$M, —OSO$_3$M, halogen, cyano and an azido.

A second object of the invention is to provide conjugates of cell binding agents with the novel benzodiazepine compounds or derivatives thereof of the present invention. These conjugates are useful as therapeutic agents, which are delivered specifically to target cells and are cytotoxic.

Specifically, a conjugate of the invention may comprise: a cytotoxic compound and a cell binding agent (CBA), wherein the cytotoxic compound comprises a linking group which covalently links the cytotoxic compound to the CBA, and wherein the cytotoxic compound is represented by any one of the following formulas:

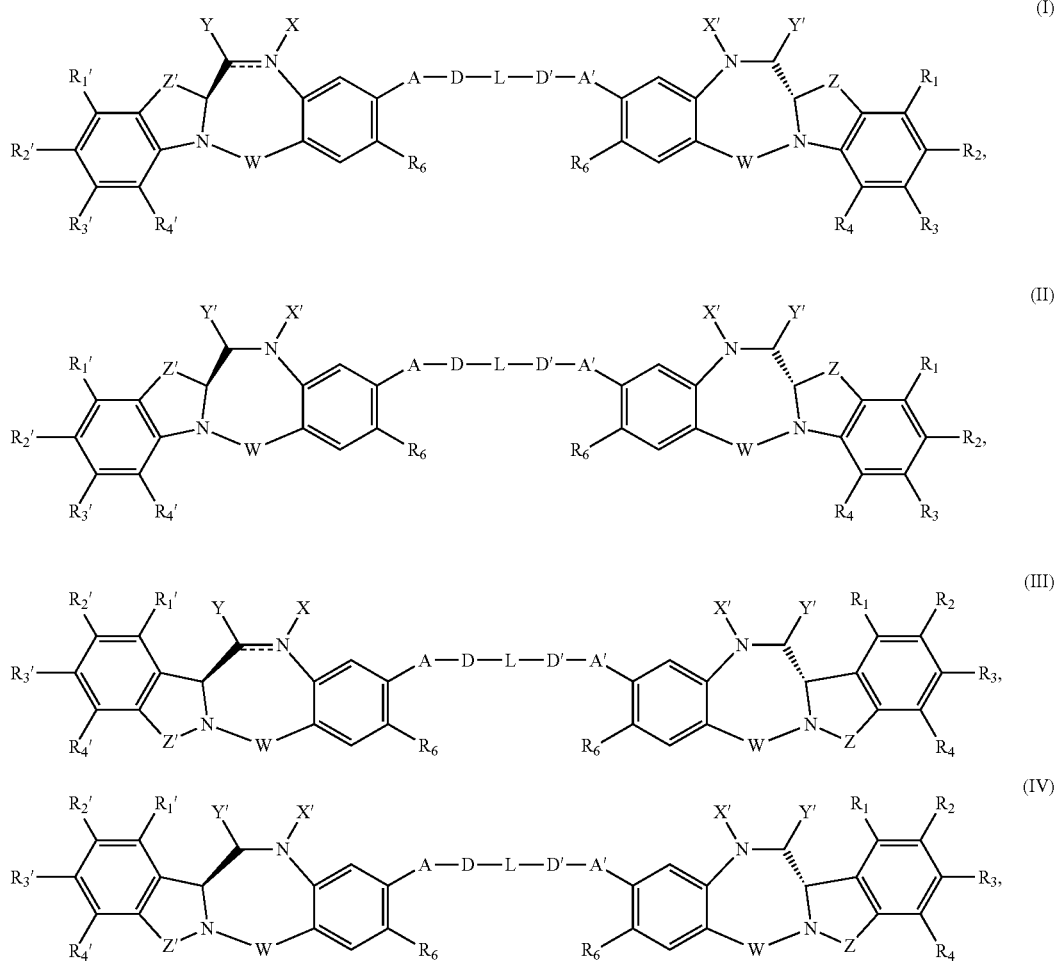

or a pharmaceutically acceptable salt thereof, wherein:

the double line $=$ between N and C represents a single bond or a double bond, provided that when it is a double bond X is absent and Y is —H, or a linear or branched alkyl having 1 to 4 carbon atoms, and when it is a single bond, X is —H, the linking group, or an amine protecting moiety;

Y is —H or a leaving group selected from —OR, —OCOR', —OCOOR', —OCONR'R", —NR'R", —NR'COR", —NR'NR'R", an optionally substituted 5 or 6-membered nitrogen-containing heterocycle (e.g., piperidine, tetrahydropyrrole, pyrazole, morpholine), a guanidinum represented by —NR'(C=NH)NR'R", an amino acid, or a peptide represented by —NRCOP', wherein P' is an amino acid or a polypeptide containing between 2 to 20 amino acid units, —SR, —SOR', —SO$_2$M, —SO$_3$M, —OSO$_3$M, halogen, cyano and an azido; or, Y is a sulfite (HSO$_3$, HSO$_2$ or a salt of HSO$_3^-$, SO$_3^{2-}$ or HSO$_2^-$ formed with a cation), metabisulfite (H$_2$S$_2$O$_5$ or a salt of S$_2$O$_5^{2-}$ formed with a cation), mono-, di-, tri-, and tetra-thiophosphate (PO$_3$SH$_3$, PO$_2$S$_2$H$_2$, POS$_3$H$_2$, PS$_4$H$_2$ or a salt of PO$_3$S$^{3-}$, PO$_2$S$_2^{3-}$, POS$_3^{3-}$ or PS$_4^{3-}$ formed with a cation), thio phosphate ester (R$^i$O)$_2$PS(OR$^i$), R$^i$S—, R$^i$SO, R$^i$SO$_2$, R$^i$SO$_3$, thiosulfate (HS$_2$O$_3$ or a salt of S$_2$O$_3^{2-}$ formed with a cation), dithionite (HS$_2$O$_4$ or a salt of S$_2$O$_4^{2-}$ formed with a cation), phosphorodithioate (P(=S)(OR$^{k'}$)(S)(OH) or a salt thereof formed with a cation), hydroxamic acid (R$^{k'}$C(=O)NOH or a salt formed with a cation), formaldehyde sulfoxylate (HOCH$_2$SO$_2^-$ or a salt of HOCH$_2$SO$_2^-$ formed with a cation, such as HOCH$_2$SO$_2^-$Na$^+$) or a mixture thereof, wherein R$^i$ is a linear or branched alkyl having 1 to 10 carbon atoms and is substituted with at least one substituent selected from —N(R$^j$)$_2$, —CO$_2$H, —SO$_3$H, and —PO$_3$H; R$^i$ can be further optionally substituted with a substituent for an alkyl described herein; R$^j$ is a linear or branched alkyl having 1 to 6 carbon atoms; R$^{k'}$ is a linear, branched or cyclic alkyl, alkenyl or alkynyl having 1 to 10 carbon atoms, aryl, heterocyclyl or heteroaryl; preferably, Y is an adduct of a bisulfite, a hydrosulfite, or a metabisulfite, or salts thereof (such as sodium salt);

M is —H or a cation;

R, for each occurrence, is independently selected from the group consisting of —H, an optionally substituted linear, branched or cyclic alkyl, alkenyl or alkynyl having from 1 to 10 carbon atoms, a polyethylene glycol unit —(CH$_2$CH$_2$O)$_n$—R$^c$, an optionally substituted aryl having 6 to 18 carbon atoms, an optionally substituted 5- to 18-membered heteroaryl ring containing one or more heteroatoms independently selected from nitrogen, oxygen, and sulfur, or an optionally substituted 3- to 18-membered heterocyclic ring containing 1 to 6 heteroatoms independently selected from O, S, N and P;

R' and R" are each independently selected from —H, —OH, —OR, —NHR, —NR$_2$, —COR, an optionally substituted linear, branched or cyclic alkyl, alkenyl or alkynyl having from 1 to 10 carbon atoms, a polyethylene glycol unit —(CH$_2$CH$_2$O)$_n$—R$^c$, and an optionally substituted 3- to 18-membered heterocyclic ring having 1 to 6 heteroatoms independently selected from O, S, N and P;

R$^c$ is —H or a substituted or unsubstituted linear or branched alkyl having 1 to 4 carbon atoms, or the linking group;

n is an integer from 1 to 24;

W is selected from C=O, C=S, CH$_2$, BH, SO and SO$_2$;

X' is selected from —H, an amine-protecting group, the linking group, an optionally substituted linear, branched or cyclic alkyl, alkenyl or alkynyl having from 1 to 10 carbon atoms, a polyethylene glycol unit —(CH$_2$CH$_2$O)$_n$—R$^c$, an optionally substituted aryl having 6 to 18 carbon atoms, an optionally substituted 5- to 18-membered heteroaryl ring containing one or more heteroatoms independently selected from nitrogen, oxygen, and sulfur, and an optionally substituted 3- to 18-membered heterocyclic ring containing 1 to 6 heteroatoms independently selected from O, S, N and P;

Y' is selected from —H, an oxo group, the linking group, an optionally substituted linear, branched or cyclic alkyl, alkenyl or alkynyl having from 1 to 10 carbon atoms, an optionally substituted 6- to 18-membered aryl, an optionally substituted 5- to 18-membered heteroaryl ring containing one or more heteroatoms independently selected from nitrogen, oxygen, and sulfur, an optionally substituted 3 to 18-membered heterocyclic ring having 1 to 6 heteroatoms;

$R_1$, $R_2$, $R_3$, $R_4$, $R_1'$, $R_2'$, $R_3'$ and $R_4'$ are each independently selected from the group consisting of —H, an optionally substituted linear, branched or cyclic alkyl, alkenyl or alkynyl having from 1 to 10 carbon atoms, a polyethylene glycol unit —(OCH$_2$CH$_2$)$_n$—R$^c$, halogen, guanidinium [—NH(C=NH)NH$_2$], —OR, —NR'R", —NO$_2$, —NCO, —NR'COR", —SR, a sulfoxide represented by —SOR', a sulfone represented by —SO$_2$R', a sulfonate —SO$_3^-$M$^+$, a sulfate —OSO$_3^-$M$^+$, a sulfonamide represented by —SO$_2$NR'R", cyano, an azido, —COR', —OCOR', —OCONR'R" and the linking group;

$R_6$ is —H, —R, —OR, —SR, —NR'R", —NO$_2$, halogen or the linking group;

Z and Z' are independently selected from —(CH$_2$)$_{n'}$—, —(CH$_2$)$_{n'}$—CR$_7$R$_8$—(CH$_2$)$_{na'}$—, —(CH$_2$)$_{n'}$—NR$_9$—(CH$_2$)$_{na'}$—, —(CH$_2$)$_{n'}$, —O—(CH$_2$)$_{na'}$— and —(CH$_2$)$_{n'}$—S—(CH$_2$)$_{na'}$—;

n' and na' are the same or different, and are selected from 0, 1, 2 and 3;

$R_7$ and $R_8$ are same or different, and are each independently selected from —H, —OH, —SH, —COOH, —NHR', a polyethylene glycol unit —(OCH$_2$CH$_2$)$_n$—, an amino acid, a peptide unit bearing 2 to 6 amino acids, an optionally substituted linear, branched or cyclic alkyl having from 1 to 10 carbon atoms;

$R_9$ is independently selected from —H, an optionally substituted linear, branched or cyclic alkyl having from 1 to 10 carbon atoms, a polyethylene glycol unit —(OCH$_2$CH$_2$)$_n$—;

A and A' are the same or different, and are independently selected from —O—, oxo (—C(=O)—), —CRR'O—, —CRR'—, —S—, —CRR'S—, —NR$_5$ and —CRR'N(R$_5$)—, $R_5$ for each occurrence is independently —H or an optionally substituted linear or branched alkyl having 1 to 10 carbon atoms;

D and D' are the same or different, and are independently absent or selected from the group consisting of an optionally substituted linear, branched or cyclic alkyl, alkenyl or alkynyl having 1 to 10 carbon atoms, an amino acid, a peptide bearing 2 to 6 amino acids, and a polyethylene glycol unit (—OCH$_2$CH$_2$)$_n$—;

L is absent, the linking group, a polyethylene glycol unit (—OCH$_2$CH$_2$)$_n$—, a linear, branched or cyclic alkyl or alkenyl having 1 to 10 carbon atoms, a phenyl group, a 3- to 18-membered heterocyclic ring or a 5- to 18-membered heteroaryl ring having 1 to 6 heteroatoms independently selected from O, S, N and P, wherein the alkyl or alkenyl is optionally substituted with the linking group; phenyl or heterocyclic or heteroaryl ring can be optionally substituted, wherein the substituent can be the linking group.

In certain embodiments, X is not the linking group. In certain embodiments, the double line == between N and C represents a single bond, Y is not —H.

In certain embodiments, Y is —H or a leaving group selected from —OR, —OCOR', —OCOOR', —OCONR'R", —NR'R", —NR'COR", —NR'NR'R", an optionally substituted 5- or 6-membered nitrogen-containing heterocycle (e.g., piperidine, tetrahydropyrrole, pyrazole, morpholine, etc.), a guanidinum represented by —NR'(C=NH)NR'R", an amino acid, or a peptide represented by —NRCOP', wherein P' is an amino acid or a polypeptide containing between 2 to 20 amino acid units, —SR, —SOR', —SO$_2$M, —SO$_3$M, —OSO$_3$M, halogen, cyano and an azido. In certain embodiments, Y is not —H.

In certain embodiments, the compound of the conjugate is not any one of the following compounds (the wavy bond represents the bond through which the compound is linked to the CBA):

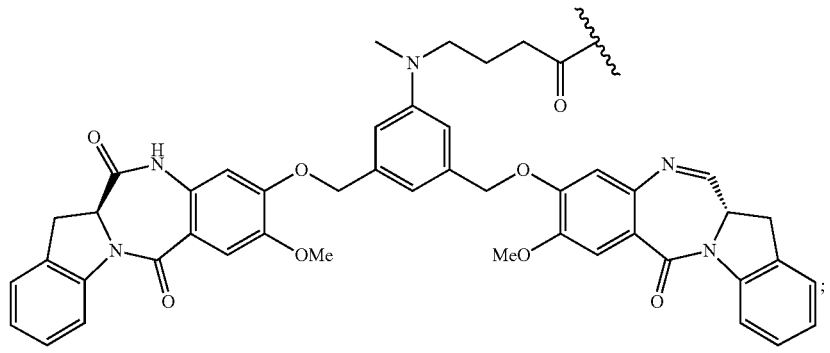

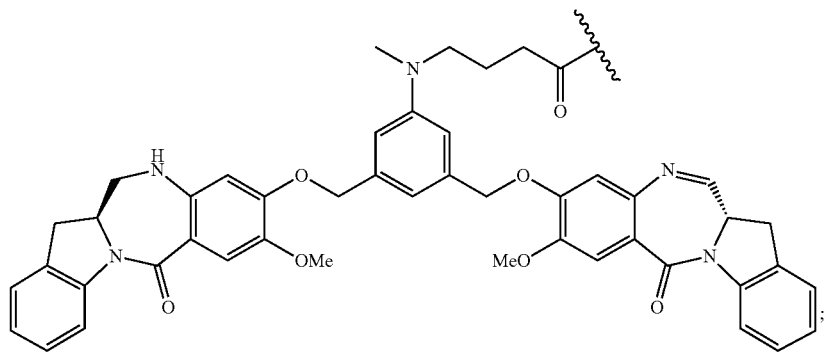

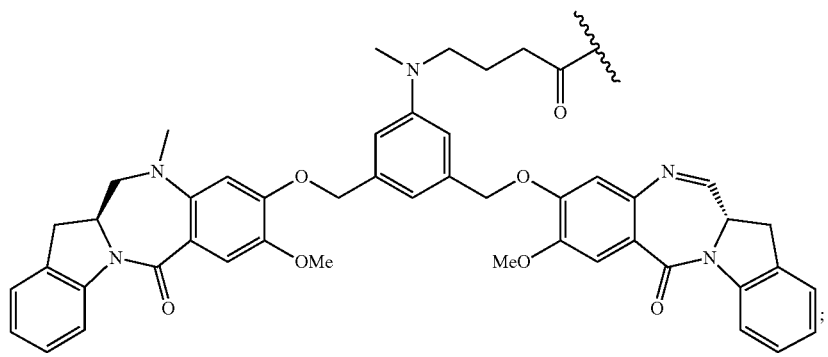

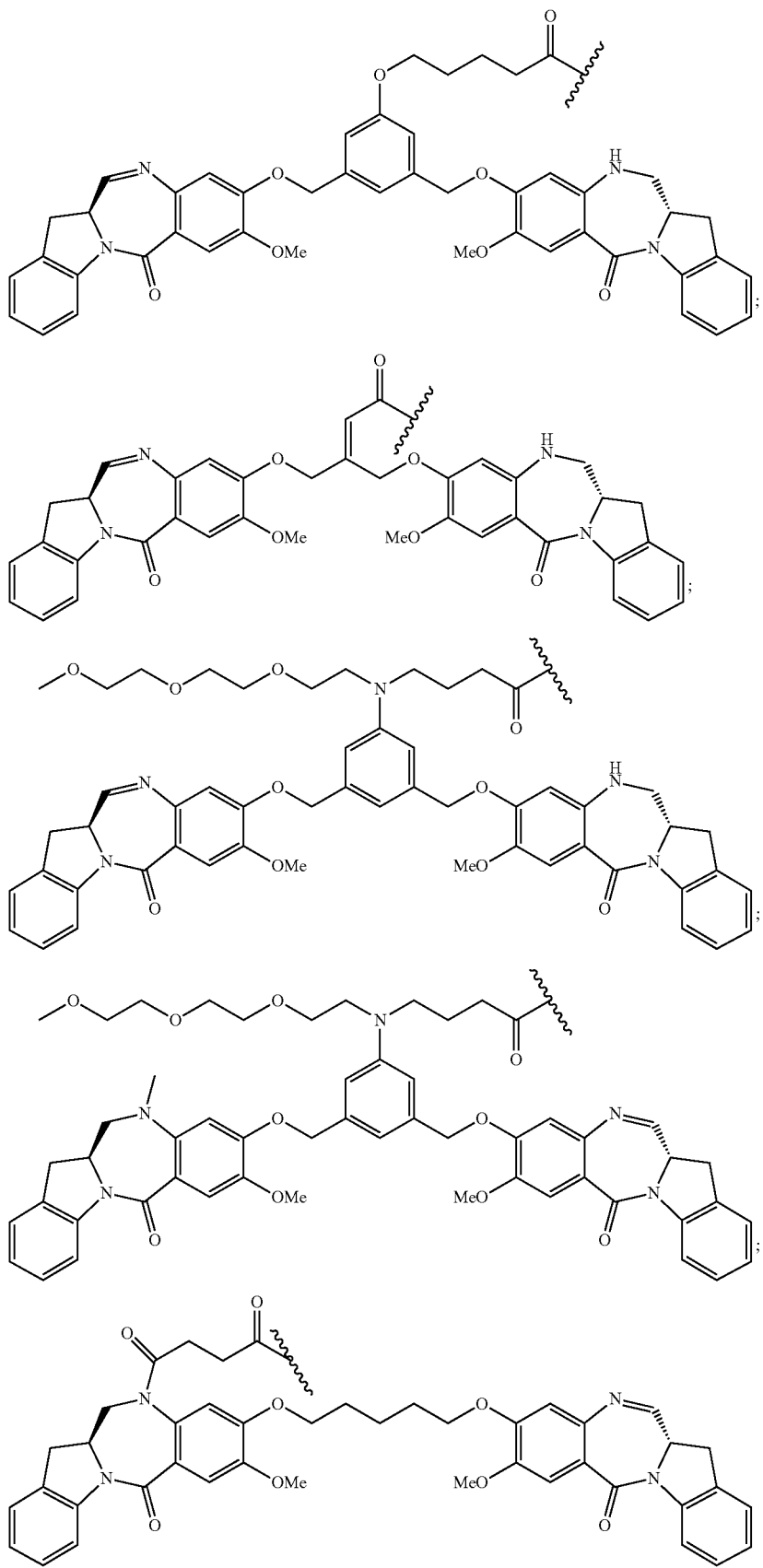

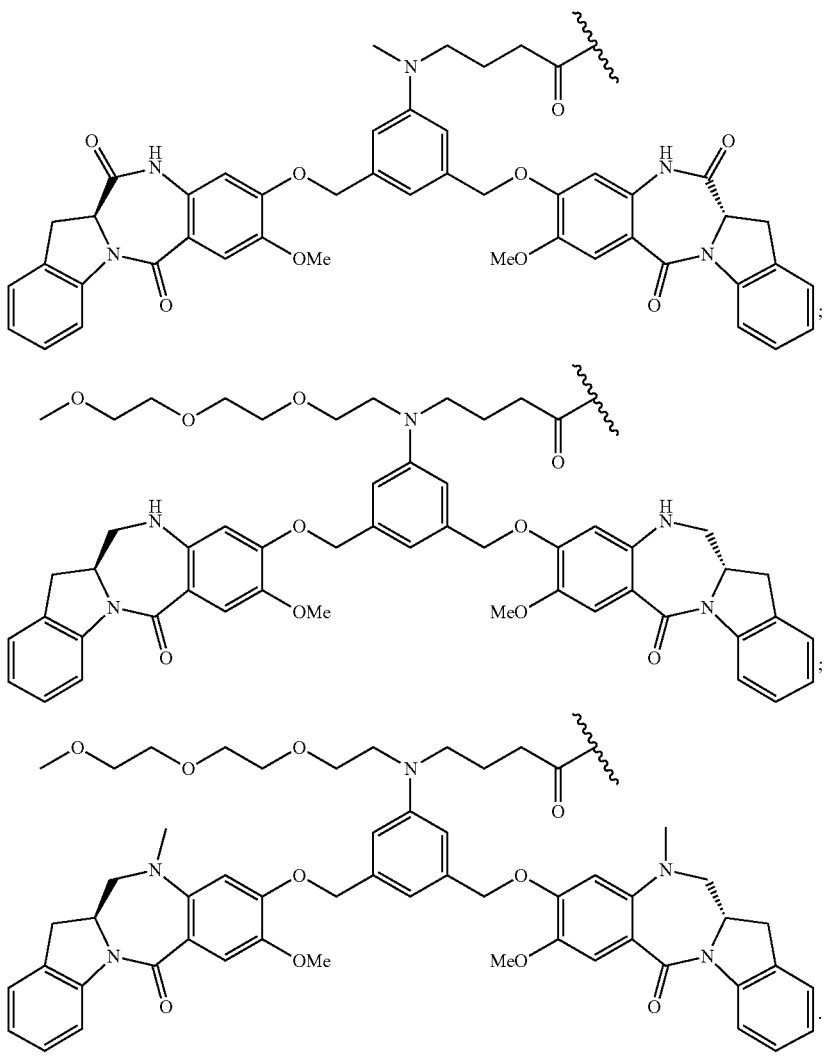

The present invention also includes a composition (e.g., a pharmaceutical composition) comprising novel benzodiazepine compounds, derivatives thereof, or conjugates thereof, (and/or solvates, hydrates and/or salts thereof) and a carrier (a pharmaceutically acceptable carrier). The present invention additionally includes a composition (e.g., a pharmaceutical composition) comprising novel benzodiazepine compounds, derivatives thereof, or conjugates thereof (and/or solvates, hydrates and/or salts thereof), and a carrier (a pharmaceutically acceptable carrier), further comprising a second therapeutic agent. The present compositions are useful for inhibiting abnormal cell growth or treating a proliferative disorder in a mammal (e.g., human) The present compositions are useful for treating conditions such as cancer, rheumatoid arthritis, multiple sclerosis, graft versus host disease (GVHD), transplant rejection, lupus, myositis, infection, immune deficiency such as AIDS, and inflammatory diseases in a mammal (e.g., human).

The present invention includes a method of inhibiting abnormal cell growth or treating a proliferative disorder in a mammal (e.g., human) comprising administering to said mammal a therapeutically effective amount of novel benzodiazepine compounds, derivatives thereof, or conjugates thereof, (and/or solvates and salts thereof) or a composition thereof, alone or in combination with a second therapeutic agent. The present invention includes a method of synthesizing and using novel benzodiazepine compounds, derivatives thereof, and conjugates thereof for in vitro, in situ, and in vivo diagnosis or treatment of mammalian cells, organisms, or associated pathological conditions.

The compounds of this invention, derivatives thereof, or conjugates thereof, and compositions comprising them, are useful for treating or lessening the severity of disorders, such as, characterized by abnormal growth of cells (e.g., cancer). Other applications for compounds and conjugates of this invention include, but are not limited to, treating conditions such as cancer, rheumatoid arthritis, multiple sclerosis, graft versus host disease (GVHD), transplant rejection, lupus, myositis, infection, immune deficiency such as AIDS and inflammatory diseases in a mammal (e.g., human).

As used herein, when referring to a group (e.g., $R^c$, L, X' etc.) "is/be" (or "is not") the linking group or the linking group with the reactive group bounded thereto, it is meant that the group "comprises" (or "does not comprise") the linking group or the linking group with the reactive group bounded thereto.

BRIEF DESCRIPTION OF THE FIGURES

FIGS. 1-6 show the schemes for the synthesis of benzodiazepine compounds and the corresponding linkable compounds suitable for conjugation of the present invention.

FIG. 7 shows the scheme for the synthesis of representative compounds with PEG modified linkers of the present invention.

FIG. 8 shows the scheme for the synthesis of representative compounds with a methylthio linker of the present invention.

FIGS. 9-10 show the schemes for the synthesis of representative compounds containing a tertiary amine of the present invention.

FIG. 11 shows the scheme for the synthesis of representative compounds with a peptide linker of the present invention.

FIGS. 12A, 12B, and 13-19 show the schemes for the synthesis of representative compounds suitable for one-step conjugation methods of the present invention.

FIG. 20 shows the scheme for a two-step mono-imine dimer synthesis.

FIG. 21 shows the scheme for a two-step di-reduced dimer synthesis.

FIG. 23 shows the scheme for the two-step synthesis of the representative antibody-drug conjugates.

FIGS. 24A, 24B, and 24C show the in vitro cytotoxicity of the methyldithio dimer 1d against Namalwa, KB and HL60/QC cell lines.

FIGS. 25A, 25B and 25C show the in vitro cytotoxicity and specificity of the huMy9-6-SPDB-1f conjugates against various cell lines. Note that sodium bisulfite was added to the conjugation reaction for making the conjugate.

FIG. 26 shows the in vitro cytotoxicity and specificity of the huFOLR1-SPDB-1f conjugates.

FIG. 27 shows conjugation of dimer does not reduce binding affinity of antibody. Note that sodium bisulfite was added to the conjugation reaction for making the conjugate.

FIG. 28 shows the in vivo antitumor activity of huMy9-6 conjugate. Note that sodium bisulfite was added to the conjugation reaction for making the conjugate.

FIGS. 29A, 29B, 29C and 29D show in vitro cytotoxicity of huMy9-6-SPDB-1f conjugate against antigen positive cells. Note that sodium bisulfite was added to the conjugation reaction for making the conjugate.

FIG. 30 shows synthetic scheme for making thioether-containing linker disulfides 27e-h.

FIG. 31 shows synthetic scheme for making dimers 28c-f.

FIG. 32 shows synthetic scheme for making phenyl linked dimers 29b-c.

FIG. 33 shows the scheme for an alternative two-step synthesis for mono-imine dimers.

FIGS. 34A, 34B and 34C show in vitro cytotoxicity for huMy9-6-SPDB-1f (A), huMy9-6-sulfoSPDB-1f (B) and huMy9-6-BMPS-1f (C) against HL60/QC (Ag$^+$) cells with and without blocking of antigen binding sites. Note that in all three experiments (34A, 34B, and 34C), sodium bisulfite were added to the conjugation reaction for making the conjugate.

FIG. 36 shows in vivo efficacy of huMy9-6-SPDB-1f in HL60/QC bearing mice. Note that sodium bisulfite was added to the conjugation reaction.

FIG. 37 shows in vivo efficacy of huFOLR1-SPDB-1f in KB tumor bearing mice.

FIG. 38 shows synthetic scheme of compound 1.

FIG. 39 shows a synthetic scheme of compound 1d with 5-ethyl-2-methylpyridine borane (PEMB).

FIG. 40 shows a synthetic scheme of compound 1d with sodium triacetoxyborohydride (STAB).

FIG. 41 shows a synthetic scheme of compound 31a-c.

FIG. 42 shows a synthetic scheme of compound 32c,d.

FIG. 43 shows a synthetic scheme of compounds 1i and 12a.

FIGS. 44A, 44B and 44C show antiproliferative activity by comparing (A) huMy9-6-SPDB-1f, (B) huMy9-6-sulfoSPDB-1f, and (C) huMy9-6-BMPS-1f, against OCI-AML3 (Ag$^+$) cells with and without blocking of antigen binding sites. Note that in all three experiments, sodium bisulfite was added to the conjugation reaction for making the conjugate.

FIG. 45 shows an alternate scheme for synthesizing 4-(benzyloxy)-5-methoxy-2-nitrobenzoic acid used in the preparation of IBD monomer.

FIG. 46 is an alternate synthesis scheme for (5-((2-(2-(2-methoxyethoxy)ethoxy)ethyl)(2-methyl-2-(methyldisulfanyl)propyl)amino)-1,3-phenylene)dimethanol (1b).

FIG. 47 is an alternate synthesis scheme for (5-((2-(2-(2-methoxyethoxy)ethoxy)ethyl)(2-methyl-2-(methyldisulfanyl)propyl)amino)-1,3-phenylene)dimethanol (1b).

FIG. 48 is an alternate synthetic scheme for a two-step mono-imine dimer synthesis.

FIG. 49 shows potency of various conjugates against various cell lines. The IC$_{50}$ values listed in the table are in the unit of nM.

FIG. 50 shows in vivo efficacy of huMy9-6-sulfo-SPDB-1f in MOLM-13 tumor bearing mice.

FIG. 51 shows in vivo efficacy of huMy9-6-sulfo-SPDB-1f in NB4 tumor bearing mice.

FIG. 52 shows in vivo efficacy of huMy9-6-BMPS-1f in HL60/QC tumor bearing mice.

FIG. 53 shows in vivo efficacy of huMy9-6-BMPS-1f in MOLM-13 tumor bearing mice. Note that sodium bisulfite was added to the conjugation reaction for making the conjugate.

FIG. 54 shows a representative synthesis scheme for a Sulfonated folate/cytotoxic compound conjugate.

FIG. 55 shows several representative sulfonated drug-antibody conjugates with different linkers.

FIG. 56 shows in vivo efficacy of huMy9-6-Drug 2 in HL60/QC tumor bearing mice. Note that sodium bisulfite was added to the conjugation reaction for making the conjugate.

FIG. 57 shows in vivo efficacy of huMy9-6-Drug 2 in MOLM-13 tumor bearing mice. Note that sodium bisulfite was added to the conjugation reaction for making the conjugate.

DETAILED DESCRIPTION OF THE INVENTION

Figures 22A, 22B, 22C:
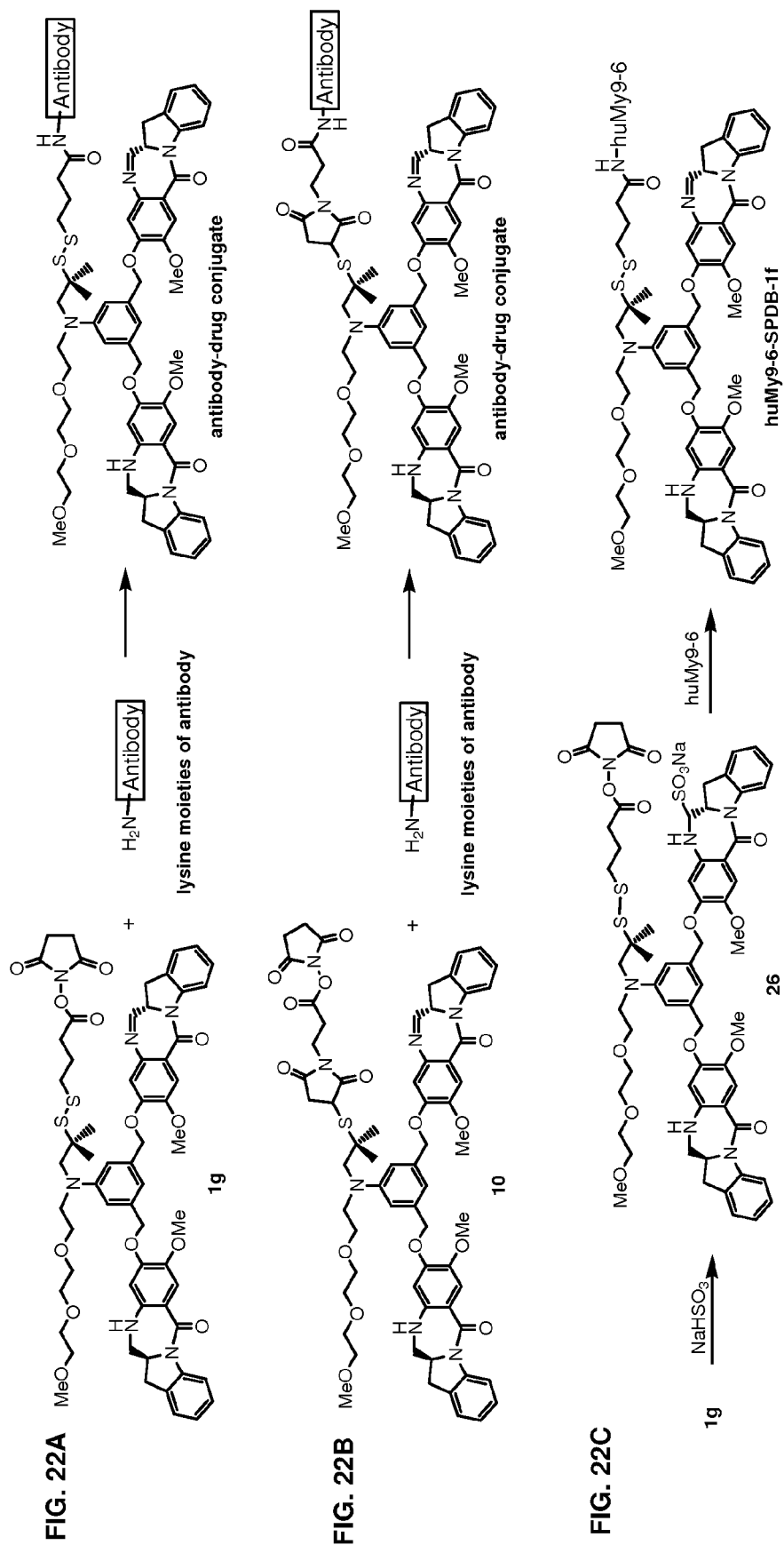
FIG. 22A, FIG. 22B and FIG. 22C show the scheme for the one-step synthesis of the representative antibody-drug conjugates.

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention.

It should be understood that any of the embodiments described herein, including those described under different aspects of the invention (e.g., compounds, compound-linker molecules, conjugates, compositions, methods of making and using) and different parts of the specification (including embodiments described only in the Examples) can be combined with one or more other embodiments of the invention, unless explicitly disclaimed or improper. Combination of embodiments are not limited to those specific combinations claimed via the multiple dependent claims.

DEFINITIONS

"Linear or branched alkyl" as used herein refers to a saturated linear or branched-chain monovalent hydrocarbon radical of one to twenty carbon atoms. Examples of alkyl include, but are not limited to, methyl, ethyl, 1-propyl, 2-propyl, 1-butyl, 2-methyl-1-propyl, —CH$_2$CH(CH$_3$)$_2$), 2-butyl, 2-methyl-2-propyl, 1-pentyl, 2-pentyl 3-pentyl, 2-methyl-2-butyl, 3-methyl-2-butyl, 3-methyl-1-butyl, 2-methyl-1-butyl, 1-hexyl), 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, 1-heptyl, 1-octyl, and the like. Preferably, the alkyl has one to ten carbon atoms. More preferably, the alkyl has one to four carbon atoms.

"Linear or branched alkenyl" refers to linear or branched-chain monovalent hydrocarbon radical of two to twenty carbon atoms with at least one site of unsaturation, i.e., a carbon-carbon, double bond, wherein the alkenyl radical includes radicals having "cis" and "trans" orientations, or alternatively, "E" and "Z" orientations. Examples include, but are not limited to, ethylenyl or vinyl (—CH═CH$_2$), allyl (—CH$_2$CH═CH$_2$), and the like. Preferably, the alkenyl has two to ten carbon atoms. More preferably, the alkyl has two to four carbon atoms.

"Linear or branched alkynyl" refers to a linear or branched monovalent hydrocarbon radical of two to twenty carbon atoms with at least one site of unsaturation, i.e., a carbon-carbon, triple bond. Examples include, but are not limited to, ethynyl, propynyl, 1-butynyl, 2-butynyl, 1-pentynyl, 2-pentynyl, 3-pentynyl, hexynyl, and the like. Preferably, the alkynyl has two to ten carbon atoms. More preferably, the alkynyl has two to four carbon atoms.

The term "carbocycle," "carbocyclyl" and "carbocyclic ring" refer to a monovalent non-aromatic, saturated or partially unsaturated ring having 3 to 12 carbon atoms as a monocyclic ring or 7 to 12 carbon atoms as a bicyclic ring. Bicyclic carbocycles having 7 to 12 atoms can be arranged, for example, as a bicyclo[4,5], [5,5], [5,6], or [6,6] system, and bicyclic carbocycles having 9 or 10 ring atoms can be arranged as a bicyclo[5,6] or [6,6] system, or as bridged systems such as bicyclo[2.2.1]heptane, bicyclo[2.2.2]octane and bicyclo[3.2.2]nonane. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like.

The terms "cyclic alkyl" and "cycloalkyl" can be used interchangeably. They refer to a monovalent saturated carbocyclic ring radical. Preferably, the cyclic alkyl is 3 to 7 membered monocyclic ring radical. More preferably, the cyclic alkyl is cyclohexyl.

The term "cyclic alkenyl" refers to a carbocyclic ring radical having at least one double bond in the ring structure.

The term "cyclic alkynyl" refers to a carbocyclic ring radical having at least one triple bond in the ring structure.

"Aryl" means a monovalent aromatic hydrocarbon radical of 6-18 carbon atoms derived by the removal of one hydrogen atom from a single carbon atom of a parent aromatic ring system. Some aryl groups are represented in the exemplary structures as "Ar." Aryl includes bicyclic radicals comprising an aromatic ring fused to a saturated, partially unsaturated ring, or aromatic carbocyclic or heterocyclic ring. Typical aryl groups include, but are not limited to, radicals derived from benzene (phenyl), substituted benzenes, naphthalene, anthracene, indenyl, indanyl, 1,2-dihydronapthalene, 1,2,3,4-tetrahydronapthyl, and the like. Preferably, aryl is phenyl group.

The terms "heterocycle," "heterocyclyl," and "heterocyclic ring" are used interchangeably herein and refer to a saturated or a partially unsaturated (i.e., having one or more double and/or triple bonds within the ring) carbocyclic radical of 3 to 18 ring atoms in which at least one ring atom is a heteroatom selected from nitrogen, oxygen, phosphorus, and sulfur, the remaining ring atoms being C, where one or more ring atoms is optionally substituted independently with one or more substituents described below. A heterocycle may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), for example: a bicyclo[4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, and azabicyclo[2.2.2]hexanyl. Spiro moieties are also included within the scope of this definition. Examples of a heterocyclic group wherein ring atoms are substituted with oxo (═O) moieties are pyrimidinonyl and 1,1-dioxo-thiomorpholinyl.

The term "heteroaryl" refers to a monovalent aromatic radical of 5- or 6-membered rings, and includes fused ring systems (at least one of which is aromatic) of 5-18 atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl.

The heterocycle or heteroaryl groups may be carbon (carbon-linked) or nitrogen (nitrogen-linked) attached where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or O-carboline.

The heteroatoms present in heteroaryl or heterocyclcyl include the oxidized forms such as NO, SO, and $SO_2$.

The term "halo" or "halogen" refers to F, Cl, Br or I.

The alkyl, alkenyl, alkynyl, cyclic alkyl, cyclic alkenyl, cyclic alkynyl, carbocyclyl, aryl, heterocyclyl and heteroaryl described above can be optionally substituted with one more (e.g., 2, 3, 4, 5, 6 or more) substituents.

If a substituent is described as being "substituted," a non-hydrogen substituent is in the place of a hydrogen substituent on a carbon, oxygen, sulfur or nitrogen of the substituent. Thus, for example, a substituted alkyl substituent is an alkyl substituent wherein at least one non-hydrogen substituent is in the place of a hydrogen substituent on the alkyl substituent. To illustrate, monofluoroalkyl is alkyl substituted with a fluoro substituent, and difluoroalkyl is alkyl substituted with two fluoro substituents. It should be recognized that if there is more than one substitution on a substituent, each non-hydrogen substituent may be identical or different (unless otherwise stated).

If a substituent is described as being "optionally substituted," the substituent may be either (1) not substituted, or (2) substituted. If a carbon of a substituent is described as being optionally substituted with one or more of a list of substituents, one or more of the hydrogens on the carbon (to the extent there are any) may separately and/or together be replaced with an independently selected optional substituent. If a nitrogen of a substituent is described as being optionally substituted with one or more of a list of substituents, one or more of the hydrogens on the nitrogen (to the extent there are any) may each be replaced with an independently selected optional substituent. One exemplary substituent may be depicted as —NR'R", wherein R' and R" together with the nitrogen atom to which they are attached, may form a heterocyclic ring. The heterocyclic ring formed from R' and R" together with the nitrogen atom to which they are attached may be partially or fully saturated. In one embodiment, the heterocyclic ring consists of 3 to 7 atoms. In another embodiment, the heterocyclic ring is selected from the group consisting of pyrrolyl, imidazolyl, pyrazolyl, triazolyl, tetrazolyl, isoxazolyl, pyridyl and thiazolyl.

This specification uses the terms "substituent," "radical," and "group" interchangeably.

If a group of substituents are collectively described as being optionally substituted by one or more of a list of substituents, the group may include: (1) unsubstitutable substituents, (2) substitutable substituents that are not substituted by the optional substituents, and/or (3) substitutable substituents that are substituted by one or more of the optional substituents.

If a substituent is described as being optionally substituted with up to a particular number of non-hydrogen substituents, that substituent may be either (1) not substituted; or (2) substituted by up to that particular number of non-hydrogen substituents or by up to the maximum number of substitutable positions on the substituent, whichever is less. Thus, for example, if a substituent is described as a heteroaryl optionally substituted with up to 3 non-hydrogen substituents, then any heteroaryl with less than 3 substitutable positions would be optionally substituted by up to only as many non-hydrogen substituents as the heteroaryl has substitutable positions. Such substituents, in non-limiting examples, can be selected from a linear, branched or cyclic alkyl, alkenyl or alkynyl having from 1 to 10 carbon atoms, aryl, heteroaryl, heterocycyclyl, halogen, guanidinium [—NH(C=NH)$NH_2$], —OR$^{100}$, NR$^{101}$R$^{102}$, —$NO_2$, —NR$^{101}$COR$^{102}$, —SR$^{100}$, a sulfoxide represented by —SOR$^{101}$, a sulfone represented by —$SO_2$R$^{101}$, a sulfonate —$SO_3$M, a sulfate —O$SO_3$M, a sulfonamide represented by —$SO_2$NR$^{101}$R$^{102}$, cyano, an azido, —COR$^{101}$, —OCOR$^{101}$, —OCONR$^{101}$R$^{102}$ and a polyethylene glycol unit (—OCH$_2$CH$_2$)—R$^{101}$ wherein M is H or a cation (such as Na$^+$ or K$^+$); R$^{101}$, R$^{102}$ and R$^{103}$ are each independently selected from H, linear, branched or cyclic alkyl, alkenyl or alkynyl having from 1 to 10 carbon atoms, a polyethylene glycol unit (—OCH$_2$CH$_2$)$_n$—R$^{104}$, wherein n is an integer from 1 to 24, an aryl having from 6 to 10 carbon atoms, a heterocyclic ring having from 3 to 10 carbon atoms and a heteroaryl having 5 to 10 carbon atoms; and R$^{104}$ is H or a linear or branched alkyl having 1 to 4 carbon atoms, wherein the alkyl, alkenyl, alkynyl, aryl, heteroaryl and heterocyclcyl in the groups represented by R$^{100}$, R$^{101}$, R$^{102}$, R$^{103}$ and R$^{104}$ are optionally substituted with one or more (e.g., 2, 3, 4, 5, 6 or more) substituents independently selected from halogen, —OH, —CN, —$NO_2$ and unsubstituted linear or branched alkyl having 1 to 4 carbon atoms. Preferably, the substituents for the optionally substituted alkyl, alkenyl, alkynyl, cyclic alkyl, cyclic alkenyl, cyclic alkynyl, carbocyclyl, aryl, heterocyclyl and heteroaryl described above include halogen, —CN, —NR$^{102}$R$^{103}$, —$CF_3$, —OR$^{101}$, aryl, heteroaryl, heterocycycl, —SR$^{101}$, —SOR$^{101}$, —$SO_2$R$^{101}$ and —$SO_3$M.

The term "compound" or "cytotoxic compound," "cytotoxic dimer" and "cytotoxic dimer compound" are used interchangeably. They are intended to include compounds for which a structure or formula or any derivative thereof has been disclosed in the present invention or a structure or formula or any derivative thereof that has been incorporated by reference. The term also includes, stereoisomers, geometric isomers, tautomers, solvates, metabolites, salts (e.g., pharmaceutically acceptable salts) and prodrugs, and prodrug salts of a compound of all the formulae disclosed in the present invention. The term also includes any solvates, hydrates, and polymorphs of any of the foregoing. The specific recitation of "stereoisomers," "geometric isomers," "tautomers," "solvates," "metabolites," "salt" "prodrug," "prodrug salt," "conjugates," "conjugates salt," "solvate," "hydrate," or "polymorph" in certain aspects of the invention described in this application shall not be interpreted as an intended omission of these forms in other aspects of the invention where the term "compound" is used without recitation of these other forms.

The term "conjugate" as used herein refers to a compound described herein or a derivative thereof that is linked to a cell binding agent.

The term "linkable to a cell binding agent" as used herein refers to the compounds described herein or derivates thereof comprising at least one linking group or a precursor thereof suitable to bond these compounds or derivatives thereof to a cell binding agent.

The term "precursor" of a given group refers to any group which may lead to that group by any deprotection, a chemical modification, or a coupling reaction.

The term "linked to a cell binding agent" refers to a conjugate molecule comprising at least one of the compounds described herein (e.g., compounds of formula (I)-(IV) and (VIII)-(XI) and drug-linker compounds describe herein), or derivative thereof bound to a cell binding agent via a suitable linking group or a precursor thereof.

The term "chiral" refers to molecules which have the property of non-superimposability of the mirror image partner, while the term "achiral" refers to molecules which are superimposable on their mirror image partner.

The term "stereoisomer" refers to compounds which have identical chemical constitution and connectivity, but different orientations of their atoms in space that cannot be interconverted by rotation about single bonds.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as crystallization, electrophoresis and chromatography.

"Enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds," John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The term "prodrug" as used in this application refers to a precursor or derivative form of a compound of the invention that is capable of being enzymatically or hydrolytically activated or converted into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," Directed Drug Delivery, Borchardt et al., (ed.), pp. 247-267, Humana Press (1985). The prodrugs of this invention include, but are not limited to, ester-containing prodrugs, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs, optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, compounds of the invention and chemotherapeutic agents such as described above.

The term "prodrug" is also meant to include a derivative of a compound that can hydrolyze, oxidize, or otherwise react under biological conditions (in vitro or in vivo) to provide a compound of this invention. Prodrugs may only become active upon such reaction under biological conditions, or they may have activity in their unreacted forms. Examples of prodrugs contemplated in this invention include, but are not limited to, analogs or derivatives of compounds of any one of the formulae disclosed herein that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of compounds of any one of the formulae disclosed herein that comprise —NO, —NO$_2$, —ONO, or —ONO$_2$ moieties. Prodrugs can typically be prepared using well-known methods, such as those described by Burger's Medicinal Chemistry and Drug Discovery (1995) 172-178, 949-982 (Manfred E. Wolff ed., 5th ed); see also Goodman and Gilman's, The Pharmacological basis of Therapeutics, 8th ed., McGraw-Hill, Int. Ed. 1992, "Biotransformation of Drugs."

One preferred form of prodrug of the invention includes compounds (with or without any linker groups) and conjugates of the invention comprising an adduct formed between an imine bond of the compounds/conjugates and an imine reactive reagent. Another preferred form of prodrug of the invention includes compounds such as those of formula (I)-(IV), wherein when the double line ═ between N and C represents a single bond, X is H or an amine protecting group, and the compound becomes a prodrug. A prodrug of the invention may contain one or both forms of prodrugs described herein (e.g., containing an adduct formed between an imine bond of the compounds/conjugates and an imine reactive reagent, and/or containing a Y leaving group when X is —H).

The term "imine reactive reagent" refers to a reagent that is capable of reacting with an imine group. Examples of imine reactive reagent includes, but is not limited to, sulfites ($H_2SO_3$, $H_2SO_2$ or a salt of $HSO_3^-$, $SO_3^{2-}$ or $HSO_2$ formed with a cation), metabisulfite ($H_2S_2O_5$ or a salt of $S_2O_5^{2-}$ formed with a cation), mono, di, tri, and tetra-thiophosphates ($PO_3SH_3$, $PO_2S_2H_3$, $POS_3H_3$, $PS_4H_3$ or a salt of $PO_3S^{3-}$, $PO_2S_2^{3-}$, $POS_3^{3-}$ or $PS_4^{3-}$ formed with a cation), thio phosphate esters (($R^iO)_2PS(OR^i)$, $R^iSH$, $R^iSOH$, $R^iSO_2H$, $R^iSO_3H$), various amines (hydroxyl amine (e.g., $NH_2OH$), hydrazine (e.g., $NH_2NH_2$), $NH_2O$—$R^i$, $R^{i'}NH$—$R^i$, $NH_2$—$R^i$), $NH_2$—CO—$NH_2$, $NH_2$—C(═S)—$NH_2$, thiosulfate ($H_2S_2O_3$ or a salt of $S_2O_3^{2-}$ formed with a cation), dithionite ($H_2S_2O_4$ or a salt of $S_2O_4^{2-}$ formed with a cation), phosphorodithioate (P(═S)($OR^k$)(SH)(OH) or a salt thereof formed with a cation), hydroxamic acid ($R^kC$(═O)NHOH or a salt formed with a cation), hydrazide ($R^kCONHNH_2$), formaldehyde sulfoxylate ($HOCH_2SO_2H$ or a salt of $HOCH_2SO_2^-$ formed with a cation, such as $HOCH_2SO_2^-Na^+$), glycated nucleotide (such as GDP-mannose), fludarabine or a mixture thereof, wherein $R^i$ and $R^{i'}$ are each independently a linear or branched alkyl having 1 to 10 carbon atoms and are substituted with at least one substituent selected from —N($R^j)_2$, —$CO_2H$, —$SO_3H$, and —$PO_3H$; $R^i$ and $R^{i'}$ can be further optionally substituted with a substituent for an alkyl described herein; $R^j$ is a linear or branched alkyl having 1 to 6 carbon atoms; and $R^k$ is a linear, branched or cyclic alkyl, alkenyl or alkynyl having 1 to 10 carbon atoms, aryl, heterocyclyl or heteroaryl (preferably, $R^k$ is a linear or branched alkyl having 1 to 4 carbon atoms; more preferably, $R^k$ is methyl, ethyl or propyl). Preferably, the cation is a monovalent cation, such as $Na^+$ or $K^+$. Preferably, the imine reactive reagent is selected from sulfites, hydroxyl amine, urea and hydrazine. More preferably, the imine reactive reagent is $NaHSO_3$ or $KHSO_3$.

As used herein and unless otherwise indicated, the terms "biohydrolyzable amide," "biohydrolyzable ester," "biohydrolyzable carbamate," "biohydrolyzable carbonate," "biohydrolyzable ureide" and "biohydrolyzable phosphate analogue" mean an amide, ester, carbamate, carbonate, ureide, or phosphate analogue, respectively, that either: 1) does not destroy the biological activity of the compound and confers upon that compound advantageous properties in vivo, such as uptake, duration of action, or onset of action; or 2) is itself biologically inactive but is converted in vivo to a biologically active compound. Examples of biohydrolyzable amides include, but are not limited to, lower alkyl amides, α-amino acid amides, alkoxyacyl amides, and alkylaminoalkylcarbonyl amides. Examples of biohydrolyzable esters include, but are not limited to, lower alkyl esters, alkoxyacyloxy esters, alkyl acylamino alkyl esters, and choline esters. Examples of biohydrolyzable carbamates include, but are not limited to, lower alkylamines, substituted ethylenediamines, amino acids, hydroxyalkylamines, heterocyclic and heteroaromatic amines, and polyether amines. Particularly favored prodrugs and prodrug salts are those that increase the bioavailability of the compounds of this invention when such compounds are administered to a mammal.

The phrase "pharmaceutically acceptable salt" as used herein, refers to pharmaceutically acceptable organic or inorganic salts of a compound of the invention. Exemplary salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate," ethanesulfonate, benzenesulfonate, p-toluenesulfonate, pamoate (i.e., 1,1'-methylene-bis-(2-hydroxy-3-naphthoate)) salts, alkali metal (e.g., sodium and potassium) salts, alkaline earth metal (e.g., magnesium) salts, and ammonium salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

As used herein, the term "solvate" means a compound which further includes a stoichiometric or non-stoichiometric amount of solvent such as water, isopropanol, acetone, ethanol, methanol, DMSO, ethyl acetate, acetic acid, and ethanolamine dichloromethane, 2-propanol, or the like, bound by non-covalent intermolecular forces. Solvates or hydrates of the compounds are readily prepared by addition of at least one molar equivalent of a hydroxylic solvent such as methanol, ethanol, 1-propanol, 2-propanol or water to the compound to result in solvation or hydration of the imine moiety.

The terms "abnormal cell growth" and "proliferative disorder" are used interchangeably in this application. "Abnormal cell growth," as used herein, unless otherwise indicated, refers to cell growth that is independent of normal regulatory mechanisms (e.g., loss of contact inhibition). This includes, for example, the abnormal growth of: (1) tumor cells (tumors) that proliferate by expressing a mutated tyrosine kinase or overexpression of a receptor tyrosine kinase; (2) benign and malignant cells of other proliferative diseases in which aberrant tyrosine kinase activation occurs; (3) any tumors that proliferate by receptor tyrosine kinases; (4) any tumors that proliferate by aberrant serine/threonine kinase activation; and (5) benign and malignant cells of other proliferative diseases in which aberrant serine/threonine kinase activation occurs.

The terms "cancer" and "cancerous" refer to or describe the physiological condition in mammals that is typically characterized by unregulated cell growth. A "tumor" comprises one or more cancerous cells, and/or benign or pre-cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, acute leukemia, head/brain and neck cancer, cancers of lymphatic organs and hematological malignancy including Leukemia (Acute lymphoblastic leukemia (ALL), Acute myelogenous leukemia (AML), Chronic lymphocytic leukemia (CLL), Chronic myelogenous leukemia (CML), Acute monocytic leukemia (AMOL), Hairy cell leukemia (HCL), T-cell prolymphocytic leukemia (T-PLL), Large granular lymphocytic leukemia, Adult T-cell leukemia), Lymphoma (small lymphocytic lymphoma (SLL), Hodgkin's lymphomas (Nodular sclerosis, Mixed cellularity, Lymphocyte-rich, Lymphocyte depleted or not depleted, and Nodular lymphocyte-predominant Hodgkin lymphoma), Non-Hodgkin's lymphomas (all subtypes), Chronic lymphocytic leukemia/Small lymphocytic lymphoma, B-cell prolymphocytic leukemia, Lymphoplasmacytic lymphoma (such as Waldenström macroglobulinemia), Splenic marginal zone lymphoma, Plasma cell neoplasms (Plasma cell myeloma, Plasmacytoma, Monoclonal immunoglobulin deposition diseases, Heavy chain diseases), Extranodal marginal zone B cell lymphoma (MALT lymphoma), Nodal marginal zone B cell lymphoma (NMZL), Follicular lymphoma, Mantle cell lymphoma, Diffuse large B cell lymphoma, Mediastinal (thymic) large B cell lymphoma, Intravascular large B cell lymphoma, Primary effusion lymphoma, Burkitt lymphoma/leukemia, T cell prolymphocytic leukemia, T cell large granular lymphocytic leukemia, Aggressive NK cell leukemia, Adult T cell leukemia/lymphoma, Extranodal NK/T cell lymphoma (nasal type), Enteropathy-type T cell lymphoma, Hepatosplenic T cell lymphoma, Blastic NK cell lymphoma, Mycosis fungoides/Sezary syndrome, Primary cutaneous CD30-positive T cell lymphoproliferative disorders, Primary cutaneous anaplastic large cell lymphoma, Lymphomatoid papulosis, Angioimmunoblastic T cell lymphoma, Peripheral T cell lymphoma (unspecified), Anaplastic large cell lymphoma), multiple myeloma (plasma cell myeloma or Kahler's disease).

A "therapeutic agent" encompasses both a biological agent such as an antibody, a peptide, a protein, an enzyme or a chemotherapeutic agent.

A "chemotherapeutic agent" is a chemical compound useful in the treatment of cancer. Examples of chemotherapeutic agents include Erlotinib (TARCEVA®, Genentech/OSI Pharm.), Bortezomib (VELCADE®, Millennium Pharm.), Fulvestrant (FASLODEX®, AstraZeneca), Sutent (SU11248, Pfizer), Letrozole (FEMARA®, Novartis), Imatinib mesylate (GLEEVEC®, Novartis), PTK787/ZK 222584 (Novartis), Oxaliplatin (Eloxatin®, Sanofi), 5-FU (5-fluorouracil), Leucovorin, Rapamycin (Sirolimus, RAPAMUNE®, Wyeth), Lapatinib (TYKERB®, GSK572016, Glaxo Smith Kline), Lonafarnib (SCH 66336), Sorafenib (BAY43-9006, Bayer Labs), and Gefitinib (IRESSA®, AstraZeneca), AG1478, AG1571 (SU 5271; Sugen), alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omegaII (Angew Chem. Intl. Ed. Engl. (1994) 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamniprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (doxetaxel; Rhone-Poulenc Rorer, Antony, France); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; a topoisomerase 1 inhibitor such as LURTOTECAN®; ABARELIX® rmRH; (ix) anti-angiogenic agents such as bevacizumab (AVASTIN®, Genentech); and (x) pharmaceutically acceptable salts, acids and derivatives of any of the above. Other anti-angiogenic agents include MMP-2 (matrix-metalloproteinase 2) inhibitors, MMP-9 (matrix-metalloproteinase 9) inhibitors, COX-II (cyclooxygenase II) inhibitors, and VEGF receptor tyrosine kinase inhibitors. Examples of such useful matrix metalloproteinase inhibitors that can be used in combination with the present compounds/compositions are described in WO 96/33172, WO 96/27583, EP 818442, EP 1004578, WO 98/07697, WO 98/03516, WO 98/34918, WO 98/34915, WO 98/33768, WO 98/30566, EP 606,046, EP 931,788, WO 90/05719, WO 99/52910, WO 99/52889, WO 99/29667, WO 99/07675, EP 945864, U.S. Pat. No. 5,863,949, U.S. Pat. No. 5,861,510, and EP 780,386, all of which are incorporated herein in their entireties by reference. Examples of VEGF receptor tyrosine kinase inhibitors include 4-(4-bromo-2-fluoroanilino)-6-methoxy-7-(1-methylpiperidin-4-ylmethoxy)quinazoline (ZD6474; Example 2 within WO 01/32651), 4-(4-fluoro-2-methylindol-5-yloxy)-6-methoxy-7-(3-pyrrolidin-1-ylpropoxy)-quinazoline (AZD2171; Example 240 within WO 00/47212), vatalanib (PTK787; WO 98/35985) and SU11248 (sunitinib; WO 01/60814), and compounds such as those disclosed in PCT Publication Nos. WO 97/22596, WO 97/30035, WO 97/32856, and WO 98/13354).

Other examples of chemotherapeutic agents that can be used in combination with the present compounds include inhibitors of PI3K (phosphoinositide-3 kinase), such as those reported in Yaguchi et al (2006) Jour. of the Nat. Cancer Inst. 98(8):545-556; U.S. Pat. No. 7,173,029; U.S. Pat. No. 7,037,915; U.S. Pat. No. 6,608,056; U.S. Pat. No. 6,608,053; U.S. Pat. No. 6,838,457; U.S. Pat. No. 6,770,641; U.S. Pat. No. 6,653,320; U.S. Pat. No. 6,403,588; WO 2006/046031; WO 2006/046035; WO 2006/046040; WO 2007/042806; WO 2007/042810; WO 2004/017950; US 2004/092561; WO 2004/007491; WO 2004/006916; WO 2003/037886; US 2003/149074; WO 2003/035618; WO 2003/034997; US 2003/158212; EP 1417976; US 2004/053946; JP 2001247477; JP 08175990; JP 08176070; U.S. Pat. No. 6,703,414; and WO 97/15658, all of which are incorporated herein in their entireties by reference. Specific examples of such PI3K inhibitors include SF-1126 (PI3K inhibitor, Semafore Pharmaceuticals), BEZ-235 (PI3K inhibitor, Novartis), XL-147 (PI3K inhibitor, Exelixis, Inc.).

Chemotherapeutic agents may also include any of the generic drugs or biosimilars of the brand-name drugs referenced herein, or improvements thereof, including improved formulations, prodrugs, delivery means (sustained release, bioadhesive coating, targeted delivery etc.), and dosage forms.

A "metabolite" is a product produced through metabolism in the body of a specified compound, a derivative thereof, or a conjugate thereof, or salt thereof. Metabolites of a compound, a derivative thereof, or a conjugate thereof, may be identified using routine techniques known in the art and their activities determined using tests such as those described herein. Such products may result for example from the oxidation, hydroxylation, reduction, hydrolysis, amidation, deamidation, esterification, deesterification, enzymatic cleavage, and the like, of the administered compound. Accordingly, the invention includes metabolites of compounds, a derivative thereof, or a conjugate thereof, of the invention, including compounds, a derivative thereof, or a conjugate thereof, produced by a process comprising contacting a compound, a derivative thereof, or a conjugate thereof, of this invention with a mammal for a period of time sufficient to yield a metabolic product thereof.

The phrase "pharmaceutically acceptable" indicates that the substance or composition must be compatible chemically and/or toxicologically, with the other ingredients comprising a formulation, and/or the mammal being treated therewith.

The term "protecting group" or "protecting moiety" refers to a substituent that is commonly employed to block or protect a particular functionality while reacting other functional groups on the compound, a derivative thereof, or a conjugate thereof. For example, an "amine-protecting group" or an "amino-protecting moiety" is a substituent attached to an amino group that blocks or protects the amino functionality in the compound. Such groups are well known in the art (see for example P. Wuts and T. Greene, 2007, Protective Groups in Organic Synthesis, Chapter 7, J. Wiley & Sons, NJ) and exemplified by carbamates such as methyl and ethyl carbamate, FMOC, substituted ethyl carbamates, carbamates cleaved by 1,6-β-elimination (also termed "self immolative"), ureas, amides, peptides, alkyl and aryl derivatives. Suitable amino-protecting groups include acetyl, trifluoroacetyl, t-butoxycarbonyl (BOC), benzyloxycarbonyl (CBZ) and 9-fluorenylmethylenoxycarbonyl (Fmoc). For a general description of protecting groups and their use, see P. G. M. Wuts & T. W. Greene, Protective Groups in Organic Synthesis, John Wiley & Sons, New York, 2007.

The term "leaving group" refers to an group of charged or uncharged moiety that departs during a substitution or displacement. Such leaving groups are well known in the art and include, but not limited to, halogens, esters, alkoxy, hydroxyl, tosylates, triflates, mesylates, nitriles, azide, carbamate, disulfides, thioesters, thioethers and diazonium compounds.

The term "bifunctional crosslinking agent," "bifunctional linker" or "crosslinking agents" refers to modifying agents that possess two reactive groups; one of which is capable of reacting with a cell binding agent while the other one reacts with the cytotoxic compound to link the two moieties together. Such bifunctional crosslinkers are well known in the art (see, for example, Isalm and Dent in *Bioconjugation* chapter 5, p 218-363, Groves Dictionaries Inc. New York, 1999). For example, bifunctional crosslinking agents that enable linkage via a thioether bond include N-succinimidyl-4-(N-maleimidomethyl)-cyclohexane-1-carboxylate (SMCC) to introduce maleimido groups, or with N-succinimidyl-4-(iodoacetyl)-aminobenzoate (SIAB) to introduce iodoacetyl groups. Other bifunctional crosslinking agents that introduce maleimido groups or haloacetyl groups on to a cell binding agent are well known in the art (see US Patent Applications 2008/0050310, 20050169933, available from Pierce Biotechnology Inc. P.O. Box 117, Rockland, Ill. 61105, USA) and include, but not limited to, bis-maleimidopolyethyleneglycol (BMPEO), BM(PEO)$_2$, BM(PEO)$_3$, N-(β-maleimidopropyloxy)succinimide ester (BMPS), γ-maleimidobutyric acid N-succinimidyl ester (GMBS), ε-maleimidocaproic acid N-hydroxysuccinimide ester (EMCS), 5-maleimidovaleric acid NHS, HBVS, N-succinimidyl-4-(N-maleimidomethyl)-cyclohexane-1-carboxy-(6-amidocaproate), which is a "long chain" analog of SMCC (LC-SMCC), m-maleimidobenzoyl-N-hydroxysuccinimide ester (MBS), 4-(4-N-maleimidophenyl)-butyric acid hydrazide or HCl salt (MPBH), N-succinimidyl 3-(bromoacetamido)propionate (SBAP), N-succinimidyl iodoacetate (SIA), κ-maleimidoundecanoic acid N-succinimidyl ester (KMUA), N-succinimidyl 4-(p-maleimidophenyl)-butyrate (SMPB), succinimidyl-6-(β-maleimidopropionamido) hexanoate (SMPH), succinimidyl-(4-vinylsulfonyl)benzoate (SVSB), dithiobis-maleimidoethane (DTME), 1,4-bis-maleimidobutane (BMB), IA bismaleimidyl-2,3-dihydroxybutane (BMDB), bis-maleimidohexane (BMH), bis-maleimidoethane (BMOE), sulfosuccinimidyl 4-(N-maleimidomethyl)cyclohexane-1-carboxylate (sulfo-SMCC), sulfosuccinimidyl(4-iodo-acetyl)aminobenzoate (sulfo-SIAB), m-maleimidobenzoyl-N-hydroxysulfosuccinimide ester (sulfo-MBS), N-(γ-maleimidobutyloxy)sulfosuccinimde ester (sulfo-GMBS), N-(ε-maleimidocaproyloxy)sulfosuccimido ester (sulfo-EMCS), N-(κ-maleimidoundecanoyloxy)sulfosuccinimide ester (sulfo-KMUS), and sulfosuccinimidyl 4-(p-maleimidophenyl)butyrate (sulfo-SMPB).

Heterobifunctional crosslinking agents are bifunctional crosslinking agents having two different reactive groups. Heterobifunctional crosslinking agents containing both an amine-reactive N-hydroxysuccinimide group (NHS group) and a carbonyl-reactive hydrazine group can also be used to link the cytotoxic compounds described herein with a cell-binding agent (e.g., antibody). Examples of such commercially available heterobifunctional crosslinking agents include succinimidyl 6-hydrazinonicotinamide acetone hydrazone (SANH), succinimidyl 4-hydrazidoterephthalate hydrochloride (SHTH) and succinimidyl hydrazinium nicotinate hydrochloride (SHNH). Conjugates bearing an acid-labile linkage can also be prepared using a hydrazine-bearing benzodiazepine derivative of the present invention. Examples of bifunctional crosslinking agents that can be used include succinimidyl-p-formyl benzoate (SFB) and succinimidyl-p-formylphenoxyacetate (SFPA).

Bifunctional crosslinking agents that enable the linkage of cell binding agent with cytotoxic compounds via disulfide bonds are known in the art and include N-succinimidyl-3-(2-pyridyldithio)propionate (SPDP), N-succinimidyl-4-(2-pyridyldithio)pentanoate (SPP), N-succinimidyl-4-(2-pyridyldithio)butanoate (SPDB), N-succinimidyl-4-(2-pyridyldithio)2-sulfo butanoate (sulfo-SPDB) to introduce dithiopyridyl groups. Other bifunctional crosslinking agents that can be used to introduce disulfide groups are known in the art and are disclosed in U.S. Pat. Nos. 6,913,748, 6,716,821 and US Patent Publications 20090274713 and 20100129314, all of which are incorporated herein by reference. Alternatively, crosslinking agents such as 2-iminothiolane, homocysteine thiolactone or S-acetylsuccinic anhydride that introduce thiol groups can also be used.

A "linker," "linker moiety," or "linking group" as defined herein refers to a moiety that connects two groups, such as a cell binding agent and a cytotoxic compound, together. Typically, the linker is substantially inert under conditions for which the two groups it is connecting are linked. A bifunctional crosslinking agent may comprise two reactive groups, one at each ends of a linker moiety, such that one reactive group can be first reacted with the cytotoxic compound to provide a compound bearing the linker moiety and a second reactive group, which can then react with a cell binding agent. Alternatively, one end of the bifunctional crosslinking agent can be first reacted with the cell binding agent to provide a cell binding agent bearing a linker moiety and a second reactive group, which can then react with a cytotoxic compound. The linking moiety may contain a chemical bond that allows for the release of the cytotoxic moiety at a particular site. Suitable chemical bonds are well known in the art and include disulfide bonds, thioether bonds, acid labile bonds, photolabile bonds, peptidase labile bonds and esterase labile bonds (see for example U.S. Pat. Nos. 5,208,020; 5,475,092; 6,441,163; 6,716,821; 6,913, 748; 7,276,497; 7,276,499; 7,368,565; 7,388,026 and 7,414, 073). Preferred are disulfide bonds, thioether and peptidase labile bonds. Other linkers that can be used in the present invention include non-cleavable linkers, such as those described in are described in detail in U.S. publication number 20050169933, or charged linkers or hydrophilic linkers and are described in US 2009/0274713, US 2010/01293140 and WO 2009/134976, each of which is expressly incorporated herein by reference, each of which is expressly incorporated herein by reference.

In one embodiment, the linking group with a reactive group attached at one end, such as a reactive ester, is selected from the following:

—O(CR$_{20}$R$_{21}$)$_m$(CR$_{22}$R$_{23}$)$_n$(OCH$_2$CH$_2$)$_p$(CR$_{40}$R$_{41}$)$_{p''}$Y" (CR$_{24}$R$_{25}$)$_q$(CO)$_t$X",

—O(CR$_{20}$R$_{21}$)$_m$(CR$_{26}$=CR$_{27}$)$_{m'}$(CR$_{22}$R$_{23}$)$_n$(OCH$_2$CH$_2$)$_p$ (CR$_{40}$R$_{41}$)$_{p''}$Y"(CR$_{24}$R$_{25}$)$_q$(CO)$_t$X",

—O(CR$_{20}$R$_{21}$)$_m$(alkynyl)$_{n'}$(CR$_{22}$R$_{23}$)$_n$(OCH$_2$CH$_2$)$_p$ (CR$_{40}$R$_{41}$)$_{p''}$Y"(CR$_{24}$R$_{25}$)$_q$(CO)$_t$X", —O(CR$_{20}$R$_{21}$)$_m$(piperazino)$_{t'}$(CR$_{22}$R$_{23}$)$_n$(OCH$_2$CH$_2$)$_p$ (CR$_{40}$R$_{41}$)$_{p''}$Y"(CR$_{24}$R$_{25}$)$_q$(CO)$_t$X", —O(CR$_{20}$R$_{21}$)$_m$(pyrrolo)$_{t'}$(CR$_{22}$R$_{23}$)$_n$(OCH$_2$CH$_2$)$_p$ (CR$_{40}$R$_{41}$)$_{p''}$Y"(CR$_{24}$R$_{25}$)$_q$(CO)$_t$X", —O(CR$_{20}$R$_{21}$)$_m$A"$_{m''}$(CR$_{22}$R$_{23}$)$_n$(OCH$_2$CH$_2$)$_p$(CR$_{40}$R$_{41}$)$_{p''}$Y"(CR$_{24}$R$_{25}$)$_q$(CO)$_t$X", —S(CR$_{20}$R$_{21}$)$_m$(CR$_{22}$R$_{23}$)$_n$(OCH$_2$CH$_2$)$_p$(CR$_{40}$R$_{41}$)$_{p''}$Y" (CR$_{24}$R$_{25}$)$_q$(CO)$_t$X", —S(CR$_{20}$R$_{21}$)$_m$(CR$_{26}$=CR$_{27}$)$_{m'}$(CR$_{22}$R$_{23}$)$_n$(OCH$_2$CH$_2$)$_p$ (CR$_{40}$R$_{41}$)$_{p''}$Y"(CR$_{24}$R$_{25}$)$_q$(CO)$_t$X", —S(CR$_{20}$R$_{21}$)$_m$(alkynyl)$_{n'}$(CR$_{22}$R$_{23}$)$_n$(OCH$_2$CH$_2$)$_p$ (CR$_{40}$R$_{41}$)$_{p''}$Y"(CR$_{24}$R$_{25}$)$_q$(CO)$_t$X", —S(CR$_{20}$R$_{21}$)$_m$(piperazino)$_{t'}$(CR$_{22}$R$_{23}$)$_n$(OCH$_2$CH$_2$)$_p$ (CR$_{40}$R$_{41}$)$_{p''}$Y"(CR$_{24}$R$_{25}$)$_q$(CO)$_t$X", —S(CR$_{20}$R$_{21}$)$_m$(pyrrolo)$_{t'}$(CR$_{22}$R$_{23}$)$_n$(OCH$_2$CH$_2$)$_p$ (CR$_{40}$R$_{41}$)$_{p''}$Y"(CR$_{24}$R$_{25}$)$_q$(CO)$_t$X", —S(CR$_{20}$R$_{21}$)$_m$A"$_{m''}$(CR$_{22}$R$_{23}$)$_n$(OCH$_2$CH$_2$)$_p$(CR$_{40}$R$_{41}$)$_{p''}$Y"(CR$_{24}$R$_{25}$)$_q$(CO)$_t$X", —NR$_{33}$(C=O)$_{p''}$(CR$_{20}$R$_{21}$)$_m$(CR$_{22}$R$_{23}$)$_n$(OCH$_2$CH$_2$)$_p$ (CR$_{40}$R$_{41}$)$_{p''}$Y"(CR$_{24}$R$_{25}$)$_q$(CO)$_t$X", —NR$_{33}$(C=O)$_{p''}$(CR$_{20}$R$_{21}$)$_m$(CR$_{26}$=CR$_{27}$)$_{m'}$(CR$_{22}$R$_{23}$)$_n$ (OCH$_2$CH$_2$)$_p$(CR$_{40}$R$_{41}$)$_{p''}$Y"(CR$_{24}$R$_{25}$)$_q$(CO)$_t$X", —NR$_{33}$(C=O)$_{p''}$(CR$_{20}$R$_{21}$)$_m$(alkynyl)$_{n'}$(CR$_{22}$R$_{23}$)$_n$ (OCH$_2$CH$_2$)$_p$(CR$_{40}$R$_{41}$)$_{p''}$Y"(CR$_{24}$R$_{25}$)$_q$—(CO)$_t$X", —NR$_{33}$(C=O)$_{p''}$(CR$_{20}$R$_{21}$)$_m$(piperazino)$_{t'}$(CR$_{22}$R$_{23}$)$_n$ (OCH$_2$CH$_2$)$_p$(CR$_{40}$R$_{41}$)$_{p''}$Y"(CR$_{24}$R$_{25}$)$_q$(CO)$_t$X", —NR$_{33}$(C=O)$_{p''}$(CR$_{20}$R$_{21}$)$_m$(pyrrolo)$_{t'}$(CR$_{22}$R$_{23}$)$_n$ (OCH$_2$CH$_2$)$_p$(CR$_{40}$R$_{41}$)$_{p''}$Y"(CR$_{24}$R$_{25}$)$_q$⁻(CO)$_t$X", —NR$_{33}$(C=O)$_{p''}$(CR$_{20}$R$_{21}$)$_m$A"$_{m''}$(CR$_{22}$R$_{23}$)$_n$(OCH$_2$CH$_2$)$_p$ (CR$_{40}$R$_{41}$)$_{p''}$Y"(CR$_{24}$R$_{25}$)$_q$(CO)$_t$X", —(CR$_{20}$R$_{21}$)$_m$(CR$_{22}$R$_{23}$)$_n$(OCH$_2$CH$_2$)$_p$(CR$_{40}$R$_{41}$)$_{p''}$Y" (CR$_{24}$R$_{25}$)$_q$(CO)$_t$X", —(CR$_{20}$R$_{21}$)$_m$(CR$_{26}$=CR$_{27}$)$_{m'}$(CR$_{22}$R$_{23}$)$_n$(OCH$_2$CH$_2$)$_p$ (CR$_{40}$R$_{41}$)$_{p''}$Y"(CR$_{24}$R$_{25}$)$_q$(CO)$_t$X", —(CR$_{20}$R$_{21}$)$_m$(alkynyl)$_{n'}$(CR$_{22}$R$_{23}$)$_n$(OCH$_2$CH$_2$)$_p$ (CR$_{40}$R$_{41}$)$_{p''}$Y"(CR$_{24}$R$_{25}$)$_q$(CO)$_t$X", —(CR$_{20}$R$_{21}$)$_m$(piperazino)$_{t'}$(CR$_{22}$R$_{23}$)$_n$(OCH$_2$CH$_2$)$_p$ (CR$_{40}$R$_{41}$)$_{p''}$Y"(CR$_{24}$R$_{25}$)$_q$(CO)$_t$X", —(CR$_{20}$R$_{21}$)$_m$A"$_{m''}$(CR$_{22}$R$_{23}$)$_n$(OCH$_2$CH$_2$)$_p$(CR$_{40}$R$_{41}$)$_{p''}$Y" (CR$_{24}$R$_{25}$)$_q$(CO)$_t$X", —(CR$_{20}$R$_{21}$)$_m$(CR$_{29}$=N—NR$_{30}$)$_{n''}$(CR$_{22}$R$_{23}$)$_n$(OCH$_2$CH$_2$)$_p$(CR$_{40}$R$_{41}$)$_{p''}$Y"(CR$_{24}$R$_{25}$)$_q$(CO)$_t$X", —(CR$_{20}$R$_{21}$)$_m$(CR$_{29}$=N—NR$_{30}$)$_{n''}$(CR$_{26}$=CR$_{27}$)$_{m'}$ (CR$_{22}$R$_{23}$)$_n$(OCH$_2$CH$_2$)$_p$(CR$_{40}$R$_{41}$)$_{p''}$Y"(CR$_{24}$R$_{25}$)$_q$(CO)$_t$X", —(CR$_{20}$R$_{21}$)$_m$(CR$_{29}$=N—NR$_{30}$)$_{n''}$(alkynyl)$_{n'}$(CR$_{22}$R$_{23}$)$_n$ (OCH$_2$CH$_2$)$_p$(CR$_{40}$R$_{41}$)$_{p''}$Y"(CR$_{24}$R$_{25}$)$_q$⁻(CO)$_t$X", —(CR$_{20}$R$_{21}$)$_m$(CR$_{29}$=N—NR$_{30}$)$_{n''}$A"$_{m''}$(CR$_{22}$R$_{23}$)$_n$ (OCH$_2$CH$_2$)$_p$(CR$_{40}$R$_{41}$)$_{p''}$Y"(CR$_{24}$R$_{25}$)$_q$(CO)$_t$X", wherein:
  m, n, p, q, m', n', t' are integer from 1 to 10, or are optionally 0;
  t, m", n", and p" are 0 or 1;
  X" is selected from OR$_{36}$, SR$_{37}$, NR$_{38}$R$_{39}$, wherein R$_{36}$, R$_{37}$, R$_{38}$, R$_{39}$ are H, or linear, branched or cyclic alkyl, alkenyl or alkynyl having from 1 to 20 carbon atoms and, or, a polyethylene glycol unit —(OCH$_2$CH$_2$)$_n$, R$_{37}$, optionally, is a thiol protecting group when t=1, COX" forms a reactive ester selected from N-hydroxy-succinimide esters, N-hydroxyphthalimide esters, N-hydroxy sulfo-succinimide esters, para-nitrophenyl esters, dinitrophenyl esters, pentafluorophenyl esters and their derivatives, wherein said derivatives facilitate amide bond formation;
  Y" is absent or is selected from O, S, S—S or NR$_{32}$, wherein R$_{32}$ has the same definition as given above for R; or
  when Y" is not S—S and t=0, X" is selected from a maleimido group, a haloacetyl group or SR$_{37}$, wherein R$_{37}$ has the same definition as above;
  A" is an amino acid selected from glycine, alanine, leucine, valine, lysine, citrulline and glutamate or a polypeptide containing between 2 to 20 amino acid units;
  R$_{20}$, R$_{21}$, R$_{22}$, R$_{23}$, R$_{24}$, R$_{25}$, R$_{26}$, and R$_{27}$ are the same or different, and are —H or a linear or branched alkyl having from 1 to 5 carbon atoms;
  R$_{29}$ and R$_{30}$ are the same or different, and are —H or alkyl from 1 to 5 carbon atoms;
  R$_{33}$ is —H or linear, branched or cyclic alkyl, alkenyl or alkynyl having from 1 to 12 carbon atoms, a polyethylene glycol unit R—(OCH$_2$CH$_2$)$_n$—, or R$_{33}$ is —COR$_{34}$, —CSR$_{34}$, —SOR$_{34}$, or —SO$_2$R$_{34}$, wherein R$_{34}$ is H or linear, branched or cyclic alkyl, alkenyl or alkynyl having from 1 to 20 carbon atoms or, a polyethylene glycol unit —(OCH$_2$CH$_2$)$_n$; and
  one of R$_{40}$ and R$_{41}$ is optionally a negatively or positively charged functional group and the other is H or alkyl, alkenyl, alkynyl having 1 to 4 carbon atoms.

Any of the above linking groups may be present in any of the compounds, drug-linker compounds, or conjugates of the invention, including replacing the linking groups of any of the formulas described herein.

The term "amino acid" refers to naturally occurring amino acids or non-naturally occurring amino acid represented by NH$_2$—C(R$^{aa'}$R$^{aa}$)—C(=O)OH, wherein R$^{aa}$ and R$^{aa'}$ are each independently H, an optionally substituted linear, branched or cyclic alkyl, alkenyl or alkynyl having 1 to 10 carbon atoms, aryl, heteroaryl or heterocyclyl. The term "amino acid" also refers to the corresponding residue when one hydrogen atom is removed from the amine and/or carboxy end of the amino acid, such as —NH—C (R$^{aa'}$R$^{aa}$)—C(=O)O—.

The term "cation" refers to an ion with positive charge. The cation can be monovalent (e.g., Na$^+$, K$^+$, etc.), bi-valent (e.g., Ca$^{2+}$, Mg$^{2+}$, etc.) or multi-valent (e.g., Al$^{3+}$ etc.). Preferably, the cation is monovalent.

The term "therapeutically effective amount" means that amount of active compound or conjugate that elicits the desired biological response in a subject. Such response includes alleviation of the symptoms of the disease or disorder being treated, prevention, inhibition or a delay in the recurrence of symptom of the disease or of the disease itself, an increase in the longevity of the subject compared with the absence of the treatment, or prevention, inhibition or delay in the progression of symptom of the disease or of the disease itself. Determination of the effective amount is well within the capability of those skilled in the art, especially in light of the detailed disclosure provided herein. Toxicity and therapeutic efficacy of compound I can be determined by standard pharmaceutical procedures in cell cultures and in experimental animals. The effective amount of compound or conjugate of the present invention or other therapeutic agent to be administered to a subject will depend on the stage, category and status of the multiple myeloma and characteristics of the subject, such as general health, age, sex, body weight and drug tolerance. The effective amount of compound or conjugate of the present invention or other therapeutic agent to be administered will also depend on administration route and dosage form. Dosage amount and interval can be adjusted individually to provide plasma levels of the active compound that are sufficient to maintain desired therapeutic effects.

Cytotoxic Compounds

The present invention is directed to cytotoxic compounds described herein (e.g., compounds of formulas (I), (II), (III), and (IV)). In one embodiment, the cytotoxic compounds of the present invention do not include any compounds described in US 2010/0203007 (the entire teaching of which is incorporated herein by reference), such as those specifically disclaimed in the proviso below.

In a first specific embodiment, the invention provides a cytotoxic compound comprising a linking group with a reactive group bonded thereto capable of covalently linking the cytotoxic compound to a cell binding agent (CBA), wherein said cytotoxic compound is represented by any one of the following formulas (I), (II), (III) or (IV):

Y is —H or a leaving group selected from —OR, —OCOR', —OCOOR', —OCONR'R'', —NR'R'', —NR'COR'', —NR'NR'R'', an optionally substituted 5- or 6-membered nitrogen-containing heterocycle (e.g., piperidine, tetrahydropyrrole, pyrazole, morpholine, etc.), a guanidinum represented by —NR'(C=NH)NR'R'', an amino acid, or a peptide represented by —NRCOP', wherein P' is an amino acid or a polypeptide containing between 2 to 20 amino acid units, —SR, —SOR', —SO$_2$M, —SO$_3$M, —OSO$_3$M, halogen, cyano and an azido, wherein M is —H or a cation; such as Na$^+$ or K$^+$. Preferably, M is —H or Na$^+$. Preferably, Y is selected from —SO$_3$M, —OH, —OMe, —OEt or —NHOH. More preferably, Y is —SO$_3$M or —OH; or, Y is a sulfite (HSO$_3$, HSO$_2$ or a salt of HSO$_3^-$, SO$_3^{2-}$ or HSO$_2^-$ formed with a cation), metabisulfite (H$_2$S$_2$O$_5$ or a salt of S$_2$O$_5^{2-}$ formed with a cation), mono-, di-, tri-, and tetra-thiophosphate (PO$_3$SH$_3$, PO$_2$S$_2$H$_2$, POS$_3$H$_2$, PS$_4$H$_2$ or a salt of PO$_3$S$^{3-}$, PO$_2$S$_2^{3-}$, POS$_3^{3-}$ or PS$_4^{3-}$ formed with a cation), thio phosphate ester (R$^i$O)$_2$PS (OR$^i$), R$^i$S—, R$^i$SO, R$^i$SO$_2$, R$^i$SO$_3$, thiosulfate (HS$_2$O$_3$ or a salt of S$_2$O$_3^{2-}$ formed with a cation), dithionite

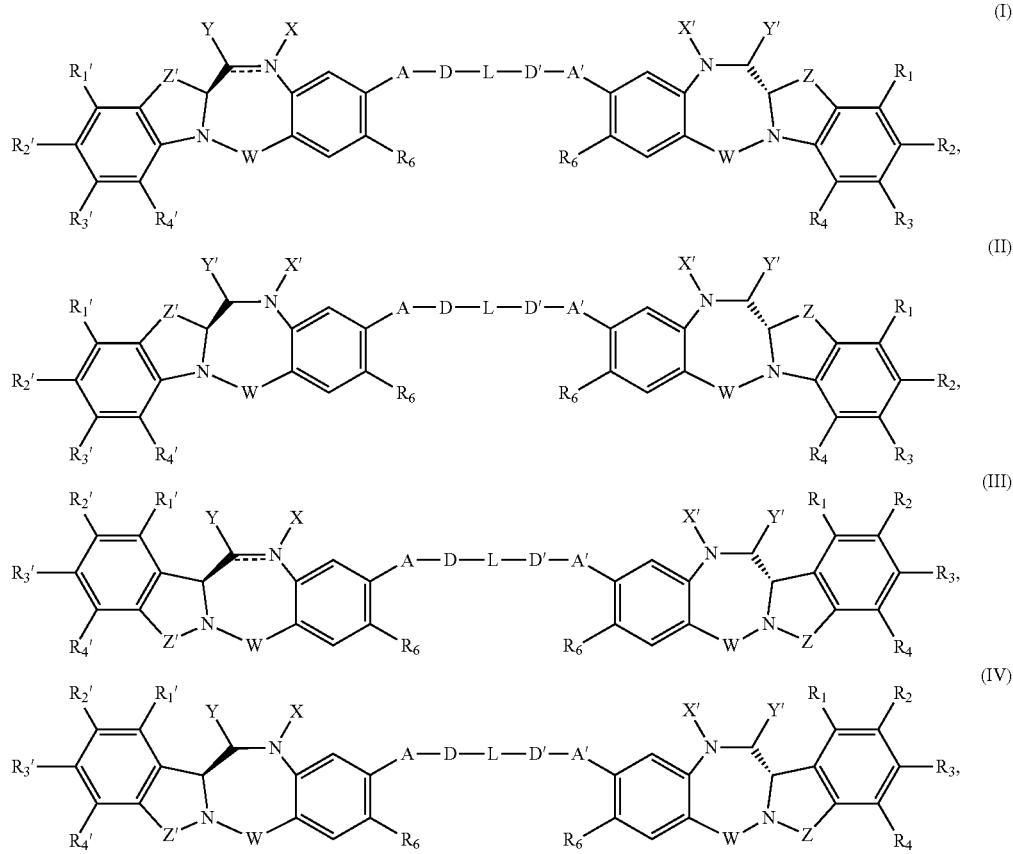

or a pharmaceutically acceptable salt thereof, wherein:
the double line == between N and C represents a single bond or a double bond, provided that when it is a double bond, X is absent and Y is —H, or a linear or branched alkyl having 1 to 4 carbon atoms, and when it is a single bond, X is —H, the linking group with the reactive group bonded thereto, or an amine protecting moiety; preferably, the double line == between N and C represents a double bond;

(HS$_2$O$_4$ or a salt of S$_2$O$_4^{2-}$ formed with a cation), phosphorodithioate (P(=S)(OR$^{k'}$)(S)(OH) or a salt thereof formed with a cation), hydroxamic acid (R$^{k'}$(=O)NOH or a salt formed with a cation), formaldehyde sulfoxylate (HOCH$_2$SO$_2^-$ or a salt of HOCH$_2$SO$_2^-$ formed with a cation, such as HOCH$_2$SO$_2^-$Na$^+$) or a mixture thereof, wherein R$^i$ is a linear or branched alkyl having 1 to 10 carbon atoms and is substituted with at least one substituent selected from —N(R$^j$)$_2$, —CO$_2$H, —SO$_3$H, and —PO$_3$H; R$^i$ can be further optionally substituted with a substituent for an alkyl described herein; R$^j$ is a linear or branched alkyl having 1 to 6 carbon atoms; R$^{k'}$ is a linear, branched or cyclic alkyl, alkenyl or alkynyl having 1 to 10 carbon atoms, aryl, heterocyclyl or heteroaryl; preferably, Y is an adduct of a bisulfite, a hydrosulfite, or a metabisulfite, or salts thereof (such as sodium salt);

R, for each occurrence, is independently selected from the group consisting of —H, an optionally substituted linear, branched or cyclic alkyl, alkenyl or alkynyl having from 1 to 10 carbon atoms, a polyethylene glycol unit —(CH$_2$CH$_2$O)$_n$—R$^c$, an optionally substituted aryl having 6 to 18 carbon atoms, an optionally substituted 5- to 18-membered heteroaryl ring containing one or more heteroatoms independently selected from nitrogen, oxygen, and sulfur, or an optionally substituted 3- to 18-membered heterocyclic ring containing 1 to 6 heteroatoms independently selected from O, S, N and P;

R' and R" are the same or different, and are independently selected from —H, —OH, —OR, —NHR, —NR$_2$, —COR, an optionally substituted linear, branched or cyclic alkyl, alkenyl or alkynyl having from 1 to 10 carbon atoms, a polyethylene glycol unit —(CH$_2$CH$_2$O)$_n$—R$^c$, and an optionally substituted 3- to 18-membered heterocyclic ring having 1 to 6 heteroatoms independently selected from O, S, N and P;

R$^c$ is —H or a substituted or unsubstituted linear or branched alkyl having 1 to 4 carbon atoms, or the linking group with the reactive group bonded thereto;

n is an integer from 1 to 24;

W is selected from C=O, C=S, CH$_2$, BH, SO, and SO$_2$;

X' is selected from the group consisting of —H, —OH, an amine-protecting group, the linking group with the reactive group bonded thereto, an optionally substituted linear, branched or cyclic alkyl, alkenyl or alkynyl having from 1 to 10 carbon atoms, a polyethylene glycol unit —(CH$_2$CH$_2$O)$_n$—R$^c$, an optionally substituted aryl having 6 to 18 carbon atoms (e.g., phenyl), an optionally substituted 5- to 18-membered heteroaryl ring containing one or more heteroatoms independently selected from nitrogen, oxygen, and sulfur, and an optionally substituted 3- to 18-membered heterocyclic ring containing 1 to 6 heteroatoms independently selected from O, S, N and P. Preferably, X' is —H, —OH, -Me or the linking group with the reactive group bonded thereto. More preferably, X' is —H;

Y' is selected from the group consisting of —H, an oxo group, the linking group with the reactive group bonded thereto, an optionally substituted linear, branched or cyclic alkyl, alkenyl or alkynyl having from 1 to 10 carbon atoms, an optionally substituted 6- to 18-membered aryl, an optionally substituted 5- to 18-membered heteroaryl ring containing one or more heteroatoms independently selected from nitrogen, oxygen, and sulfur, an optionally substituted 3- to 18-membered heterocyclic ring having 1 to 6 heteroatoms. Preferably, Y' is selected from —H or oxo. More preferably, Y' is —H;

R$_1$, R$_2$, R$_3$, R$_4$, R$_1$', R$_2$', R$_3$' and R$_4$' are each independently selected from the group consisting of —H, an optionally substituted linear, branched or cyclic alkyl, alkenyl or alkynyl having from 1 to 10 carbon atoms, a polyethylene glycol unit —(OCH$_2$CH$_2$)$_n$—R$^c$, halogen, guanidinium [—NH(C=NH)NH$_2$], —OR, —NR'R", —NO$_2$, —NCO, —NR'COR", —SR, a sulfoxide represented by —SOR', a sulfone represented by —SO$_2$R', a sulfonate —SO$_3$$^-$M$^+$, a sulfate —OSO$_3$$^-$M$^+$, a sulfonamide represented by —SO$_2$NR'R", cyano, an azido, —COR', —OCOR', —OCONR'R" and the linking group with the reactive group bonded thereto. Preferably, one of R$_2$, R$_3$, R$_2$' and R$_3$' is the linking group with the reactive group bonded thereto and the rest are —H;

R$_6$ is —H, —R, —OR, —SR, —NR'R", —NO$_2$, halogen, the linking group with the reactive group bonded thereto, —OR$^c$ or —SR$^c$, wherein R$^c$ is —H, a linear or branched alkyl having 1 to 4 carbon atoms. Preferably, R$_6$ is —OMe or —SMe. Even more preferably, R$_6$ is —OMe;

Z and Z' are independently selected from —(CH$_2$)$_{n'}$—, —(CH$_2$)$_{n'}$—CR$_7$R$_8$—(CH$_2$)$_{na'}$—, —(CH$_2$)$_{n'}$—NR$_9$—(CH$_2$)$_{na'}$—, —(CH$_2$)$_{n'}$—O—(CH$_2$)$_{na'}$— and —(CH$_2$)$_{n'}$—S—(CH$_2$)$_{na'}$—;

n' and na' are same or different, and are selected from 0, 1, 2 and 3;

R$_7$ and R$_8$ are the same or different, and are each independently selected from —H, —OH, —SH, —COOH, —NHR', a polyethylene glycol unit —(OCH$_2$CH$_2$)$_n$—, an amino acid, a peptide unit bearing 2 to 6 amino acids, an optionally substituted linear, branched or cyclic alkyl having from 1 to 10 carbon atoms;

R$_9$ is independently selected from —H, an optionally substituted linear, branched or cyclic alkyl having from 1 to 10 carbon atoms, a polyethylene glycol unit —(OCH$_2$CH$_2$)$_n$—;

A and A' are the same or different, and are independently selected from —O—, oxo (—C(=O)—), —CRR'O—, —CRR'—, —S—, —CRR'S—, —N(R$_5$)— and —CRR'N(R$_5$)—. Preferably, A and A' are the same or different, and are selected from —O— and —S—. More preferably, A and A' are —O—;

R$_5$ for each occurrence is independently —H or an optionally substituted linear or branched alkyl having 1 to 10 carbon atoms;

D and D' are the same or different, and are independently absent or selected from the group consisting of an amino acid, a peptide bearing 2 to 6 amino acids, and a polyethylene glycol unit (—OCH$_2$CH$_2$)$_n$—, an optionally substituted linear, branched or cyclic alkyl, alkenyl or alkynyl having 1 to 10 carbon atoms, wherein the alkyl, alkenyl and alkynyl are optionally substituted with one or more (e.g., 2, 3, 4, 5, 6 or more) substituents independently selected from the group consisting of halogen, —OR, —NR'COR", —SR and —COR';

Preferably, D and D' are the same or different, and are independently selected from linear, branched or cyclic alkyl, alkenyl or alkynyl having from 1 to 10 carbon atoms. More preferably, D and D' are linear or branched alkyl bearing 1 to 4 carbon atoms. Still more preferably, D and D' are the same or different, and are selected from a linear alkyl having 1 to 4 carbon atoms;

L is absent, the linking group with the reactive group bonded thereto, a polyethylene glycol unit (—OCH$_2$CH$_2$)$_n$—, a linear, branched or cyclic alkyl or alkenyl having 1 to 10 carbon atoms (e.g., 1-6 carbon atoms), a phenyl group, a 3- to 18-membered heterocyclic ring or a 5- to 18-membered heteroaryl ring having 1 to 6 heteroatoms independently selected from O, S, N and P, wherein the alkyl or alkenyl is optionally substituted with the linking group with the reactive group bonded thereto; phenyl or heterocyclic or heteroaryl ring can be optionally substituted, wherein the substituent can be the linking group with the reactive group bonded thereto.

In certain embodiments, X is not the linking group with the reactive group bonded thereto. In certain embodiments, the double line ═ between N and C represents a single bond, Y is not —H.

In certain embodiments, the cytotoxic compounds of the present invention are not any one of the following compounds:

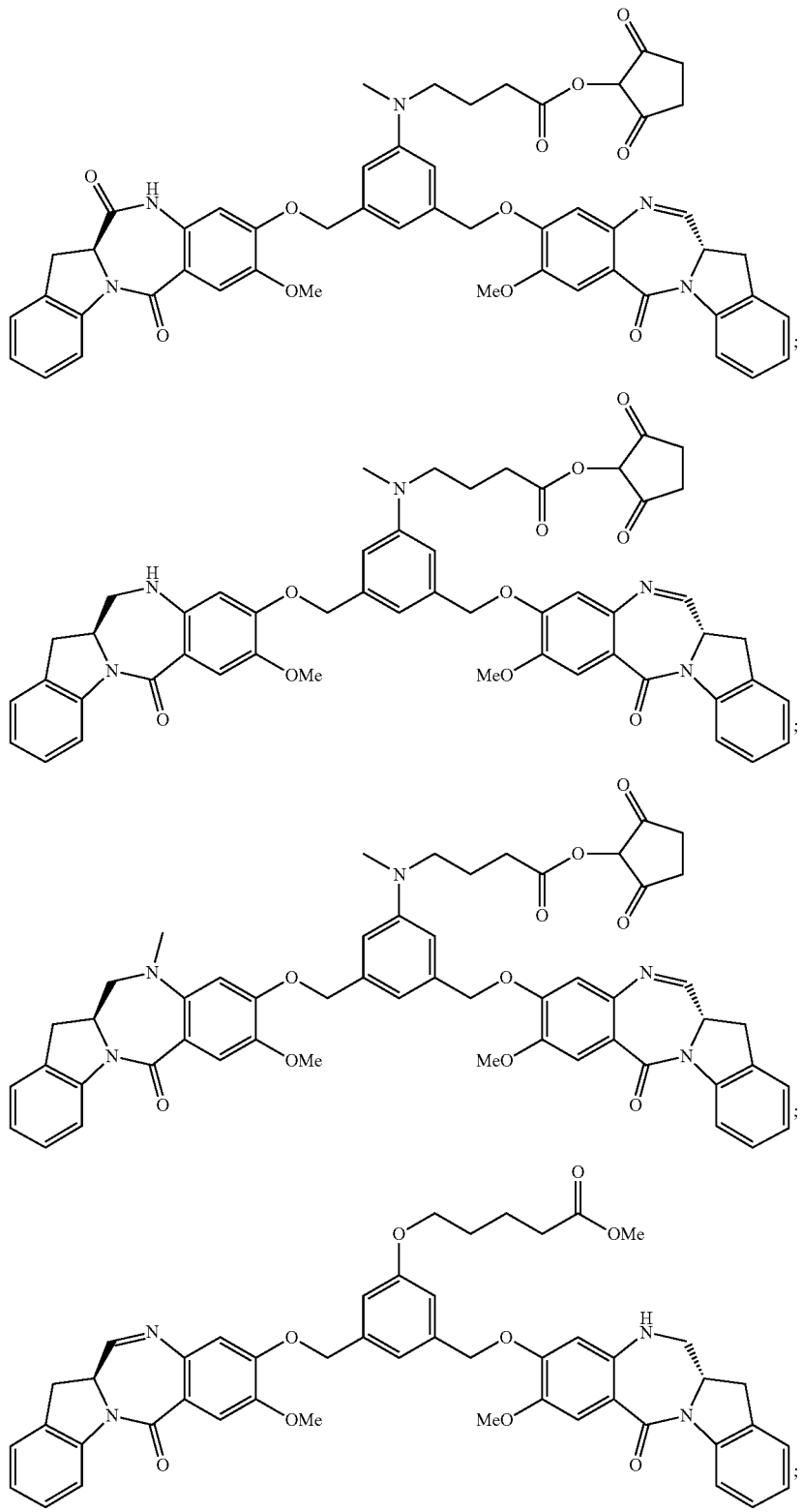

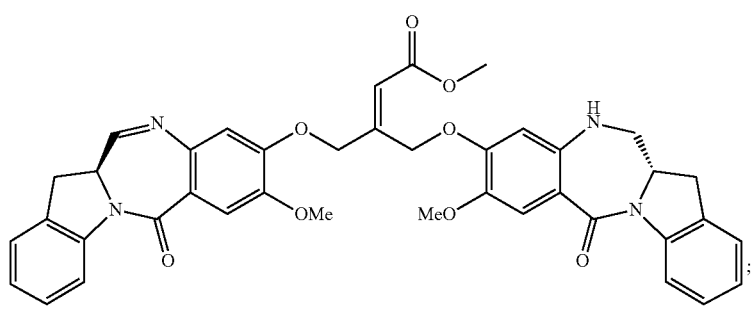
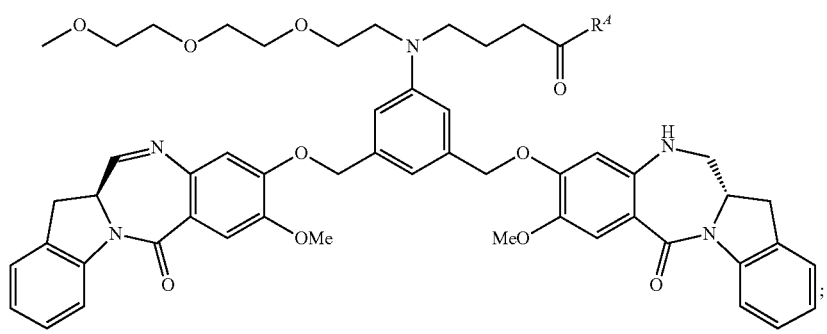
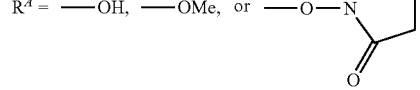
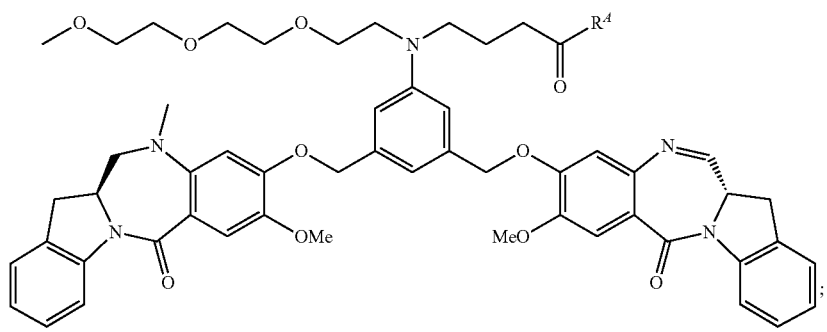
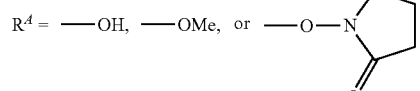
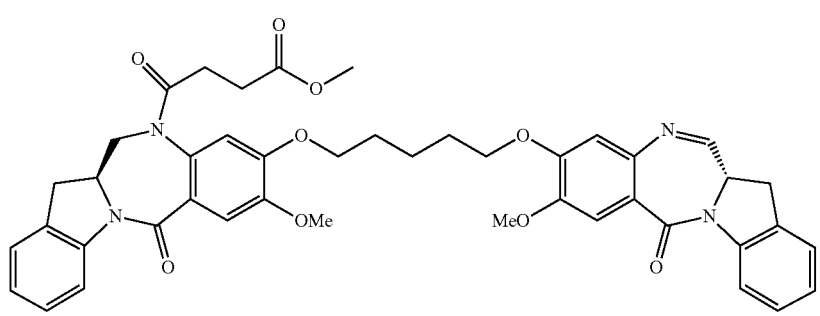

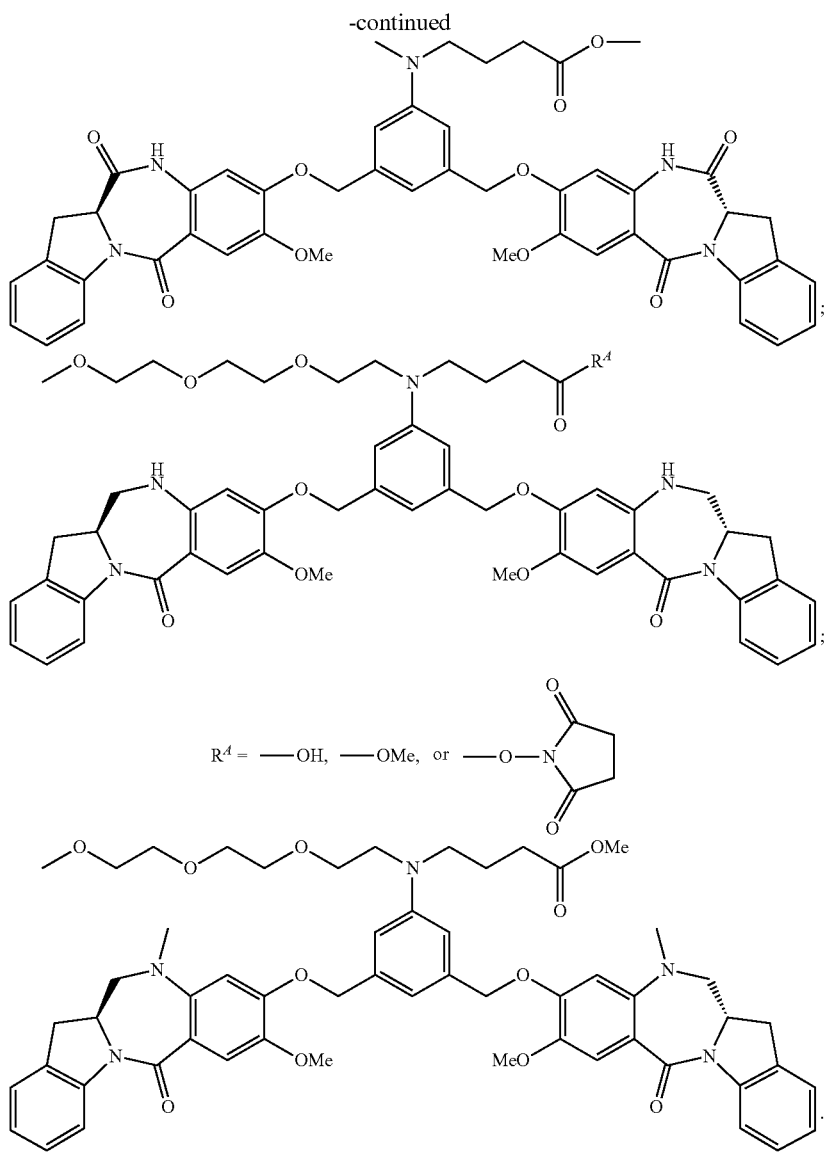

In certain embodiments, Y is —H or a leaving group selected from —OR, —OCOR', —OCOOR', —OCONR'R", —NR'R", —NR'COR", —NR'NR'R", an optionally substituted 5 or 6-membered nitrogen-containing heterocycle (e.g., piperidine, tetrahydropyrrole, pyrazole, morpholine, etc.), a guanidinum represented by —NR'(C=NH)NR'R", an amino acid, or a peptide represented by —NRCOP', wherein P' is an amino acid or a polypeptide containing between 2 to 20 amino acid units, —SR, —SOR', —SO$_2$M, —SO$_3$M, —OSO$_3$M, halogen, cyano and an azido. Preferably, Y is Sodium Bisulfite adduct, Sodium Hydrosulfite adduct, or Sodium Metabisulfite adduct. In certain embodiments, Y is not —H.

In certain embodiments, L is absent, or is selected from an optionally substituted phenyl group and an optionally substituted pyridyl group, wherein the phenyl and the pyridyl group bears the linking group with the reactive group bonded thereto, or L is an amine group bearing the linking group with the reactive group bonded thereto (i.e., —N(linking group)-), or L is a linear, branched or cyclic alkyl or alkenyl having from 1 to 6 carbon atoms and bearing the linking group with the reactive group bonded thereto.

In a second specific embodiment, for cytotoxic dimers (I), (II), (III) and (IV), the variables are as described below:

the double line ⚌ between N and C represents a double bond;

Y is —H;

W is C=O;

$R_1$, $R_2$, $R_1'$, $R_2'$, $R_4$ and $R_4'$ are —H;

one of $R_3$, or $R_3'$ is optionally a linking group and the other is —H;

$R_6$ is —OMe;

Z and Z' are —CH$_2$—;

X' is —H;

Y' is —H;

A and A' are —O—; and the remainder of the variables are as described in the first specific embodiment.

In a third specific embodiment, the cytotoxic dimers of formula (I), (II), (III) and (IV) are represented by the following formulas:

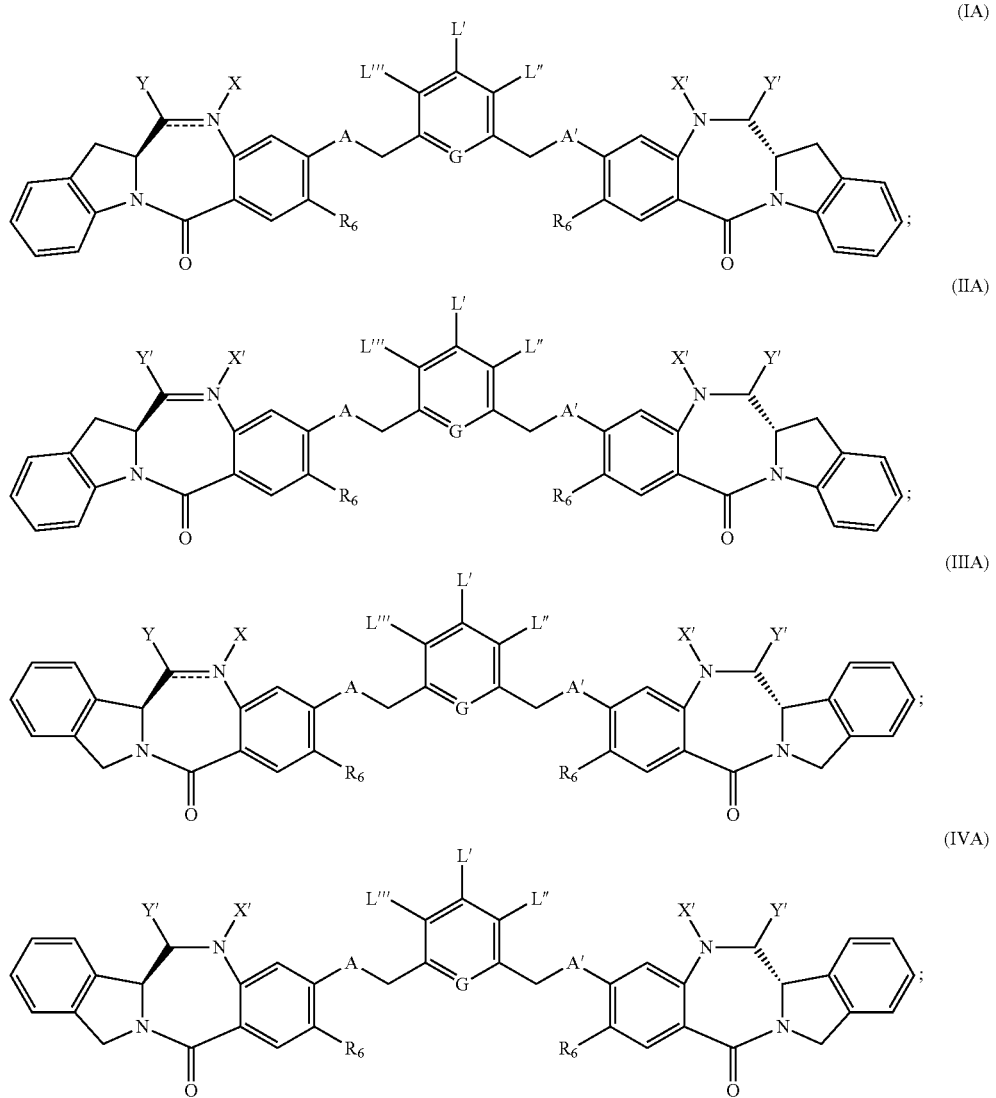

wherein:
- the double line ═ between N and C represents a single bond or a double bond, provided that when it is a double bond X is absent and Y is —H, and when it is a single bond, X is selected from —H, the linking group with the reactive group bonded thereto, or an amine protecting group (preferably X is —H);
- Y is selected from —H, —OR, —OCOR', —SR, —NR'R", —SO$_3$M, —SO$_2$M, or —OSO$_3$M, wherein M is —H or a cation such as Na$^+$. K$^+$. Preferably, Y is selected from —OH, —OMe, —OEt, —NHOH or —SO$_3$M. Even more preferably, Y is —OH or —SO$_3$M, preferably M is —H or Na$^+$;
- R is —H, an optionally substituted linear, branched or cyclic alkyl, alkenyl or alkynyl having from 1 to 10 carbon atoms or a PEG group —(CH$_2$CH$_2$O)$_n$—R$^c$, wherein n is an integer from 1 to 24 and R$^c$ is a linear or branched alkyl having 1 to 4 carbon atoms;
- R' and R" are the same or different, and are selected from —H, —OH, —OR, —NRR$^{g'}$, —COR, an optionally substituted linear, branched or cyclic alkyl, alkenyl or alkynyl having from 1 to 10 carbon atoms, an optionally substituted aryl having from 6 to 18 carbon atoms, an optionally substituted 3- to 18-membered heterocyclic ring having 1 to 6 heteroatoms selected from O, S, N and P, a PEG group —(CH$_2$CH$_2$O)$_n$—R$^c$, wherein n is an integer from 1 to 24, preferably n is 2, 4 or 8; and R$^{g'}$ is —H, an optionally substituted linear, branched or cyclic alkyl, alkenyl or alkynyl having from 1 to 10 carbon atoms or a PEG group —(CH$_2$CH$_2$O)$_n$—R$^c$;
- X' is selected from the group consisting of —H, —OH, a substituted or unsubstituted linear, branched or cyclic alkyl, alkenyl or alkynyl having from 1 to 10 carbon atoms, phenyl, and an amine-protecting group. Preferably, X' is —H, —OH or -Me. More preferably, X' is —H;
- Y' is selected from the group consisting of —H, an oxo group, a substituted or unsubstituted linear, branched or cyclic alkyl, alkenyl or alkynyl having from 1 to 10 carbon atoms. Preferably, Y' is selected from —H or -Me. More preferably Y' is —H;
- R$_6$ is —OR$^c$ or —SR$^c$, wherein R$^c$ is a linear or branched alkyl having 1 to 4 carbon atoms. Preferably, R$_6$ is —OMe or —SMe. Even more preferably, R$_6$ is —OMe;

A and A' are selected from —O— and —S—. Preferably, A and A' are —O—;

L', L", and L'" are the same or different, and are independently selected from —H, an optionally substituted linear, branched or cyclic alkyl, alkenyl or alkynyl having from 1 to 10 carbon atoms, a polyethylene glycol unit —(OCH$_2$CH$_2$)$_n$—R$^c$, halogen, guanidinium [—NH(C=NH)NH$_2$], —OR, —NR'R", —NO$_2$, —NR'COR", —SR, a sulfoxide represented by —SOR', a sulfone represented by —SO$_2$R', a sulfonate —SO$_3$$^-$M$^+$, a sulfate —OSO$_3$$^+$M$^-$, a sulfonamide represented by SO$_2$NR'R", cyano, an azido, —COR', —OCOR', —OCONR'R" and the linking group with the reactive group bonded thereto, provided only one of L', L", and L'" is the linking group with the reactive group bonded thereto. Preferably, L' is the linking group with the reactive group bonded thereto. Alternatively, one of L', L" or L'" is the linking group with the reactive group bonded thereto, while the others are —H. More preferably, L' is the linking group with the reactive group bonded thereto, and L" and L'" are —H;

G is selected from —CH— or —N—; and the remainder of the variables are as described in the first specific embodiment.

In certain embodiments, X is not the linking group with the reactive group bonded thereto. In certain embodiments, the double line == between N and C represents a single bond, Y is not —H.

In certain embodiments, A and A' are both —O—, R$_6$ is —OMe, and G is —CH—.

In a fourth specific embodiment, for the cytotoxic dimers of formula (IA), (IIA), (IIIA) or (IVA), L' is represented by the formula:

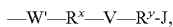
—W'—R$^x$—V—R$^y$-J, wherein:

W' and V are the same or different, and are each independently absent, or selected from —CR$^e$R$^{e'}$—, —O—, —O—C(=O)—, —C(=O)—O—, —S—, —SO—, —SO$_2$—, —CH$_2$—S—, —CH$_2$O—, —CH$_2$NR$^e$—, —O—(C=O)O—, —O—(C=O)N(R$^e$)—, —N(R$^e$)—, —N(R$^e$)—C(=O)—, —C(=O)—N(R$^e$)—, —N(R$^e$)—C(=O)O—, —N(C(=O)R$^e$)C(=O)—, —N(C(=O)R$^e$)—, —(O—CH$_2$—CH$_2$)$_n$—, —SS—, or —C(=O)—, or an amino acid, or a peptide having 2 to 8 amino acids;

R$^x$ and R$^y$ are the same or different, and are each independently absent or an optionally substituted linear, branched or cyclic alkyl, alkenyl or alkynyl having 1 to 10 carbon atoms, an aryl bearing 6 to 10 carbon atoms or a 3- to 8-membered heterocyclic ring bearing 1 to 3 heteroatoms selected from O, N or S;

R$^e$ and R$^{e'}$ are the same or different, and are selected from —H, a linear, branched or cyclic alkyl, alkenyl or alkynyl having 1 to 10 carbon atoms or —(CH$_2$—CH$_2$—O)$_n$—R$^k$, wherein R$^k$ is a —H, a linear, branched cyclic alkyl having 1 to 6 carbon atoms, optionally bearing a secondary amino (e.g., —NHR$^{101}$) or tertiary amino (—NR$^{101}$R$^{102}$) group or a 5 or 6-membered nitrogen containing heterocycle, such as piperidine or morpholine, wherein R$^{101}$ and R$^{102}$ are each independently a linear, branched, or cyclic alkyl, alkenyl or alkynyl having 1 to 10 carbon atoms. Preferably, R$^{101}$ and R$^{102}$ are each independently a linear or branched alkyl having 1 to 6 carbon atoms;

n is an integer from 1 to 24; and

J comprises the reactive group bonded thereto, and is selected from a maleimide, a haloacetamido, —SH, —SSR$^d$, —CH$_2$SH, —CH(Me)SH, —C(Me)$_2$SH, —NHR$^{c1}$, —CH$_2$NHR$^{c1}$, —NR$^{c1}$NH$_2$, —COOH, and —COE, wherein —COE represents a reactive ester selected from, but not limited to, N-hydroxysuccinimde ester, N-hydroxy sulfosuccinimide ester, nitrophenyl (e.g., 2 or 4-nitrophenyl) ester, dinitrophenyl (e.g., 2,4-dinitrophenyl) ester, sulfo-tetrafluorophenyl (e.g., 4-sulfo-2,3,5,6-tetrafluorophenyl) ester, and pentafluorophenyl ester, and wherein R$^{c1}$ is —H or a substituted or unsubstituted linear or branched alkyl having 1 to 4 carbon atoms, and R$^d$ is selected from phenyl, nitrophenyl (e.g., 2 or 4-nitrophenyl), dinitrophenyl (e.g., 2 or 4-nitrophenyl), carboxynitrophenyl (e.g., 3-carboxy-4-nitrophenyl), pyridyl or nitropyridyl (e.g., 4-nitropyridyl).

In certain embodiments, J is —SH, —SSR$^d$, a maleimide, or a N-hydroxysuccinimide ester.

In certain embodiments, R$^{e'}$ is —H or -Me; R$^e$ is a linear or branched alkyl having 1 to 6 carbon atoms or —(CH$_2$—CH$_2$—O)$_n$—R$^k$; n is an integer from 2 to 8; preferably R$^k$ is —H, -Me or —CH$_2$CH$_2$—NMe$_2$, and the remainder of the variables are as described above in the fourth specific embodiment.

In certain embodiments, V is an amino acid or a peptide having 2 to 8 amino acids. In certain embodiments, V is valine-citrulline, gly-gly-gly, or ala-leu-ala-leu.

In certain embodiments,

W' is —O—, —N(R$^e$)— or —N(R$^e$)—C(=O)—;

R$^e$ is H, a linear or branched alkyl having 1 to 4 carbon atoms, or —(CH$_2$—CH$_2$—O)$_n$—R$^k$;

R$^x$ is a linear or branched alkyl having 1 to 6 carbon atoms;

V is absent, —(O—CH$_2$—CH$_2$)$_n$—, —C(=O)—NH—, —S—, —NH—C(=O)—;

R$^y$ is absent or a linear or branched alkyl having 1 to 4 carbon atoms; and

J is —SH, —SSR$^d$ or —COE (preferably, N-hydroxysuccinimide ester). The remainder of the variables is as described in the fourth specific embodiment.

In certain embodiments,

W' is —O—, —N(R$^e$)— or —N(R$^e$)—C(=O)—;

R$^e$ is H, Me, or —(CH$_2$—CH$_2$—O)$_n$-Me;

n is an integer from 2 to 6;

R$^x$ is linear or branched alkyl bearing 1 to 6 carbon atoms;

V and R$^y$ are absent; and

J is —COE, preferably N-hydroxysuccinimide ester. The remainder of the variables is as described in the fourth specific embodiment.

In a fifth specific embodiment, L' is represented by the following formula:

—W'—[CR$_{1"}$R$_{2"}$]$_a$—V-[Cy]$_{0-1}$-[CR$_{3"}$—R$_{4"}$]$_b$-COE, wherein:

R$_{1"}$, R$_{2"}$, and R$_{3"}$ are each independently —H or a linear or branched alkyl bearing 1 to 4 carbon atoms, preferably -Me;

R$_{4"}$ is —H, a linear or branched alkyl bearing 1 to 4 carbon atoms (preferably -Me), —SO$_3$H, or —SO$_3$$^-$M$^+$, wherein M$^+$ is a pharmaceutically acceptable cation;

a is an integers from 0-5 (e.g., from 0 to 2, 3, 4, or 5), and b is an integer from 0-6 (e.g., from 0 to 3, 4, 5, or 6); and, Cy is an optionally substituted 5-membered heterocyclic ring bearing an N heteroatom, preferably Cy is

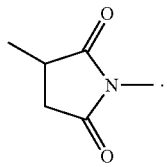

In certain embodiments, W' is —N($R^e$)—.

In certain embodiments, such as in the fourth and/or the fifth specific embodiment, $R^e$ is —(CH$_2$—CH$_2$—O)$_{2-6}$—$R^k$, wherein $R^k$ is a —H, a linear, branched cyclic alkyl having 1 to 6 carbon atoms.

In certain embodiments, such as in the fourth and/or the fifth specific embodiment, V is —S— or —SS—.

In a sixth specific embodiments, such as in the fourth and/or the fifth specific embodiment, L' is represented by the following formula:

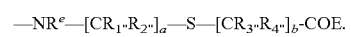

In certain embodiments, the compound is any of the following:

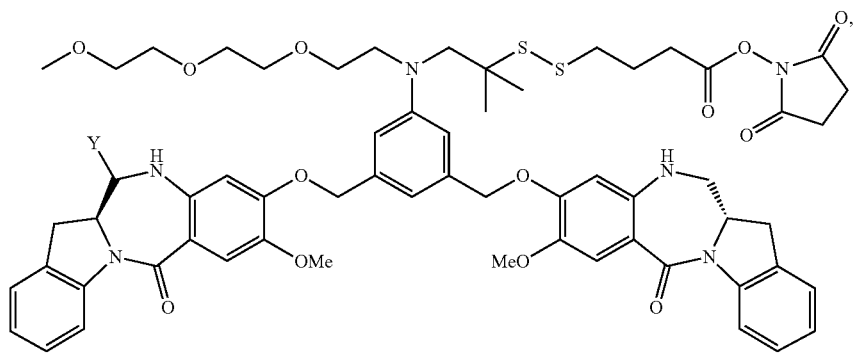

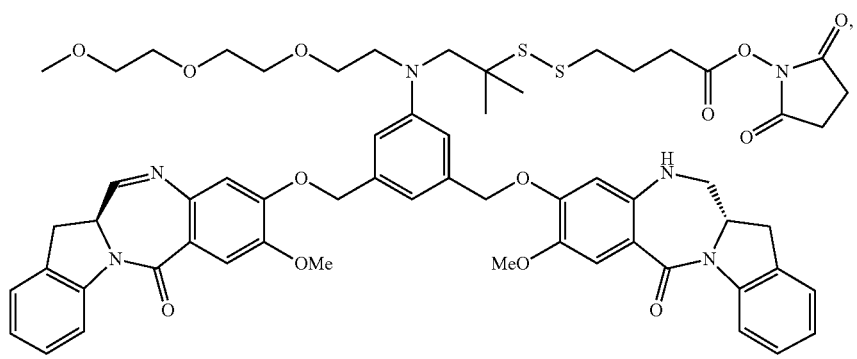

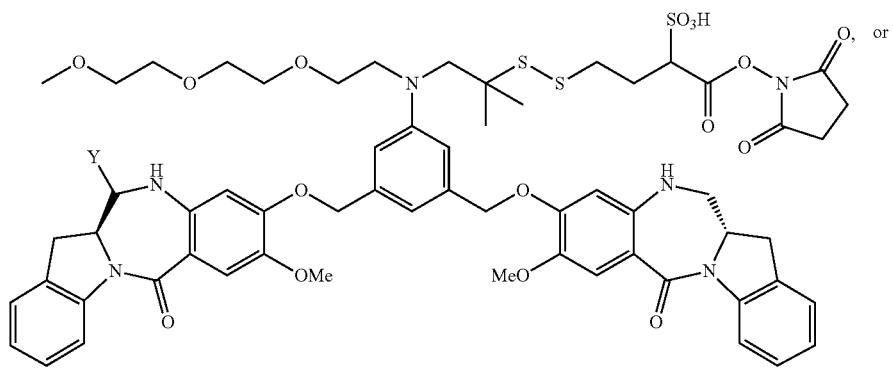

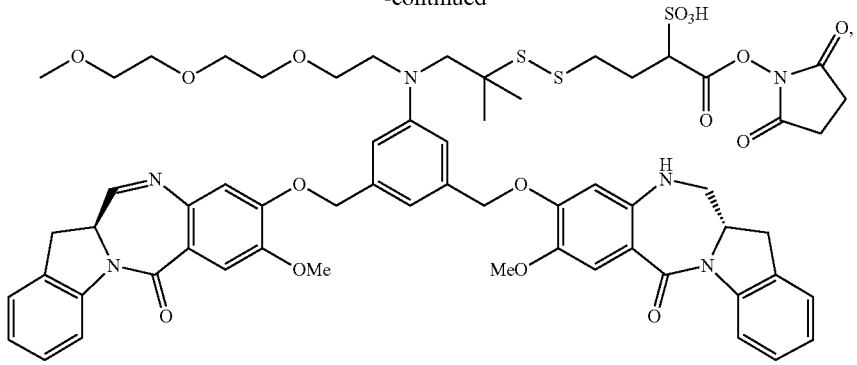
wherein Y is —H or —SO₃M, and M is —H or a pharmaceutically acceptable cation. In certain embodiments, Y is —SO₃M.
In a seventh specific embodiments, such as in the fourth and/or the fifth specific embodiment, L' is represented by the following formula:
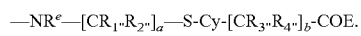
—NR$^e$—[CR$_1$"R$_2$"]$_a$—S-Cy-[CR$_3$"R$_4$"]$_b$-COE.
In certain embodiments, the compound is any one of the following:
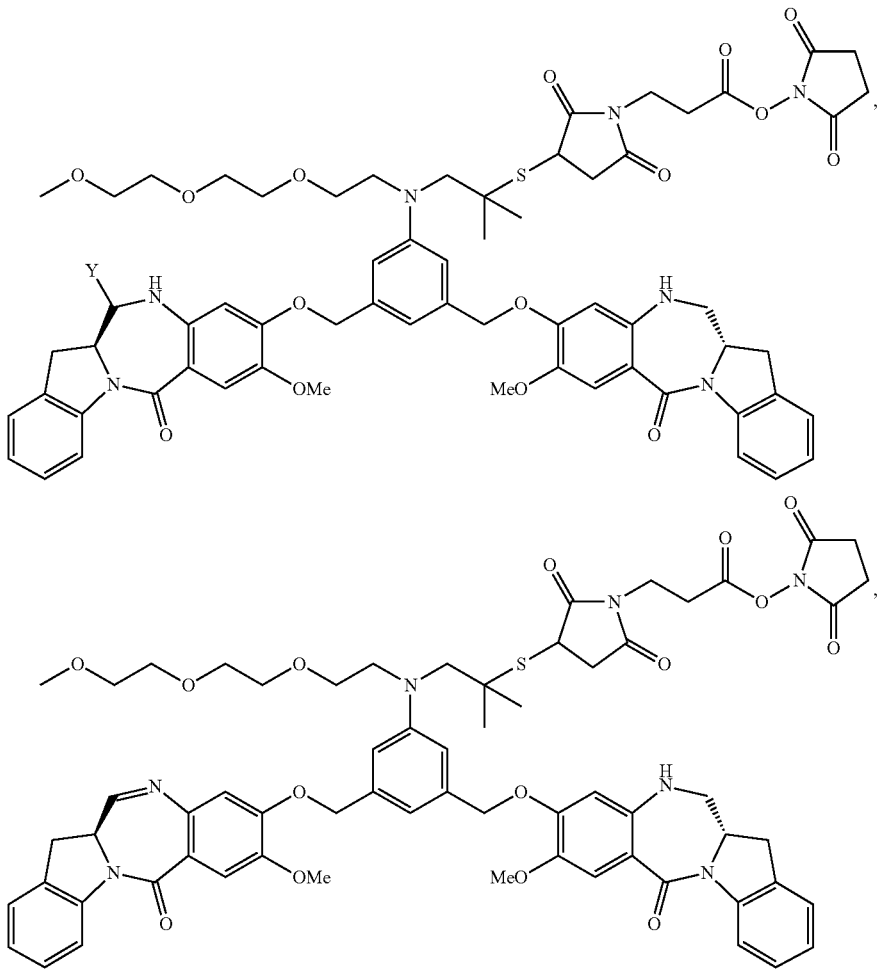

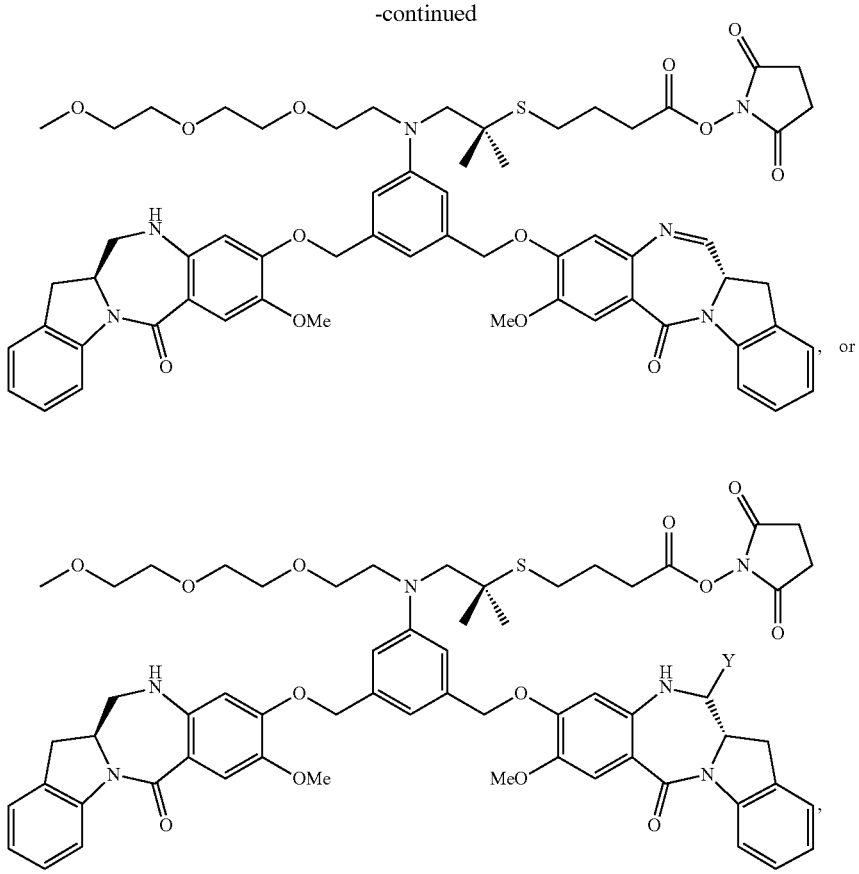
wherein Y is —H or —SO₃M, and M is —H or a pharmaceutically acceptable cation. In certain embodiments, Y is —SO₃M.
In a eighth specific embodiment, the cytotoxic dimers of formula (I), (II), (III) and (IV) are represented by the following formulas:
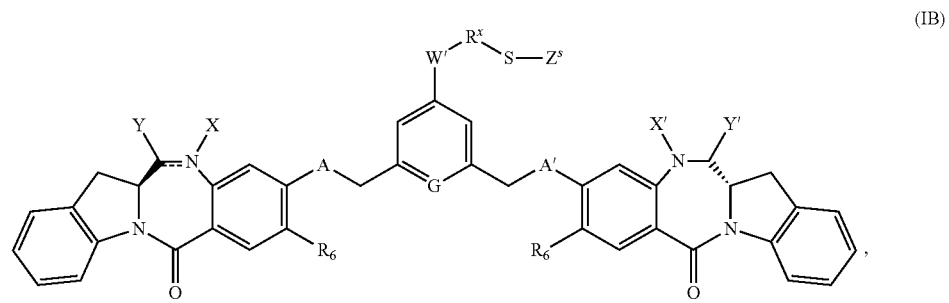
(IB)
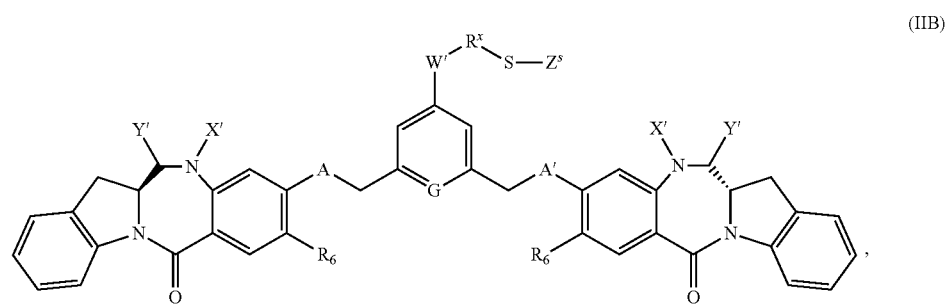
(IIB)

-continued

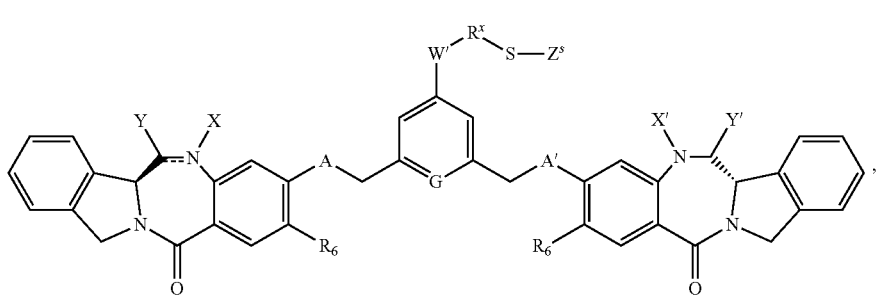
(IIIB)

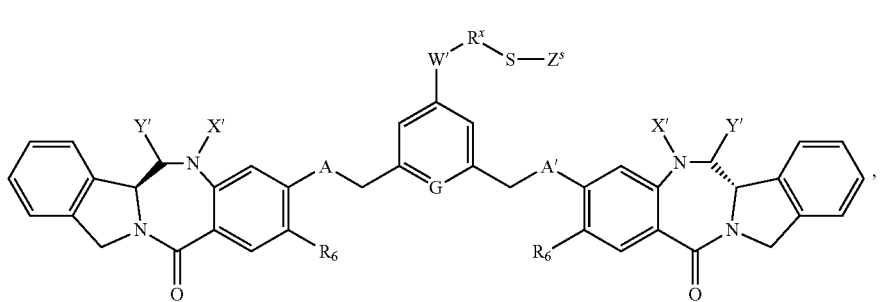
(IVB)

wherein:

W' is absent, or selected from —O—, —N($R^e$)—, —N($R^e$)—C(=O)—, —N(C(=O)$R^e$)—, —S— or —CH$_2$—S—, —CH$_2$NR$^e$—;

$R^x$ is absent or selected from a linear, branched or cyclic alkyl having 1 to 10 carbon atoms;

$R^e$ is —H, a linear, branched or cyclic alkyl, alkenyl or alkynyl having 1 to 10 carbon atoms or —(CH$_2$—CH$_2$—O)$_n$—$R^k$, wherein $R^k$ is a —H, a linear, branched cyclic alkyl having 1 to 6 carbon atoms, optionally bearing a secondary amino (e.g., —NHR$^{101}$) or tertiary amino (—NR$^{101}$R$^{102}$) group or a 5- or 6-membered nitrogen containing heterocycle, such as piperidine or morpholine, wherein R$^{101}$ and R$^{102}$ are each independently a linear, branched, or cyclic alkyl, alkenyl or alkynyl having 1 to 10 carbon atoms. Preferably, R$^{101}$ and R$^{102}$ are each independently a linear or branched alkyl having 1 to 6 carbon atoms;

$Z^s$ is —H, —SR$^m$;

$R^m$ is $R^d$ or a substituted or unsubstituted linear or branched alkyl having 1 to 4 carbon atoms bearing a reactive ester, selected from N-hydroxysuccinimide esters, N-hydroxyphtalimide esters, N-hydroxy sulfosuccinimide esters, para-nitrophenyl esters, dinitrophenyl esters, pentafluorophenyl esters;

$R^d$ is selected from phenyl, nitrophenyl, dinitrophenyl, carboxynitrophenyl, pyridyl or nitropyridyl; and, n is an integer from 1 to 24; and the remainder of the variables are as described above in the third specific embodiment.

Preferably, $R^k$ is —H or -Me, and n is an integer from 2 to 8. Preferably, $R^x$ is a linear or branched alkyl having 1 to 6 carbon atoms; and the remainder of the variables is as described above in the third, fourth, and/or the fifth specific embodiment.

In a ninth specific embodiment, the cytotoxic dimers of formula (I), (II), (III) and (IV) are represented by the following formulas:

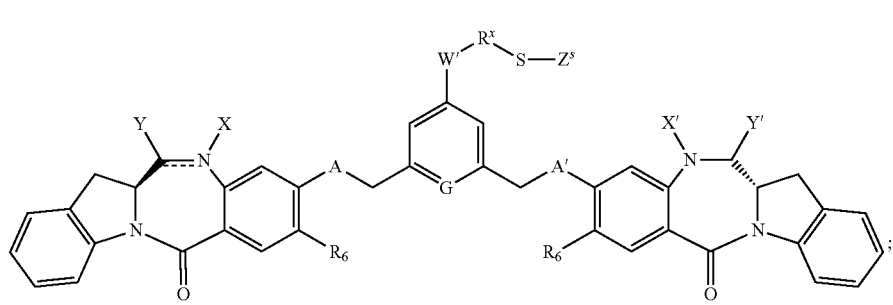
(VIII)

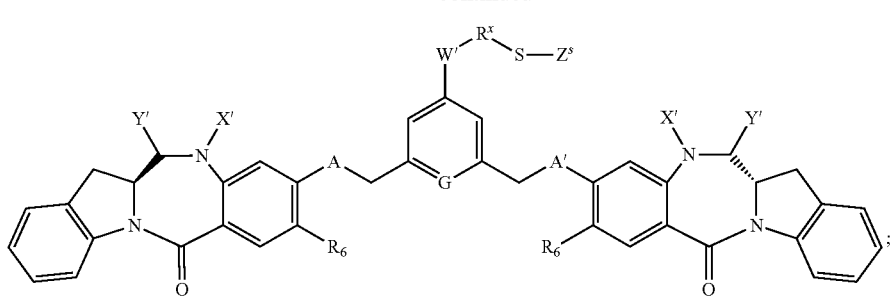

(IX)

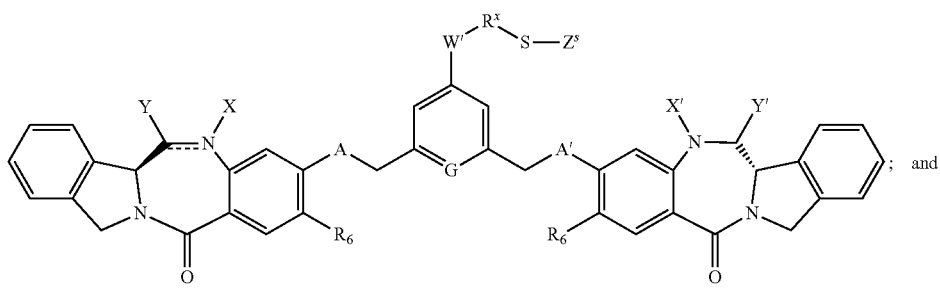

(X)
; and

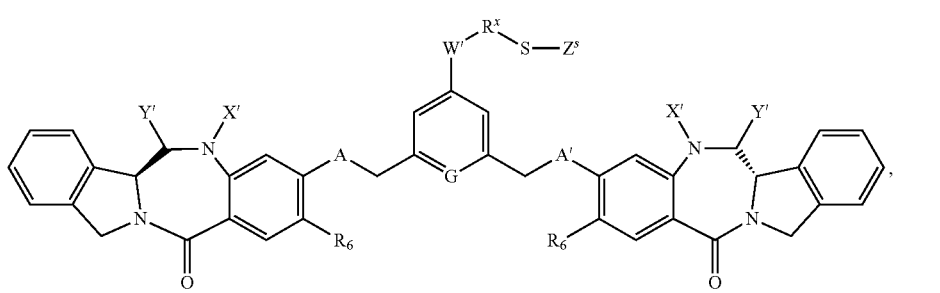

(XI)
, wherein:
the double line ⚌ between N and C represents a single bond or a double bond, provided that when it is a double bond, X is absent and Y is —H, and when it is a single bond, X is selected from —H, the linking group with the reactive group bonded thereto, or an amine protecting group (preferably X is —H or an amine protecting group; more preferably, X is —H);

Y is selected from —H, —OR, —OCOR', —SR, —NR'R", —SO$_3$M, —SO$_2$M or —OSO$_3$M (e.g., Y is —OR, —OCOR', —SR, —NR'R", —SO$_3$M, —SO$_2$M or —OSO$_3$M), wherein M is —H or a cation such as Na$^+$ or K$^+$;

R is —H, an optionally substituted linear, branched or cyclic alkyl, alkenyl or alkynyl having from 1 to 10 carbon atoms or a PEG group —(CH$_2$CH$_2$O)$_n$—R$^c$, wherein n is an integer from 1 to 24, and R$^c$ is a linear or branched alkyl having 1 to 4 carbon atoms;

R' and R" are the same or different, and are selected from —H, —OH, —OR, —NRR$^{g'}$, —COR, an optionally substituted linear, branched or cyclic alkyl, alkenyl or alkynyl having from 1 to 10 carbon atoms, an optionally substituted aryl having from 6 to 18 carbon atoms, an optionally substituted 3- to 18-membered heterocyclic ring having 1 to 6 heteroatoms selected from O, S, N and P, a PEG group —(CH$_2$CH$_2$O)$_n$—R$^c$, wherein n is an integer from 1 to 24, preferably n is 2, 4 or 8; and R$^{g'}$ is —H, an optionally substituted linear, branched or cyclic alkyl, alkenyl or alkynyl having from 1 to 10 carbon atoms or a PEG group —(CH$_2$CH$_2$O)$_n$—R$^c$;

X' is selected from the group consisting of —H, —OH, a substituted or unsubstituted linear, branched or cyclic alkyl, alkenyl or alkynyl having from 1 to 10 carbon atoms, phenyl, and an amine-protecting group;

Y' is selected from the group consisting of —H, an oxo group, a substituted or unsubstituted linear, branched or cyclic alkyl, alkenyl or alkynyl having from 1 to 10 carbon atoms;

A and A' are selected from —O— and —S—;

W' is absent, or selected from —O—, —N(R$^e$)—, —N(R$^e$)—C(=O)—, —N(C(=O)R$^e$)—, —S— or —CH$_2$—S—, —CH$_2$NR$^e$—;

R$^x$ is absent or selected from a linear, branched or cyclic alkyl having 1 to 10 carbon atoms;

R$^e$ is —H, a linear, branched or cyclic alkyl, alkenyl or alkynyl having 1 to 10 carbon atoms or —(CH$_2$—CH$_2$—O)$_n$—R$^k$, wherein R$^k$ is a —H, a linear, branched cyclic alkyl having 1 to 6 carbon atoms, optionally bearing a secondary amino (e.g., —NHR$^{101}$) or tertiary amino (NR$^{101}$R$^{102}$) group or a 5 or 6-membered nitrogen containing heterocycle, such as piperidine or morpholine, wherein R$^{101}$ and R$^{102}$ are each independently a linear, branched, or cyclic alkyl, alkenyl or alkynyl having 1 to 10 carbon atoms;

G is selected from —CH— or —N—;

Z$^s$ is —H, or is selected from any one of the following formulas:

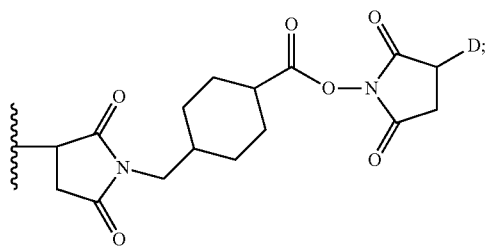 (A1)
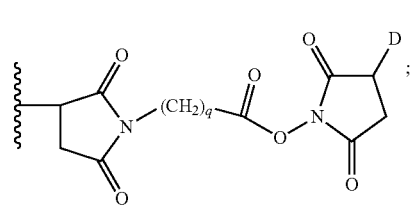 (A2)
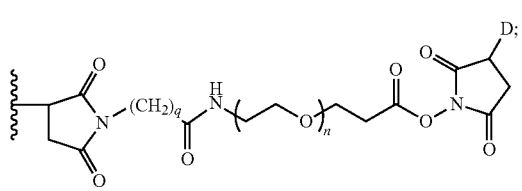 (A3)
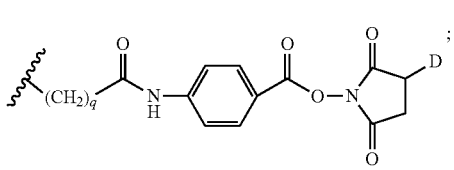 (A4)
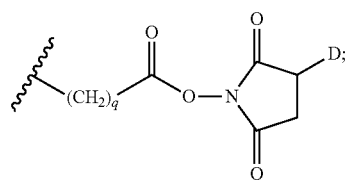 (A5)
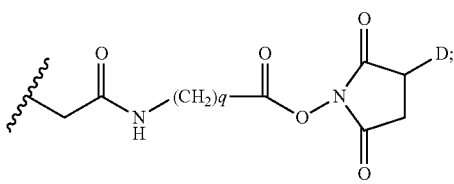 (A6)
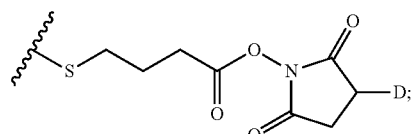 (A7)
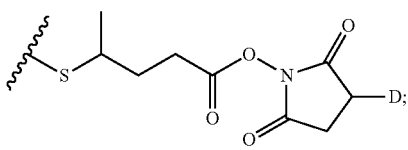 (A8)
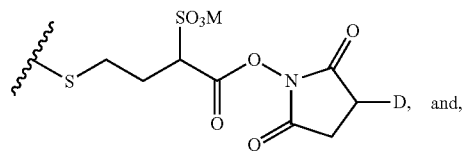 (A9)
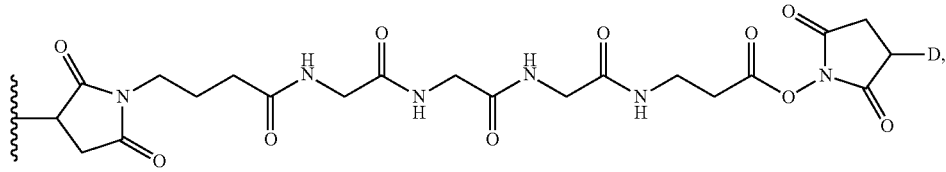 (A10)
wherein:
q is an integer from 1 to 5;
n is an integer from 2 to 6;
D is —H or —SO$_3$M;
M is —H or a cation, such as Na$^+$ or K$^+$.
In certain embodiments, $Z^s$ is represented by any one of the following formulas:
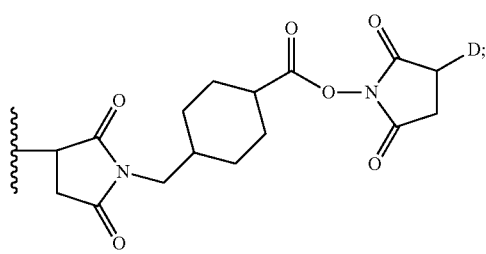 (a1)
-continued
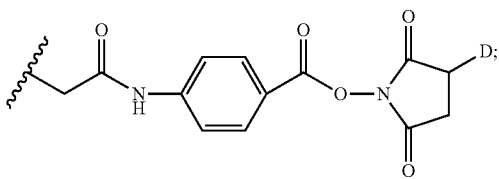 (a4')
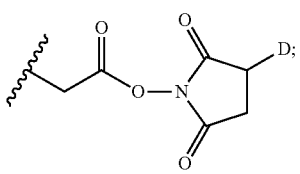 (a5')

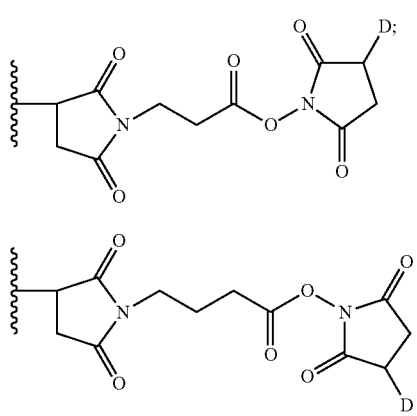

In certain embodiments, W' is —N(R$^e$)—.

In certain embodiments, R$^e$ is —(CH$_2$—CH$_2$—O)$_n$—R$^k$, wherein R$^k$ is a —H, a linear, branched cyclic alkyl having 1 to 6 carbon atoms.

In certain embodiments, R$^k$ is —H or -Me, n is 4, and q is 2.

In certain embodiments, R$^x$ is a linear or branched alkyl having 1 to 6 carbon atoms.

In certain embodiments, R$^x$ may be —(CH$_2$)$_p$—(CR$^f$R$^g$)—, wherein R$^f$ and R$^g$ are each independently selected from H or a linear or branched alkyl having 1 to 4 carbon atoms; and p is 0, 1, 2 or 3.

In certain embodiments, R$^f$ and R$^g$ are the same or different, and are selected from —H and -Me; and p is 1.

In a tenth specific embodiment, the compounds of formula (VIII), (IX), (X) and (XI) described in the ninth specific embodiment, the variables are as described below:
the double line == between N and C represents a single bond or a double bond, provided that when it is a double bond X is absent and Y is —H, and when it is a single bond, X is —H; Y is —H, —OH or —SO$_3$M;
M is —H or a pharmaceutically acceptable cation (e.g., Na$^+$);
X' and Y' are both —H;
A and A' are both —O—;
R$_6$ is —OMe; and
R$^x$ is a linear or branched alkyl having 1 to 6 carbon atoms.

In a related embodiment, Y is —OH or —SO$_3$M.

In another embodiment, the compounds of formula (VIII), (IX), (X) and (XI) described in the ninth specific embodiment, the variables are as described below:
W' is —O—, —N(R$^e$)—, —N(R$^e$)—C(=O)—, —N(COR$^e$)—, —S— or —CH$_2$—S—;
R$^x$ is absent or selected from a linear, branched or cyclic alkyl having 1 to 6 carbon atoms;
R$^e$ is —H, a linear, branched or cyclic alkyl, alkenyl or alkynyl having 1 to 10 carbon atoms or —(CH$_2$—CH$_2$—O)$_n$—R$^k$, wherein R$^k$ is a —H, a linear, branched cyclic alkyl having 1 to 6 carbon atoms, optionally bearing a primary, secondary or tertiary amino group or a 5- or 6-membered Nitrogen containing heterocycle, such as piperidine or morpholine;
n is an integer from 1 to 24; and the remainder of the variables are as described above in the ninth specific embodiment.

Preferably, R$^k$ is —H or -Me, and n is an integer from 2 to 8. Preferably, R$^x$ is a linear or branched alkyl having 1 to 6 carbon atoms.

Preferably, R$^x$ is —(CH$_2$)$_p$—(CR$^f$R$^g$)—, wherein R$^f$ and R$^g$ are each independently selected from H or a linear or branched alkyl having 1 to 4 carbon atoms; p is 0, 1, 2 or 3.

More preferably, R$^f$ and R$^g$ are the same or different, and are selected from —H and -Me; and p is 1.

In another preferred embodiment, the linker is represented by any one of the formula selected from formulas (a1), (a4), (a5), (a10) and (a11) shown above; and the remainder of the variables are as described above in the tenth specific embodiment.

In a eleventh specific embodiment, for compounds of formula (IB), (IIB), (IIIB) and (IVB) described in the eighth specific embodiment, the variables are as described below:
the double line == between N and C represents a single bond or a double bond, provided that when it is a double bond X is absent and Y is —H, and when it is a single bond, X is —H; Y is —H, —OH or —SO$_3$M (e.g., Y is —OH or —SO$_3$M);
M is —H or Na$^+$;
X' and Y' are both —H;
A and A' are both —O—;
R$_6$ is —OMe;
R$^x$ is a linear or branched alkyl having 1 to 6 carbon atoms; and the remainder of the variables is as described above in the third, fourth, or the fifth specific embodiment.

Preferably, R$^x$ is —(CH$_2$)$_p$—(CR$^f$R$^g$)—, wherein R$^f$ and R$^g$ are each independently selected from H or a linear or branched alkyl having 1 to 4 carbon atoms; p is 0, 1, 2 or 3. More preferably, R$^f$ and R$^g$ are the same or different, and are selected from —H and -Me; and p is 1.

In any of the specific embodiments above (e.g., the first to the 11$^{th}$ specific embodiments), the double line == between N and C may represent a double bond.

In any of the specific embodiments above (e.g., the first to the 11$^{th}$ specific embodiments), the double line == between N and C may represent a single bond, X is —H, the linking group with the reactive group bonded thereto, or an amine protecting group (e.g., X is —H or an amine protecting group); and Y is selected from —H, —OR, —OCOR', —SR, —NR'R", an optionally substituted 5- or 6-membered nitrogen-containing heterocycle, —SO$_3$M, —SO$_2$M and a sulfate —OSO$_3$M (e.g., Y is —OR, —OCOR', —SR, —NR'R", an optionally substituted 5- or 6-membered nitrogen-containing heterocycle, —SO$_3$M, —SO$_2$M and a sulfate —OSO$_3$M).

In certain embodiments, Y is selected from —H, —SO$_3$M, —OH, —OMe, —OEt or —NHOH (e.g., Y is —SO$_3$M, —OH, —OMe, —OEt or —NHOH).

In certain embodiments, Y is —H, —SO$_3$M or —OH (e.g., Y is —SO$_3$M or —OH).

In certain embodiments, M is —H, Na$^+$ or K$^+$.

In any of the specific embodiments above (e.g., the first to the 11$^{th}$ specific embodiments), W, when present, is C=O.

In any of the specific embodiments above (e.g., the first to the 11$^{th}$ specific embodiments), Z and Z', when present, are —CH$_2$.

In any of the specific embodiments above (e.g., the first to the 11$^{th}$ specific embodiments), X' is selected from the group consisting of —H, —OH, an optionally substituted linear, branched or cyclic alkyl, alkenyl or alkynyl having from 1 to 10 carbon atoms, phenyl, the linking group with the reactive group bounded thereto, and an amine-protecting group.

In certain embodiments, X' is —H, —OH, -Me or the linking group with the reactive group bounded thereto.

In certain embodiments, X' is —H.

In any of the specific embodiments above (e.g., the first to the 11$^{th}$ specific embodiments), Y' is selected from the group consisting of —H, an oxo group, a substituted or unsubstituted linear, branched or cyclic alkyl, alkenyl or alkynyl having from 1 to 10 carbon atoms.

In certain embodiments, Y' is —H or oxo.

In certain embodiments, Y' is —H.

In any of the specific embodiments above (e.g., the first to the 11th specific embodiments), A and A' are the same or different, and are selected from O, S, NR$_5$ and oxo (C=O). A and A' may be same or different and selected from —O— and —S—. Preferably, both A and A' are —O—.

In any of the specific embodiments above (e.g., the first to the 11th specific embodiments), D and D', when present, are the same or different, and are independently selected from a polyethylene glycol unit (—OCH$_2$CH$_2$)$_n$, wherein n is an integer from 1 to 24, an amino acid, a peptide bearing 2 to 6 amino acids, or a linear, branched or cyclic alkyl, alkenyl or alkynyl having 1 to 10 carbon atoms, wherein the alkyl, alkenyl and alkynyl are optionally substituted with one or more substituents independently selected from the group consisting of halogen, —OR, —NR'COR'', —SR and —COR'. Preferably, D and D' are linear or branched alkyl bearing 1 to 4 carbon atoms.

In a twelfth embodiment, the cytotoxic compound of the present invention as described in the first, third, and ninth embodiment is represented by the following:

the double line == between N and C represents a double bond;
Y is —H;
W is C=O;
$R_1$, $R_2$, $R_1'$, $R_2'$, $R_4$ and $R_4'$ are —H;
one of $R_3$, or $R_3'$ is optionally the linking group with the reactive group bounded thereto and the other is —H;
$R_6$ is —OMe;
Z and Z' are —CH$_2$;
X' is —H;
Y' is —H; and
A and A' are —O—.

In a thirteenth embodiment, the cytotoxic compound of the present invention is:

In one embodiment, compound 29b can used in methods of the present invention described herein. In a preferred embodiment, compound 29b can be used for treating a proliferative disorder, such as cancer.

In another embodiment, compound 29b can be used for screening cell lines to identify cell lines that are sensitive to benzodiazepine compounds, such as benzodiazepine derivatives described herein.

Drug Compounds & Drug-Linker Compounds

The cytotoxic compounds described above comprise a linking group with a reactive group bonded thereto, which compounds may result from reacting a bifunctional cross-linking reagent with "linker-less" compounds to form the so-called drug-linker compounds. Alternatively, drug compounds that are otherwise identical to the drug-linker compounds, but without the linker moiety are also encompassed by the present invention.

Thus in certain embodiments, the invention provides a cytotoxic compound without linking group, but may be capable of reacting with a bifunctional crosslinking agent to form a compound of the invention, such as any one of the 1$^{st}$ to the 12$^{th}$ specific embodiments described above; or to form a cell-binding agent conjugate of the invention (such as those described below). An exemplary linkerless cytotoxic compound of the invention includes compound 29b of the 13$^{th}$ specific embodiment above. The linkerless cytotoxic compounds of the invention are represented by any one of the following formulas (I'), (II'), (III') or (IV'):

(compound 29b)

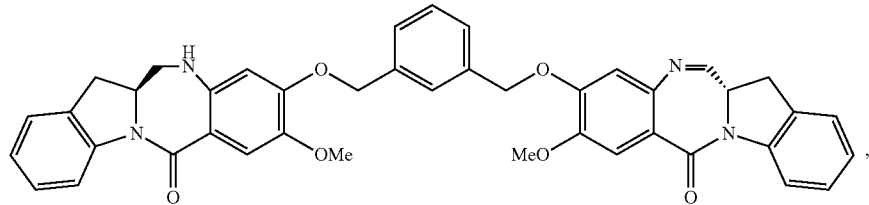

or a pharmaceutically acceptable salt thereof.

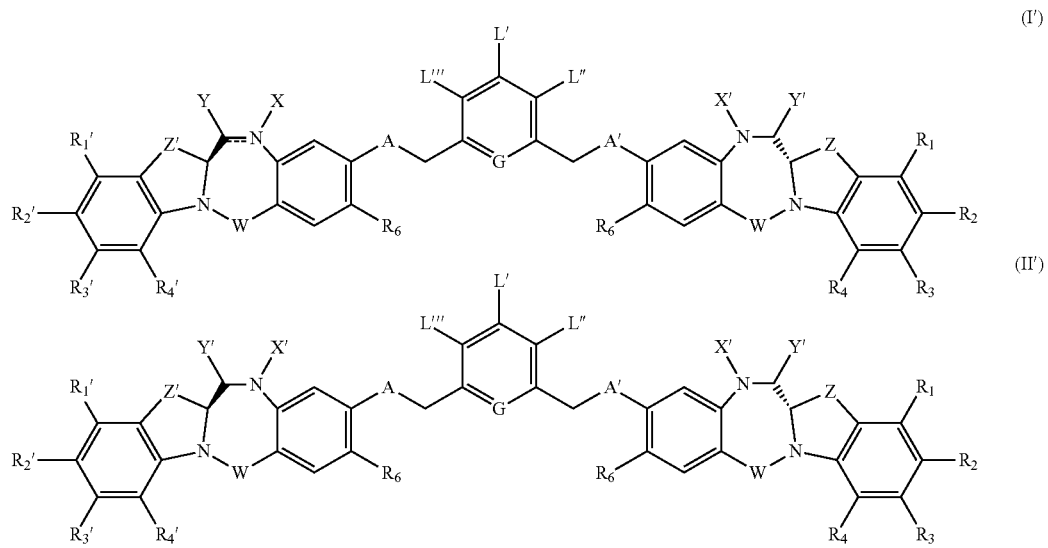

(I')

(II')

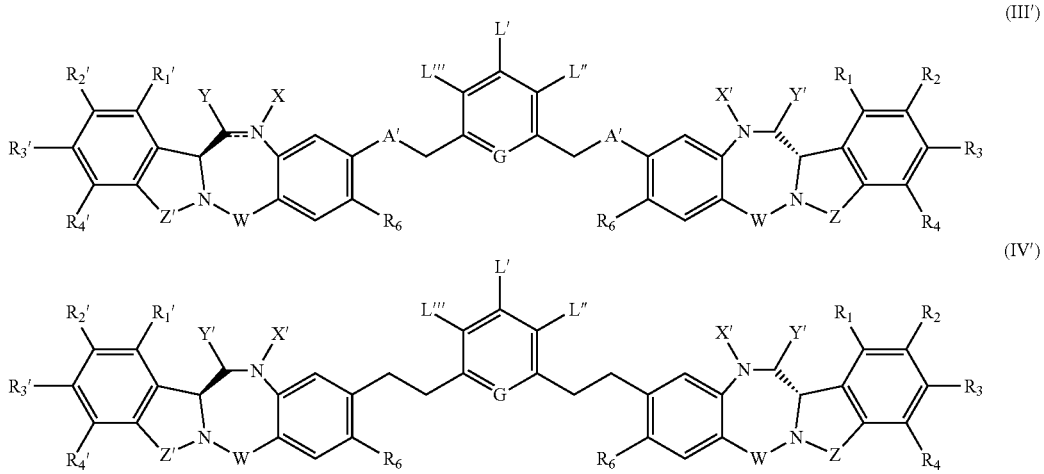

or a pharmaceutically acceptable salt thereof, wherein:
the double line ═ between N and C represents a single bond or a double bond, provided that when it is a double bond, X is absent and Y is —H, or a linear or branched alkyl having 1 to 4 carbon atoms, and when it is a single bond, X is —H, or an amine protecting moiety; preferably, the double line ═ between N and C represents a double bond;

Y is —H or a leaving group selected from —OR, —OCOR', —OCOOR', —OCONR'R", —NR'R", —NR'COR", —NR'NR'R", an optionally substituted 5- or 6-membered nitrogen-containing heterocycle (e.g., piperidine, tetrahydropyrrole, pyrazole, morpholine, etc.), a guanidinum represented by —NR'(C═NH)NR'R", an amino acid, or a peptide represented by —NRCOP', wherein P' is an amino acid or a polypeptide containing between 2 to 20 amino acid units, —SR, —SOR', —SO$_2$M, —SO$_3$M, —OSO$_3$M, halogen, cyano and an azido, wherein M is —H or a cation; such as Na$^+$ or K$^+$. Preferably, M is —H or Na$^+$. Preferably, Y is selected from —SO$_3$M, —OH, —OMe, —OEt or —NHOH. More preferably, Y is —SO$_3$M or —OH; or, Y is a sulfite (HSO$_3$, HSO$_2$ or a salt of HSO$_3^-$, SO$_3^{2-}$ HSO$_2^-$ formed with a cation), metabisulfite (H$_2$S$_2$O$_5$ or a salt of S$_2$O$_5^{2-}$ formed with a cation), mono-, di-, tri-, and tetra-thiophosphate (PO$_3$SH$_3$, PO$_2$S$_2$H$_2$, POS$_3$H$_2$, PS$_4$H$_2$ or a salt of PO$_3$S$^{3-}$, PO$_2$S$_2^{3-}$, POS$_3^{3-}$ or PS$_4^{3-}$ formed with a cation), thio phosphate ester (R$^i$O)$_2$PS(OR$^i$), R$^i$S—, R$^i$SO, R$^i$SO$_2$, R$^i$SO$_3$, thiosulfate (HS$_2$O$_3$ or a salt of S$_2$O$_3^{2-}$ formed with a cation), dithionite (HS$_2$O$_4$ or a salt of S$_2$O$_4^{2-}$ formed with a cation), phosphorodithioate (P(═S)(OR$^{k'}$)(S)(OH) or a salt thereof formed with a cation), hydroxamic acid (R$^{k'}$C(═O)NOH or a salt formed with a cation), formaldehyde sulfoxylate (HOCH$_2$SO$_2^-$ or a salt of HOCH$_2$SO$_2^-$ formed with a cation, such as HOCH$_2$SO$_2^-$Na$^+$) or a mixture thereof, wherein R' is a linear or branched alkyl having 1 to 10 carbon atoms and is substituted with at least one substituent selected from —N(R$^j$)$_2$, —CO$_2$H, —SO$_3$H, and —PO$_3$H; R$^j$ can be further optionally substituted with a substituent for an alkyl described herein; R$^j$ is a linear or branched alkyl having 1 to 6 carbon atoms; R$^{k'}$ is a linear, branched or cyclic alkyl, alkenyl or alkynyl having 1 to 10 carbon atoms, aryl, heterocyclyl or heteroaryl; preferably, Y is an adduct of a bisulfite, a hydrosulfite, or a metabisulfite, or salts thereof (such as sodium salt);

R, for each occurrence, is independently selected from the group consisting of —H, an optionally substituted linear, branched or cyclic alkyl, alkenyl or alkynyl having from 1 to 10 carbon atoms, a polyethylene glycol unit —(CH$_2$CH$_2$O)$_n$—R$^c$, an optionally substituted aryl having 6 to 18 carbon atoms, an optionally substituted 5- to 18-membered heteroaryl ring containing one or more heteroatoms independently selected from nitrogen, oxygen, and sulfur, or an optionally substituted 3- to 18-membered heterocyclic ring containing 1 to 6 heteroatoms independently selected from O, S, N and P;

R' and R" are the same or different, and are independently selected from —H, —OH, —OR, —NHR, —NR$_2$, —COR, an optionally substituted linear, branched or cyclic alkyl, alkenyl or alkynyl having from 1 to 10 carbon atoms, a polyethylene glycol unit —(CH$_2$CH$_2$O)$_n$—R$^c$, and an optionally substituted 3- to 18-membered heterocyclic ring having 1 to 6 heteroatoms independently selected from O, S, N and P;

R$^c$ is —H or a substituted or unsubstituted linear or branched alkyl having 1 to 4 carbon atoms;

n is an integer from 1 to 24;

W is selected from C═O, C═S, CH$_2$, BH, SO, and SO$_2$;

X' is selected from the group consisting of —H, —OH, an amine-protecting group, an optionally substituted linear, branched or cyclic alkyl, alkenyl or alkynyl having from 1 to 10 carbon atoms, a polyethylene glycol unit —(CH$_2$CH$_2$O)$_n$—R$^c$, an optionally substituted aryl having 6 to 18 carbon atoms (e.g., phenyl), an optionally substituted 5- to 18-membered heteroaryl ring containing one or more heteroatoms independently selected from nitrogen, oxygen, and sulfur, and an optionally substituted 3- to 18-membered heterocyclic ring containing 1 to 6 heteroatoms independently selected from O, S, N and P. Preferably, X' is —H, —OH, or -Me. More preferably, X' is —H;

Y' is selected from the group consisting of —H, an oxo group, an optionally substituted linear, branched or cyclic alkyl, alkenyl or alkynyl having from 1 to 10 carbon atoms, an optionally substituted 6- to 18-membered aryl, an optionally substituted 5- to 18-membered heteroaryl ring containing one or more heteroatoms independently selected from nitrogen, oxygen, and sulfur, an optionally substituted 3- to 18-membered heterocyclic ring having 1 to 6 heteroatoms. Preferably, Y' is selected from —H or oxo. More preferably, Y' is —H;

$R_1$, $R_2$, $R_3$, $R_4$, $R_1'$, $R_2'$, $R_3'$ and $R_4'$ are each independently selected from the group consisting of —H, an optionally substituted linear, branched or cyclic alkyl, alkenyl or alkynyl having from 1 to 10 carbon atoms, a polyethylene glycol unit —$(OCH_2CH_2)_n$—$R^e$, halogen, guanidinium [—NH(C=NH)NH$_2$], —OR, —NR'R", —NO$_2$, —NCO, —NR'COR", —SR, a sulfoxide represented by —SOR', a sulfone represented by —SO$_2$R', a sulfonate —SO$_3^-$M$^+$, a sulfate —OSO$_3^-$M$^+$, a sulfonamide represented by —SO$_2$NR'R", cyano, an azido, —COR', —OCOR', and —OCONR'R". Preferably, 1, 2, 3, or all of $R_2$, $R_3$, $R_2'$ and $R_3'$ is —H;

$R_6$ is —H, —R, —OR, —SR, —NR'R", —NO$_2$, halogen, —OR$^c$ or —SR$^c$, wherein R$^c$ is —H, a linear or branched alkyl having 1 to 4 carbon atoms. Preferably, $R_6$ is —OMe or —SMe. Even more preferably, $R_6$ is —OMe;

Z and Z' are independently selected from —$(CH_2)_{n'}$—, —$(CH_2)_{n'}$—CR$_7$R$_8$—$(CH_2)_{na'}$—, —$(CH_2)_{n'}$—NR$_9$—$(CH_2)_{na'}$—, —$(CH_2)_{n'}$—O—$(CH_2)_{na'}$— and —$(CH_2)_{n'}$—S—$(CH_2)_{na'}$—;

n' and na' are same or different, and are selected from 0, 1, 2 and 3;

$R_7$ and $R_8$ are the same or different, and are each independently selected from —H, —OH, —SH, —COOH, —NHR', a polyethylene glycol unit —$(OCH_2CH_2)_n$—, an amino acid, a peptide unit bearing 2 to 6 amino acids, an optionally substituted linear, branched or cyclic alkyl having from 1 to 10 carbon atoms;

$R_9$ is independently selected from —H, an optionally substituted linear, branched or cyclic alkyl having from 1 to 10 carbon atoms, a polyethylene glycol unit —$(OCH_2CH_2)_n$—;

A and A' are the same or different, and are independently selected from —O—, oxo (—C(=O)—), —CRR'O—, —CRR'—, —S—, —CRR'S—, —N(R$_5$)— and —CRR'N(R$_5$)—. Preferably, A and A' are the same or different, and are selected from —O— and —S—. More preferably, A and A' are —O—;

$R_5$ for each occurrence is independently —H or an optionally substituted linear or branched alkyl having 1 to 10 carbon atoms;

L', L", and L'" are the same or different, and are independently selected from —H, halogen, an optionally substituted linear, branched or cyclic alkyl, haloalkyl, alkoxy, haloalkoxy, —NO$_2$, or —CN;

G is selected from —CH— or —N—.

In certain embodiments, the double line ⚌ between N and C represents a single bond, Y is not —H.

In certain embodiments, the double line ⚌ between N and C represents a single bond or a double bond, provided that when it is a double bond X is absent and Y is —H, and when it is a single bond, X is selected from —H, or an amine protecting group (preferably X is —H); W is C=O; $R_1$, $R_2$, $R_3$, $R_4$, $R_1'$, $R_2'$, $R_3'$, and $R_4'$ are —H; Z and Z' are —CH$_2$—; A and A' are both —O—; W is —(C=O)—; G is —CH—; $R_6$ is —H, or optionally substituted C1-C10 linear, C1-C10 branched, or C3-C7 cyclic alkyl, —O-alkyl, or —O-haloalkyl, such as —OMe; X' is selected from the group consisting of —H, —OH, a substituted or unsubstituted linear, branched or cyclic alkyl, alkenyl or alkynyl having from 1 to 10 carbon atoms, phenyl, and an amine-protecting group; and Y' is selected from the group consisting of —H, an oxo group, a substituted or unsubstituted linear, branched or cyclic alkyl, alkenyl or alkynyl having from 1 to 10 carbon atoms.

Preferably, when Y is not —H, Y is selected from —OR, —OCOR', —SR, —NR'R", —SO$_3$M, —SO$_2$M, or —OSO$_3$M, wherein M is —H or a cation such as Na$^+$, K$^+$. Preferably, Y is selected from —H, —OH, —OMe, —OEt, —NHOH or —SO$_3$M (e.g., Y is —OH, —OMe, —OEt, —NHOH or —SO$_3$M). Even more preferably, Y is —H, —OH or —SO$_3$M (e.g., Y is —OH or —SO$_3$M), preferably M is —H or Na$^+$.

In certain embodiments, the double line ⚌ between N and C represents a single bond or a double bond, provided that when it is a double bond X is absent and Y is —H, and when it is a single bond, X is selected from —H, or an amine protecting group (preferably X is —H); W is C=O; $R_1$, $R_2$, $R_3$, $R_4$, $R_1'$, $R_2'$, $R_3'$, $R_4'$, X' and Y' are —H; Z and Z' are —CH$_2$—; A and A' are both —O—; W is —(C=O)—; G is —CH—; $R_6$ is —H, or optionally substituted C1-C10 linear, C1-C10 branched, or C3-C7 cyclic alkyl, —O-alkyl, or —O-haloalkyl, such as —OMe.

The bifunctional crosslinking agents can be any bifunctional linker known in the art. For example, the bifunctional linkers can be used for making the drug-linker compounds are those that form disulfide bonds, thioether bonds, acid labile bonds, photolabile bonds, peptidase labile bonds and esterase labile bonds with the cytotoxic compounds (see for example, U.S. Pat. Nos. 5,208,020; 5,475,092; 6,441,163; 6,716,821; 6,913,748; 7,276,497; 7,276,499; 7,368,565; 7,388,026 and 7,414,073, all of which are incorporated herein by reference). Preferably, the bifunctional crosslinking agents are those that form disulfide bonds, thioether and peptidase labile bonds with the cytotoxic compounds. Other bifunctional crosslinking agents that can be used in the present invention include non-cleavable linkers, such as those described in U.S. publication number US 2005/0169933, or charged linkers or hydrophilic linkers and are described in US 2009/0274713, US 2010/01293140 and WO 2009/134976, each of which is expressly incorporated herein by reference. The bifunctional crosslinking agents that can be used for making the (drug-linker) compounds of the present invention also include those described in *Thermo Scientific Pierce Crosslinking Technical Handbook*, the entire teaching of which is incorporated herein by reference.

Synthesis of Cytotoxic Compounds

Representative processes for preparing the cytotoxic dimer compounds of the present invention are shown in FIGS. 1-11. The dimers were prepared by reacting a monomer with linker compounds which possess two leaving groups such as halogen, triflate, mesylate, or tosylate such as that described for the synthesis of 1c in FIG. 1. Synthesis of representative dimers which bear a thiol or disulfide moiety to enable linkage to cell binding agents via reducible or non-reducible bonds are shown in FIGS. 1-5, 7, 8, and 10. In FIG. 1 a linker containing a short polyethylene glycol moiety and an alkyl disulfide was prepared through reductive amination of 1a. Conversion of 1b to its corresponding mesylate and coupling with the IBD (indolinobenzodiazepine) monomer unit gave dimer 1c which was reduced to the mono-imine, converted to the free thiol, and coupled with 2 to give compound 1g of the present invention. In FIG. 3, a modified form of IBD monomer was prepared and coupled to give a dimer of the present invention in which the reduced imine was converted to a linker FIG. 4 describes a dimer possessing a short polyethylene glycol moiety and an amide disulfide which was reduced to thiol 4c and converted to a reactive ester. FIG. 5 describes the synthesis of pyridyl disulfide containing linker 5e which was converted to the mono-imine thiol 5i of the present invention before being converted to a reactive ester. Synthesis of representative dimers which possess linkers that can react with cell binding agents are prepared by converting the methyl esters to the corresponding reactive esters of a leaving group such as, but not limited to, N-hydroxysuccinimide esters, N-hydroxyphthalimide esters, N-hydroxy sulfo-succinimide esters, para-nitrophenyl esters, pentafluorophenyl esters are shown in FIGS. 6, 9, and 11.

Representative processes for preparing the cytotoxic dimer compounds of the present invention suitable for one-step conjugation with a cell binding agent are shown in FIGS. 1 and 12-19. In all of these examples a dimer containing a thiol moiety is reacted with a bifunctional crosslinking reagent possessing a reactive group such as, but not limited to, a thiopyridyl, a maleimide, iodide, bromide, or tosylate on one side and a reactive substituent suitable for reaction with a cell binding agent such as, but not limited to, N-hydroxysuccinimide esters, N-hydroxyphtalimide esters, N-hydroxy sulfo-succinimide esters, paranitrophenyl esters, pentafluorophenyl esters.

Alternative synthetic processes for preparing representative cytotoxic dimer compounds of the present invention are shown in FIGS. 20-21. In FIG. 20, the synthesis of the mono reduced dimer (i.e., having one imine group) is accomplished by a two step coupling method, in which a reduced form of monomer is either initially coupled to the linker followed by coupling with the IBD monomer or the dimer is prepared using a mixture of both reduced monomer and the IBD monomer in the coupling with the reactive linker. While the di-reduced dimer is potentially a byproduct of the second synthetic pathway previously described, a more direct route is shown in FIG. 21 in which the reduced monomer is coupled to both with the linker directly.

Cell-Binding Agents

The effectiveness of the conjugates of the invention as therapeutic agents depends on the careful selection of an appropriate cell-binding agent. Cell-binding agents may be of any kind presently known, or that become known and includes peptides and non-peptides. Generally, these can be antibodies (especially monoclonal antibodies), lymphokines, hormones, growth factors, vitamins (such as folate etc., which may bind to a cell surface receptor thereof, e.g., a folate receptor), nutrient-transport molecules (such as transferrin), or any other cell-binding molecule or substance.

In certain embodiments, the cell-binding agents are proteins or polypeptides, or compounds comprising proteins or polypeptides. Preferably, the proteins or polypeptides comprise one or more Lys residues with side chain —NH$_2$ groups. Alternatively or in addition, the proteins or polypeptides comprise one or more Cys residues. The side chain —SH groups of the Cys residues may be intact, or may be in a disulfide bond that can be reduced. Preferably, reduction of the disulfide bond(s) does not significantly negatively impact the cell-binding function of the proteins or polypeptides (e.g., in the case of antibody or antigen-binding portion thereof, reduction of the disulfide bonds does not substantially increase the dissociation of light chains/heavy chains).

The Lys side chain —NH$_2$ groups and/or the Cys side chain —SH groups may be covalently linked to the linkers, which are in turn linked to the dimer compounds of the invention, thus conjugating the cell-binding agents to the dimer compounds of the invention. Each protein-based cell-binding agents may contain multiple Lys side chain —NH$_2$ groups and/or the Cys side chain —SH groups available for linking the compounds of the invention through the bifunctional crosslinkers.

More specific examples of cell-binding agents that can be used include:

polyclonal antibodies;

monoclonal antibodies;

fragments of antibodies such as Fab, Fab', and F(ab')$_2$, Fv, minibodies, diabodies, tribodies, tetrabodies (Parham, *J. Immunol.* 131:2895-2902 (1983); Spring et al. *J. Immunol.* 113:470-478 (1974); Nisonoff et al. *Arch. Biochem. Biophys.* 89:230-244 (1960), Kim et al., Mol, Cancer Ther., 7: 2486-2497 (2008), Carter, Nature Revs., 6: 343-357 (2006));

interferons (e.g. α, β, γ);

lymphokines such as IL-2, IL-3, IL-4, IL-6;

hormones such as insulin, TRH (thyrotropin releasing hormone), MSH (melanocyte-stimulating hormone), steroid hormones, such as androgens and estrogens;

growth factors and colony-stimulating factors such as EGF, TGF-alpha, FGF, VEGF, G-CSF, M-CSF and GM-CSF (Burgess, *Immunology Today* 5:155-158 (1984));

transferrin (O'Keefe et al. *J. Biol. Chem.* 260:932-937 (1985));

vitamins, such as folate;

Protein scaffolds based on a consensus sequence of fibronectin type III (FN3) repeats (also known as Centyrins; See U.S. Patent Publication 2010/0255056, incorporated herein by reference);

Designer Ankyrin Repeat Proteins (DARPins; U.S. Patent Application Nos. 20040132028; 20090082274; 20110118146; 20110224100, incorporated herein by reference), C. Zahnd et al. 2010, Cancer Res., 70; 1595-1605, incorporated herein by reference); and, Fibronectin domain scaffold proteins (Adnectins: US Patent Application Nos. 20070082365; 20080139791, incorporated herein by reference).

Monoclonal antibody techniques allow for the production of extremely specific cell-binding agents in the form of specific monoclonal antibodies. Particularly well known in the art are techniques for creating monoclonal antibodies produced by immunizing mice, rats, hamsters or any other mammal with the antigen of interest such as the intact target cell, antigens isolated from the target cell, whole virus, attenuated whole virus, and viral proteins such as viral coat proteins. Sensitized human cells can also be used. Another method of creating monoclonal antibodies is the use of phage libraries of scFv (single chain variable region), specifically human scFv (see e.g., Griffiths et al., U.S. Pat. Nos. 5,885,793 and 5,969,108; McCafferty et al., WO 92/01047; Liming et al., WO 99/06587). In addition, resurfaced antibodies disclosed in U.S. Pat. No. 5,639,641 may also be used, as may chimeric antibodies and humanized antibodies. Selection of the appropriate cell-binding agent is a matter of choice that depends upon the particular cell population that is to be targeted, but in general human monoclonal antibodies are preferred if an appropriate one is available.

For example, the monoclonal antibody MY9 is a murine IgG1 antibody that binds specifically to the CD33 Antigen {J. D. Griffin et al 8 Leukemia Res., 521 (1984)} and can be used if the target cells express CD33 as in the disease of acute myelogenous leukemia (AML). The cell-binding agent may be any compound that can bind a cell, either in a specific or non-specific manner. Generally, these can be antibodies (especially monoclonal antibodies and antibody fragments), interferons, lymphokines, hormones, growth factors, vitamins, nutrient-transport molecules (such as transferrin), or any other cell-binding molecule or substance.

Where the cell-binding agent is an antibody, it binds to an antigen that is a polypeptide and may be a transmembrane molecule (e.g. receptor) or a ligand such as a growth factor. Exemplary antigens include molecules such as renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor vmc, factor IX, tissue factor (TF), and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin, such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; protein A or D; rheumatoid factors; a neurotrophic factor such as bone-derived neurotrophic factor (BDNF), neurotrophin-3, -4, -5, or -6 (NT-3, NT4, NT-5, or NT-6), or a nerve growth factor such as NGF-β; platelet-derived growth factor (PDGF); fibroblast growth factor such as aFGF and bFGF; fibroblast growth factor receptor 2 (FGFR2), epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins, melanotransferrin, EpCAM, GD3, FLT3, PSMA, PSCA, MUC1, MUC16, STEAP, CEA, TENB2, EphA receptors, EphB receptors, folate receptor, FOLR1, mesothelin, cripto, alpha$_v$beta$_6$, integrins, VEGF, VEGFR, EGFR, transferrin receptor, IRTA1, IRTA2, IRTA3, IRTA4, IRTA5; CD proteins such as CD2, CD3, CD4, CD5, CD6, CD8, CD11, CD14, CD19, CD20, CD21, CD22, CD25, CD26, CD28, CD30, CD33, CD36, CD37, CD38, CD40, CD44, CD52, CD55, CD56, CD59, CD70, CD79, CD80. CD81, CD103, CD105, CD134, CD137, CD138, CD152 or an antibody which binds to one or more tumor-associated antigens or cell-surface receptors disclosed in US Publication No. 20080171040 or US Publication No. 20080305044 and are incorporated in their entirety by reference; erythropoietin; osteoinductive factors; immunotoxins; a bone morphogenetic protein (BMP); an interferon, such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the HIV envelope; transport proteins; homing receptors; addressins; regulatory proteins; integrins, such as CD11a, CD11b, CD11c, CD18, an ICAM, VLA-4 and VCAM; a tumor associated antigen such as HER2, HER3 or HER4 receptor; endoglin, c-Met, c-kit, 1GF1R, PSGR, NGEP, PSMA, PSCA, LGR5, B7H4, and fragments of any of the above-listed polypeptides.

Additionally, GM-CSF, which binds to myeloid cells can be used as a cell-binding agent to diseased cells from acute myelogenous leukemia. IL-2 which binds to activated T-cells can be used for prevention of transplant graft rejection, for therapy and prevention of graft-versus-host disease, and for treatment of acute T-cell leukemia. MSH, which binds to melanocytes, can be used for the treatment of melanoma, as can antibodies directed towards melanomas. Folic acid can be used to target the folate receptor expressed on ovarian and other tumors. Epidermal growth factor can be used to target squamous cancers such as lung and head and neck. Somatostatin can be used to target neuroblastomas and other tumor types.

Cancers of the breast and testes can be successfully targeted with estrogen (or estrogen analogues) or androgen (or androgen analogues) respectively as cell-binding agents.

In one embodiment, the cell-binding agent is humanized monoclonal antibodies. In another embodiment, the cell-binding agent is huMy9-6, or other related antibodies, which are described in U.S. Pat. Nos. 7,342,110 and 7,557,189 (incorporated herein by reference). In another embodiment, the cell-binding agent is an anti-folate receptor antibody described in U.S. Provisional Application Nos. 61/307,797, 61/346,595, 61/413,172 and U.S. application Ser. No. 13/033,723 (published as US 2012-0009181 A1). The teachings of all these applications are incorporated herein by reference in its entirety.

In certain embodiments, the cell-binding agent may be a monoclonal antibody or antigen-binding portions thereof sharing sequences critical for antigen-binding with an antibody disclosed herein, such as huMy9-6 or its related antibodies described in U.S. Pat. Nos. 7,342,110 and 7,557, 189 (incorporated herein by reference). These derivative antibodies may have substantially the same or identical (1) light chain and/or heavy chain CDR3 regions; (2) light chain and/or heavy chain CDR1, CDR2, and CDR3 regions; or (3) light chain and/or heavy chain regions, compared to an antibody described herein. Sequences within these regions may contain conservative amino acid substitutions, including substitutions within the CDR regions. Preferably, there is no more than 1, 2, 3, 4, or 5 conservative substitutions. In certain embodiments, the derivative antibodies have a light chain region and/or a heavy chain region that is at least about 90%, 95%, 99% or 100% identical to an antibody described herein. These derivative antibodies may have substantially the same binding specificity and/or affinity to the target antigen compared to an antibody described herein. Preferably, the $K_d$ and/or $k_{off}$ values of the derivative antibodies are within 10-fold (either higher or lower), 5-fold (either higher or lower), 3-fold (either higher or lower), or 2-fold (either higher or lower) of an antibody described herein. These derivative antibodies may be fully human antibodies, or humanized antibodies, or chimeric antibodies. The derivative antibodies may be produced according to any art-recognized methods.

In one embodiment, the anti-folate receptor antibody is a humanized antibody or antigen binding fragment thereof that specifically binds a human folate receptor 1, wherein the antibody comprises: (a) a heavy chain CDR1 comprising GYFMN (SEQ ID NO: 1); a heavy chain CDR2 comprising RIHPYDGDTFYNQXaa$_1$FXaa$_2$Xaa$_3$ (SEQ ID NO: 2); and a heavy chain CDR3 comprising YDGSRAMDY (SEQ ID NO: 3); and (b) a light chain CDR1 comprising KASQS-VSFAGTSLMH (SEQ ID NO: 4); a light chain CDR2 comprising RASNLEA (SEQ ID NO: 5); and a light chain CDR3 comprising QQSREYPYT (SEQ ID NO: 6); wherein Xaa$_1$ is selected from K, Q, H, and R; Xaa$_2$ is selected from Q, H, N, and R; and Xaa$_3$ is selected from G, E, T, S, A, and V. Preferably, the heavy chain CDR2 sequence comprises RIHPYDGDTFYNQKFQG (SEQ ID NO: 7).

In another embodiment, the anti-folate receptor antibody is a humanized antibody or antigen binding fragment thereof that specifically binds the human folate receptor 1 comprising the heavy chain having the amino acid sequence of QVQLVQSGAEVVKPGASVKISCKASGYTFTGYFMNWVKQSPGQSLEWIGRIHPY DGDTFYNQKFQGKATLTVDKSSNTAHMELLSLTSEDFAVYYCTRYDGSRAMDY WGQGTTVTVSSASTKGPSVFPLAPSSKSTSGGTAALGCLVKDYFPEPVTVSWNS GALTSGVHTFPAVLQSSGLYSLSSVVTVPSSSLGTQTYICNVNHKPSNTKVDKKV EPKSCDKTHTCPPCPAPELLGGPSVFLFPPKPKDTLMISRTPEVTCVVVDVSHEDP EVKFNWYVDGVEVHNAKTKPREEQYNSTYRVVSVLTVLHQDWLNGKEYKCKV SNKALPAPIEKTISKAKGQPREPQVYTLPPSRDELTKNQVSLTCLVKGFYPSDIAV EWESNGQPENNYKTTPPVLDSDGSFFLYSKLTVDKSRWQQGNVFSCSVMHEAL HNHYTQKSLSLSPGK (SEQ ID NO: 8).

In another embodiment, the anti-folate antibody is a humanized antibody or antigen binding fragment thereof encoded by the plasmid DNA deposited with the ATCC on Apr. 7, 2010 and having ATCC deposit nos. PTA-10772 and PTA-10773 or 10774.

In another embodiment, the anti-folate receptor antibody is a humanized antibody or antigen binding fragment thereof that specifically binds the human folate receptor 1 comprising the light chain having the amino acid sequence of DIVLTQSPLSLAVSLGQPAIISCKASQSVSFAGTSLMHWYHQKPGQQPRLLIYRAS NLEAGVPDRFSGSGSKTDFTLNISPVEAEDAATYYCQQSREYPYTFGGGTKLEIK RTVAAPSVFIFPPSDEQLKSGTASVVCLLNNFYPREAKVQWKVDNALQSGNSQE SVTEQDSKDSTYSLSSTLTLSKADYEKHKVYACEVTHQGLSSPVTKSFNRGEC (SEQ ID NO: 9); or DIVLTQSPLSLAVSLGQPAIISCKASQSVSFAGTSLMHWYHQKPGQQPRLLIYRAS NLEAGVPDRFSGSGSKTDFTLTISPVEAEDAATYYCQQSREYPYTFGGGTKLEIK RTVAAPSVFIFPPSDEQLKSGTASVVCLLNNFYPREAKVQWKVDNALQSGNSQE SVTEQDSKDSTYSLSSTLTLSKADYEKHKVYACEVTHQGLSSPVTKSFNRGEC (SEQ ID NO: 10).

In another embodiment the anti-folate receptor antibody is a humanized antibody or antigen binding fragment thereof that specifically binds the human folate receptor 1 comprising the heavy chain having the amino acid sequence of SEQ ID NO: 8, and the light chain having the amino acid sequence of SEQ ID NO: 9 or SEQ ID NO: 10. Preferably, the antibody comprises the heavy chain having the amino acid sequence of SEQ ID NO: 8 and the light chain having the amino acid sequence of SEQ ID NO: 10 (hu FOLR1).

In another embodiment, the anti-folate receptor antibody is a humanized antibody or antigen binding fragment thereof encoded by the plasmid DNA deposited with the ATCC on Apr. 7, 2010 and having ATCC deposit nos. PTA-10772 and PTA-10773 or 10774.

In another embodiment, the anti-folate receptor antibody is a humanized antibody or antigen binding fragment thereof comprising a heavy chain variable domain at least about 90%, 95%, 99% or 100% identical to QVQLVQSGAEVVKPGASVKISCKASGYTFTGYFMNWVKQSPG QSLEWIGRIHPY DGDTFYNQKFQGKATLTVDKSSNTAHMELLSLTSEDFAVYYCTRYDGSRAMDY WGQGTTVTVSS (SEQ ID NO: 11), and a light chain variable domain at least about 90%, 95%, 99% or 100% identical to DIVLTQSPLSLAVSLGQPAIISCKASQSVSFAGTSLMHWYHQKPGQQPRLLIYRAS NLEAGVPDRFSGSGSKTDFTLNISPVEAEDAATYYCQQSREYPYTFGGGTKLEIK R (SEQ ID NO: 12); or DIVLTQSPLSLAVSLGQPAIISCKASQSVSFAGTSLMHWYHQKPGQQPRLLIYR ASNLEAGVPDRFSGSGSKTDFTLTISPVEAEDAATYYCQQSREYPYTFGGGTKLEI KR (SEQ ID NO: 13).

Cell-Binding Agent-Drug Conjugates

The present invention also provides cell-binding agent-drug conjugates comprising a cell-binding agent linked to one or more cytotoxic compounds of the present invention via a variety of linkers, including, but not limited to, disulfide linkers, thioether linkers, amide bonded linkers, peptidase-labile linkers, acid-labile linkers, esterase-labile linkers.

Representative conjugates of the invention are antibody/cytotoxic compound, antibody fragment/cytotoxic compound, epidermal growth factor (EGF)/cytotoxic compound, melanocyte stimulating hormone (MSH)/cytotoxic compound, thyroid stimulating hormone (TSH)/cytotoxic compound, somatostatin/cytotoxic compound, folate/cytotoxic compound, estrogen/cytotoxic compound, estrogen analogue/cytotoxic compound, androgen/cytotoxic compound, and androgen analogue/cytotoxic compound. A representative folate/cytotoxic compound conjugate is depicted below, with the optional —$SO_3^-Na^+$ adduct on the imine bond of one of the two drug monomers. A representative synthesis scheme for this conjugate is shown in FIG. 54.

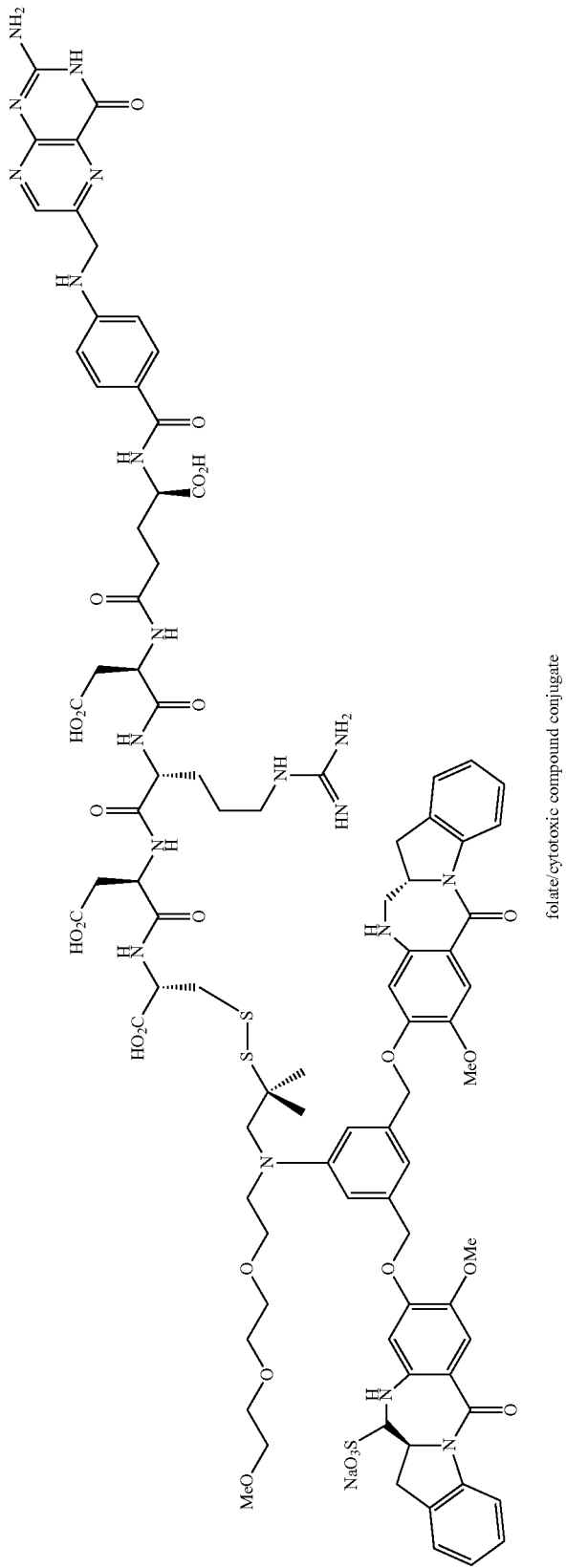
folate/cytotoxic compound conjugate

In a preferred embodiment, the present invention provides conjugates comprising an indolinobenzodiazepine dimer compound (e.g., compounds of formulas (I)-(IV), (IA)-(IVA) and (IB)-(IVB)) and the cell-binding agent linked through a covalent bond. The linker can be cleaved at the site of the tumor/unwanted proliferating cells to deliver the cytotoxic agent to its target in a number of ways. The linker can be cleaved, for example, by low pH (hydrazone), reductive environment (disulfide), proteolysis (amide/peptide link), or through an enzymatic reaction (esterase/glycosidase).

In a preferred aspect, representative cytotoxic conjugates of the invention are antibody/indolinobenzodiazepine dimer compound, antibody fragment/indolinobenzodiazepine dimer compound, epidermal growth factor (EGF)/indolinobenzodiazepine dimer compound, melanocyte stimulating hormone (MSH)/indolinobenzodiazepine dimer compound, thyroid stimulating hormone (TSH)/indolinobenzodiazepine dimer compound, somatostatin/indolinobenzodiazepine dimer compound, folate/indolinobenzodiazepine dimer compound, estrogen/indolinobenzodiazepine dimer compound, estrogen analogue/indolinobenzodiazepine dimer compound, prostate specific membrane antigen (PSMA) inhibitor/indolinobenzodiazepine dimer compound, matriptase inhibitor/indolinobenzodiazepine dimer compound, designed ankyrin repeat proteins (DARPins)/indolinobenzodiazepine dimer compound, androgen/indolinobenzodiazepine dimer compound, and androgen analogue/indolinobenzodiazepine dimer compound.

Thus in the fourteenth specific embodiment, the invention provides a conjugate comprising: a cytotoxic compound and a cell binding agent (CBA), wherein the cytotoxic compound comprises a linking group which covalently links the cytotoxic compound to the CBA, and wherein the cytotoxic compound is represented by any one of the following formulas:

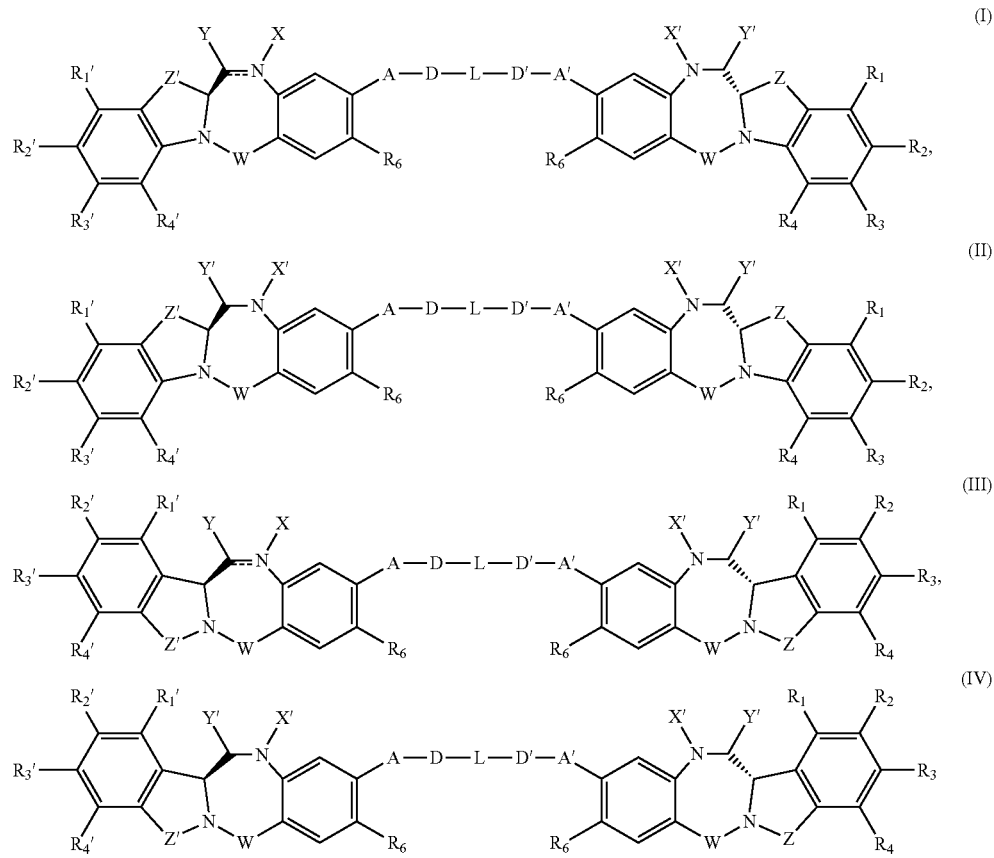

or a pharmaceutically acceptable salt thereof, wherein:

the double line $=\!=$ between N and C represents a single bond or a double bond, provided that when it is a double bond X is absent and Y is —H, or a linear or branched alkyl having 1 to 4 carbon atoms, and when it is a single bond, X is —H, the linking group, or an amine protecting moiety;

Y is —H or a leaving group selected from —OR, —OCOR', —OCOOR', —OCONR'R", —NR'R", —NR'COR", —NR'NR'R", an optionally substituted 5 or 6-membered nitrogen-containing heterocycle (e.g., piperidine, tetrahydropyrrole, pyrazole, morpholine), a guanidinum represented by —NR'(C=NH)NR'R", an amino acid, or a peptide represented by —NRCOP', wherein P' is an amino acid or a polypeptide containing between 2 to 20 amino acid units, —SR, —SOR', —SO$_2$M, —SO$_3$M, —OSO$_3$M, halogen, cyano and an azido; or, Y is a sulfite (HSO$_3$, HSO$_2$ or a salt of HSO$_3^-$, SO$_3^{2-}$ or HSO$_2^-$ formed with a cation), metabisulfite (H$_2$S$_2$O$_5$ or a salt of S$_2$O$_5^{2-}$ formed with a cation), mono-, di-, tri-, and tetra-thiophosphate (PO$_3$SH$_3$, PO$_2$S$_2$H$_2$, POS$_3$H$_2$, PS$_4$H$_2$ or a salt of PO$_3$S$^{3-}$, PO$_2$S$_2^{3-}$, POS$_3^{3-}$ or PS$_4^{3-}$ formed with a cation), thio phosphate ester $(R^iO)_2PS(OR^i)$, $R^iS—$, $R^iSO$, $R^iSO_2$, $R^iSO_3$, thiosulfate ($HS_2O_3$ or a salt of $S_2O_3^{2-}$ formed with a cation), dithionite ($HS_2O_4$ or a salt of $S_2O_4^{2-}$ formed with a cation), phosphorodithioate $(P(=S)(OR^{k'})(S)(OH)$ or a salt thereof formed with a cation), hydroxamic acid ($R^{k'}C(=O)NOH$ or a salt formed with a cation), formaldehyde sulfoxylate ($HOCH_2SO_2^-$ or a salt of $HOCH_2SO_2^-$ formed with a cation, such as $HOCH_2SO_2^-Na^+$) or a mixture thereof, wherein $R^i$ is a linear or branched alkyl having 1 to 10 carbon atoms and is substituted with at least one substituent selected from $—N(R^j)_2$, $—CO_2H$, $—SO_3H$, and $—PO_3H$; $R^i$ can be further optionally substituted with a substituent for an alkyl described herein; $R^j$ is a linear or branched alkyl having 1 to 6 carbon atoms; $R^{k'}$ is a linear, branched or cyclic alkyl, alkenyl or alkynyl having 1 to 10 carbon atoms, aryl, heterocyclyl or heteroaryl; preferably, Y is an adduct of a bisulfite, a hydrosulfite, or a metabisulfite, or salts thereof (such as sodium salt);

M is —H or a cation;

R, for each occurrence, is independently selected from the group consisting of —H, an optionally substituted linear, branched or cyclic alkyl, alkenyl or alkynyl having from 1 to 10 carbon atoms, a polyethylene glycol unit $—(CH_2CH_2O)_n—R^c$, an optionally substituted aryl having 6 to 18 carbon atoms, an optionally substituted 5- to 18-membered heteroaryl ring containing one or more heteroatoms independently selected from nitrogen, oxygen, and sulfur, or an optionally substituted 3- to 18-membered heterocyclic ring containing 1 to 6 heteroatoms independently selected from O, S, N and P;

R' and R" are each independently selected from —H, —OH, —OR, —NHR, —NR$_2$, —COR, an optionally substituted linear, branched or cyclic alkyl, alkenyl or alkynyl having from 1 to 10 carbon atoms, a polyethylene glycol unit $—(CH_2CH_2O)_n—R^c$, and an optionally substituted 3- to 18-membered heterocyclic ring having 1 to 6 heteroatoms independently selected from O, S, N and P;

$R^c$ is —H or a substituted or unsubstituted linear or branched alkyl having 1 to 4 carbon atoms, or the linking group;

n is an integer from 1 to 24;

W is selected from C=O, C=S, $CH_2$, BH, SO and $SO_2$;

X' is selected from —H, an amine-protecting group, the linking group, an optionally substituted linear, branched or cyclic alkyl, alkenyl or alkynyl having from 1 to 10 carbon atoms, a polyethylene glycol unit $—(CH_2CH_2O)_n—R^c$, an optionally substituted aryl having 6 to 18 carbon atoms, an optionally substituted 5- to 18-membered heteroaryl ring containing one or more heteroatoms independently selected from nitrogen, oxygen, and sulfur, and an optionally substituted 3- to 18-membered heterocyclic ring containing 1 to 6 heteroatoms independently selected from O, S, N and P;

Y' is selected from —H, an oxo group, the linking group, an optionally substituted linear, branched or cyclic alkyl, alkenyl or alkynyl having from 1 to 10 carbon atoms, an optionally substituted 6- to 18-membered aryl, an optionally substituted 5- to 18-membered heteroaryl ring containing one or more heteroatoms independently selected from nitrogen, oxygen, and sulfur, an optionally substituted 3- to 18-membered heterocyclic ring having 1 to 6 heteroatoms;

$R_1$, $R_2$, $R_3$, $R_4$, $R_1'$, $R_2'$, $R_3'$ and $R_4'$ are each independently selected from the group consisting of —H, an optionally substituted linear, branched or cyclic alkyl, alkenyl or alkynyl having from 1 to 10 carbon atoms, a polyethylene glycol unit $—(OCH_2CH_2)_n—R^c$, halogen, guanidinium [$—NH(C=NH)NH_2$], —OR, —NR'R", —NO$_2$, —NCO, —NR'COR", —SR, a sulfoxide represented by —SOR', a sulfone represented by —SO$_2$R', a sulfonate —SO$_3^-$M$^+$, a sulfate —OSO$_3^-$M$^+$, a sulfonamide represented by —SO$_2$NR'R", cyano, an azido, —COR', —OCOR', —OCONR'R" and the linking group;

$R_6$ is —H, —R, —OR, —SR, —NR'R", —NO$_2$, halogen or the linking group;

Z and Z' are independently selected from $—(CH_2)_{n'}—$, $—(CH_2)_{n'}—CR_7R_8—(CH_2)_{na'}—$, $—(CH_2)_{n'}—$, $—NR_9—(CH_2)_{na'}—$, $—(CH_2)_{n'}$, $—O—(CH_2)_{na'}—$ and $—(CH_2)_{n'}—S—(CH_2)_{na'}—$;

n' and na' are the same or different, and are selected from 0, 1, 2 and 3;

$R_7$ and $R_8$ are the same or different, and are each independently selected from —H, —OH, —SH, —COOH, —NHR', a polyethylene glycol unit $—(OCH_2CH_2)_n—$, an amino acid, a peptide unit bearing 2 to 6 amino acids, an optionally substituted linear, branched or cyclic alkyl having from 1 to 10 carbon atoms;

$R_9$ is independently selected from —H, an optionally substituted linear, branched or cyclic alkyl having from 1 to 10 carbon atoms, a polyethylene glycol unit $—(OCH_2CH_2)_n—$;

A and A' are the same or different, and are independently selected from —O—, oxo (—C(=O)—), —CRR'O—, —CRR'—, —S—, —CRR'S—, —NR$_5$ and —CRR'N(R$_5$)—;

$R_5$ for each occurrence is independently —H or an optionally substituted linear or branched alkyl having 1 to 10 carbon atoms;

D and D' are the same or different, and are independently absent or selected from the group consisting of an optionally substituted linear, branched or cyclic alkyl, alkenyl or alkynyl having 1 to 10 carbon atoms, an amino acid, a peptide bearing 2 to 6 amino acids, and a polyethylene glycol unit $(—OCH_2CH_2)_n—$;

L is absent, the linking group, a polyethylene glycol unit $(—OCH_2CH_2)_n—$, a linear, branched or cyclic alkyl or alkenyl having 1 to 10 carbon atoms, a phenyl group, a 3- to 18-membered heterocyclic ring or a 5- to 18-membered heteroaryl ring having 1 to 6 heteroatoms independently selected from O, S, N and P, wherein the alkyl or alkenyl is optionally substituted with the linking group; phenyl or heterocyclic or heteroaryl ring can be optionally substituted, wherein the substituent can be the linking group.

In certain embodiments, X is not the linking group. In certain embodiments, the double line ═ between N and C represents a single bond, Y is not —H.

In certain embodiments, Y is a leaving group selected from —OR, —OCOR', —OCOOR', —OCONR'R", —NR'R", —NR'COR", —NR'NR'R", an optionally substituted 5 or 6-membered nitrogen-containing heterocycle (e.g., piperidine, tetrahydropyrrole, pyrazole, morpholine, etc.), a guanidinum represented by —NR'(C=NH)NR'R", an amino acid, or a peptide represented by —NRCOP', wherein P' is an amino acid or a polypeptide containing between 2 to 20 amino acid units, —SR, —SOR', —SO$_2$M, —SO$_3$M, —OSO$_3$M, halogen, cyano and an azido.

In certain embodiments, the compound is not any one of the following compounds:
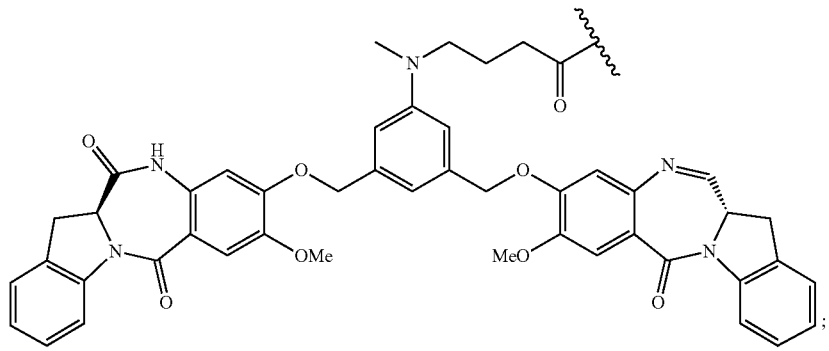
;
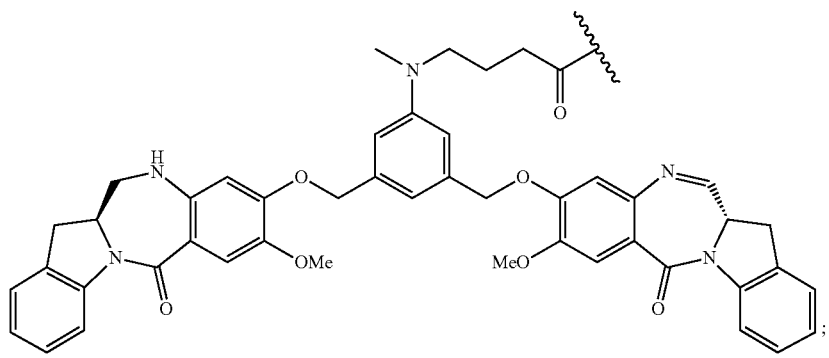
;
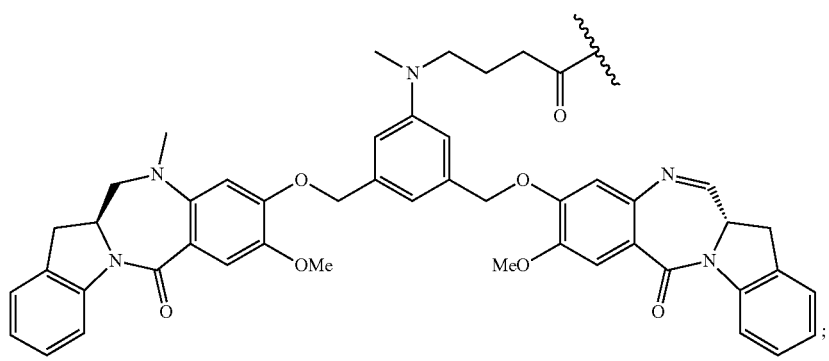
;
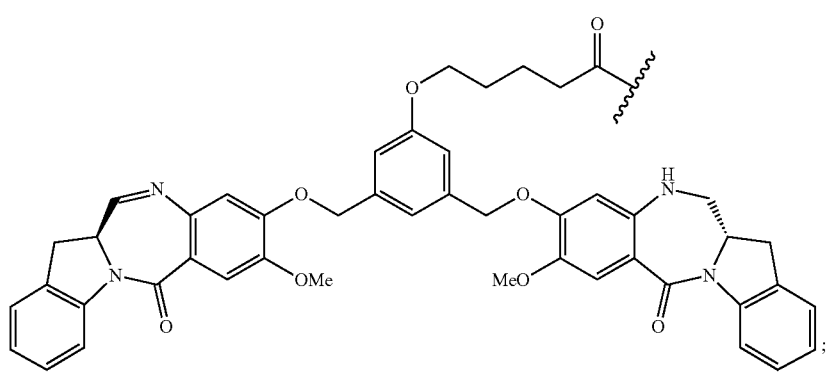
;

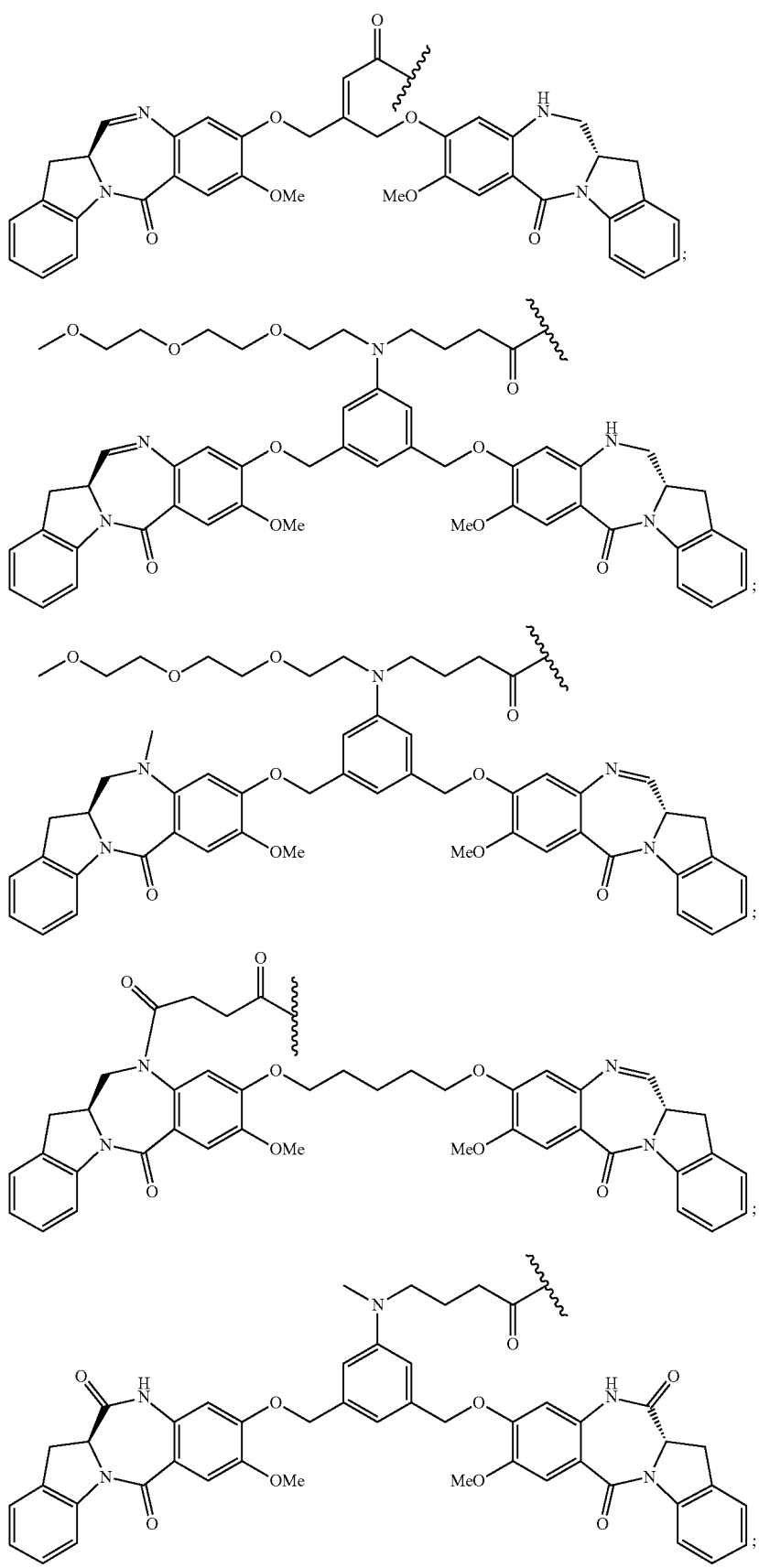

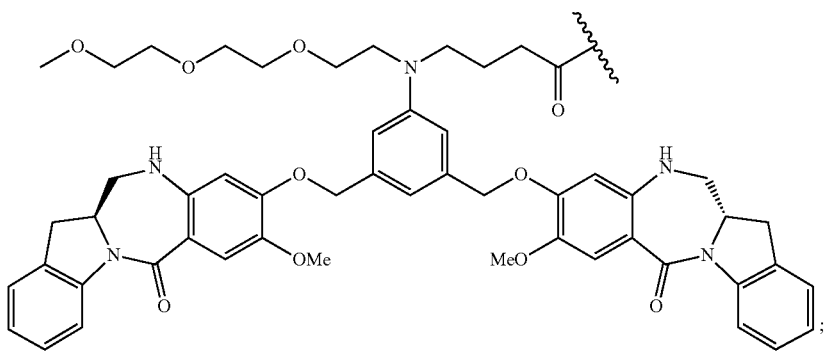
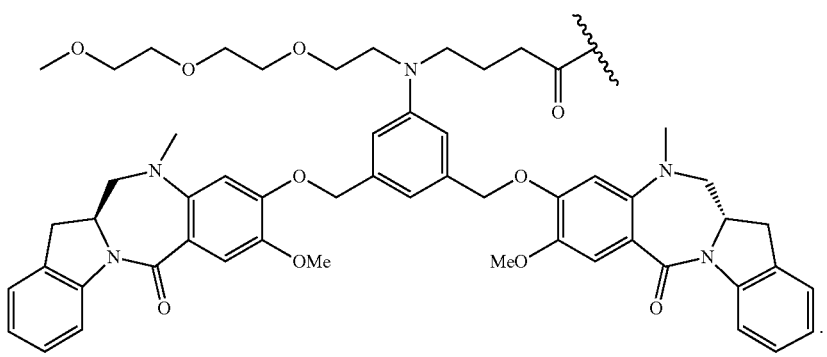
In certain embodiments, the conjugates of the invention include the following:
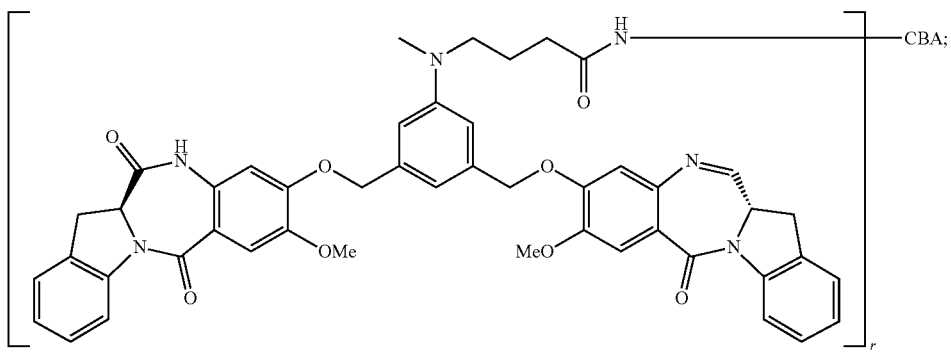
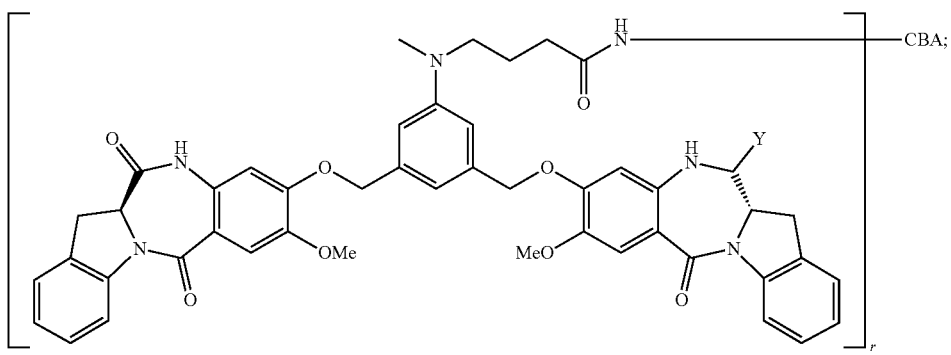

-continued
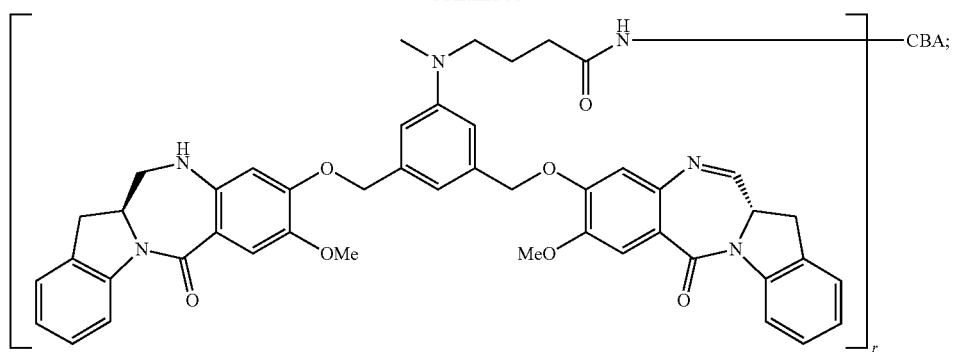
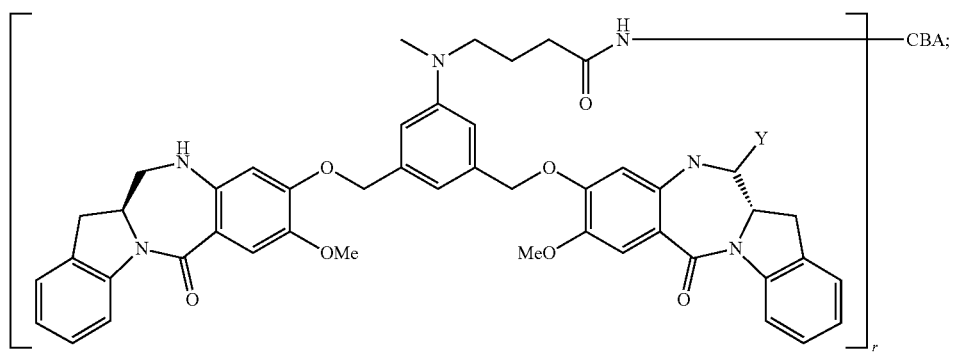
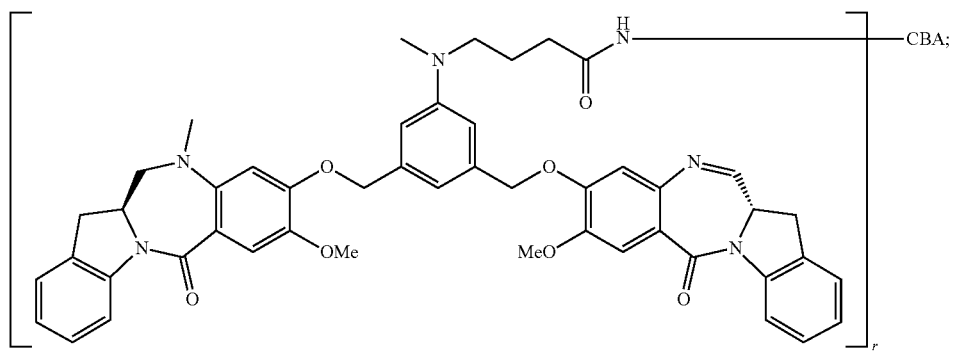
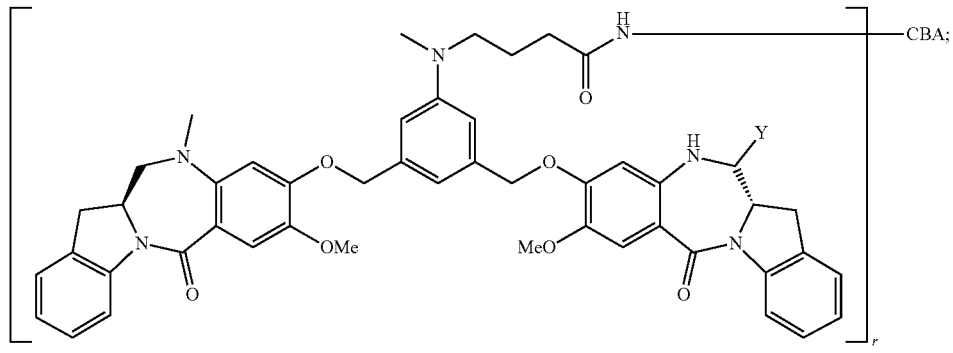

-continued
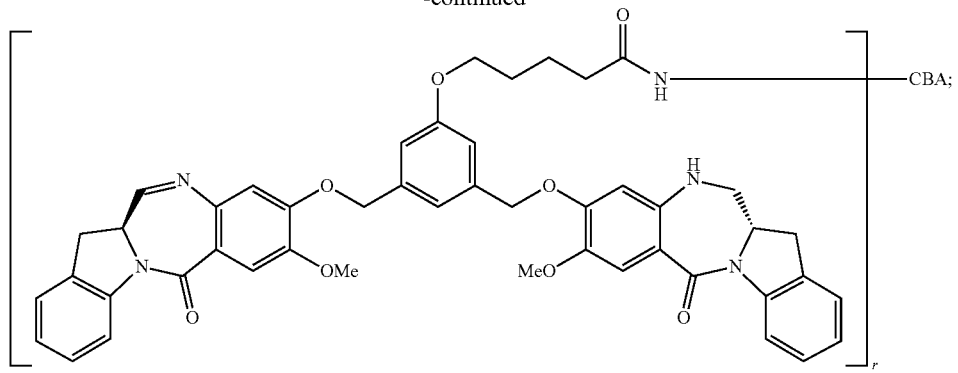
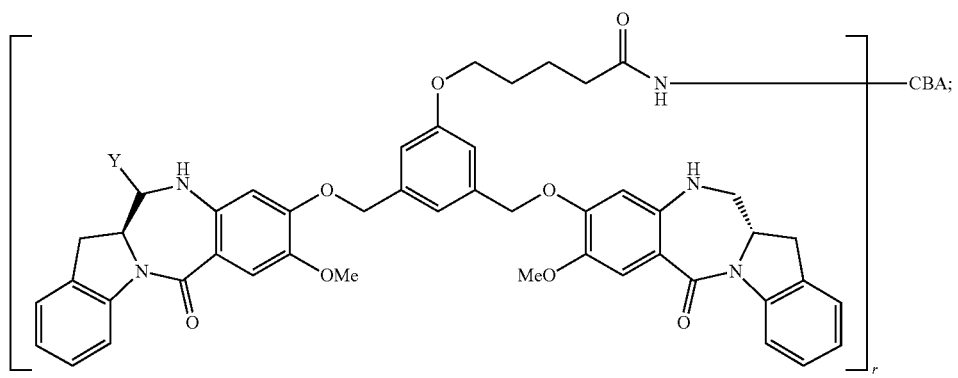
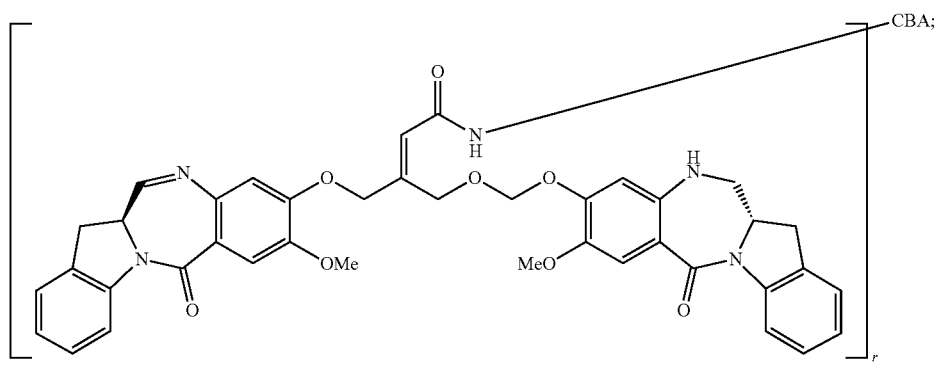
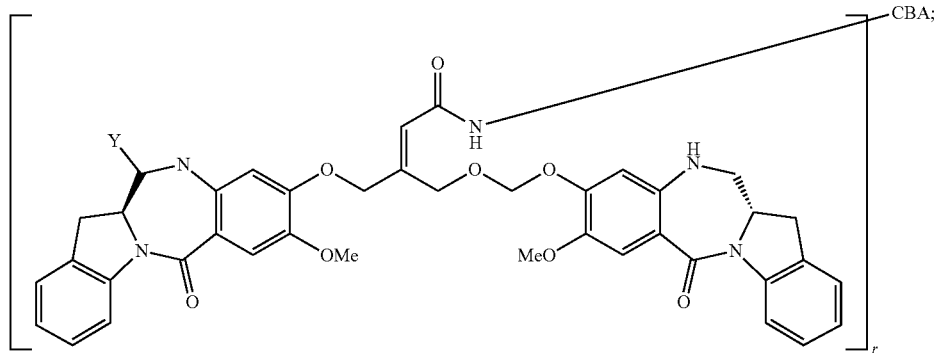

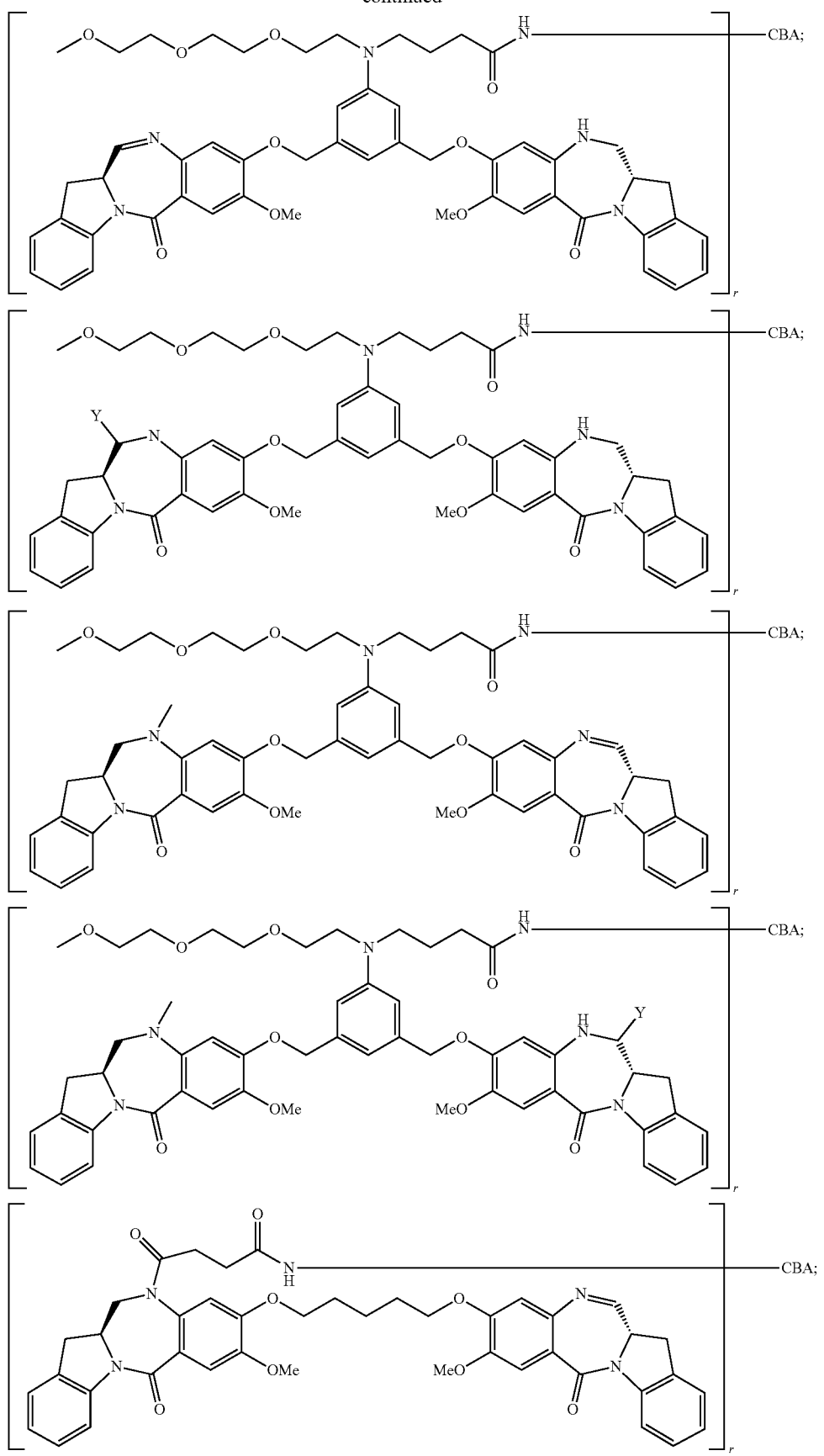

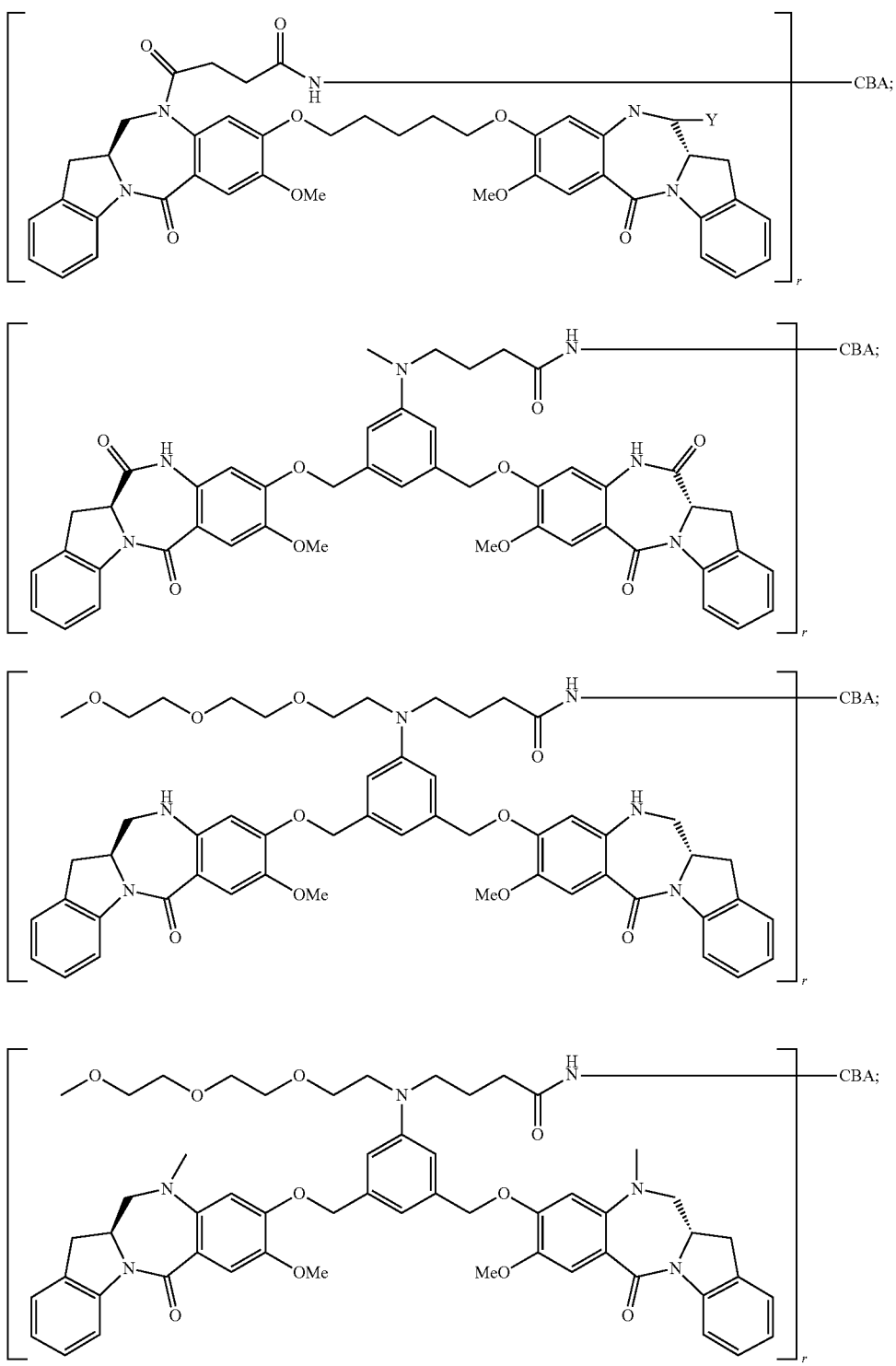

wherein:
CBA is the cell-binding agent, r is an integer from 1 to 10, Y is —H, an adduct of a bisulfite, a hydrosulfite, or a metabisulfite, or salts thereof, or —SO$_3$M, and M is —H or a pharmaceutically acceptable cation.

In certain embodiments, L is absent, or is selected from an optionally substituted phenyl group and an optionally substituted pyridyl group, wherein the phenyl and the pyridyl group bears the linking group, or L is an amine group bearing the linking group (i.e., —N(linking group)-), or L is a linear, branched or cyclic alkyl or alkenyl having from 1 to 6 carbon atoms and bearing the linking group.

In the fifteenth specific embodiment, the compound is represented by any one of the following formulas:

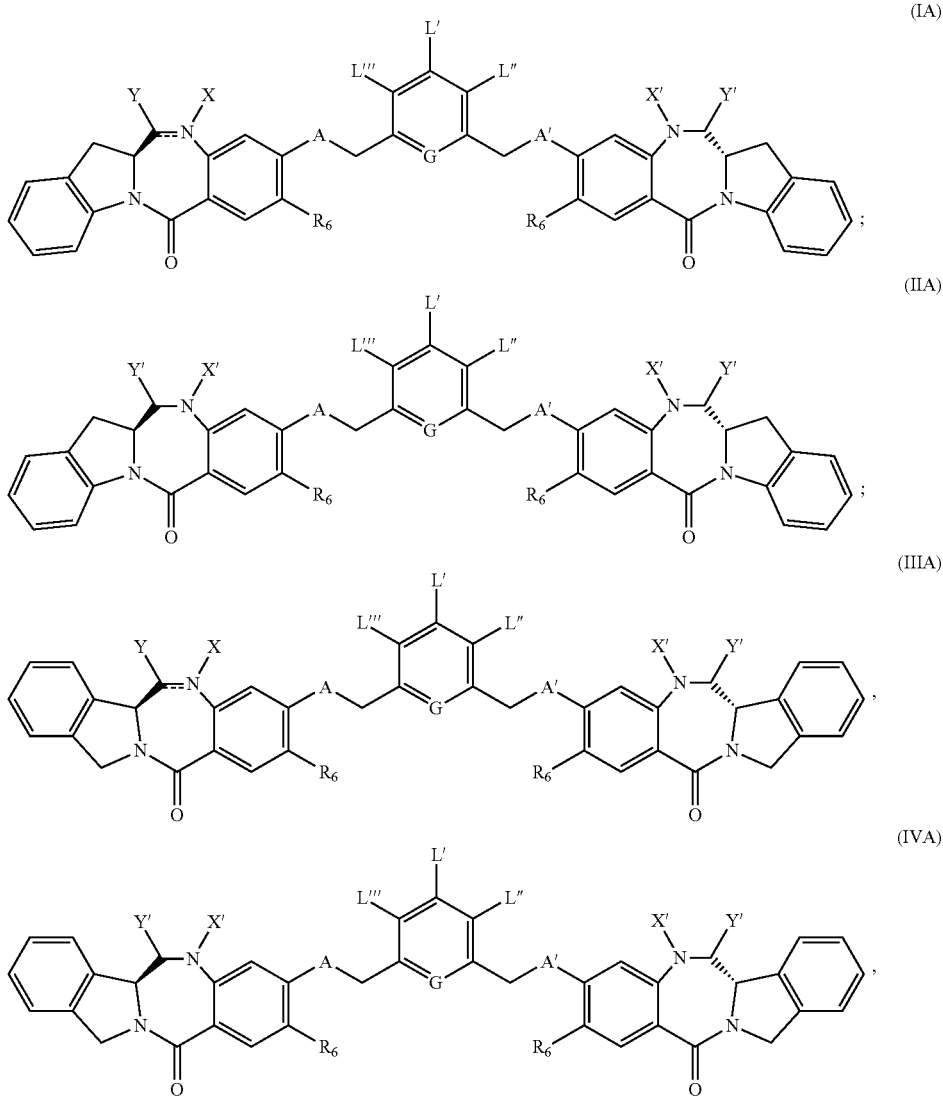

(IA)

(IIA)

(IIIA)

(IVA)

wherein:

L', L", and L'" are the same or different, and are independently selected from —H, an optionally substituted linear, branched or cyclic alkyl, alkenyl or alkynyl having from 1 to 10 carbon atoms, a polyethylene glycol unit —$(OCH_2CH_2)_n$—$R^c$, halogen, guanidinium [—NH(C=NH)$NH_2$], —OR, —NR'R", —$NO_2$, —NR'COR", —SR, a sulfoxide represented by —SOR', a sulfone represented by —$SO_2$R', a sulfonate —$SO_3$M, a sulfate —$OSO_3$M, a sulfonamide represented by —$SO_2$NR'R", cyano, an azido, —COR', —OCOR', —OCONR'R" and the linking group, provided only one of L', L", and L'" is the linking group; and G is selected from —CH— or —N—. The remaining groups are as described in the fourteenth specific embodiment above.

In certain embodiments, one of L', L", or L'" is the linking group, while the others are —H. Preferably, L' is the linking group, and L" and L'" are —H.

In certain embodiments, A and A' are both —O—, $R_6$ is —OMe, and G is —CH—.

In a sixteenth specific embodiment, L' is represented by the following formula:

wherein:

W' and V are the same or different, and are each independently absent, or selected from —$CR^eR^{e'}$—, —O—, —O—C(=O)—, —C(=O)—O—, —S—, —SO—, —$SO_2$—, —$CH_2$—S—, —$CH_2$O—, —$CH_2NR^e$—, —O—(C=O)O—, —O—(C=O)N($R^e$)—, —N($R^e$)—, —N($R^e$)—C(=O)—, —C(=O)—N($R^e$)—, —N($R^e$)—C(=O)O—, —N(C(=O)$R^e$)C(=O)—, —N(C(=O)$R^e$)—, —(O—$CH_2$—$CH_2$)$_n$—, —SS—, or —C(=O)—, or an amino acid, or a peptide having 2 to 8 amino acids;

$R^x$ and $R^y$ are the same or different, and are each independently absent or an optionally substituted linear, branched or cyclic alkyl, alkenyl, or alkynyl having 1 to 10 carbon atoms, an aryl bearing 6 to 10 carbon atoms or a 3- to 8-membered heterocyclic ring bearing 1 to 3 heteroatoms selected from O, N or S;

$R^e$ and $R^{e'}$ are the same or different, and are selected from —H, a linear, branched or cyclic alkyl, alkenyl, or alkynyl having 1 to 10 carbon atoms or —(CH$_2$—CH$_2$—O)$_n$—R$^k$, wherein R$^k$ is a —H, a linear, branched cyclic alkyl having 1 to 6 carbon atoms, optionally bearing a secondary amino (e.g., —NHR$^{101}$) or tertiary amino (—NR$^{101}$R$^{102}$) group or a 5- or 6-membered nitrogen containing heterocycle, such as piperidine or morpholine, wherein R$^{101}$ and R$^{102}$ are each independently a linear, branched, or cyclic alkyl, alkenyl or alkynyl having 1 to 10 carbon atoms; preferably, R$^{101}$ and R$^{102}$ are each independently a linear or branched alkyl having 1 to 6 carbon atoms;

n is an integer from 1 to 24; and

J is covalently linked to the CBA, and is selected from a succinimide, a acetamido, —S—, —SS—, —CH$_2$S—, —CH(Me)S—, —C(Me)$_2$S—, —NR$^{c1}$—, —CH$_2$NR$^{c1}$—, —NR$^{c1}$N—, and —C(=O)—, wherein R$^{c1}$ is —H or a substituted or unsubstituted linear or branched alkyl having 1 to 4 carbon atoms.

In certain embodiments, J is —S—, —SS—, a succinimide, or —C(=O)—.

In certain embodiments, $R^{e'}$ is —H or -Me; $R^e$ is a linear or branched alkyl having 1 to 6 carbon atoms or —(CH$_2$—CH$_2$—O)$_n$—R$^k$; n is an integer from 2 to 8; and R$^k$ is —H, -Me or —CH$_2$CH$_2$—NMe$_2$, and the remainder of the variables are as described above in the fifteenth specific embodiment.

In certain embodiments, V is an amino acid or a peptide having 2 to 8 amino acids.

In certain embodiments, V is valine-citrulline, gly-gly-gly, or ala-leu-ala-leu.

In certain embodiments,

W' is —O—, —N(R$^e$)— or —N(R$^e$)—C(=O)—;

R$^e$ is H, a linear or branched alkyl having 1 to 4 carbon atoms, or —(CH$_2$—CH$_2$—O)$_n$—R$^k$;

R$^x$ is a linear or branched alkyl having 1 to 6 carbon atoms;

V is absent, —(O—CH$_2$—CH$_2$)$_n$—, —C(=O)—NH—, —S—, —NH—C(=O)—;

R$^y$ is absent or a linear or branched alkyl having 1 to 4 carbon atoms; and

J is —S—, —SS—, or —C(=O)—, and the remaining groups are as defined in the sixteenth specific embodiment.

In certain embodiments,

W' is —O—, —N(R$^e$)— or —N(R$^e$)—C(=O)—;

R$^e$ is —H, -Me, or —(CH$_2$—CH$_2$—O)$_n$-Me;

n is an integer from 2 to 6;

R$^x$ is linear or branched alkyl bearing 1 to 6 carbon atoms;

V and R$^y$ are absent; and

J is —C(=O)—. The remaining groups are as defined in the sixteenth specific embodiment.

In a seventeenth specific embodiment, L' in the sixteenth specific embodiment is represented by the following formula:

—W'—[CR$_1$''R$_2$'']$_a$—V-[Cy]$_{0-1}$-[CR$_3$''R$_4$'']$_b$—C(=O)—, wherein:

R$_1$''', R$_2$''', and R$_3$''' are each independently —H or a linear or branched alkyl bearing 1 to 4 carbon atoms, preferably -Me;

R$_4$'' is —H, a linear or branched alkyl bearing 1 to 4 carbon atoms (preferably -Me), —SO$_3$H, or —SO$_3^-$M$^+$, wherein M$^+$ is a pharmaceutically acceptable cation;

a is an integers from 0-5 (e.g., from 0 to 2, 3, 4, or 5), and b is an integer from 0-6 (e.g., from 0 to 3, 4, 5, or 6); and, Cy is an optionally substituted 5-membered heterocyclic ring bearing an N heteroatom, preferably Cy is

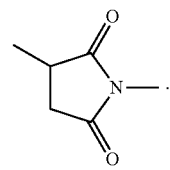

In certain embodiments, such as in the sixteenth or the seventeenth specific embodiment, W' is —N(R$^e$)—.

In certain embodiments, such as in the sixteenth or the seventeenth specific embodiment, R$^e$ is —(CH$_2$—CH$_2$—O)$_{2-6}$—R$^k$, wherein R$^k$ is a linear or branched alkyl having 1 to 6 carbon atoms.

In certain embodiments, such as in the sixteenth or the seventeenth specific embodiment, V is —S— or —SS—.

In an eighteenth specific embodiment, L' in the sixteenth or the seventeenth specific embodiment is represented by the following formula:

—NR$^e$—[CR$_1$''R$_2$'']$_a$—S—[CR$_3$''R$_4$'']$_b$—C(=O)—.

In certain embodiments, such as in the sixteenth to eighteenth specific embodiments, the conjugate is:

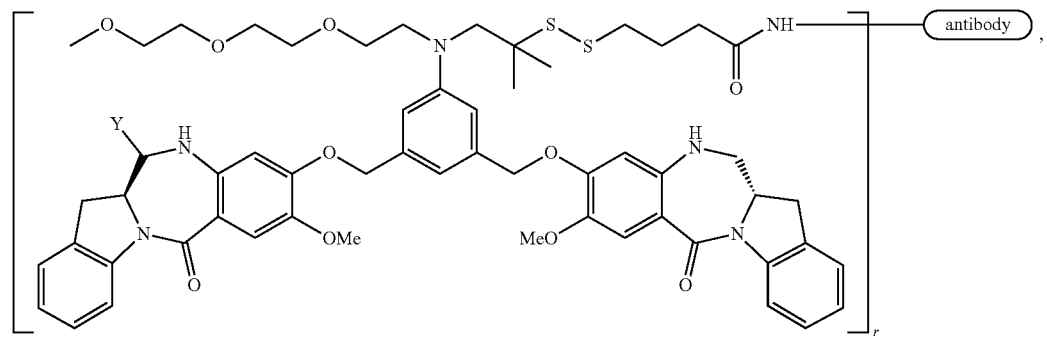

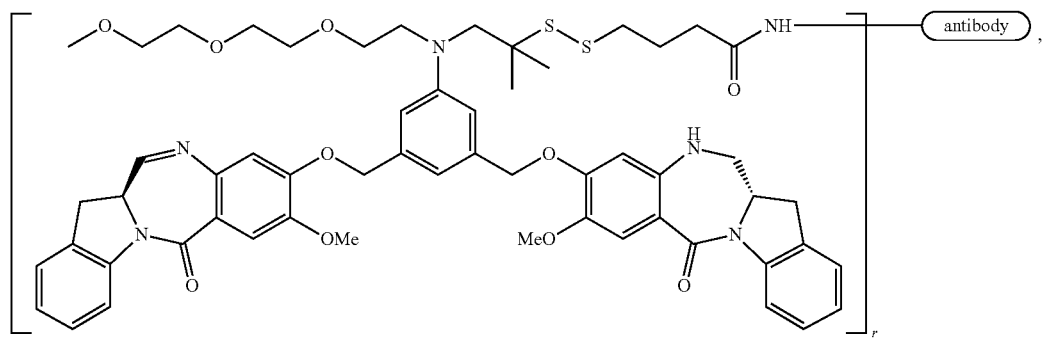

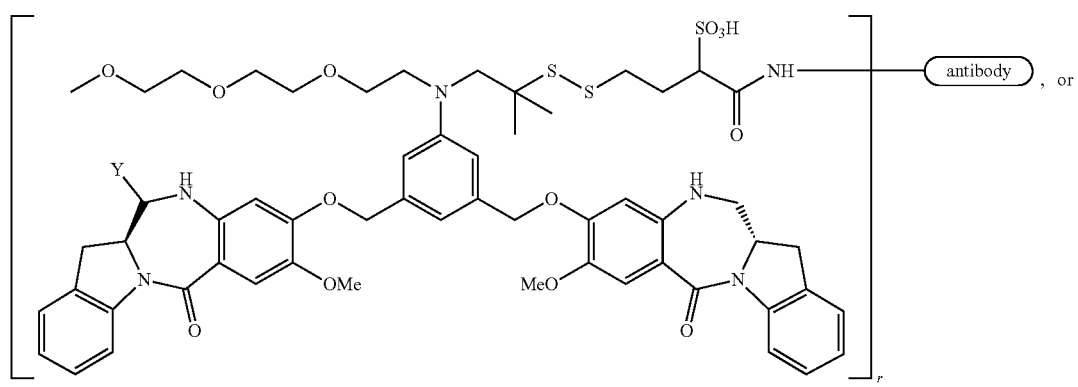

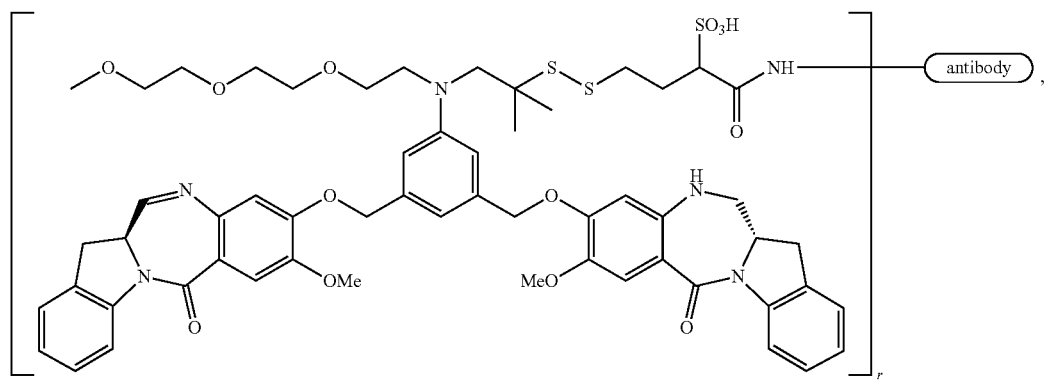

wherein r is an integer from 1 to 10, Y is —H or —SO$_3$M (e.g., Y is —SO$_3$M), and M is —H or a pharmaceutically acceptable cation.

In certain embodiments, such as in the sixteenth to eighteenth specific embodiments, the antibody is huMy9-6.

In a nineteenth specific embodiment, L' in the sixteenth or the seventeenth specific embodiment is represented by the following formula:

—NR$^e$—[CR$_1$''R$_2$'']$_a$—S-Cy-[CR$_3$''R$_4$'']$_b$—C(=O)—.

In certain embodiments, such as in the sixteenth, seventeenth, and the nineteenth specific embodiments, the conjugate is:

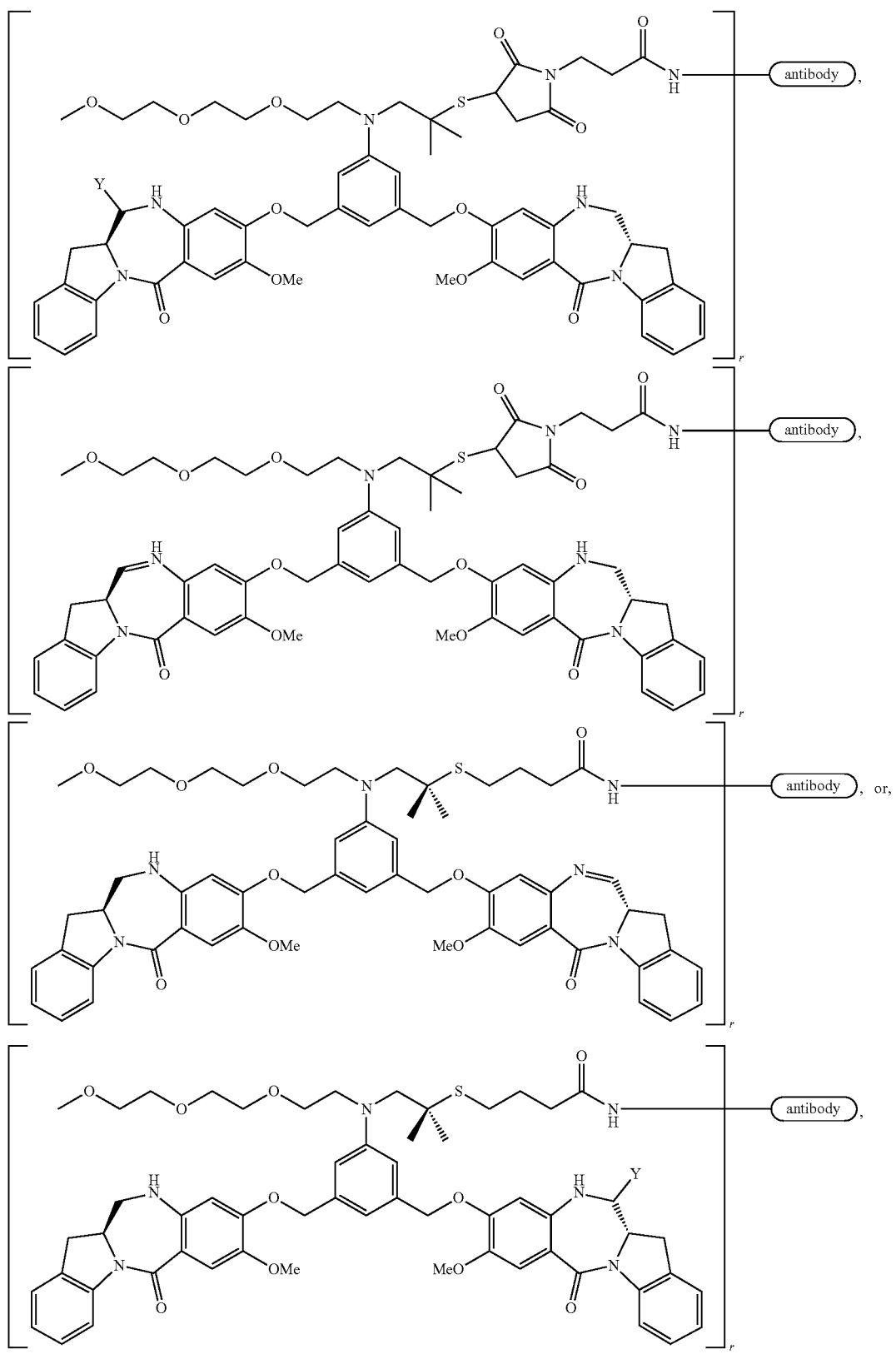
wherein r is an integer from 1 to 10, Y is —H or —SO$_3$M (e.g., Y is —SO$_3$M), and M is —H or a pharmaceutically acceptable cation.
In certain embodiments, such as in the sixteenth, seventeenth, and the nineteenth specific embodiments, the antibody is huMy9-6.

In a twentieth specific embodiment, the compound is represented by the following formula:

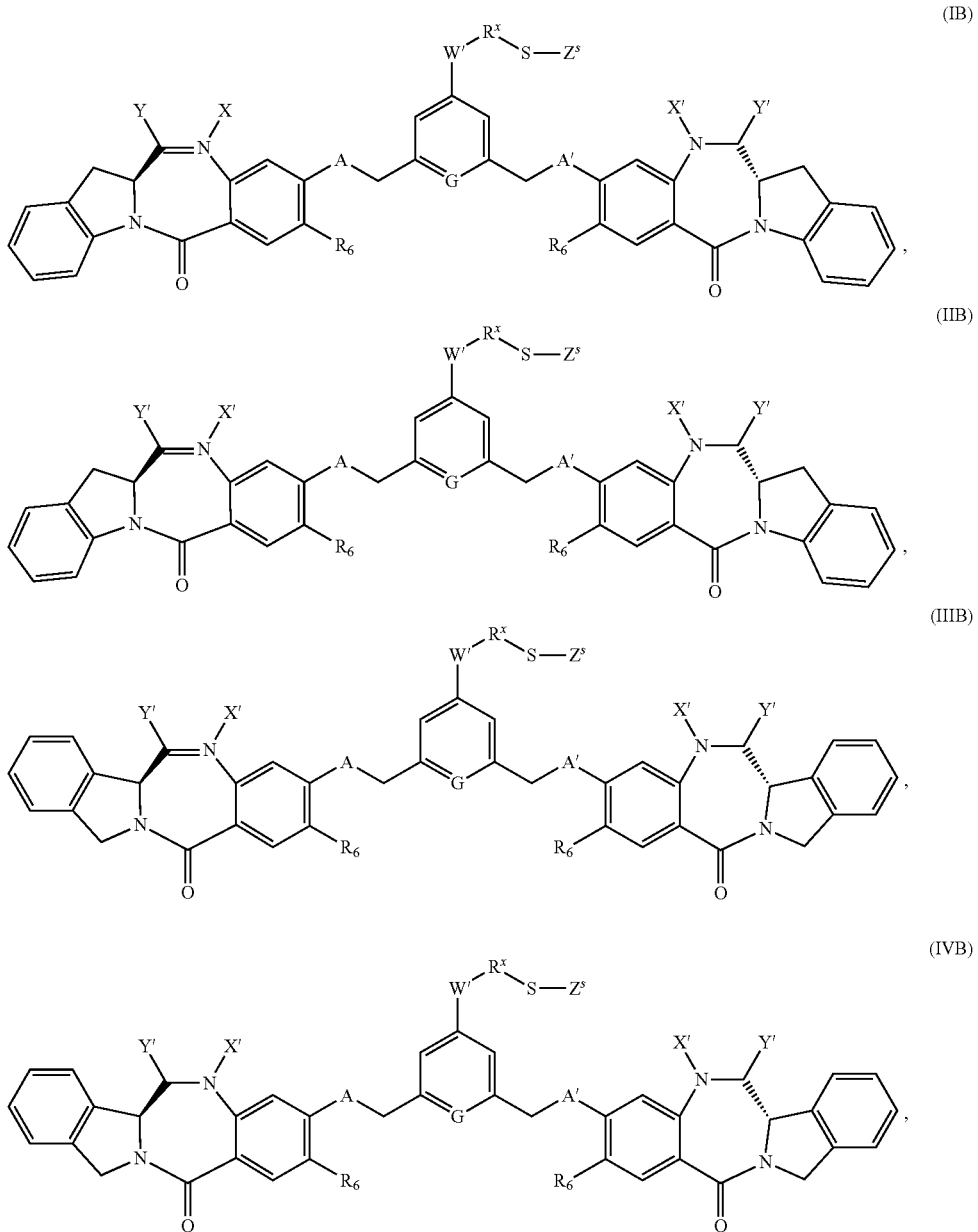

wherein:
W' is absent, or selected from —O—, —N(R$^e$)—, —N(R$^e$)—C(=O)—, —N(C(=O)R$^e$)—, —S—, —CH$_2$—S—, or —CH$_2$NR$^e$—;
R$^x$ is absent or selected from a linear, branched or cyclic alkyl having 1 to 10 carbon atoms;
R$^e$ is —H, a linear, branched or cyclic alkyl, alkenyl or alkynyl having 1 to 10 carbon atoms or —(CH$_2$—CH$_2$—O)$_n$—R$^k$, wherein R$^k$ is a —H, a linear, branched cyclic alkyl having 1 to 6 carbon atoms, optionally bearing a secondary amino (e.g., —NHR$^{101}$) or tertiary amino (NR$^{101}$R$^{102}$) group or a 5 or 6-membered nitrogen containing heterocycle, such as piperidine or morpholine, wherein R$^{101}$ and R$^{102}$ are each independently a linear, branched, or cyclic alkyl, alkenyl or alkynyl having 1 to 10 carbon atoms;

Z$^s$ is linked to the CBA, and is either a bond, or —SR$^m$—;
R$^m$ is R$^d$ or a substituted linear or branched alkyl having 1 to 4 carbon atoms bearing a reactive ester, selected from N-hydroxysuccinimide esters, N-hydroxyphtalimide esters, N-hydroxy sulfo-succinimide esters, paranitrophenyl esters, dinitrophenyl esters, and pentafluorophenyl esters;
R$^d$ is selected from phenyl, nitrophenyl, dinitrophenyl, carboxynitrophenyl, pyridyl or nitropyridyl; and
n is an integer from 1 to 24; and the remainder of the variables are as described above in the eighth or the fifteenth specific embodiment.

In a twenty-first specific embodiment, the compound is represented by the following formula:

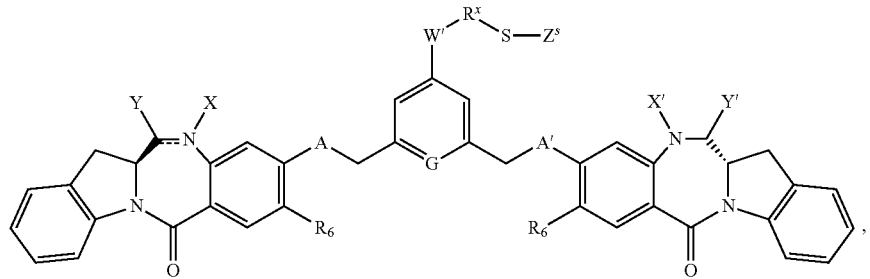

(VIII)

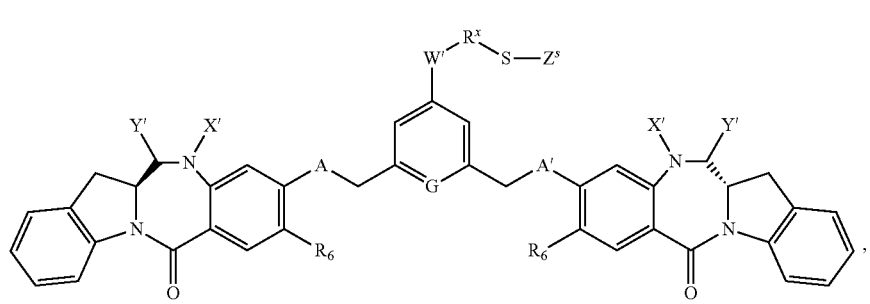

(IX)

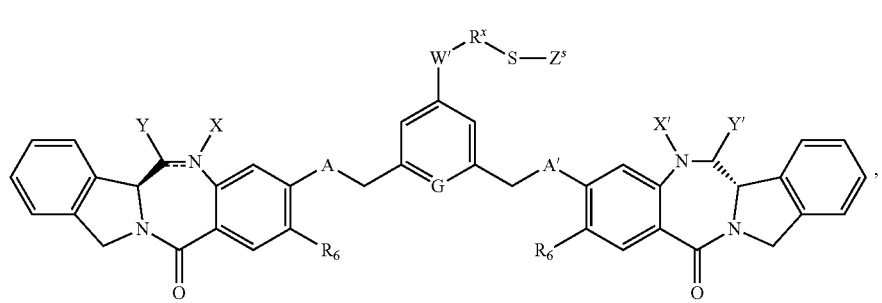

(X)

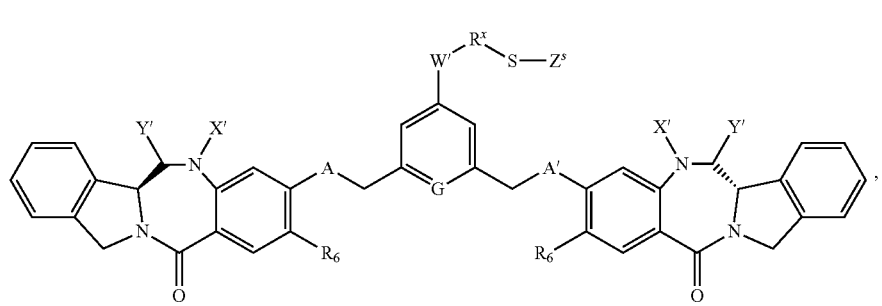

(XI)

wherein:

W' is absent, or selected from —O—, —N($R^e$)—, —N($R^e$)—C(=O)—, —N(C(=O)$R^e$)—, —S—, —CH$_2$—S—, or —CH$_2$N$R^e$—;

$R^x$ is absent or selected from a linear, branched or cyclic alkyl having 1 to 10 carbon atoms;

$R^e$ is —H, a linear, branched or cyclic alkyl, alkenyl or alkynyl having 1 to 10 carbon atoms or —(CH$_2$—CH$_2$—O)$_n$—$R^k$, wherein $R^k$ is a —H, a linear, branched cyclic alkyl having 1 to 6 carbon atoms, optionally bearing a secondary amino (e.g., —NHR[101]) or tertiary amino (—NR[101]R[102]) group or a 5 or 6-membered nitrogen containing heterocycle, such as piperidine or morpholine, wherein R[101] and R[102] are each independently a linear, branched, or cyclic alkyl, alkenyl or alkynyl having 1 to 10 carbon atoms;

n is an integer from 2 to 6;

$Z^s$ is linked to the CBA, and is selected from:

a bond;

(b1)
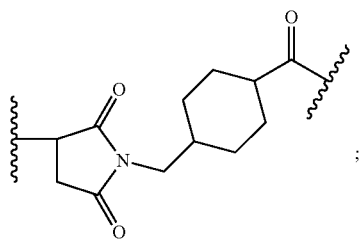
(b2)
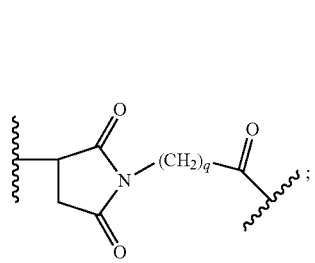
(b3)
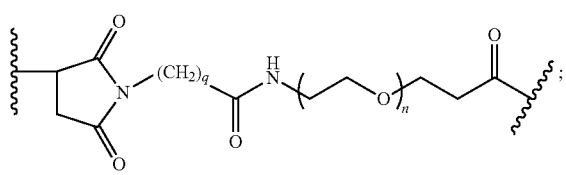
(b4)
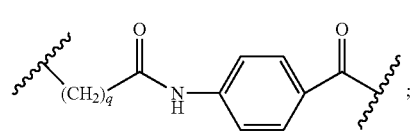
(b5)
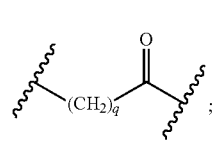
(b6)
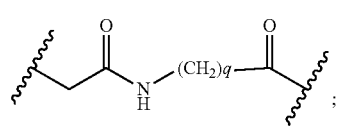
(b7)
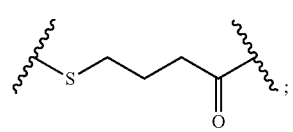
(b8)
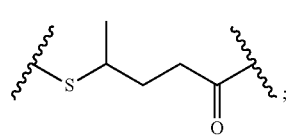
(b9)
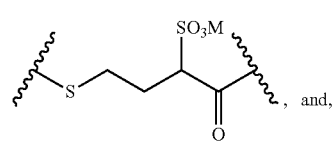, and,
(b10)
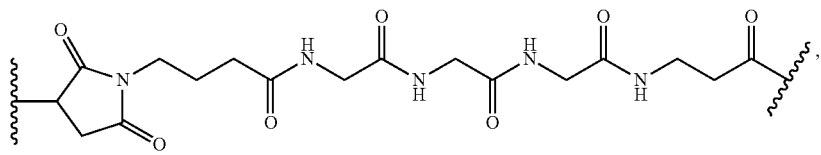
wherein:
q is an integer from 1 to 5; and,
M is —H or a cation, such as Na⁺ or K⁺.
In certain embodiments, $Z^s$ is represented by any one of the following formulas:
(b1)
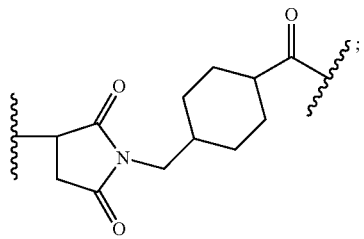
(b5')
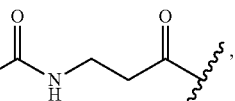
(b12)
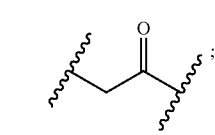
(b4')
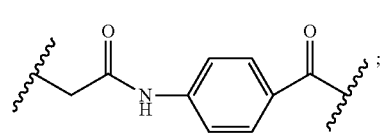
(b13)
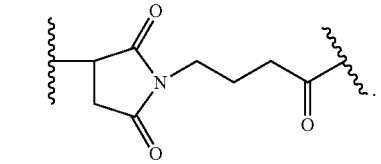

In certain embodiments, W' is —N(R$^e$)—.

In certain embodiments, R$^e$ is —(CH$_2$—CH$_2$—O)$_n$—R$^k$, wherein R$^k$ is a —H, a linear, branched cyclic alkyl having 1 to 6 carbon atoms.

In certain embodiments, R$^k$ is —H or -Me, n is 4, and q is 2.

In certain embodiments, R$^x$ is a linear or branched alkyl having 1 to 6 carbon atoms.

In certain embodiments, R$^x$ is —(CH$_2$)$_p$—(CR$^f$R$^g$)—, wherein R$^f$ and R$^g$ are each independently selected from H or a linear or branched alkyl having 1 to 4 carbon atoms; and p is 0, 1, 2 or 3.

In certain embodiments, R$^f$ and R$^g$ are the same or different, and are selected from —H and -Me; and p is 1.

In a twenty-second specific embodiment, the conjugate of formula (VIII), (IX), (X) and (XI) described in the twenty-first specific embodiment, the variables are as described below:
  the double line $=\!=$ between N and C represents a single bond or a double bond, provided that when it is a double bond X is absent and Y is —H, and when it is a single bond, X is —H; Y is —H, —OH or —SO$_3$M (e.g., Y is —OH or —SO$_3$M);
  M is —H or a pharmaceutically acceptable cation (e.g., Na$^+$);
  X' and Y' are both —H;
  A and A' are both —O—;
  R$_6$ is —OMe; and
  R$^x$ is a linear or branched alkyl having 1 to 6 carbon atoms.

In a twenty-third specific embodiment, for compounds of formula (IB), (IIB), (IIIB) and (IVB) described in the twentieth specific embodiment, the variables are as described below:
  the double line $=\!=$ between N and C represents a single bond or a double bond, provided that when it is a double bond X is absent and Y is —H, and when it is a single bond, X is —H; Y is —H, —OH or —SO$_3$M (e.g., Y is —OH or —SO$_3$M);
  M is —H or Na$^+$;
  X' and Y' are both —H;
  A and A' are both —O—;
  R$_6$ is —OMe;
  R$^x$ is a linear or branched alkyl having 1 to 6 carbon atoms.
  Preferably, R$^x$ is —(CH$_2$)$_p$—(CR$^f$R$^g$)—, wherein R$^f$ and R$^g$ are each independently selected from —H or a linear or branched alkyl having 1 to 4 carbon atoms; p is 0, 1, 2 or 3. More preferably, R$^f$ and R$^g$ are the same or different, and are selected from —H and -Me; and p is 1.

In any of the specific embodiments for the conjugate of the invention above, such as the fourteenth to the twenty-third specific embodiments, the double line $=\!=$ between N and C may represent a double bond.

In any of the specific embodiments for the conjugate of the invention above, such as the fourteenth to the twenty-third specific embodiments, the double line $=\!=$ between N and C may represent a single bond, X is —H, the linking group, or an amine protecting group (e.g., X is —H); and Y is —H or selected from —OR, —OCOR', —SR, —NR'R", an optionally substituted 5- or 6-membered nitrogen-containing heterocycle, —SO$_3$M, —SO$_2$M and a sulfate —OSO$_3$M. In certain embodiments, Y is not —H.

In certain embodiments, Y is selected from —H, —SO$_3$M, —OH, —OMe, —OEt or —NHOH (e.g., Y is —SO$_3$M, —OH, —OMe, —OEt or —NHOH).

In certain embodiments, Y is —H, —SO$_3$M or —OH (e.g., Y is —SO$_3$M or —OH).

In certain embodiments, M is —H, Na$^+$ or K$^+$.

In any of the specific embodiments for the conjugate of the invention above, such as the fourteenth to the twenty-third specific embodiments, W, when present, is C=O.

In any of the specific embodiments for the conjugate of the invention above, such as the fourteenth to the twenty-third specific embodiments, Z and Z', when present, are —CH$_2$—.

In any of the specific embodiments for the conjugate of the invention above, such as the fourteenth to the twenty-third specific embodiments, X' is selected from the group consisting of —H, —OH, an optionally substituted linear, branched or cyclic alkyl, alkenyl or alkynyl having from 1 to 10 carbon atoms, phenyl, the linking group, and an amine-protecting group.

In certain embodiments, X' is —H, —OH, -Me or the linking group.

In certain embodiments, X' is —H.

In any of the specific embodiments for the conjugate of the invention above, such as the fourteenth to the twenty-third specific embodiments, Y' is selected from the group consisting of —H, an oxo group, a substituted or unsubstituted linear, branched or cyclic alkyl, alkenyl or alkynyl having from 1 to 10 carbon atoms.

In certain embodiments, Y' is —H or oxo.

In certain embodiments, Y' is —H.

In any of the specific embodiments for the conjugate of the invention above, such as the fourteenth to the twenty-third specific embodiments, A and A' are the same or different, and are selected from —O—, —S—, —N(R$_5$)—, and oxo (C=O).

In certain embodiments, A and A' are the same or different, and are selected from —O— and —S—.

In certain embodiments, A and A' are —O—.

In any of the specific embodiments for the conjugate of the invention above, such as the fourteenth to the twenty-third specific embodiments, D and D', when present, are the same or different, and are independently selected from a polyethylene glycol unit (—OCH$_2$CH$_2$)$_n$, wherein n is an integer from 1 to 24, an amino acid, a peptide bearing 2 to 6 amino acids, or a linear, branched or cyclic alkyl, alkenyl or alkynyl having 1 to 10 carbon atoms, wherein the alkyl, alkenyl and alkynyl are optionally substituted with one or more substituents independently selected from the group consisting of halogen, —OR, —NR'COR", —SR and —COR'.

In certain embodiments, D and D' are linear or branched alkyl bearing 1 to 4 carbon atoms.

In a twenty-fourth specific embodiment, the conjugate of the present invention as described in the fourteenth, fifteenth, or the twenty-first specific embodiment is represented by the following:
  the double line $=\!=$ between N and C represents a double bond;
  Y is —H;
  W is C=O;
  R$_1$, R$_2$, R$_1$', R$_2$', R$_4$ and R$_4$' are —H;
  one of R$_3$, or R$_3$' is optionally the linking group and the other is —H;
  R$_6$ is —OMe;
  Z and Z' are —CH$_2$;
  X' is —H;
  Y' is —H; and
  A and A' are —O—.

In certain embodiments, the conjugate of any one of the described embodiments, such as the fourteenth to the twenty-fourth specific embodiments, may comprise 1-10 cytotoxic compounds, 2-9 cytotoxic compounds, 3-8 cytotoxic compounds, 4-7 cytotoxic compounds, or 5-6 cytotoxic compounds, each cytotoxic compound comprising the linking group linking the cytotoxic compound to the CBA, and each cytotoxic compound on the conjugate is the same.

In any of the conjugates embodiments, such as the fourteenth to the twenty-fourth specific embodiments, the cell-binding agent may bind to target cells selected from tumor cells, virus infected cells, microorganism infected cells, parasite infected cells, autoimmune cells, activated cells, myeloid cells, activated T-cells, B cells, or melanocytes; cells expressing the CD4, CD6, CD19, CD20, CD22, CD30, CD33, CD37, CD38, CD40, CD44, CD56, EpCAM, CanAg, CALLA, or Her-2 antigens; Her-3 antigens; or cells expressing insulin growth factor receptor, epidermal growth factor receptor, and folate receptor.

In any of the conjugates embodiments, such as the fourteenth to the twenty-fourth specific embodiments, the cell-binding agent may be an antibody, a single chain antibody, an antibody fragment that specifically binds to the target cell, a monoclonal antibody, a single chain monoclonal antibody, or a monoclonal antibody fragment that specifically binds to a target cell, a chimeric antibody, a chimeric antibody fragment that specifically binds to the target cell, a domain antibody, a domain antibody fragment that specifically binds to the target cell, a lymphokine, a hormone, a vitamin, a growth factor, a colony stimulating factor, or a nutrient-transport molecule.

The antibody may be a resurfaced antibody, a resurfaced single chain antibody, or a resurfaced antibody fragment.

The antibody may be a monoclonal antibody, a single chain monoclonal antibody, or a monoclonal antibody fragment thereof.

The antibody may be a humanized antibody, a humanized single chain antibody, or a humanized antibody fragment.

The invention further provides a pharmaceutical composition comprising any of the conjugates described herein, and a pharmaceutically acceptable carrier.

The invention further provides a drug-linker compound comprising any of the subject compound covalently linked to a bifunctional linker.

The invention additional provides a conjugate comprising any of the subject compounds, or the subject drug-linker compounds, linked to a cell-binding agent.

The invention further provides a method of inhibiting abnormal cell growth or treating a proliferative disorder, an autoimmune disorder, destructive bone disorder, infectious disease, viral disease, fibrotic disease, neurodegenerative disorder, pancreatitis or kidney disease in a mammal comprising administering to the mammal a therapeutically effective amount of any of the compounds (with or without any linker group) or conjugates of the invention, and, optionally, a second chemotherapeutic agent.

In certain embodiments, the compound or the conjugate is:

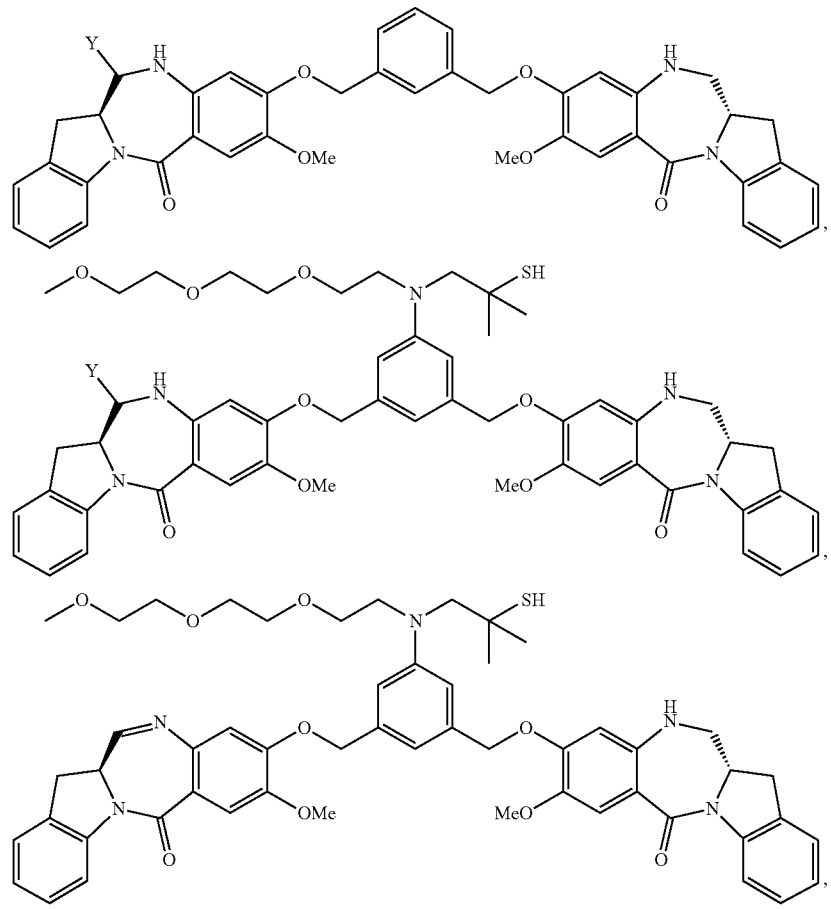

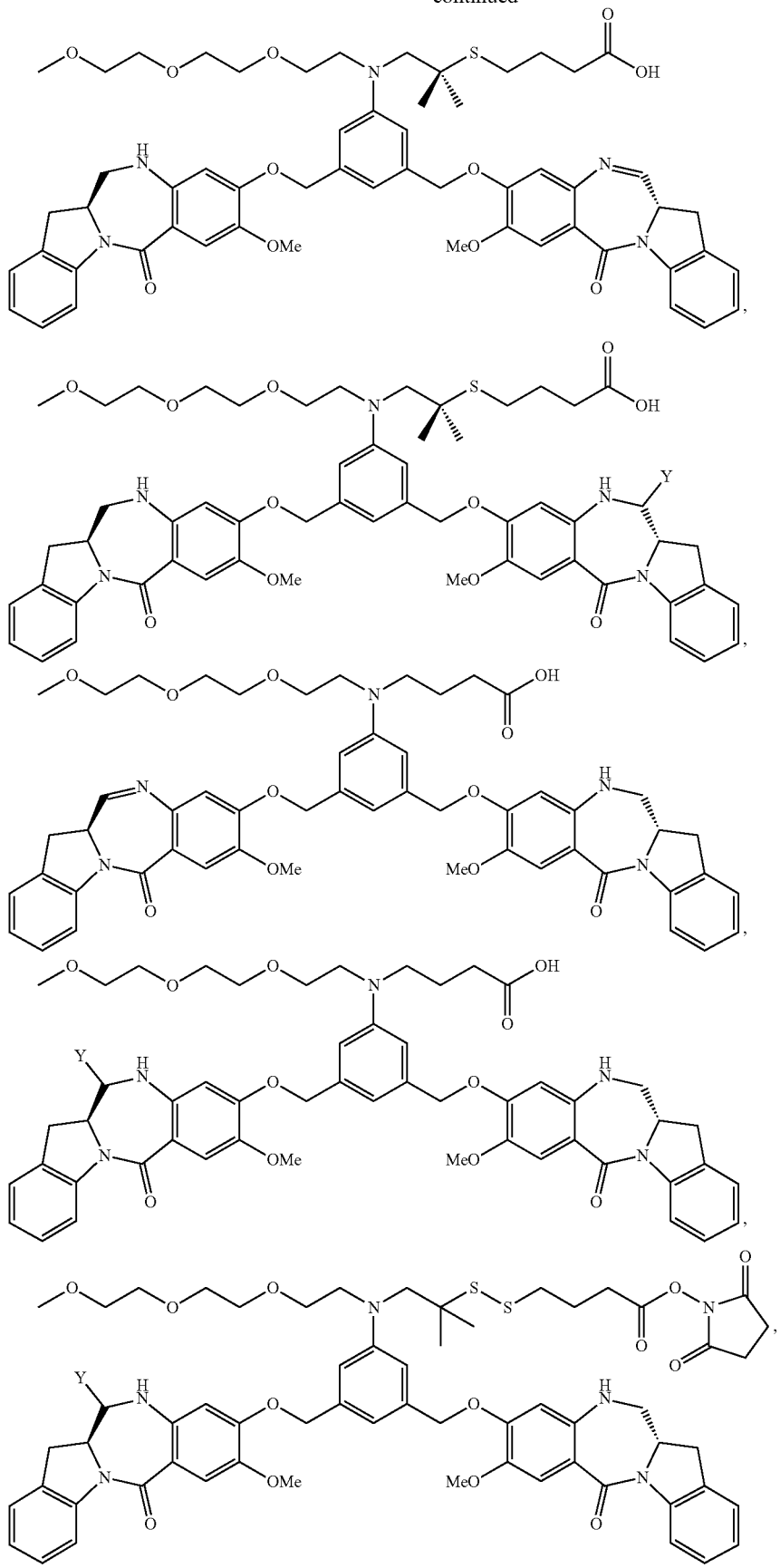

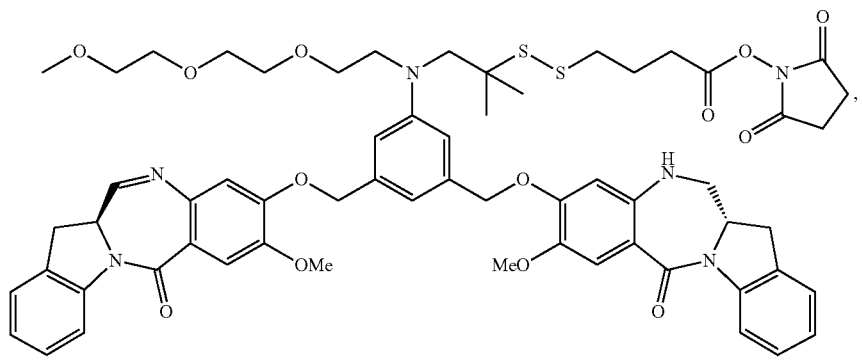
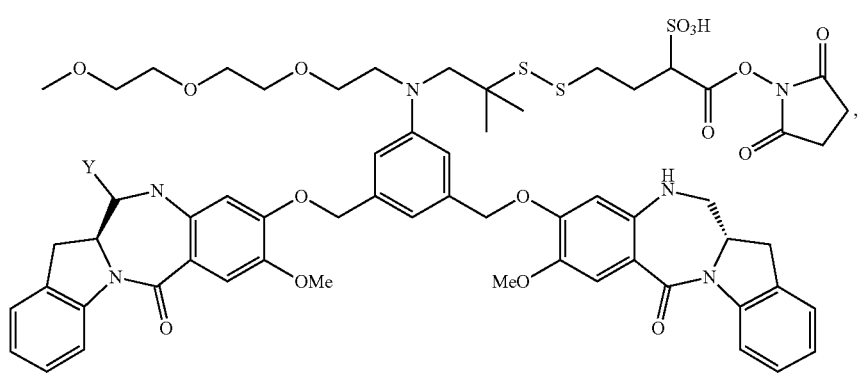
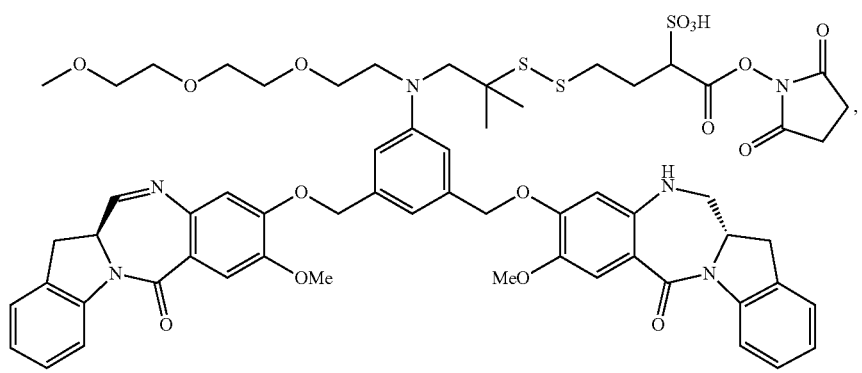
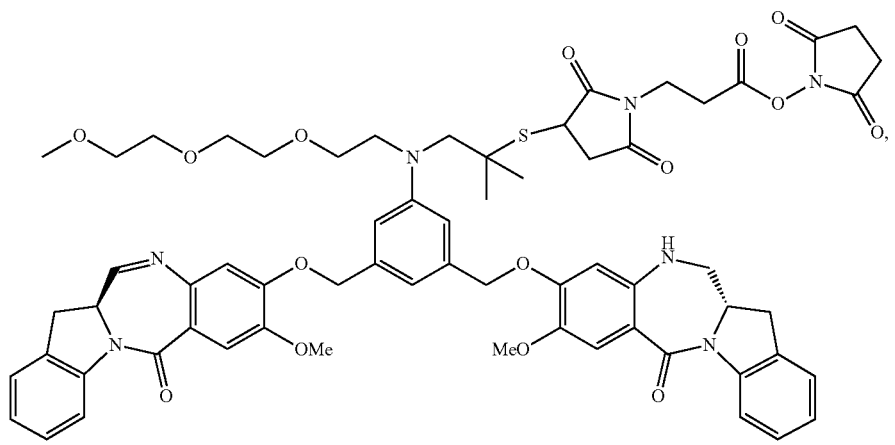

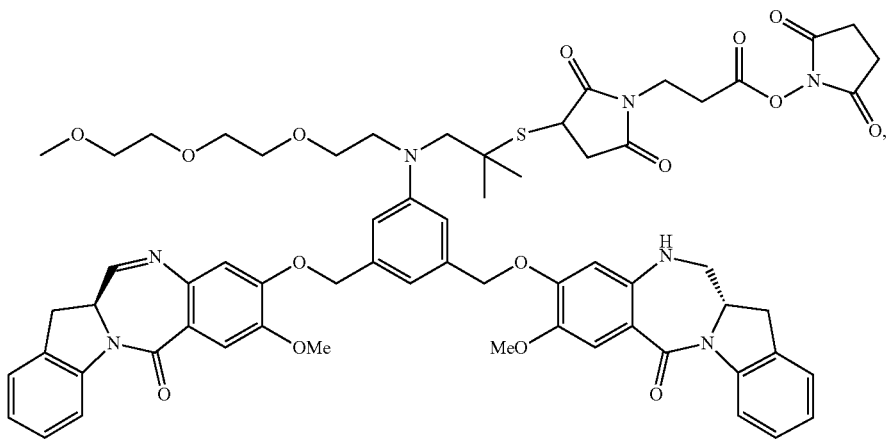
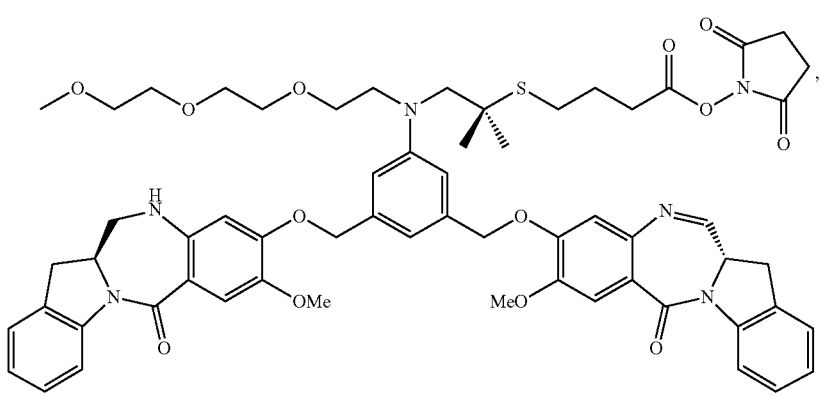
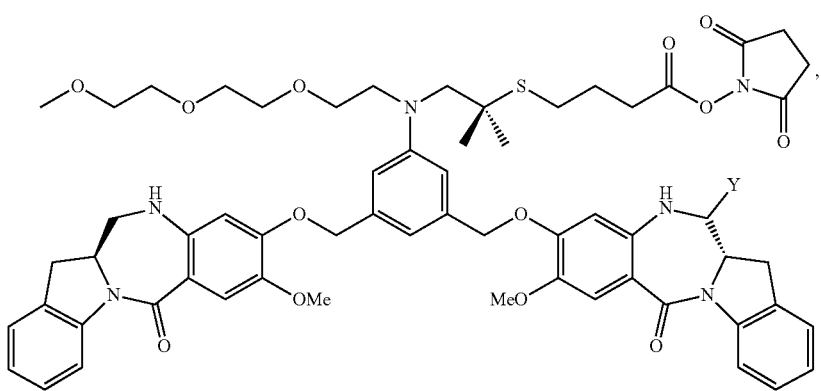
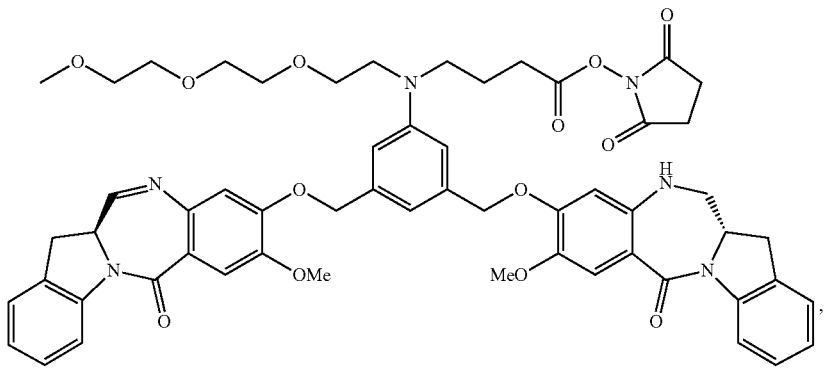

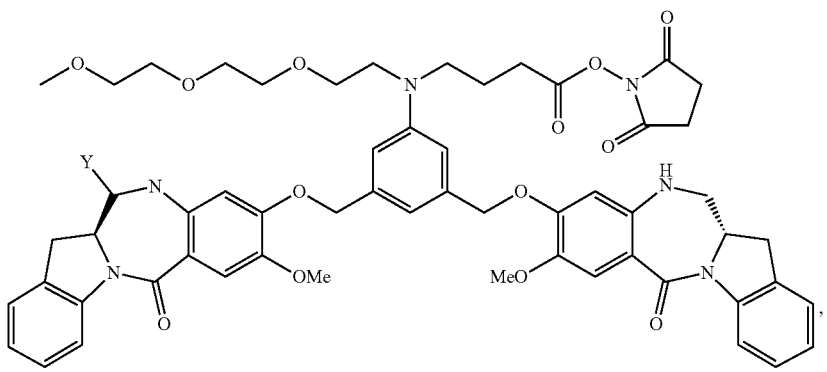
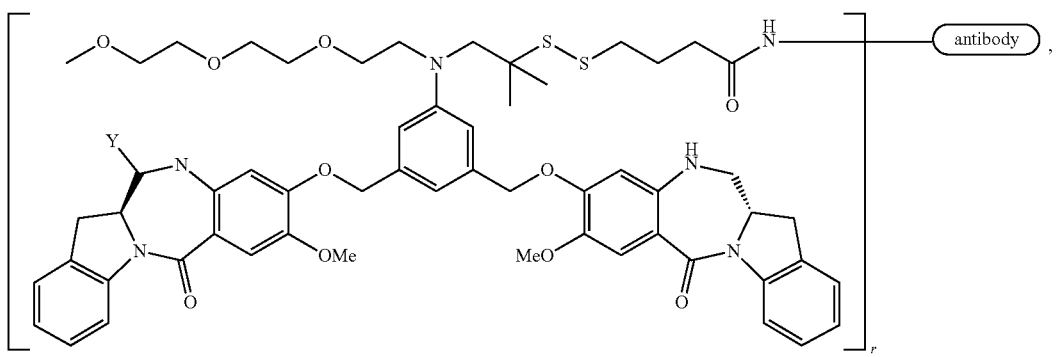
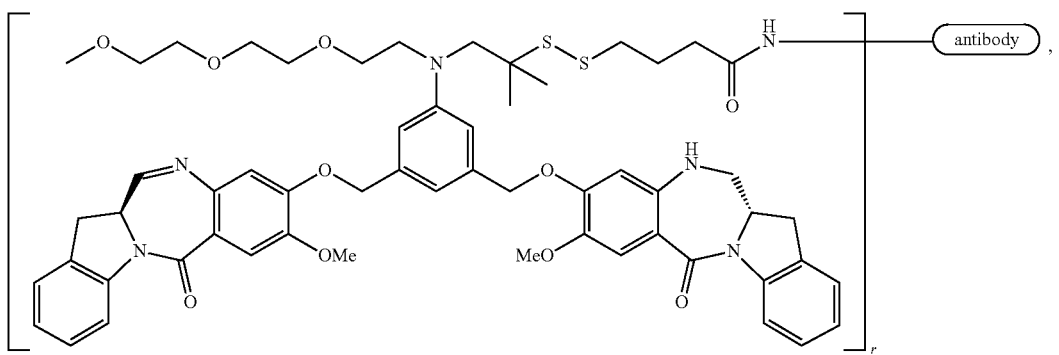
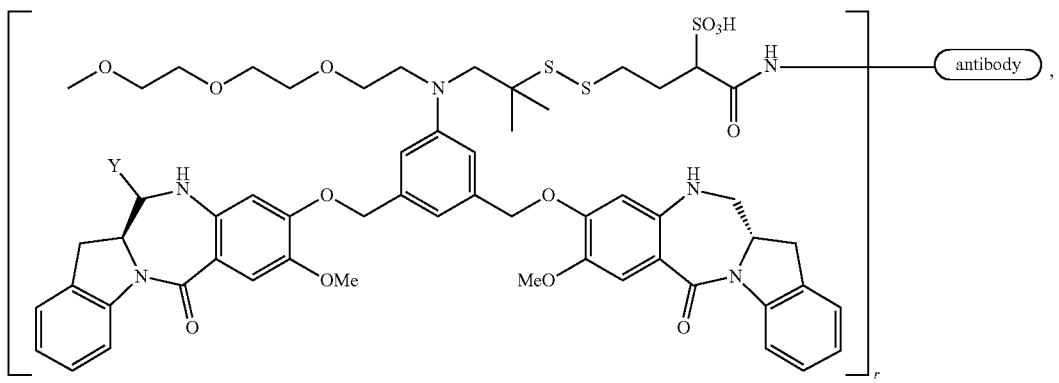

-continued
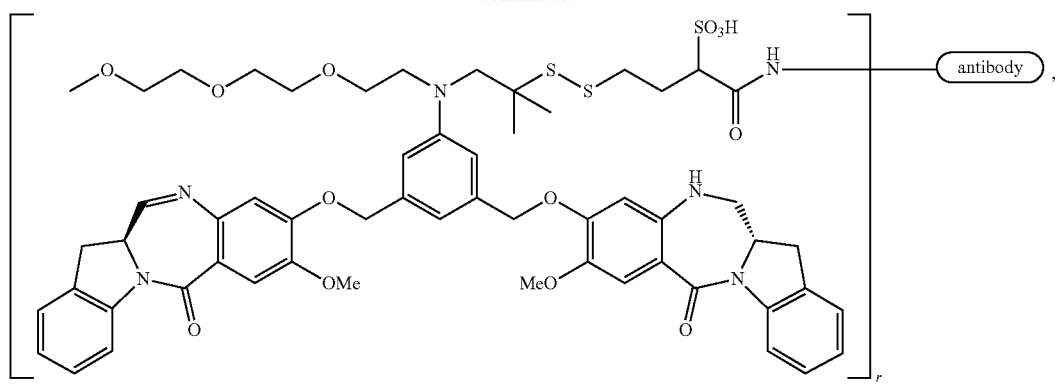
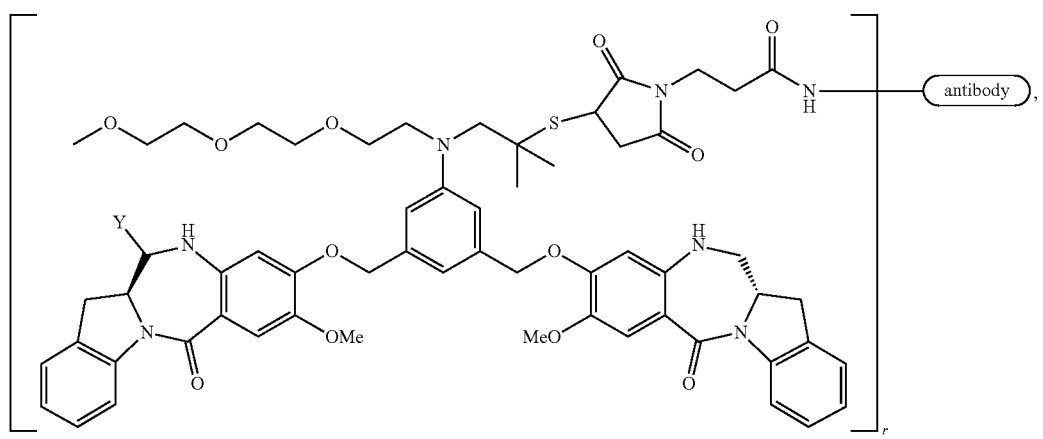
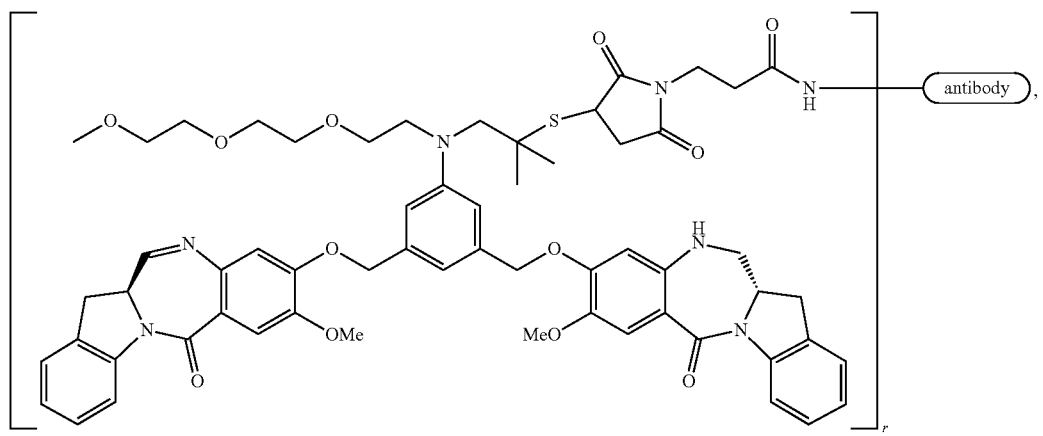
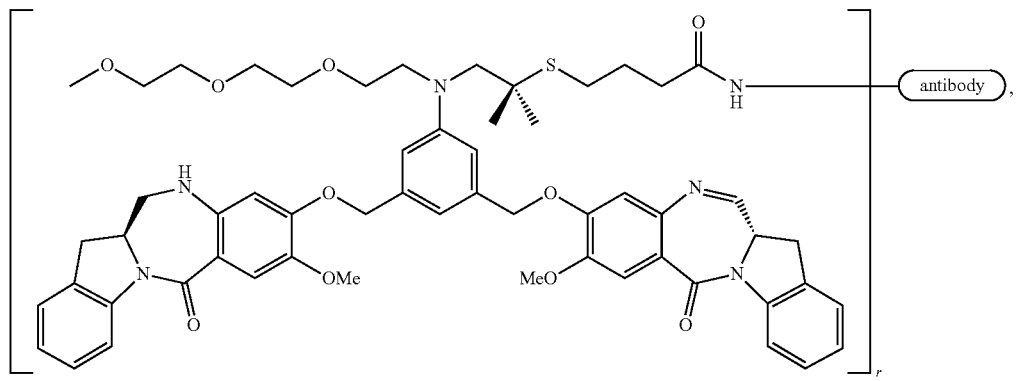

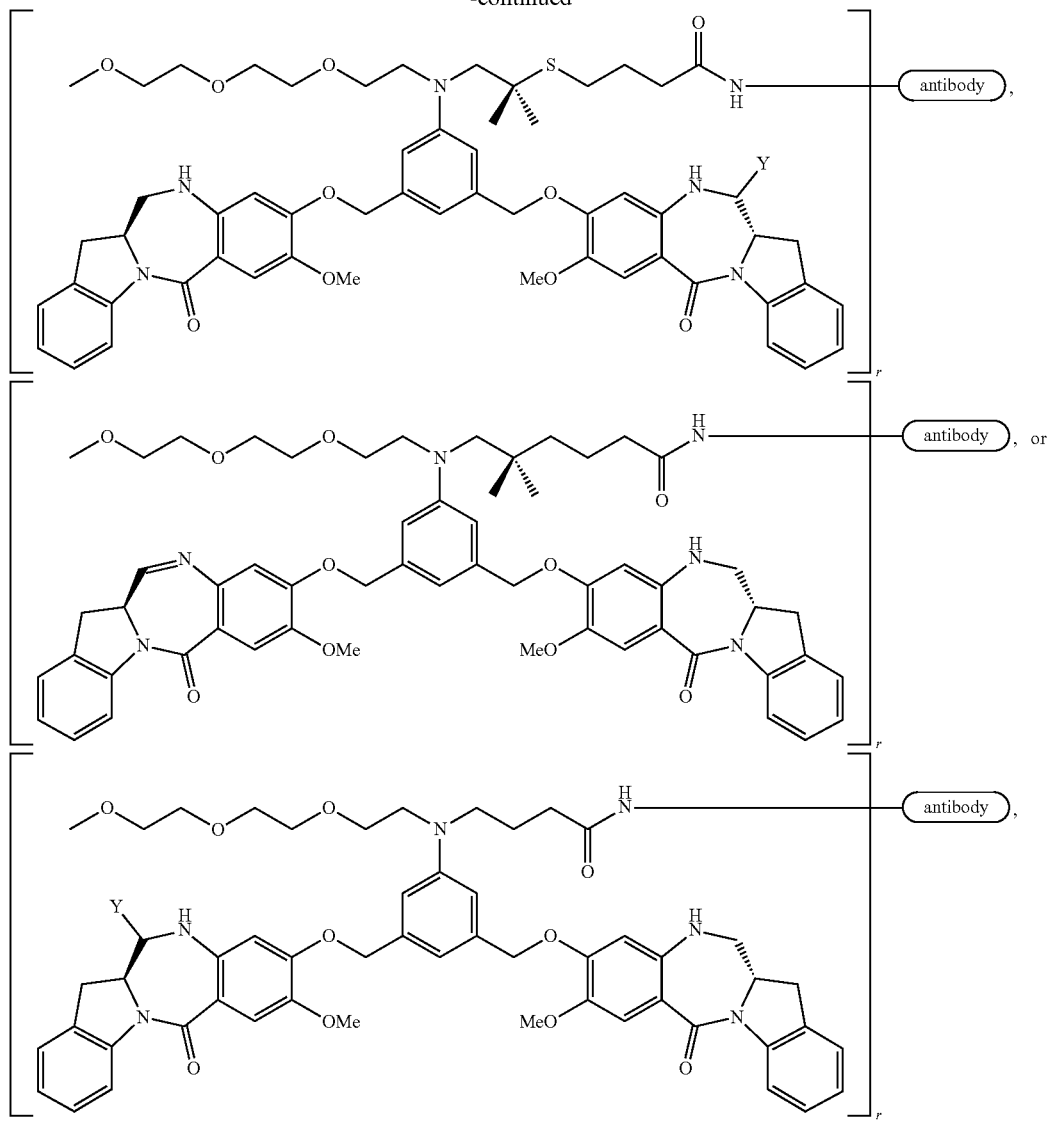

wherein r is an integer from 1 to 10, Y is —H or —SO₃M (e.g., Y is —SO₃M), and M is —H or a pharmaceutically acceptable cation.

In certain embodiments, the second chemotherapeutic agent is administered to the mammal sequentially or consecutively.

In certain embodiments, the method is for treating a condition selected from cancer, rheumatoid arthritis, multiple sclerosis, graft versus host disease (GVHD), transplant rejection, lupus, myositis, infection, and immune deficiency.

In certain embodiments, the method or conjugate is for treating a cancer.

In certain embodiments, the cancer is selected from breast cancer, colon cancer, brain cancer, prostate cancer, kidney cancer, pancreatic cancer, ovarian cancer, head and neck cancer, melanoma, colorectal cancer, gastric cancer, squamous cancer, small-cell lung cancer, non small-cell lung cancer, testicular cancer, Merkel cell carcinoma, glioblastoma, neuroblastoma, cancers of lymphatic organs and hematological malignancy including Leukemia (Acute lymphoblastic leukemia (ALL), Acute myelogenous leukemia (AML), Chronic lymphocytic leukemia (CLL), Chronic myelogenous leukemia (CML), Acute monocytic leukemia (AMOL), Hairy cell leukemia (HCL), T-cell prolymphocytic leukemia (T-PLL), Large granular lymphocytic leukemia, Adult T-cell leukemia), Lymphoma (small lymphocytic lymphoma (SLL), Hodgkin's lymphomas (Nodular sclerosis, Mixed cellularity, Lymphocyte-rich, Lymphocyte depleted or not depleted, and Nodular lymphocyte-predominant Hodgkin lymphoma), Non-Hodgkin's lymphomas (all subtypes), Chronic lymphocytic leukemia/Small lymphocytic lymphoma, B-cell prolymphocytic leukemia, Lymphoplasmacytic lymphoma (such as Waldenström macroglobulinemia), Splenic marginal zone lymphoma, Plasma cell neoplasms (Plasma cell myeloma, Plasmacytoma, Monoclonal immunoglobulin deposition diseases, Heavy chain diseases), Extranodal marginal zone B cell lymphoma (MALT lymphoma), Nodal marginal zone B cell lymphoma (NMZL), Follicular lymphoma, Mantle cell lymphoma, Diffuse large B cell lymphoma, Mediastinal (thymic) large B cell lymphoma, Intravascular large B cell lymphoma, Primary effusion lymphoma, Burkitt lymphoma/leukemia, T cell prolymphocytic leukemia, T cell large granular lymphocytic leukemia, Aggressive NK cell leukemia, Adult T cell leukemia/lymphoma, Extranodal NK/T cell lymphoma (nasal type), Enteropathy-type T cell lymphoma, Hepatosplenic T cell lymphoma, Blastic NK cell lymphoma, Mycosis fungoides/Sezary syndrome, Primary cutaneous CD30-positive T cell lymphoproliferative disorders, Primary cutaneous anaplastic large cell lymphoma, Lymphomatoid papulosis, Angioimmunoblastic T cell lymphoma, Peripheral T cell lymphoma (unspecified), Anaplastic large cell lymphoma), multiple myeloma (plasma cell myeloma or Kahler's disease).

Production of Cell-Binding Agent-Drug Conjugates

In order to link the cytotoxic compounds or derivative thereof of the present invention to the cell-binding agent, the cytotoxic compound may comprise a linking moiety with a reactive group bonded thereto. In one embodiment, a bifunctional crosslinking reagent can be first reacted with the cytotoxic compound to provide the compound bearing a linking moiety with one reactive group bonded thereto (i.e., drug-linker compound), which can then react with a cell binding agent. Alternatively, one end of the bifunctional crosslinking reagent can first react with the cell binding agent to provide the cell binding agent bearing a linking moiety with one reactive group bonded thereto, which can then react with a cytotoxic compound. The linking moiety may contain a chemical bond that allows for the release of the cytotoxic moiety at a particular site. Suitable chemical bonds are well known in the art and include disulfide bonds, thioether bonds, acid labile bonds, photolabile bonds, peptidase labile bonds and esterase labile bonds (see for example U.S. Pat. Nos. 5,208,020; 5,475,092; 6,441,163; 6,716,821; 6,913,748; 7,276,497; 7,276,499; 7,368,565; 7,388,026 and 7,414,073). Preferred are disulfide bonds, thioether and peptidase labile bonds. Other linkers that can be used in the present invention include non-cleavable linkers, such as those described in are described in detail in U.S. publication number 2005/0169933, or charged linkers or hydrophilic linkers and are described in US 2009/0274713, US 2010/01293140 and WO 2009/134976, each of which is expressly incorporated herein by reference, each of which is expressly incorporated herein by reference.

The compounds of formula (I)-(IV), (IA)-(IVA), and (IB)-(IVB) can be linked through $R_1$, $R_2$, $R_3$, $R_4$, $R_1'$, $R_2'$, $R_3'$, $R_4'$, $L'$, $L''$, $L'''$, or X (when present). Of these, preferred linkable groups are $R_2'$, $R_3'$, $R_4'$, $L'$, $L''$, $L'''$ and most preferred linkable groups are $R_2'$, $R_3'$, and $L'$. Examples of linking groups for compounds of formula (I)-(IV), (IA)-(IVA), and (IB)-(IVB) are described above.

In one embodiment, a solution of an antibody in aqueous buffer may be incubated with a molar excess of an antibody modifying agent such as N-succinimidyl-3-(2-pyridyldithio)propionate (SPDP) or with N-succinimidyl-4-(2-pyridyldithio)butanoate (SPDB) to introduce dithiopyridyl groups. The modified antibody is then reacted with the thiol-containing cytotoxic compound, such as compound 2a, to produce a disulfide-linked antibody-indolinobenzodiazepine dimer conjugate. The cell binding agent-drug conjugate may then be purified using any purification methods known in the art, such as those described in U.S. Pat. No. 7,811,572 and US Publication No. 2006/0182750, both of which are incorporated herein by reference. For example, the cell-binding agent-drug conjugate can be purified using tangential flow filtration, adsorptive chromatography, adsorptive filtration, selective precipitation, non-absorptive filtration or combination thereof. Preferably, tangential flow filtration (TFF, also known as cross flow filtration, ultrafiltration and diafiltration) and/or adsorptive chromatography resins are used for the purification of the conjugates.

Alternatively, the antibody may be incubated with a molar excess of an antibody modifying agent such as 2-iminothiolane, L-homocysteine thiolactone (or derivatives), or N-succinimidyl-S-acetylthioacetate (SATA) to introduce sulfhydryl groups. The modified antibody is then reacted with the appropriate disulfide-containing cytotoxic agent, to produce a disulfide-linked antibody-cytotoxic agent conjugate. The antibody-cytotoxic agent conjugate may then be purified by methods described above. The cell binding may also be engineered to introduce thiol moieties, such as cysteine-engineered antibodies disclosed in U.S. Pat. Nos. 7,772,485 and 7,855,275.

In another embodiment, a solution of an antibody in aqueous buffer may be incubated with a molar excess of an antibody-modifying agent such as N-succinimidyl-4-(N-maleimidomethyl)-cyclohexane-1-carboxylate to introduce maleimido groups, or with N-succinimidyl-4-(iodoacetyl)-aminobenzoate (SIAB) to introduce iodoacetyl groups. The modified antibody is then reacted with the thiol-containing cytotoxic agent to produce a thioether-linked antibody-cytotoxic conjugate. The antibody-cytotoxic conjugate may then be purified by methods described above.

The number of cytotoxic molecules bound per antibody molecule can be determined spectrophotometrically by measuring the ratio of the absorbance at 280 nm and 330 nm. An average of 1-10 cytotoxic compounds/antibody molecule(s) can be linked by the methods described herein. The preferred average number of linked cytotoxic compounds per antibody molecule is 2-5, and the most preferred is 2.5-4.0.

Cytotoxic agents containing linkers terminating in an N-hydroxy succinimidyl (NHS) ester, such as compounds 1g and 10, can react with the antibody to produce direct amide linked conjugates such as huMy9-6-SPDB-1f or huMy9-6-BMPS-1f. The antibody-cytotoxic agent conjugate may then be purified by gel-filtration by any methods described above.

Representative processes for preparing the cell-binding agent-drug conjugates of the present invention are shown in FIGS. 22 and 23. A cytotoxic dimer compound of the present invention can be conjugated with a cell binding agent through either a one-step or a two-step conjugation method. In FIGS. 22a and 22b, representative examples are described, wherein a dimer compound that possesses a linker such as an N-hydroxysuccinimide ester is reacted directly with a cell binding agent, such as an antibody, generating the desired conjugate. In FIG. 22c linkable dimer 1g was first treated with sodium bisulfate to provide a modified dimer compound 26 before adding antibody to form the conjugate huMy9-6-SBDP-1f of the present invention.

A representative example of a two-step conjugation method is described in FIG. 23, wherein an antibody is first modified with a bifunctional crosslinking agent resulting in an antibody that possesses a desired number of linkers suitable for reaction with a dimer compound having a free thiol moiety. In this example the antibody huMy9-6 was first modified with SPDB to give an antibody with linkers containing the dithiopyridyl moiety. The modified antibody was then exposed to a free thiol, such as 2a, generating the desired conjugate huMy9-6-SPDB-2a.

Processes for synthesizing the drug-linker compounds and conjugates of the invention are also described in U.S. provisional patent application No. 61/443,092, filed on Feb. 15, 2011, and a U.S. utility application claiming the benefit of filing date thereof and filed on the same day of the instant application, entitled "METHODS OF PREPARATION OF CONJUGATES," the entire contents of which applications, including all drawings, formulae, synthesis schemes, specifications, and claims, are incorporated herein by reference.

The structures of representative compounds and conjugates of the present invention are shown in Tables 1-8. These compounds and conjugates can be prepared according to the methods described herein.

TABLE 1

Structures of representative compounds in the present invention.

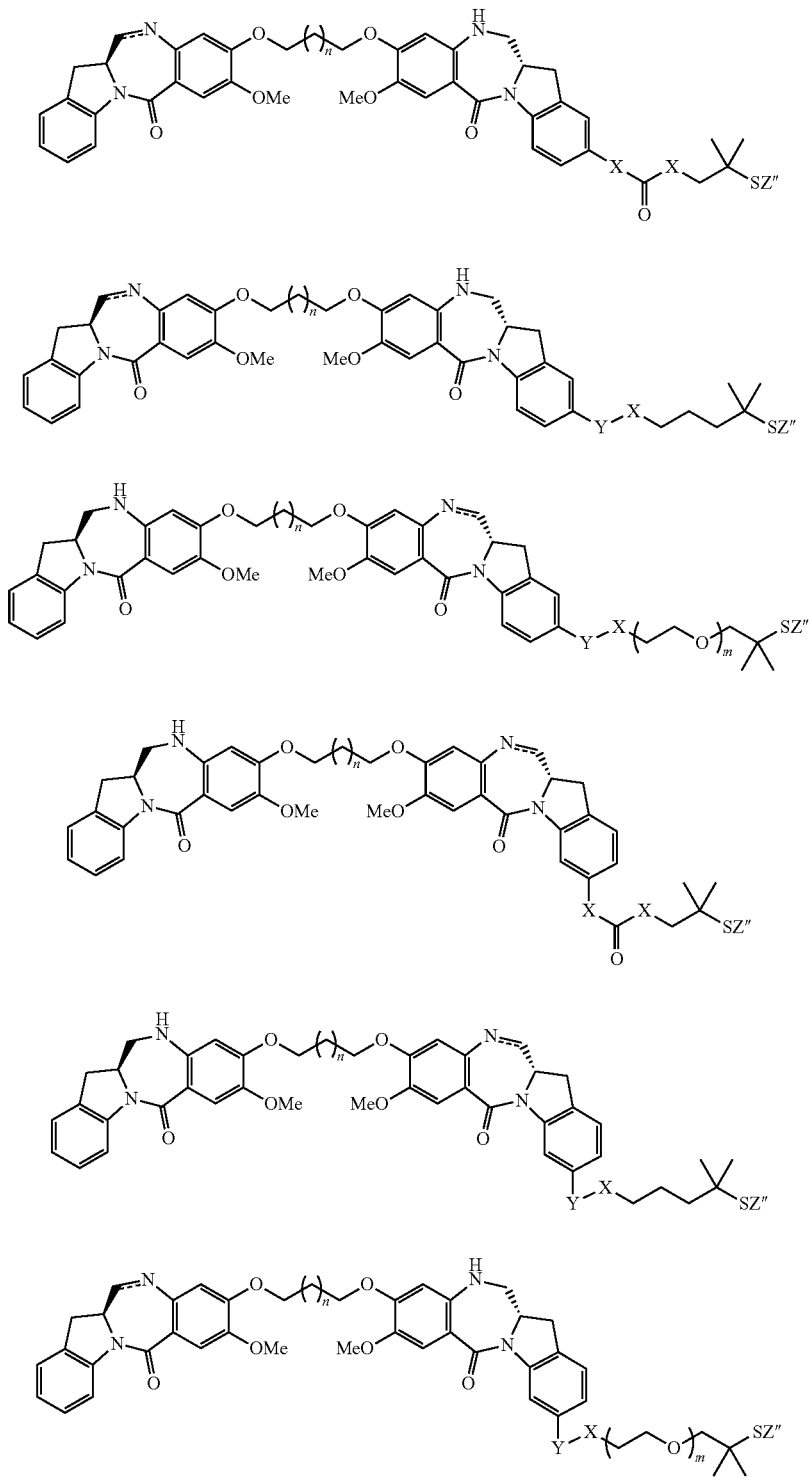

TABLE 1-continued
Structures of representative compounds in the present invention.
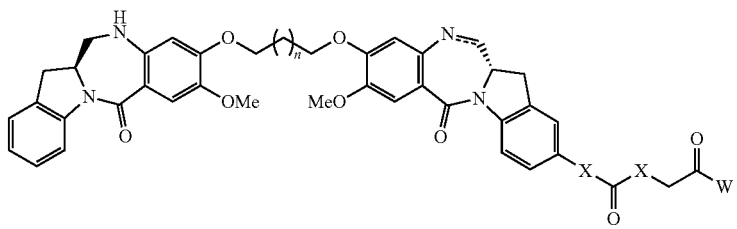
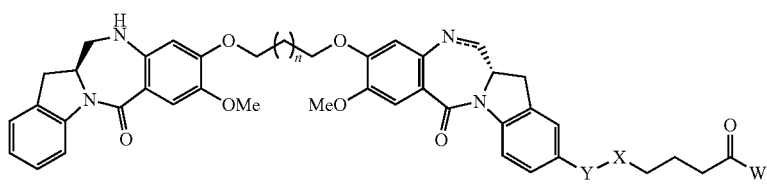
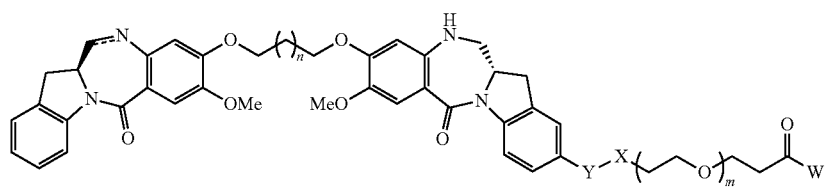
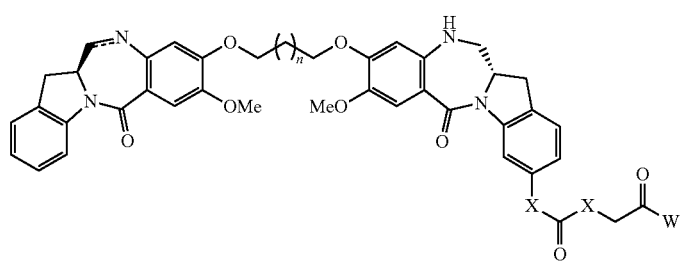
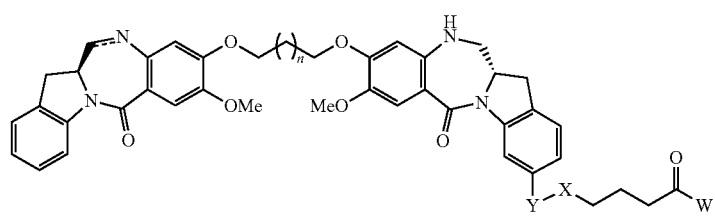
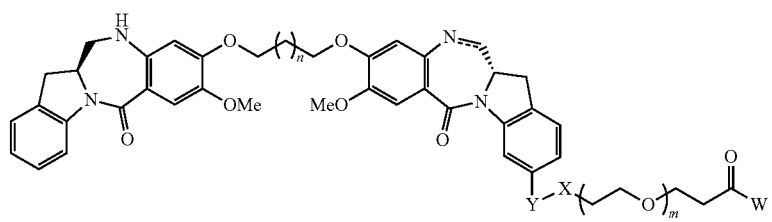
Notes:
n = 1 or 3; m = 3 or 4
W = OH, OMe, ONHS, NHNH$_2$, H, Me, Ph, Peptide
X = CH$_2$, O, S, NH or NMe
Y = CH$_2$ or absent
Z" = H, Me, SMe, S(CH$_2$)$_3$C(O)NHS or CH$_2$C(O)NHS or BMPS or SMCC or SPy or SPy-NO$_2$ TABLE 2
Structures of representative compounds in the present invention (Continued).
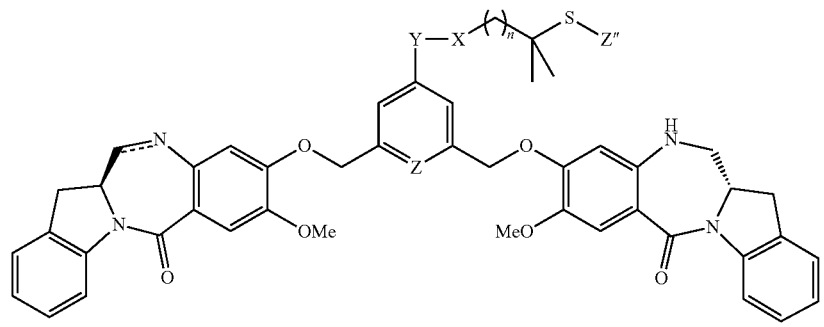
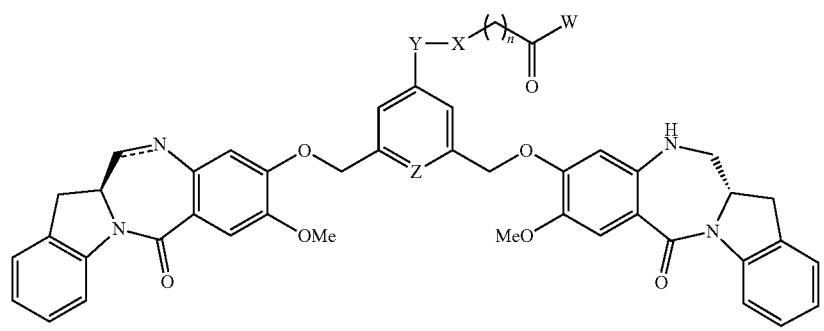
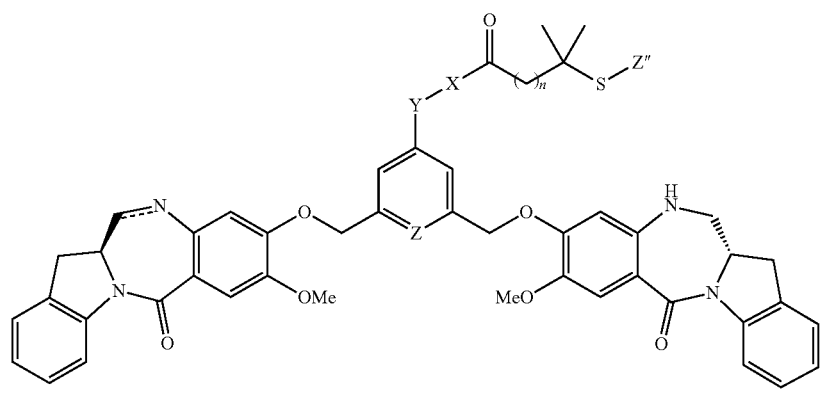
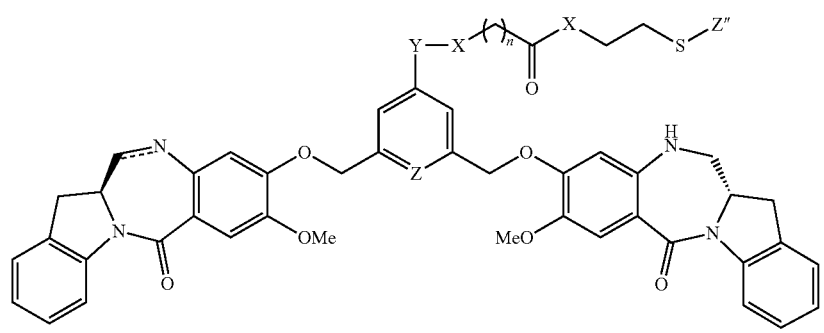

TABLE 2-continued
Structures of representative compounds in the present invention (Continued).
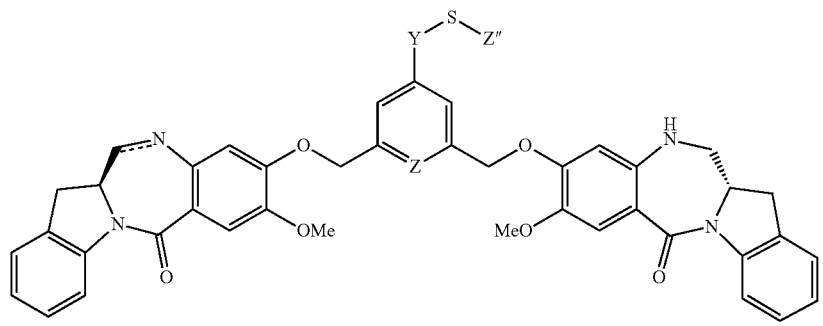
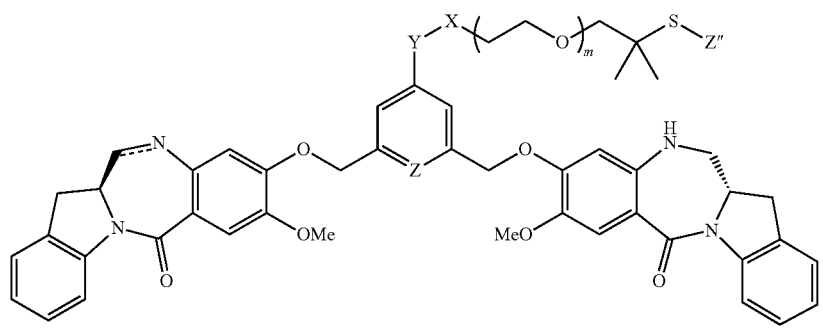
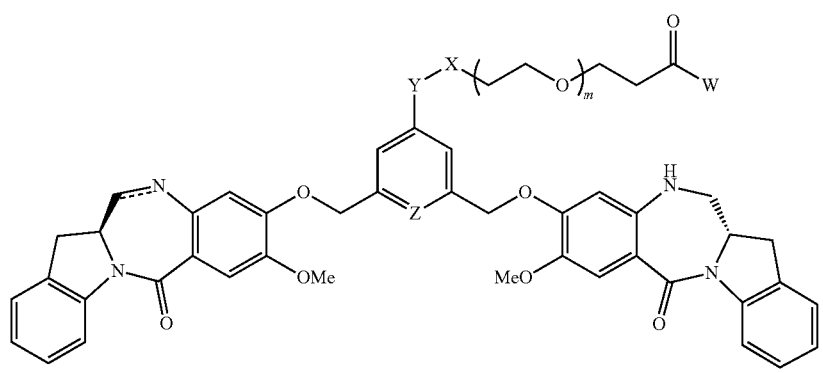
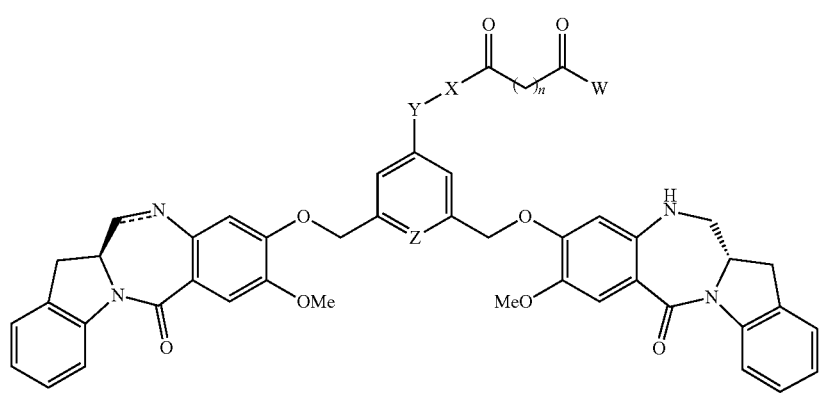

TABLE 2-continued
Structures of representative compounds in the present invention (Continued).
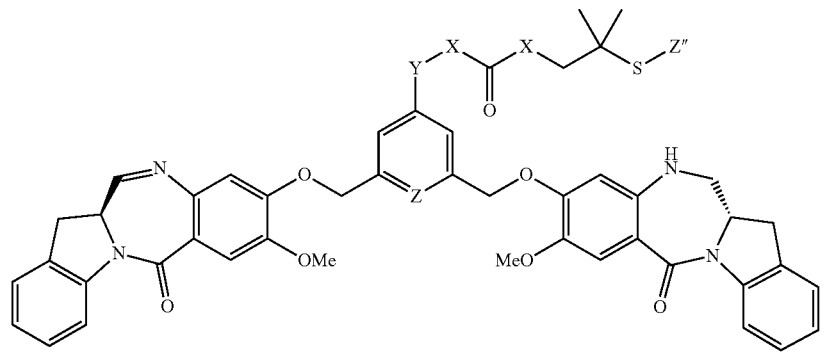
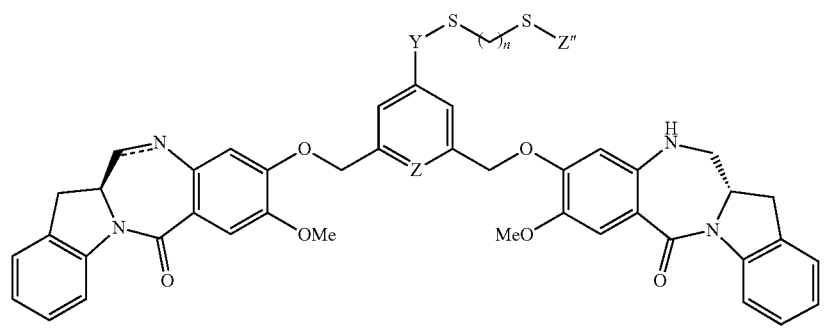
Note:
n = 1, 2 or 3
m = 3 or 4
W = OH, OMe, ONHS, NHNH$_2$, H, Me, Ph, Peptide
X = CH$_2$, O, S, NH, NMe
Y = absent or CH$_2$
Z = CH or N
Z" = H, Me, SMe, S(CH$_2$)$_3$C(O)NHS or CH$_2$C(O)NHS or BMPS or SMCC or SPy or SPy-NO$_2$
TABLE 3
Structures of representative compounds in the present invention (Continued).
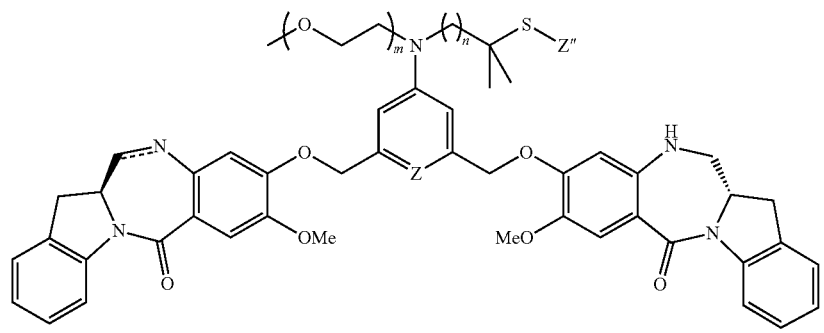

TABLE 3-continued
Structures of representative compounds in the present invention (Continued).
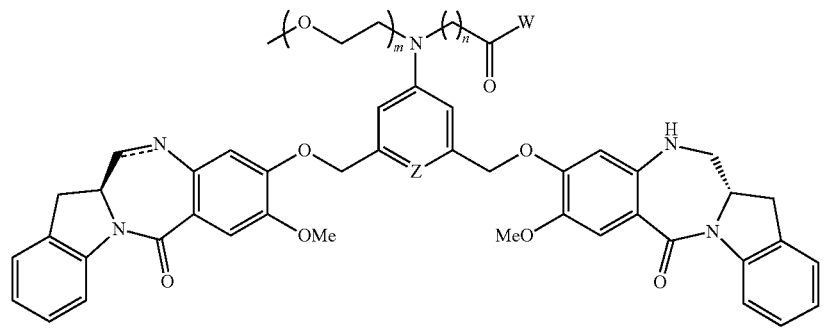
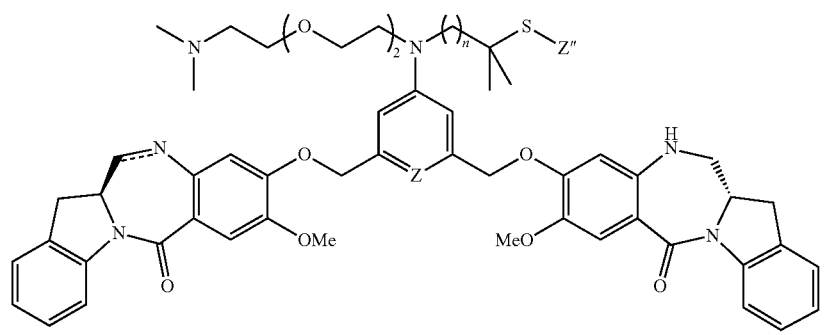
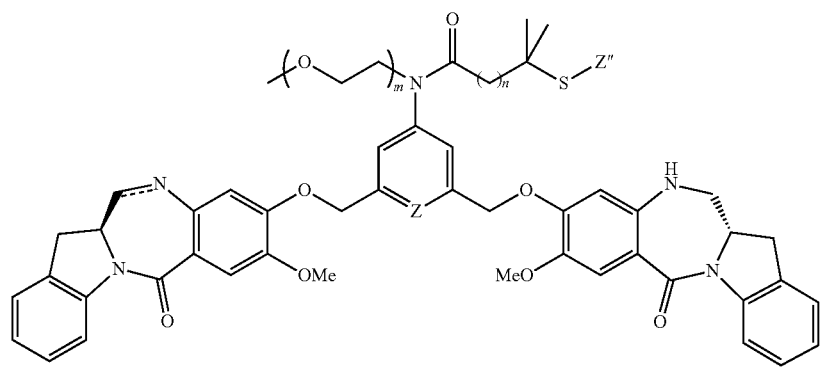
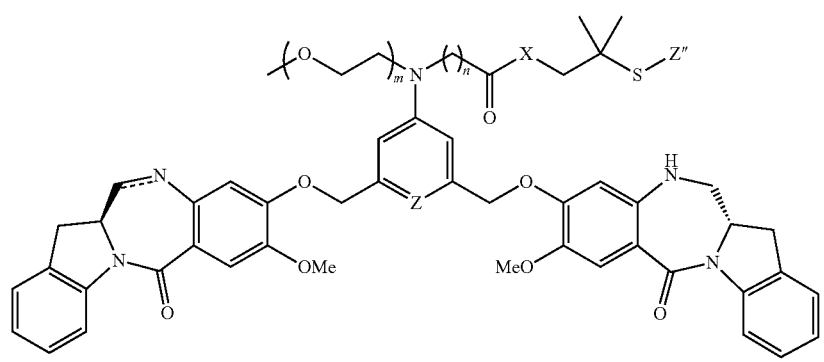

TABLE 3-continued
Structures of representative compounds in the present invention (Continued).
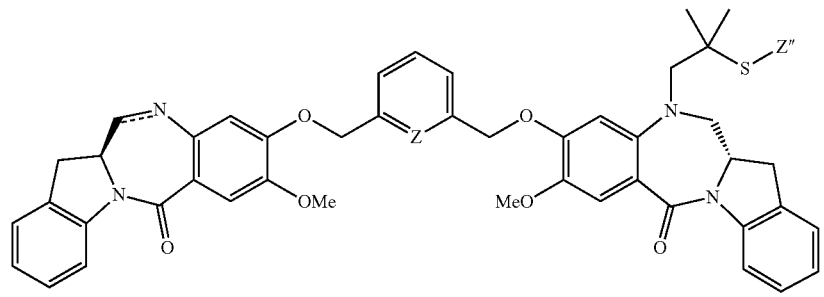
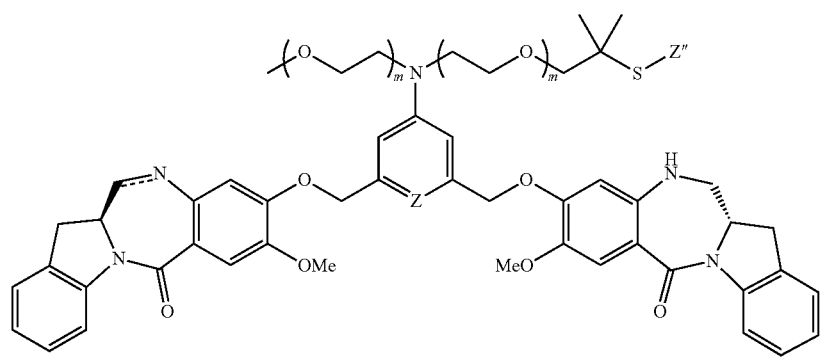
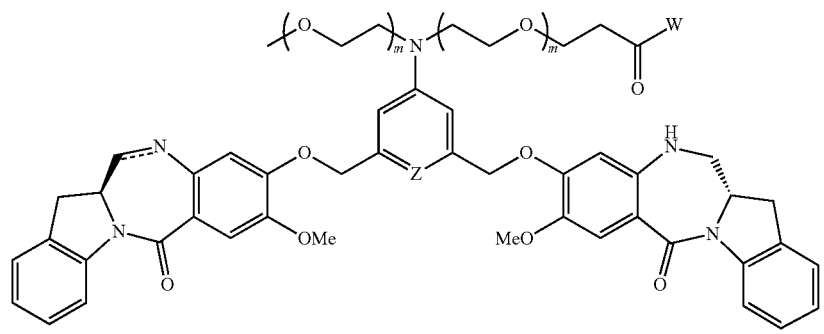
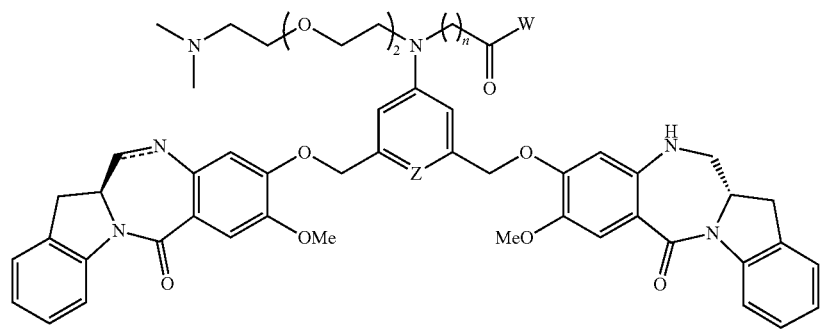

TABLE 3-continued
Structures of representative compounds in the present invention (Continued).
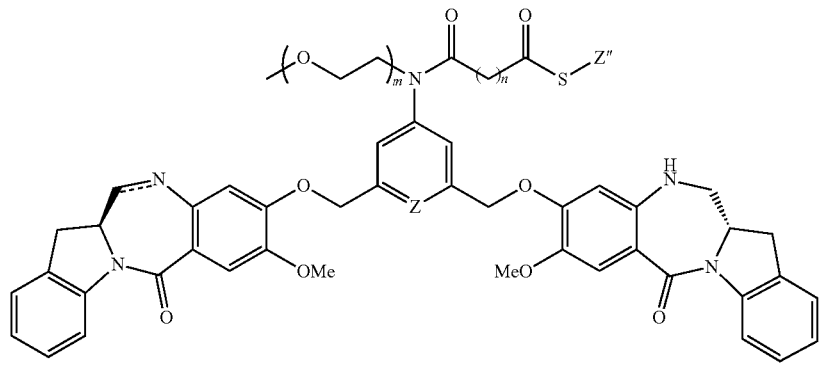
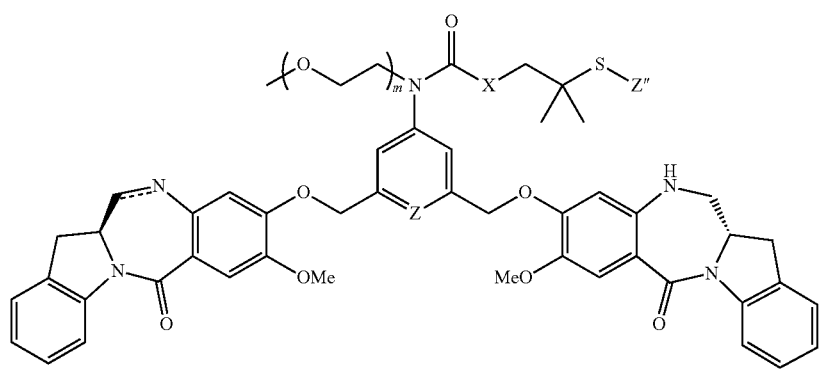
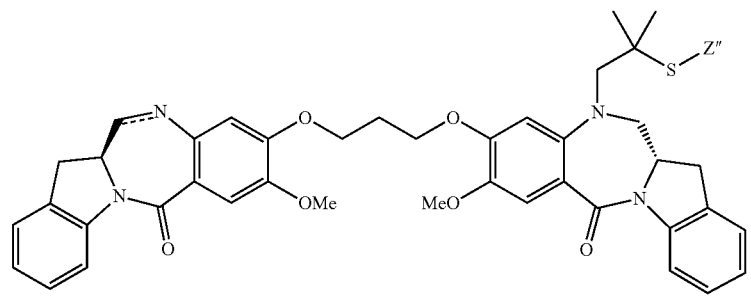
Note:
n = 1, 2 or 3
m = 3 or 4
W = OH, OMe, ONHS, NHNH$_2$, H, Me, Ph, Peptide
X = CH$_2$, O, S, NH, NMe
Z = CH or N
Z" = H, Me, SMe, S(CH$_2$)$_3$C(O)NHS or CH$_2$C(O)NHS or BMPS or SMCC or SPy or SPy-NO$_2$ TABLE 4
Structures of representative compounds in the present invention (Continued).
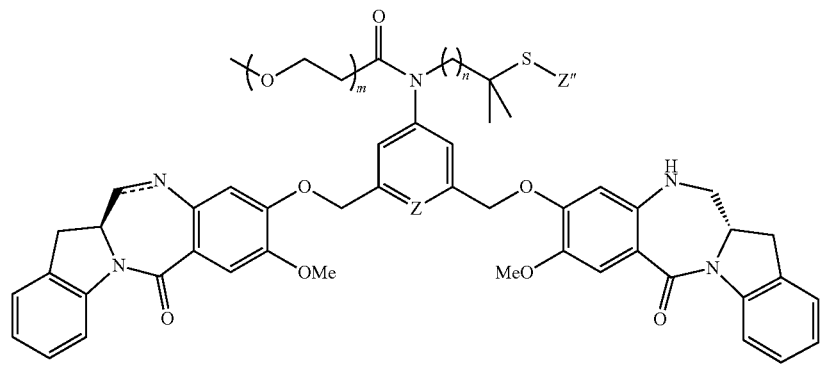
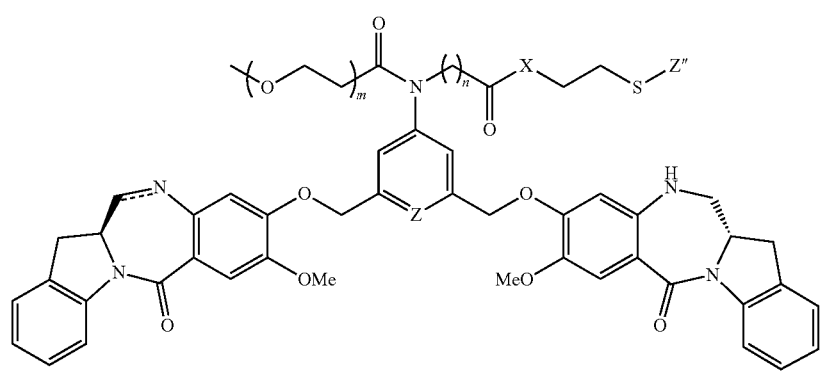
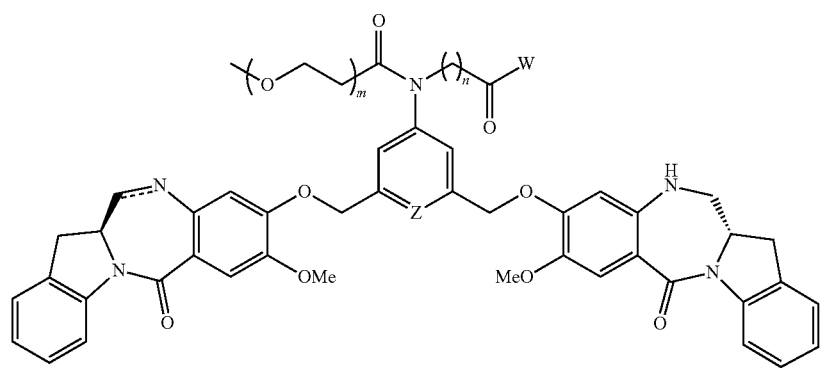
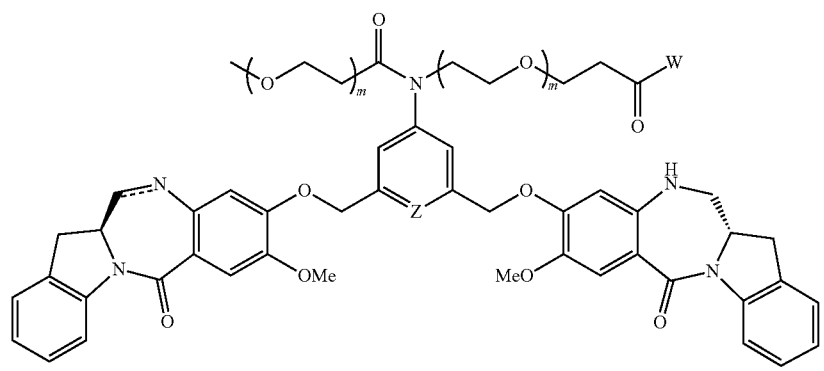

TABLE 4-continued
Structures of representative compounds in the present invention (Continued).
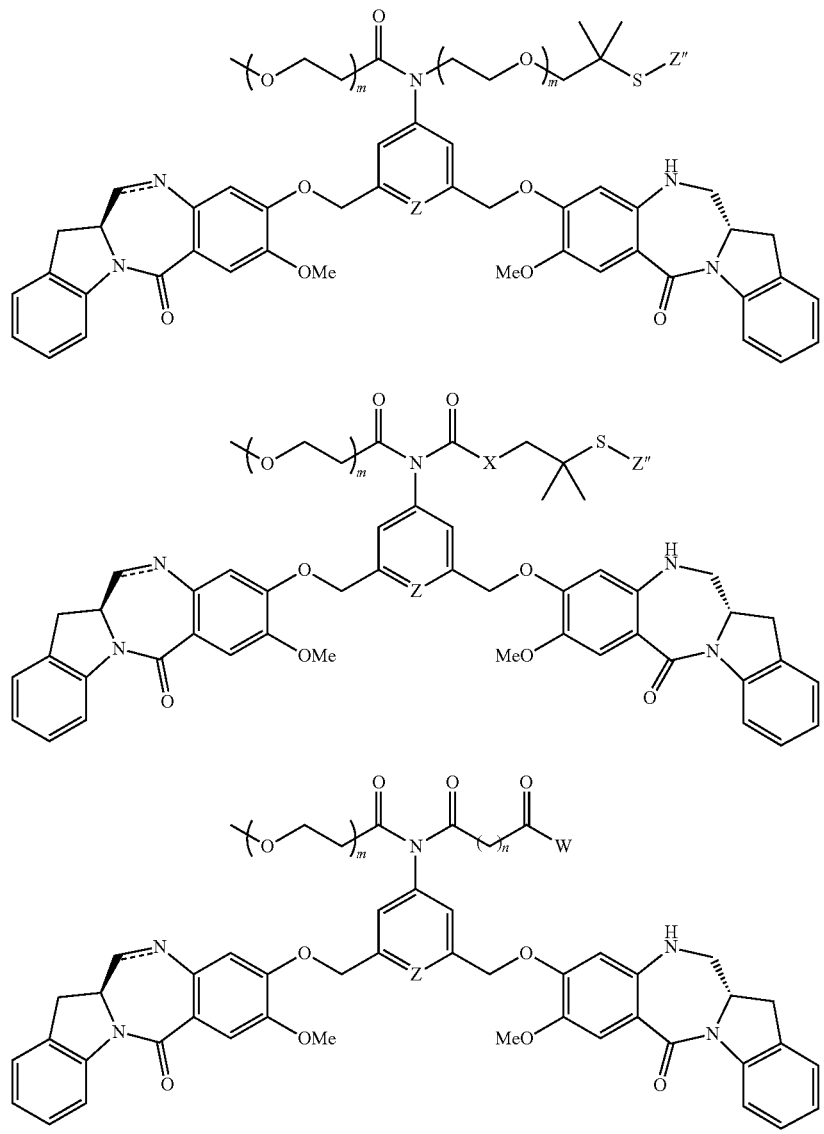
Note:
n = 1, 2 or 3
m = 3 or 4
W = OH, OMe, ONHS, NHNH₂, H, Me, Ph, Peptide
X = CH₂, O, S, NH, NMe
Z = CH or N
Z" = H, Me, SMe, S(CH₂)₃C(O)NHS or CH₂C(O)NHS or BMPS or SMCC or SPy or SPy-NO₂
TABLE 5
Structures of representative compounds in the present invention.
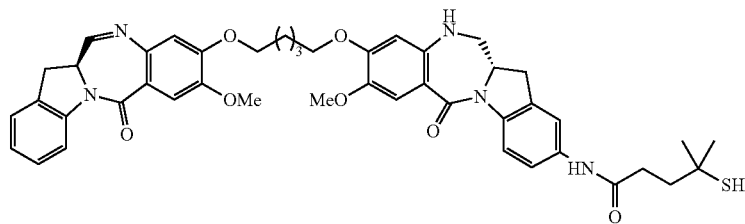

TABLE 5-continued
Structures of representative compounds in the present invention.
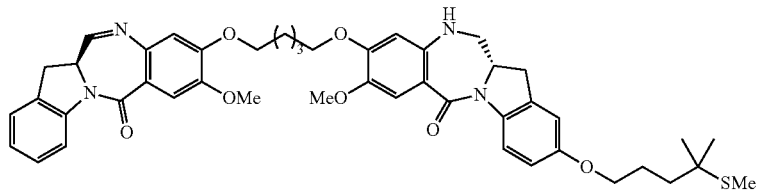
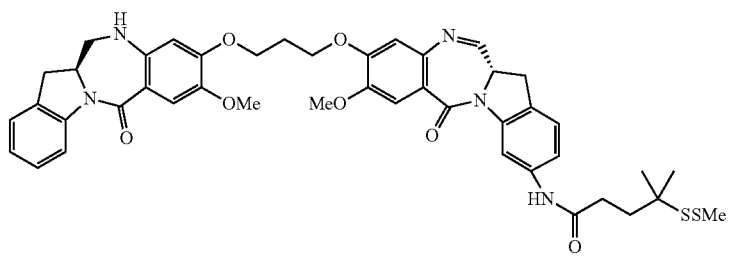
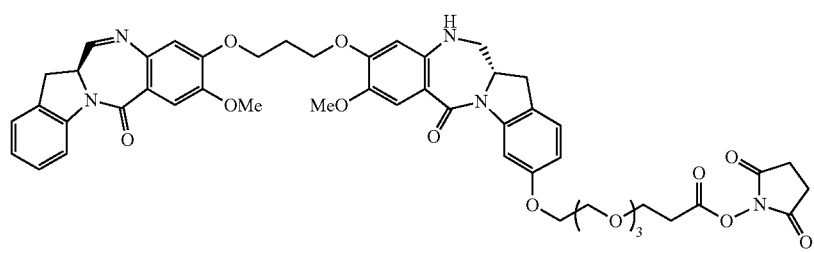
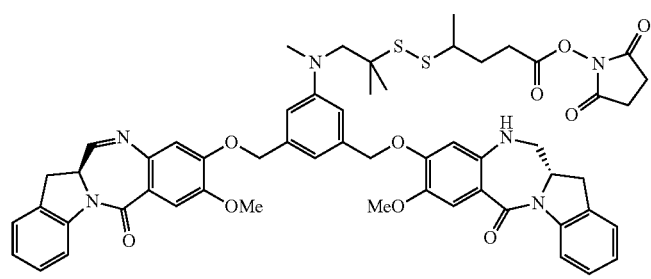 [SMILES: COc1cc2c(cc1OCc1cc(COc3cc4c(cc3OC)C(=O)N3c5ccccc5C[C@H]3CN4)cc(N(C)CC(C)(C)SSC(C)CCC(=O)ON3C(=O)CCC3=O)c1)N=C[C@@H]1Cc3ccccc3N1C2=O]
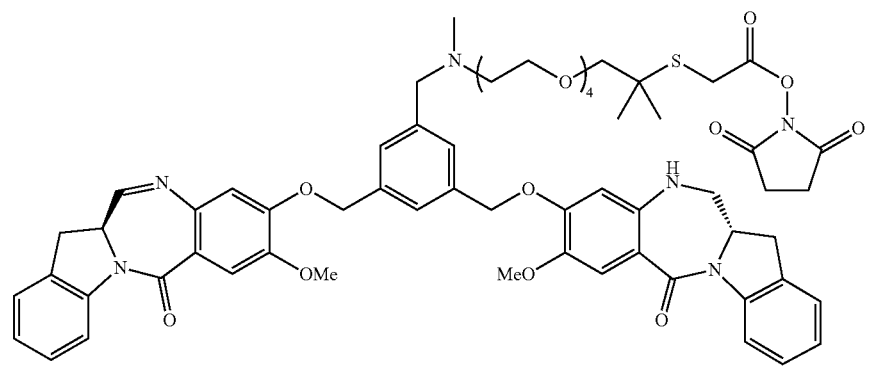

TABLE 5-continued
Structures of representative compounds in the present invention.
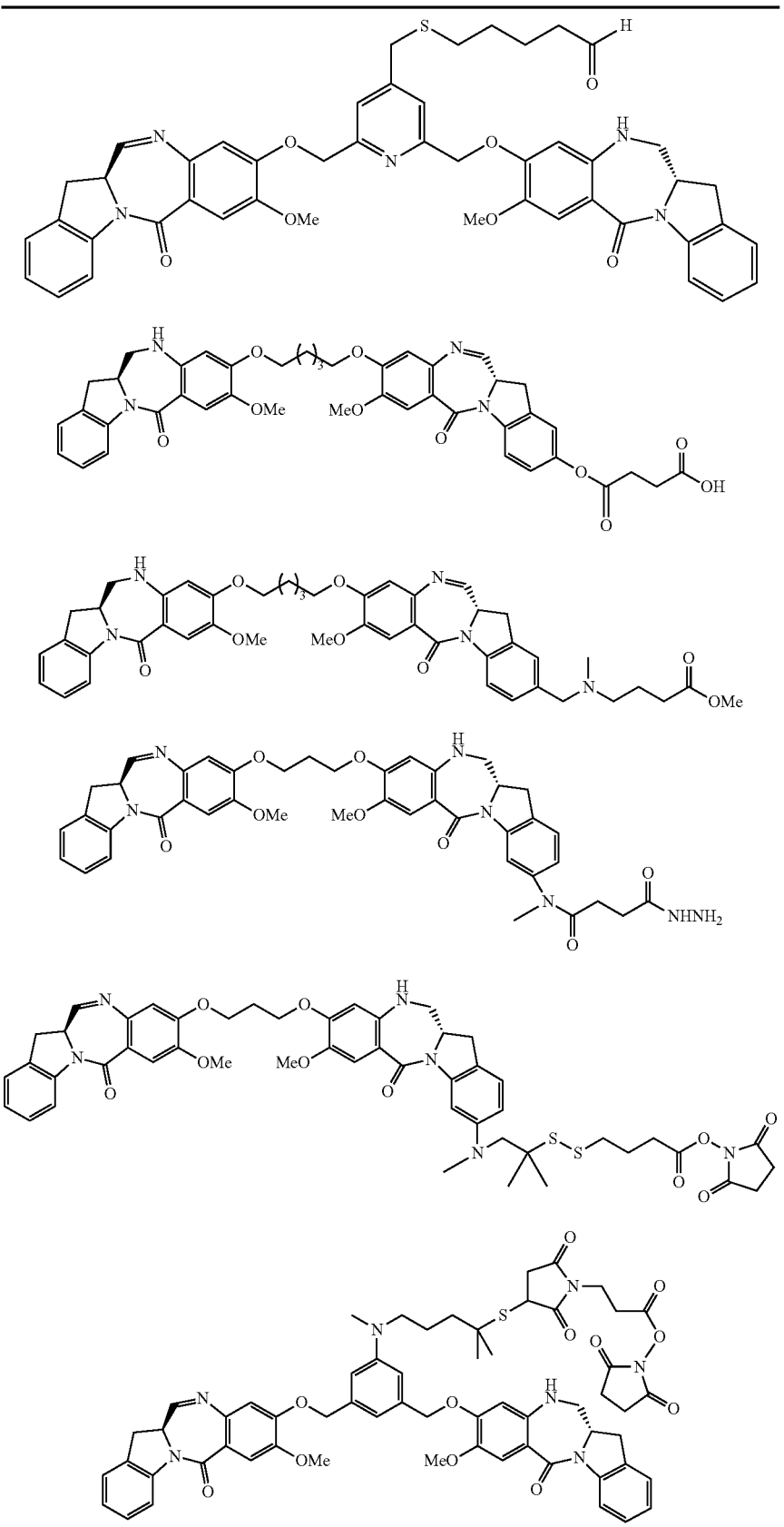

TABLE 5-continued
Structures of representative compounds in the present invention.
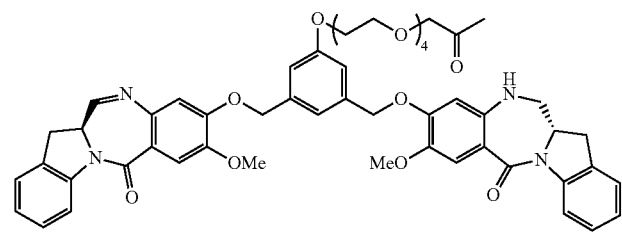
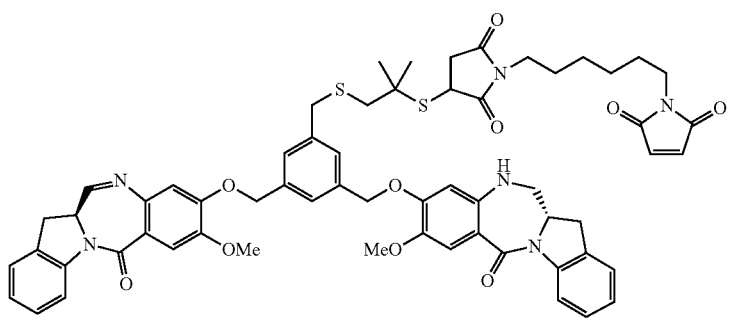 [SMILES: COc1cc2c(cc1OCc1cc(COc3cc4c(cc3OC)C(=O)N3c5ccccc5C[C@H]3CN4)cc(CSCC(C)(C)SC3CC(=O)N(CCCCCCN4C(=O)C=CC4=O)C3=O)c1)N=C[C@@H]1Cc3ccccc3N1C2=O]
TABLE 6
Structures of representative compounds in the present invention (Continued).
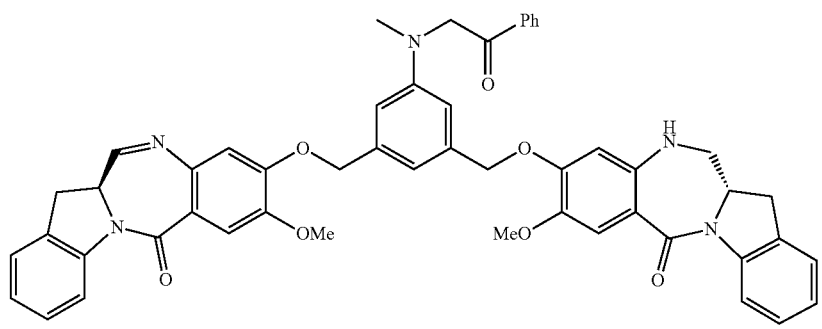 [SMILES: COc1cc2c(cc1OCc1cc(COc3cc4c(cc3OC)C(=O)N3c5ccccc5C[C@H]3CN4)cc(N(C)CC(=O)c3ccccc3)c1)N=C[C@@H]1Cc3ccccc3N1C2=O]
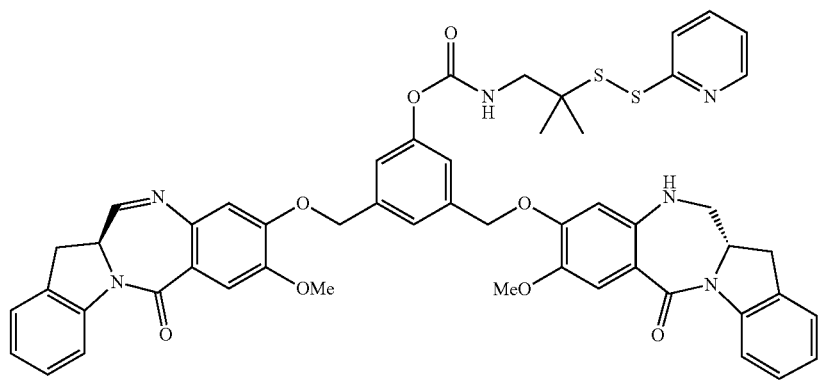 [SMILES: COc1cc2c(cc1OCc1cc(COc3cc4c(cc3OC)C(=O)N3c5ccccc5C[C@H]3CN4)cc(OC(=O)NCC(C)(C)SSc3ccccn3)c1)N=C[C@@H]1Cc3ccccc3N1C2=O]

TABLE 6-continued
Structures of representative compounds in the present invention (Continued).
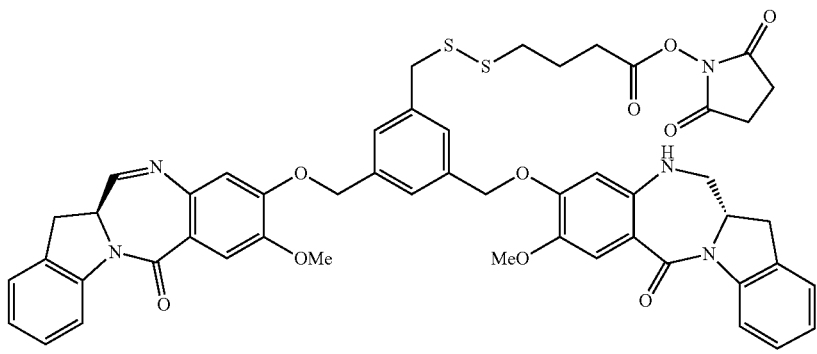 [SMILES: COc1cc2c(cc1OCc1cc(COc3cc4c(cc3OC)C(=O)N3c5ccccc5C[C@H]3CN4)cc(CSSCCCC(=O)ON3C(=O)CCC3=O)c1)N=C[C@@H]1Cc3ccccc3N1C2=O]
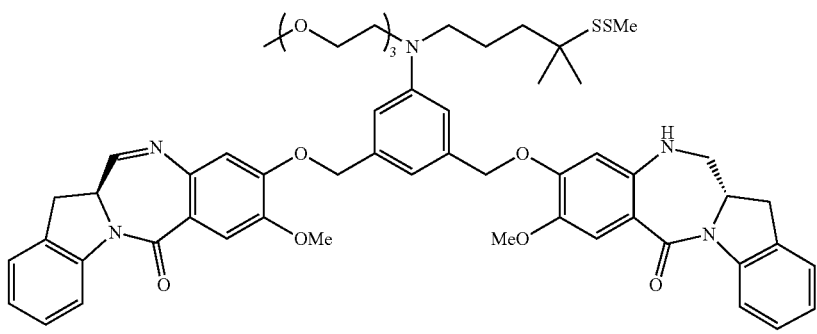
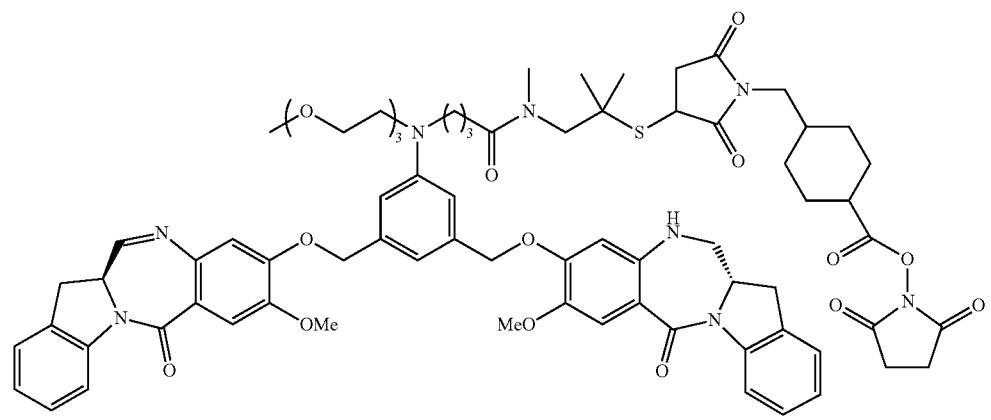
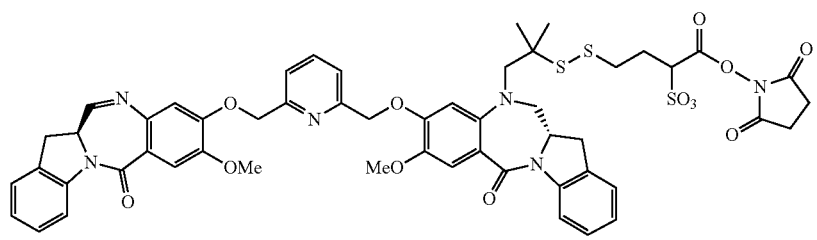

TABLE 6-continued
Structures of representative compounds in the present invention (Continued).
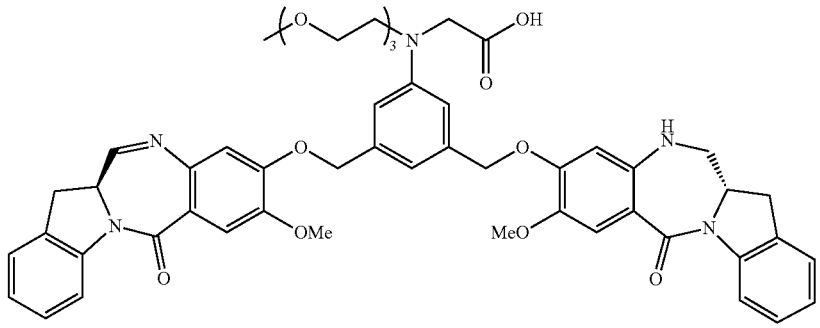
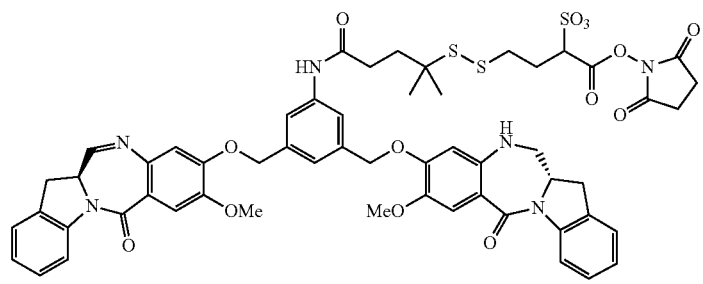
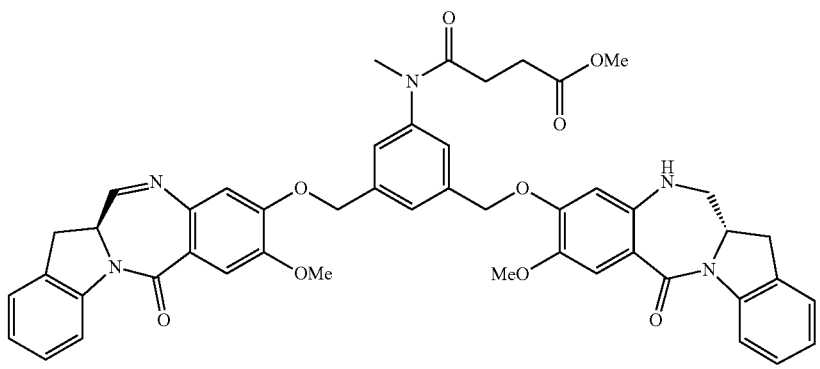 [SMILES: COC(=O)CCC(=O)N(C)c1cc(COc2cc3c(cc2OC)C(=O)N2c4ccccc4C[C@H]2C=N3)cc(COc2cc3c(cc2OC)C(=O)N2c4ccccc4C[C@H]2CN3)c1]
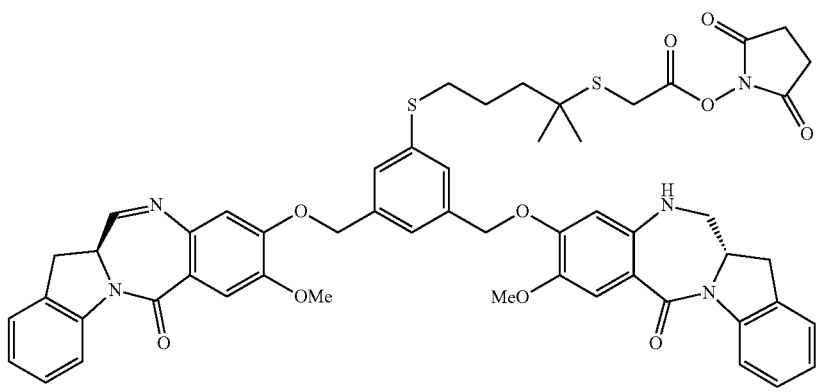 [SMILES: COc1cc2c(cc1OCc1cc(COc3cc4c(cc3OC)C(=O)N3c5ccccc5C[C@H]3CN4)cc(SCCCC(C)(C)SCC(=O)ON3C(=O)CCC3=O)c1)N=C[C@@H]1Cc3ccccc3N1C2=O]

TABLE 6-continued
Structures of representative compounds in the present invention (Continued).
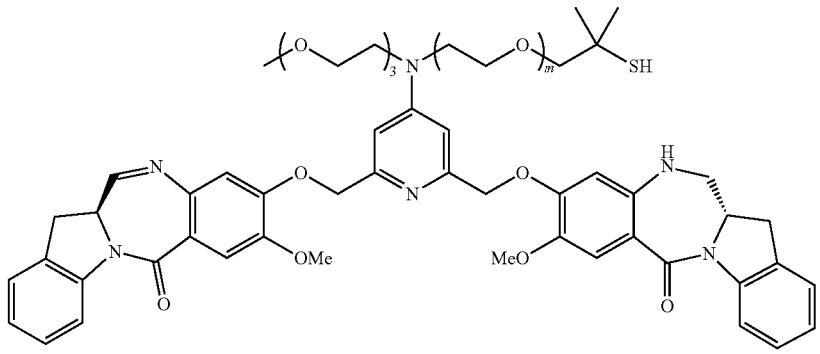
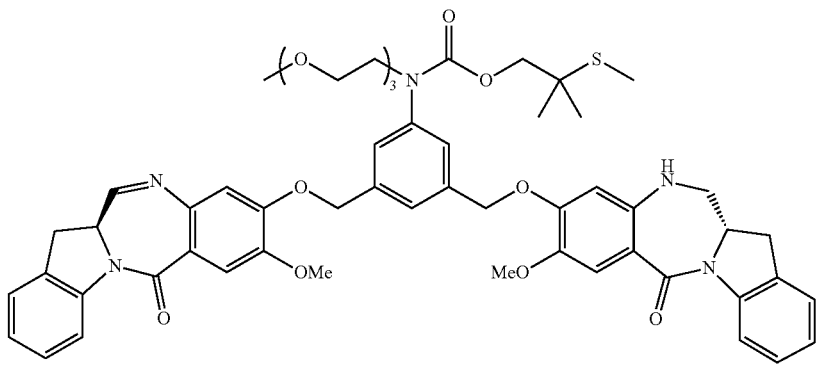
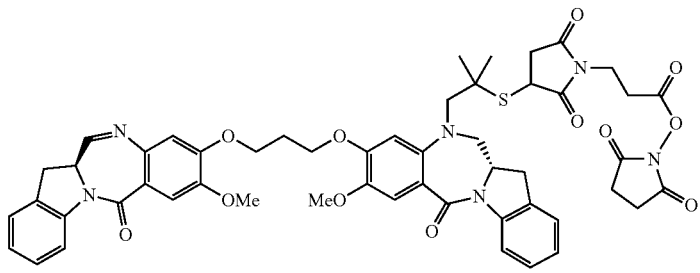 [SMILES: COc1cc2c(cc1OCCCOc1cc3c(cc1OC)C(=O)N1c4ccccc4C[C@H]1CN3CC(C)(C)SC1CC(=O)N(CCC(=O)ON3C(=O)CCC3=O)C1=O)N=C[C@@H]1Cc3ccccc3N1C2=O]
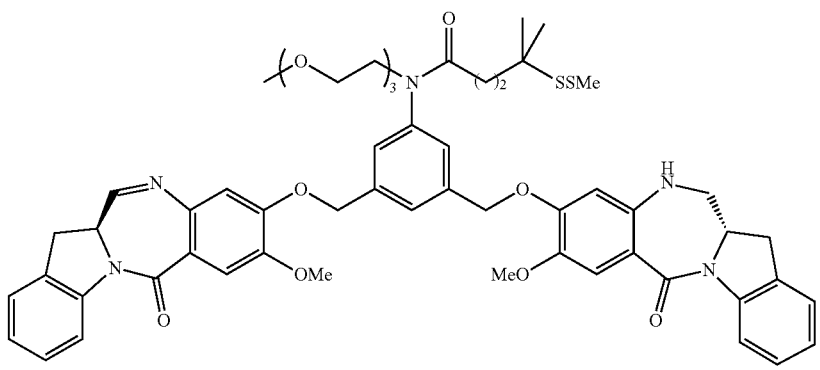

TABLE 7
Structures of representative compounds in the present invention (Continued).
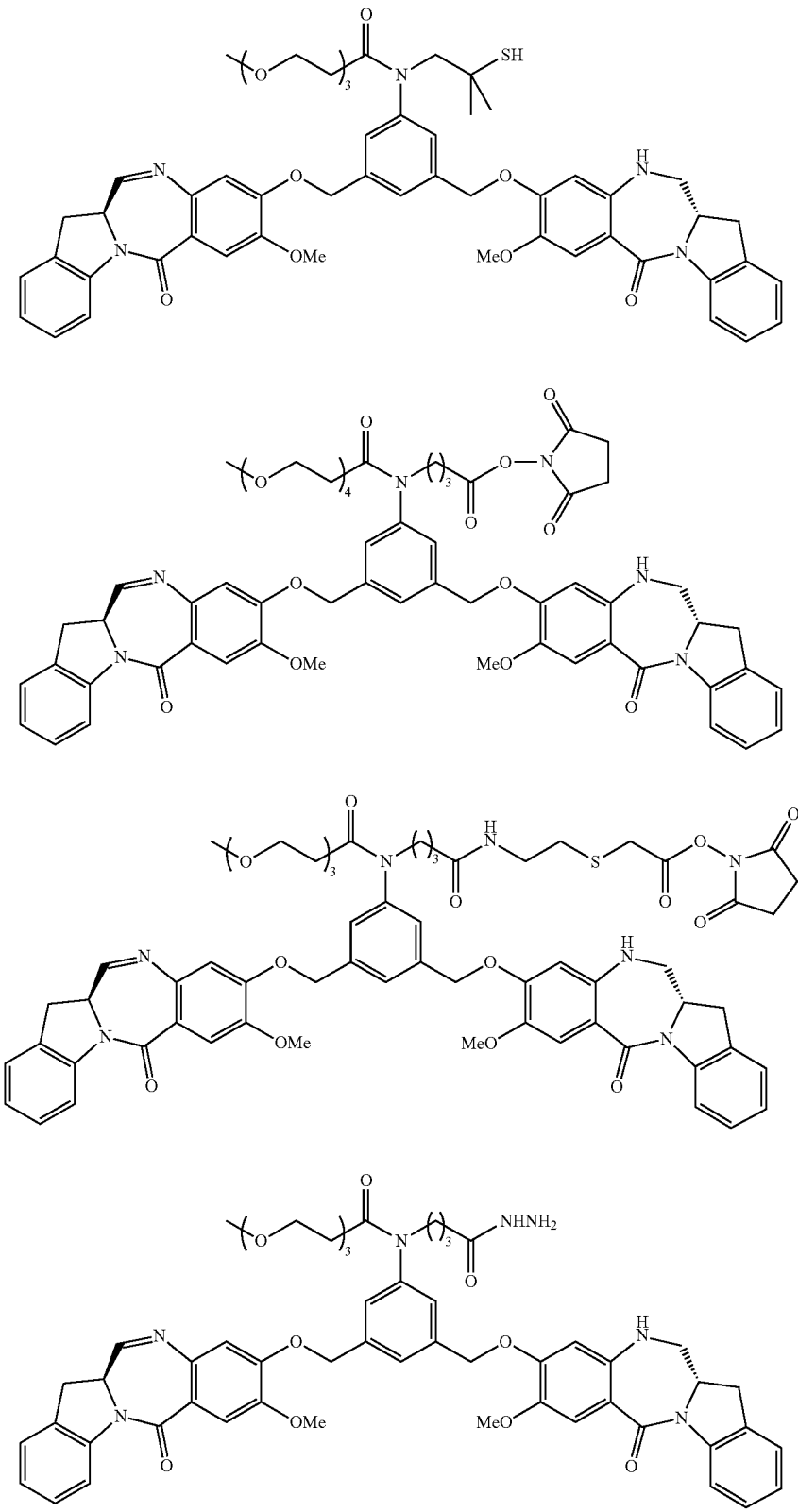

TABLE 8
Structures of representative conjugates of the present invention.
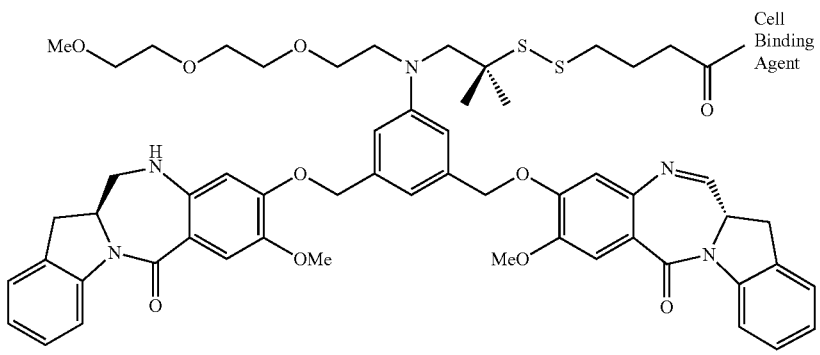
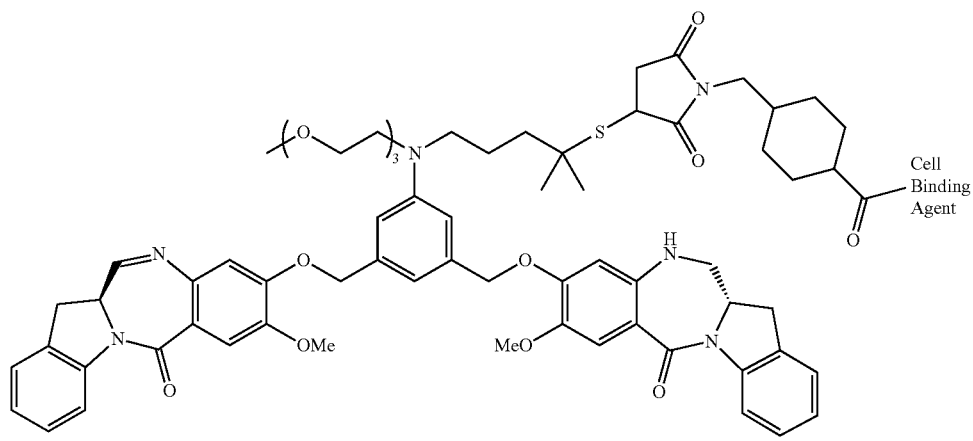
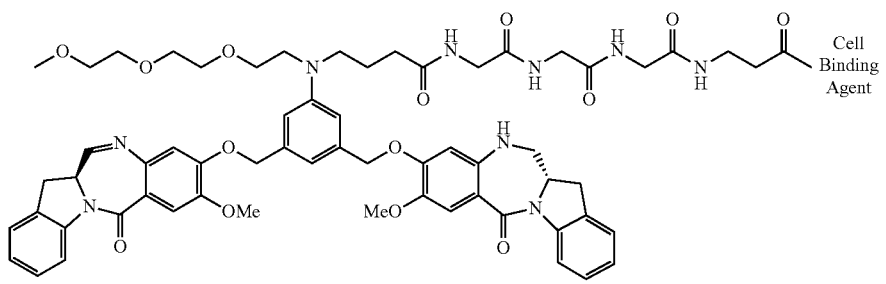 [SMILES: COCCOCCOCCN(CCCC(=O)NCC(=O)NCC(=O)NCC(=O)NCCC(C)=O)c1cc(COc2cc3c(cc2OC)C(=O)N2c4ccccc4C[C@H]2C=N3)cc(COc2cc3c(cc2OC)C(=O)N2c4ccccc4C[C@H]2CN3)c1]
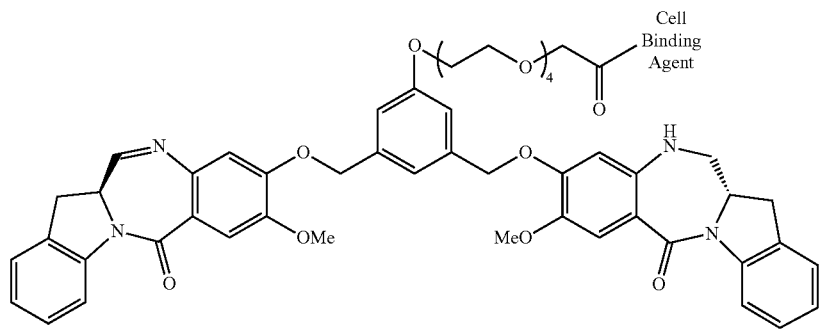

TABLE 8-continued
Structures of representative conjugates of the present invention.
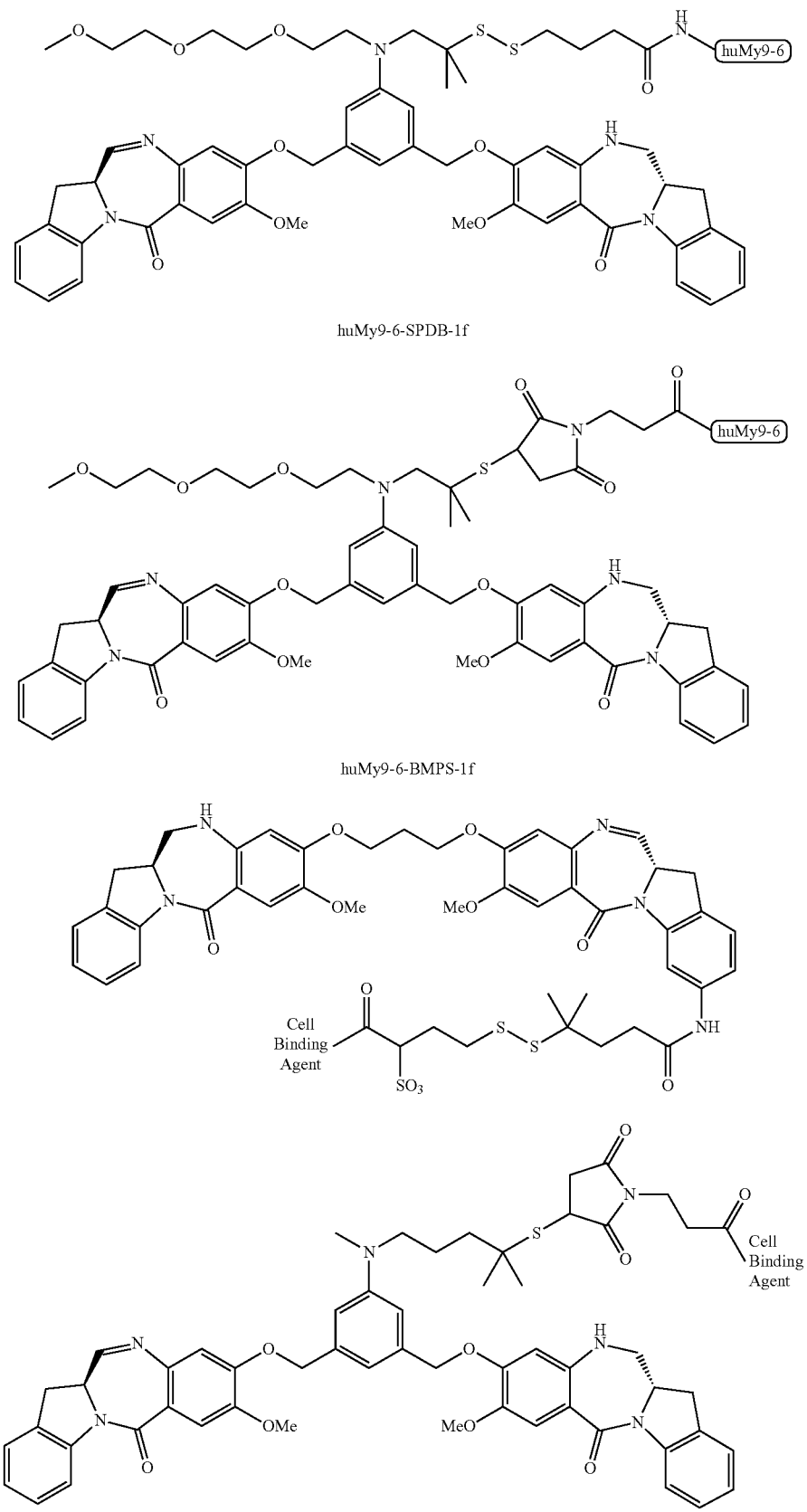
huMy9-6-SPDB-1f
huMy9-6-BMPS-1f TABLE 8-continued Structures of representative conjugates of the present invention.

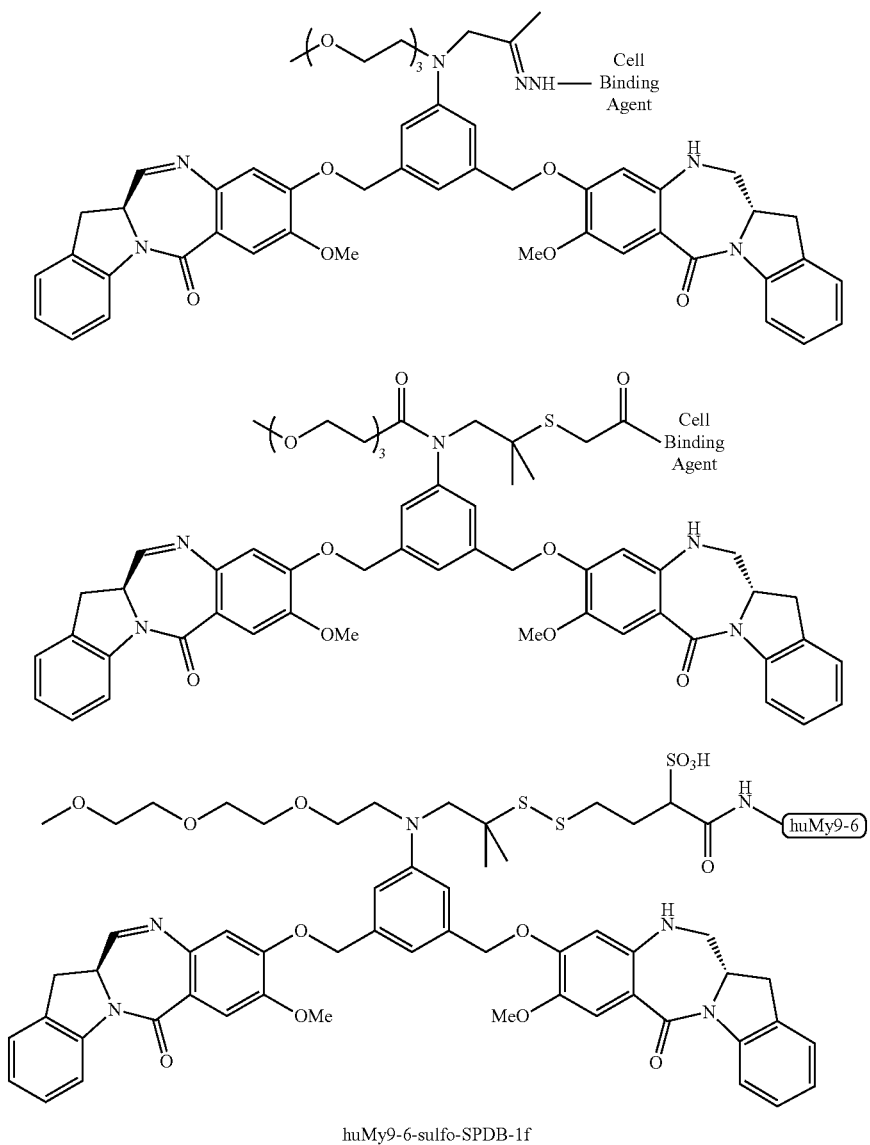

huMy9-6-sulfo-SPDB-1f

In Vitro Cytotoxicity of Compounds and Conjugates

The cytotoxic compounds and cell-binding agent-drug conjugates of the invention can be evaluated for their ability to suppress proliferation of various cancer cell lines in vitro. For example, cell lines such as the human colon carcinoma line COLO 205, the rhabdomyosarcoma cell line RH-30, and the multiple myeloma cell line MOLP-8 can be used for the assessment of cytotoxicity of these compounds and conjugates. Cells to be evaluated can be exposed to the compounds or conjugates for 1-5 days and the surviving fractions of cells measured in direct assays by known methods. $IC_{50}$ values can then be calculated from the results of the assays. Alternatively or in addition, an in vitro cell line sensitivity screen, such as the one described by the U.S. National Cancer Institute (see Voskoglou-Nomikos et al., 2003, Clinical Cancer Res. 9: 42227-4239, incorporated herein by reference) can be used as one of the guides to determine the types of cancers that may be sensitive to treatment with the compounds or conjugates of the invention.

Examples of in vitro potency and target specificity of antibody-cytotoxic agent conjugates of the present invention are shown in FIGS. 25-26. All of the conjugates are extremely cytotoxic on the antigen positive cancer cells with an $IC_{50}$ in the low picomolar range. Antigen negative cell lines remained viable when exposed to the same conjugates. The indolinobenzodiazepine dimers showed target specific potency being 160 fold less potent when blocked with unconjugated antibody huMy9-6 (anti-CD33) and 40 less potent when blocked with unconjugated antibody FOLR1 (anti-folate receptor antibody). For example, the huMy9-6-SPDB-1f conjugate killed antigen positive HL60/QC cells with an $IC_{50}$ value of 10.5 pM, while the addition of an excess of unconjugated huMy9-6 antibody reduced this cytotoxic effect (IC$_{50}$=1.69 nM), demonstrating antigen specificity (FIG. 25A). In addition, the huMy9-6-SPDB-1f conjugate is also highly potent towards both the HL60/ATCC cell line with an IC$_{50}$ value of 21 pM and the NB-4 cell line with an IC$_{50}$ value of 190 pM (FIGS. 25B and 25C).

Similarly, the huFOLR1-SPDB-1f conjugate was highly potent, with an IC$_{50}$ value of 55 pM for antigen positive KB cells (FIG. 26). Addition of an excess of unconjugated huFOLR1 antibody reduced this cytotoxic effect >40 fold, demonstrating antigen-specificity.

The effect of conjugation on antibody binding was measured by comparing the binding of both unconjugated huMy9-6 antibody and the huMy9-6-SPDB-1f conjugate towards the HL60/QC cell line (FIG. 27). FACS analysis revealed that there is no change in binding capability of the conjugate to naked antibody indicating that there is no compromise in binding due to conjugation of the cytotoxic agent to the antibody.

In one example, in vivo efficacy of a cell binding agent/cytotoxic agent conjugate was measured. Nude mice bearing human HL60/QC tumors were treated with huMy9-6-SPDB-1f conjugate and significant tumor regression was observed at multiple doses while untreated mice grew tumors rapidly (FIG. 28). Activity was observed at doses as low as 20 μg/kg which is at least 35-fold lower than the maximum tolerated dose.

The effect of imine saturation towards tolerability is shown in Table 9. Di-imine huFOLR1-drug1 was tested at multiple doses all of which were found to be highly toxic leaving only survivors in the lowest group tested at 50 μg/kg. In contrast the partially reduced mono-imine huFOLR1-Drug 2 and huFOLR1-SPDB-IGN (huFOLR1-SPDB-1f) conjugates were found to have significantly improved tolerability with the huFOLR1-SPDB-IGN (huFOLR1-SPDB-1f) conjugate showing 100% animal survival at the highest doses tested of 560 μg/kg.

Compositions and Methods of Use

The present invention includes a composition (e.g., a pharmaceutical composition) comprising novel benzodiazepine compounds described herein (e.g., indolinobenzodiazepine or oxazolidinobenzodiazepine), derivatives thereof, or conjugates thereof, (and/or solvates, hydrates and/or salts thereof) and a carrier (a pharmaceutically acceptable carrier). The present invention also includes a composition (e.g., a pharmaceutical composition) comprising novel benzodiazepine compounds described herein, derivatives thereof, or conjugates thereof, (and/or solvates, hydrates and/or salts thereof) and a carrier (a pharmaceutically acceptable carrier), further comprising a second therapeutic agent. The present compositions are useful for inhibiting abnormal cell growth or treating a proliferative disorder in a mammal (e.g., human) The present compositions are also useful for treating depression, anxiety, stress, phobias, panic, dysphoria, psychiatric disorders, pain, and inflammatory diseases in a mammal (e.g., human).

The present invention includes a method of inhibiting abnormal cell growth or treating a proliferative disorder in a mammal (e.g., human) comprising administering to said mammal a therapeutically effective amount of novel benzodiazepine compounds described herein (e.g., indolinobenzodiazepine or oxazolidinobenzodiazepine), derivatives thereof, or conjugates thereof, (and/or solvates and salts thereof) or a composition thereof, alone or in combination with a second therapeutic agent.

The present invention also provides methods of treatment comprising administering to a subject in need of treatment an effective amount of any of the conjugates described above.

Similarly, the present invention provides a method for inducing cell death in selected cell populations comprising contacting target cells or tissue containing target cells with an effective amount of a cytotoxic agent comprising any of the cytotoxic compound-cell-binding agents (e.g., indolinobenzodiazepine or oxazolidinobenzodiazepine dimer linked to a cell binding agent) of the present invention, a salt or solvate thereof. The target cells are cells to which the cell-binding agent can bind.

If desired, other active agents, such as other anti-tumor agents, may be administered along with the conjugate.

Suitable pharmaceutically acceptable carriers, diluents, and excipients are well known and can be determined by those of ordinary skill in the art as the clinical situation warrants.

Examples of suitable carriers, diluents and/or excipients include: (1) Dulbecco's phosphate buffered saline, pH about 7.4, containing or not containing about 1 mg/mL to 25 mg/mL human serum albumin, (2) 0.9% saline (0.9% w/v NaCl), and (3) 5% (w/v) dextrose; and may also contain an antioxidant such as tryptamine and a stabilizing agent such as Tween 20.

The method for inducing cell death in selected cell populations can be practiced in vitro, in vivo, or ex vivo.

Examples of in vitro uses include treatments of autologous bone marrow prior to their transplant into the same patient in order to kill diseased or malignant cells: treatments of bone marrow prior to their transplantation in order to kill competent T cells and prevent graft-versus-host-disease (GVHD); treatments of cell cultures in order to kill all cells except for desired variants that do not express the target antigen; or to kill variants that express undesired antigen.

The conditions of non-clinical in vitro use are readily determined by one of ordinary skill in the art.

Examples of clinical ex vivo use are to remove tumor cells or lymphoid cells from bone marrow prior to autologous transplantation in cancer treatment or in treatment of autoimmune disease, or to remove T cells and other lymphoid cells from autologous or allogenic bone marrow or tissue prior to transplant in order to prevent GVHD. Treatment can be carried out as follows. Bone marrow is harvested from the patient or other individual and then incubated in medium containing serum to which is added the cytotoxic agent of the invention, concentrations range from about 10 μM to 1 pM, for about 30 minutes to about 48 hours at about 37° C. The exact conditions of concentration and time of incubation, i.e., the dose, are readily determined by one of ordinary skill in the art. After incubation the bone marrow cells are washed with medium containing serum and returned to the patient intravenously according to known methods. In circumstances where the patient receives other treatment such as a course of ablative chemotherapy or total-body irradiation between the time of harvest of the marrow and reinfusion of the treated cells, the treated marrow cells are stored frozen in liquid nitrogen using standard medical equipment.

For clinical in vivo use, the cytotoxic agent of the invention will be supplied as a solution or a lyophilized powder that are tested for sterility and for endotoxin levels. Examples of suitable protocols of conjugate administration are as follows. Conjugates are given weekly for 4 weeks as an intravenous bolus each week. Bolus doses are given in 50 to 1000 mL of normal saline to which 5 to 10 mL of human serum albumin can be added. Dosages will be 10 μg to 2000 mg per administration, intravenously (range of 100 ng to 20 mg/kg per day). After four weeks of treatment, the patient can continue to receive treatment on a weekly basis. Specific clinical protocols with regard to route of administration, excipients, diluents, dosages, times, etc., can be determined by one of ordinary skill in the art as the clinical situation warrants.

Examples of medical conditions that can be treated according to the in vivo or ex vivo methods of inducing cell death in selected cell populations include malignancy of any type including, for example, cancer of the lung (small cell and non-small cell), breast, colon, brain, prostate, kidney, pancreas, ovary, head and neck, skin (melanoma), Merkel cell carcinoma, glioblastoma, neuroblastoma, and cancers of lymphatic organs; autoimmune diseases, such as systemic lupus, rheumatoid arthritis, and multiple sclerosis; graft rejections, such as renal transplant rejection, liver transplant rejection, lung transplant rejection, cardiac transplant rejection, and bone marrow transplant rejection; graft versus host disease; viral infections, such as CMV infection, HIV infection, AIDS, etc.; and parasite infections, such as giardiasis, amoebiasis, schistosomiasis, and others as determined by one of ordinary skill in the art.

Cancer therapies and their dosages, routes of administration and recommended usage are known in the art and have been described in such literature as the Physician's Desk Reference (PDR). The PDR discloses dosages of the agents that have been used in treatment of various cancers. The dosing regimen and dosages of these aforementioned chemotherapeutic drugs that are therapeutically effective will depend on the particular cancer being treated, the extent of the disease and other factors familiar to the physician of skill in the art and can be determined by the physician. The contents of the PDR are expressly incorporated herein in its entirety by reference. One of skill in the art can review the PDR, using one or more of the following parameters, to determine dosing regimen and dosages of the chemotherapeutic agents and conjugates that can be used in accordance with the teachings of this invention. These parameters include:
Comprehensive index
By Manufacturer
Products (by company's or trademarked drug name)
Category index
Generic/chemical index (non-trademark common drug names)
Color images of medications
Product information, consistent with FDA labeling
Chemical information
Function/action
Indications & Contraindications
Trial research, side effects, warnings
Analogues and Derivatives One skilled in the art of cytotoxic agents will readily understand that each of the cytotoxic agents described herein can be modified in such a manner that the resulting compound still retains the specificity and/or activity of the starting compound. The skilled artisan will also understand that many of these compounds can be used in place of the cytotoxic agents described herein. Thus, the cytotoxic agents of the present invention include analogues and derivatives of the compounds described herein.

All references cited herein and in the examples that follow are expressly incorporated by reference in their entireties.

EXAMPLES

The invention will now be illustrated by reference to non-limiting examples. Unless otherwise stated, all percents, ratios, parts, etc. are by weight. All reagents were purchased from the Aldrich Chemical Co., New Jersey, or other commercial sources. Nuclear Magnetic Resonance ($^1$H NMR) spectra were acquired on a Bruker 400 MHz instrument and mass spectra were acquired on a Bruker Daltonics Esquire 3000 instrument using electrospray ionization.

Example 1

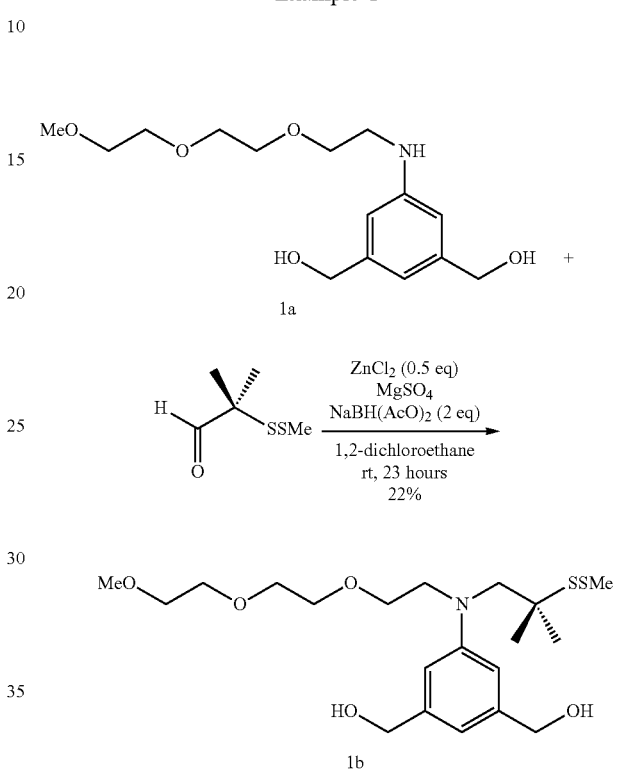

Compound 1b:

To a stirred solution of the aniline 1a (1.55 g, 5.18 mmol) and 2-(methyldithio)-isobutyraldehyde (0.7 mL, 5.18 mmol) in anhydrous 1,2-dichloromethane (20 mL) was added sodium triacetoxyborohydride (1.1 g, 5.18 mmol) and zinc chloride powder (353 mg, 2.59 mmol) followed by the addition of anhydrous magnesium sulfate (800 mg). The mixture was stirred at room temperature (rt) for 6 hours then a second portion of 2-(methyldithio)-isobutyraldehyde (0.7 mL, 5.18 mmol) and sodium triacetoxyborohydride (1.1 g, 5.18 mmol) were added. It continued to be stirred at rt overnight. The reaction mixture was filtered through celite and washed with dichloromethane. The filtrate was concentrated and the remainder was purified by silica gel chromatography (Combiflash, 40 g column, dichloromethane/MeOH) to give compound 1b (487 mg y=22%) as colorless oil. Unreacted starting material aniline 1a (1.02 g) was also recovered in 65% yield. $^1$H NMR (400 Hz, CDCl$_3$): δ 6.76 (s, 2H), 6.63 (s, 1H), 4.55 (s, 4H), 3.65-3.51 (m, 14H), 3.35 (s, 3H), 2.44 (s, 3H), 1.33 (s, 6H); $^{13}$C NMR (400 Hz, CDCl$_3$): δ 149.0, 142.35, 114.0, 111.1, 71.98, 70.7, 70.6, 70.5, 67.6, 65.5, 59.75, 59.1, 53.9, 51.9, 26.6, 25.7, 20.75; MS (m/z). found 456.2 (M+Na)$^+$. See FIG. 1.

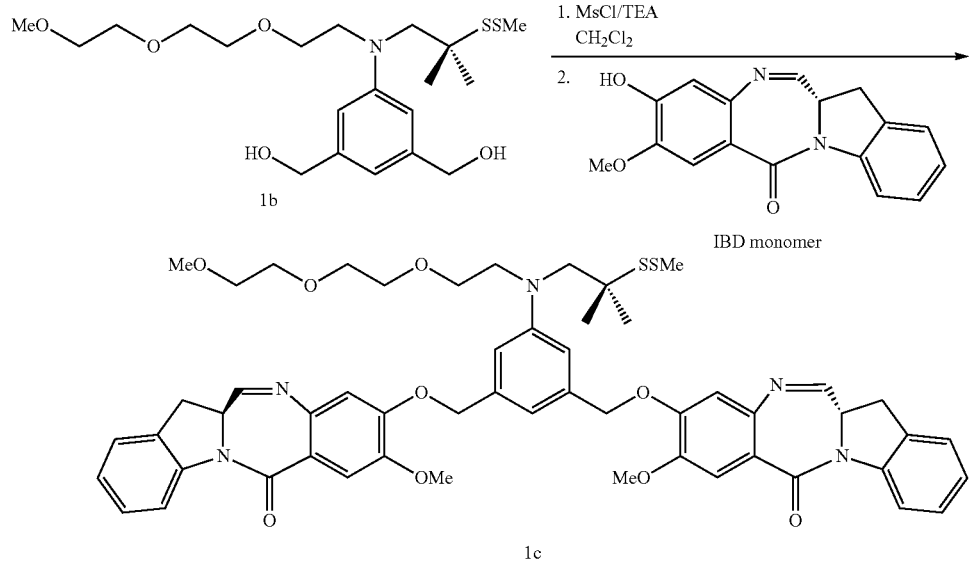

Compound 1c:

To a stirred solution of 1b (243 mg, 0.56 mmol) in anhydrous dichloromethane (3.5 mL) was added triethylamine (234 µl, 1.68 mmol). The mixture was cooled to −10° C. and methanesulfonyl chloride (113 µl, 1.46 mmol) was added slowly over 15 minutes via a syringe. The solution continued to be stirred for 60 minutes at −10~−7° C. and quenched by addition of ice/water. It was diluted with ethyl acetate and washed with cold water. The organic layer was dried over anhydrous sodium sulfate, filtered, concentrated and high vacuumed to give the mesylates as light yellowish oil (340 mg). The mesylates was transferred into a 10 mL round-bottomed flask with ethyl acetate/dichloromethane, concentrated and high vacuumed. IBD monomer (412 mg, 1.4 mmol) was added followed by the addition of anhydrous dimethylformamide (3 mL) and anhydrous potassium carbonate (232 mg, 1.68 mmol). The obtained yellowish mixture was stirred at room temperature overnight. It was diluted with dichloromethane and washed with brine. The organic layer was dried over anhydrous sodium sulfate, filtered and concentrated. The residue was dissolved in dichloromethane and loaded on silica gel column and eluted with dichloromethane/methanol (15:1 then 10:1). The fractions that contained compound 1c were combined and concentrated to give 705 mg of crude product which was further purified by preparative reverse phase HPLC (C18 column, eluted with acetonitrile/water) to give compound 1c as a yellowish fluffy solid (181 mg, y=33%). $^1$H NMR (400 Hz, CDCl$_3$): δ 8.28 (d, J=8.0 Hz, 2H), 7.86 (d, J=3.6 Hz, 2H), 7.59 (s, 2H), 7.31-7.26 (m, 4H), 7.12 (t, J=7.6 Hz, 2H), 6.87-6.80 (m, 5H), 5.18 (dd, J$_1$=20.8 Hz, J$_2$=12.4 Hz, 4H), 4.50-4.47 (m, 2H), 3.99 (s, 6H), 3.75-3.48 (m, 18H), 3.37 (s, 3H), 2.44 (s, 3H), 1.32 (s, 6H); MS (m/z). found 1025.9 (M+H$_2$O+Na)$^+$, 1043.9 (M+2H$_2$O+Na)$^+$, 983.8 (M−H)$^−$, 1055.8 (M+4H$_2$O−H)$^−$. See FIG. 1.

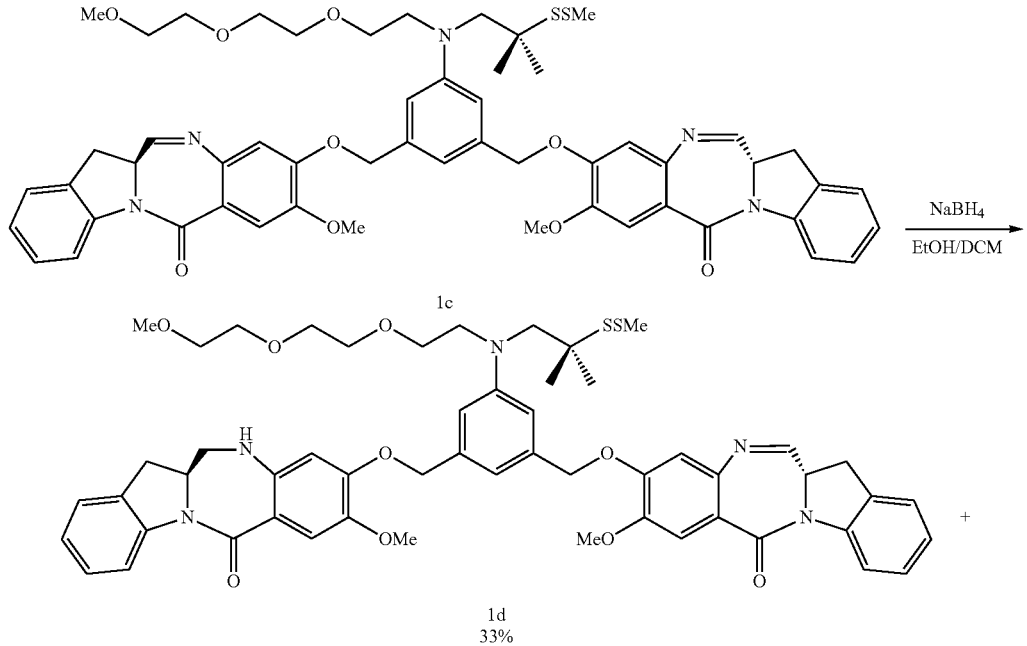

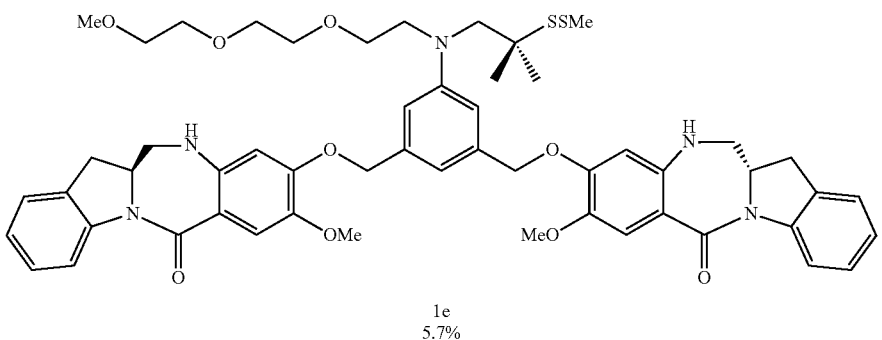

1e
5.7%

Compound 1d:

To a stirred solution of compound 1c (112 mg, 0.114 mmol) in anhydrous dichloromethane (0.3 mL) and absolute ethanol (0.6 mL) was added sodium borohydride (0.9 mg, 0.023 mmol) at 0° C. The ice bath was removed after 5 minutes and the mixture was stirred at room temperature for 3 hours and then cooled to 0° C. and quenched with saturated ammonium chloride, diluted with dichloromethane, separated and the organic layer was washed with brine, dried over anhydrous $Na_2SO_4$ and filtered through celite and concentrated. The residue was purified by reverse phase HPLC (C18 column, acetonitrile/water). The corresponding fractions were extracted with dichloromethane and concentrated to obtain the products 1d, 1e and the unreacted starting material 1c. Compound 1d: 37.1 mg (y=33%), MS (m/z). found 1010.4 $(M+Na)^+$, 1028.4 $(M+H_2O+Na)^+$, 1040.3 $(M+3H_2O-H)^-$; compound 1e: 6.4 mg (y=5.7%), MS (m/z). found 1012.4 $(M+Na)^+$; compound 1c: 44.1 mg (y=39%). See FIG. 1.

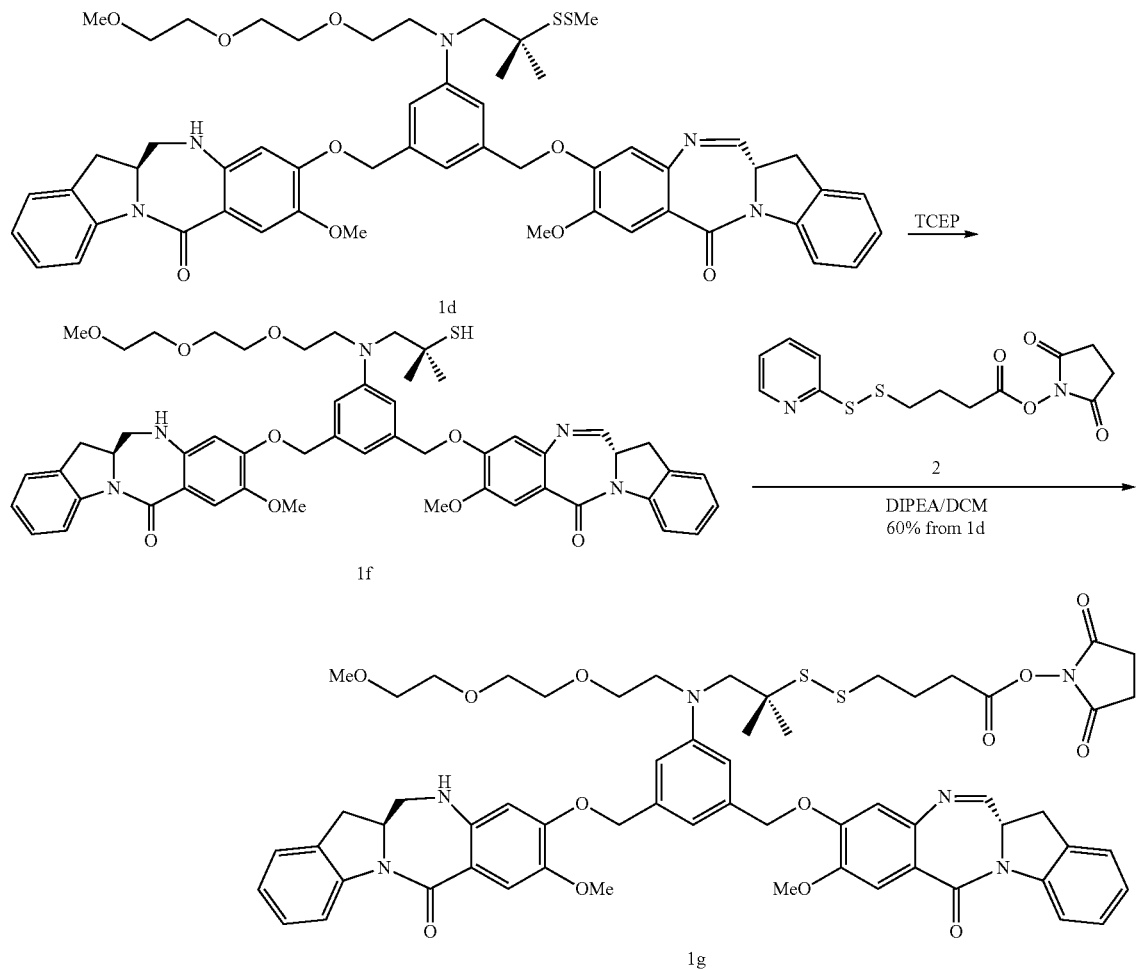

Compound 1g:

To a stirred solution of 1d (23.6 mg, 0.024 mmol) in acetonitrile (3 mL) and methanol (3 mL) was added freshly prepared TCEP solution (17 mg of TCEP HCl salt was neutralized with saturated sodium bicarbonate to pH 6~6.5 then diluted with 0.5 mL of pH 6.5 phosphate buffer) at room temperature. The mixture was stirred at room temperature for 3 hours and then diluted with dichloromethane and deionized water, separated and the organic layer was washed with brine, dried over anhydrous sodium sulfate and filtered. The filtrate was concentrated and high vacuumed to give 22 mg of 1f as light yellowish foam. Another 18 mg of 1f was prepared from 19 mg of 1d following the same procedure. The combined 40 mg (0.042 mmol) of if was dissolved in anhydrous dichloromethane (0.5 mL) and stirred. To this stirred solution was added SPDB NHS ester 2 (34.6 mg, 80% purity, 0.085 mmol) and diisopropylethylamine (15 μl, 0.085 mmol). It continued to be stirred at room temperature overnight, quenched with saturated ammonium chloride and diluted with dichloromethane, separated and washed with brine, dried over sodium sulfate, filtered and concentrated. The residue was purified by preparative reverse phase HPLC (C18 column, acetonitrile/water). The fractions containing product were combined, extracted with dichloromethane and concentrated to give compound 1g as white solid (29.7 mg, y=60%). $^1$H NMR (400 Hz, CD$_3$CN): δ 8.28-8.25 (m, 1H), 8.20-8.17 (m, 1H), 7.87-7.84 (m, 1H), 7.49 (d, J=4.4 Hz, 1H), 7.39 (d, J=4.4 Hz, 1H), 7.31-7.19 (m, 4H), 7.13-7.01 (m, 2H), 6.92-6.87 (m, 3H), 6.77 (bs, 1H), 6.31-6.29 (m, 1H), 5.16-5.09 (m, 2H), 5.00 (d, J=4.4 Hz, 2H), 4.94 (bs, —NH), 4.48-4.43 (m, 1H), 4.40-4.34 (m, 1H), 3.90 (d, J=4.4 Hz, 3H), 3.77 (d, J=4.4 Hz, 3H), 3.64-3.39 (m, 18H), 3.26 (d, J=4.4 Hz, 3H), 2.82-2.70 (m, 8H), 2.17 (d, J=4.4 Hz, 1H), 2.08-2.01 (m, 3H), 1.30 (d, J=4.4 Hz, 6H); MS (m/z). found 1025.9 (M+H$_2$O+Na)$^+$, 1043.9 (M+2H$_2$O+Na)$^+$, 983.8 (M–H)$^−$, 1055.8 (M+4H$_2$O–H)$^−$; MS (m/z). found 1179.5 (M+Na)$^+$. See FIG. 1.

Example 2

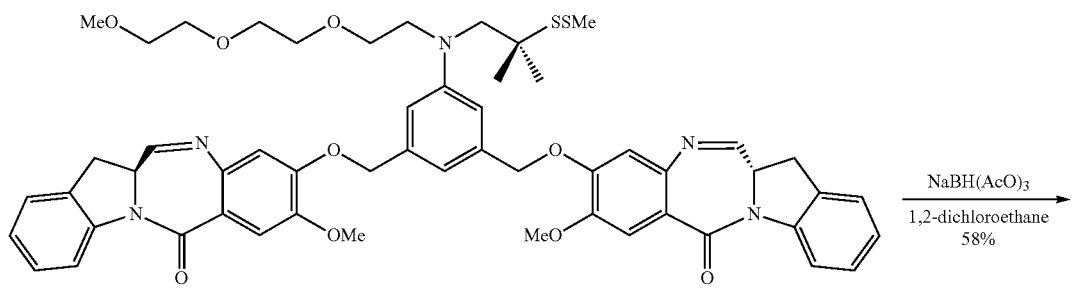

1c

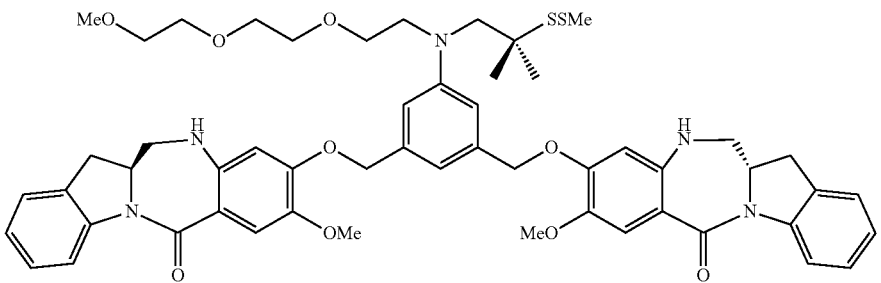

1e

Compound 1e:

To a stirred solution of 1c (8 mg, 0.0081 mmol) in anhydrous 1,2-dichloromethane (0.2 mL) was added sodium triacetoxyborohydride (3.8 mg, 0.018 mmol). The mixture was stirred at room temperature for 1.5 hours, then the mixture was diluted with dichloromethane and quenched with saturated sodium bicarbonate, separated and the organic layer was washed with brine, dried over sodium sulfate, and filtered. The filtrate was concentrated and the remainder was purified by reverse phase HPLC (C18 column, acetonitrile/water) to give compound 1e as a white solid (4.7 mg, y=58%). MS (m/z). found 1012.4 (M+Na)$^+$, 1024.2 (M+2H$_2$O−H)$^−$. See FIG. 2.

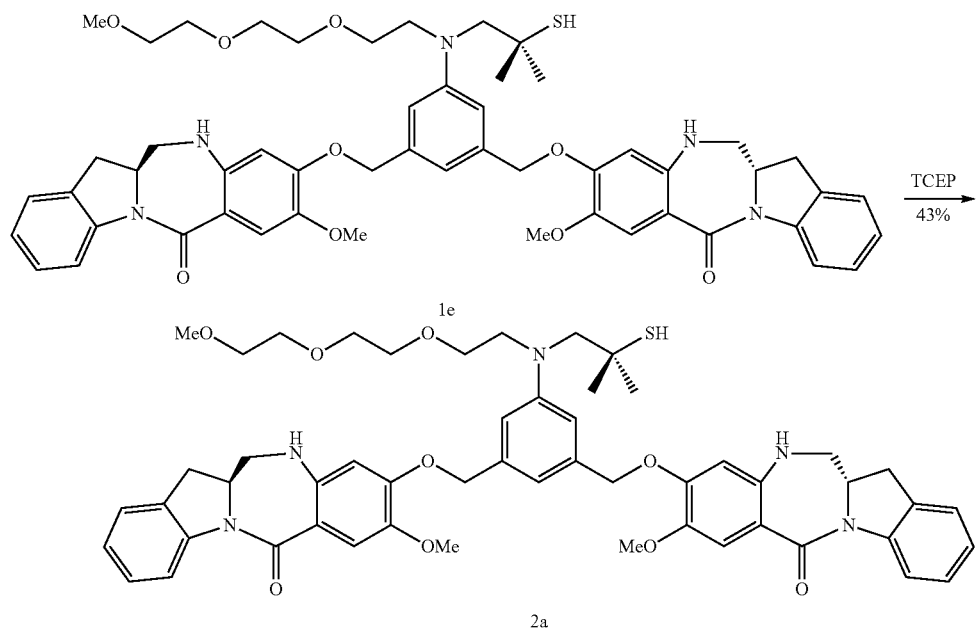

Compound 2a:

To a stirred solution of compound 1e (12 mg, 0.012 mmol) in acetonitrile (1 mL) and methanol (3 mL) was added freshly prepared TCEP solution (11 mg of TCEP HCl salt was neutralized with saturated sodium bicarbonate to pH ~6.5 then diluted with 0.4 mL of pH 6.5 phosphate buffer) at room temperature. The mixture was stirred at room temperature for 3.5 hours and then diluted with dichloromethane and deionized water, separated and the organic layer was washed with brine, dried over anhydrous sodium sulfate and filtered. The filtrate was concentrated and the remainder was purified by reverse phase HPLC (C18 column, acetonitrile/water) to give compound 2a as a white solid (4.9 mg, y=43%). MS (m/z). found 966.4 (M+Na)$^+$, 978.2 (M+2H$_2$O−H)$^−$. See FIG. 2.

Example 3

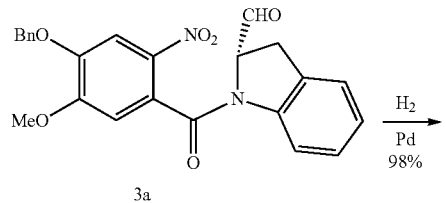

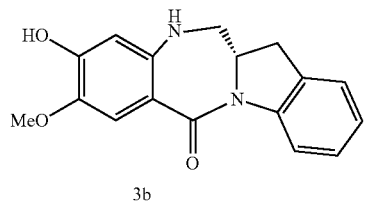

Compound 3b:

To a solution of compound 3a (830 mg, 1.9 mmol) in methanol (15 mL) was added Pd/C (10%, 204 mg, 0.19 mmol). The air in the flask was removed by vacuum and then replaced with hydrogen in a balloon. The mixture was stirred at room temperature overnight. The mixture was filtered through celite and washed the celite/Pd/C with dichloromethane and methanol. The filtrate was concentrated and the residue diluted with dichloromethane and evaporated for a few cycles and then was purified by silica gel chromatography (dichloromethane/methanol) to give compound 3b as a light yellowish solid (558 mg, y=98%). $^1$H NMR (400 Hz, CDCl$_3$): δ 8.34 (d, J=8.0 Hz, 1H), 7.40 (s, 1H), 7.22 (dd, J$_1$=8.0 Hz, J$_2$=7.6 Hz, 1H), 7.17 (d, J=7.2 Hz, 1H), 7.02 (dd, J$_1$=7.2 Hz, J$_2$=7.6 Hz, 1H), 6.16 (s, 1H), 4.37 (tt, J$_1$=10.4 Hz, J$_2$=7.2 Hz, 1H), 3.76 (s, 3H), 3.49-3.36 (m, 3H), 2.73 (dd, J$_1$=16.8 Hz, J$_2$=3.6 Hz, 1H); $^{13}$C NMR (400 Hz, CDCl$_3$): δ 167.0, 150.4, 142.6, 141.2, 140.8, 129.9, 127.7, 124.8, 123.96, 117.4, 113.7, 112.5, 104.7, 57.3, 56.3, 54.7, 33.0; MS (m/z). found 295.1 (M−H)$^−$. See FIG. 3.

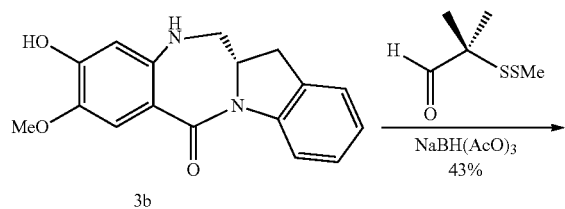
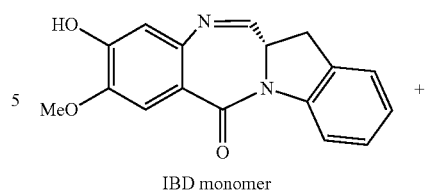

Compound 3c:

To a solution of the 2-(methyldithio)-isobutyraldehyde (113 mg, 0.75 mmol) and compound 3b (148 mg, 0.5 mmol) in anhydrous 1,2-dichloroethane (2 mL) was added sodium triacetoxyborohydride (212 mg, 1.0 mmol). The mixture was stirred at room temperature for 2 days. During the time, another two portions (0.05 mL, 0.5 mmol/portion) of 2-(methyldithio)-isobutyraldehyde along with one portion of sodium triacetoxyborohydride (106 mg, 0.5 mmol) were added. The reaction was quenched with saturated sodium bicarbonate, diluted with dichloromethane and water. The organic layer was washed with brine, dried over sodium sulfate and filtered. The filtrate was concentrated under reduced pressure and the residue was purified by silica gel chromatography (Combiflash, 24 g column, hexanes/ethyl acetate) to give compound 3c as a white fluffy solid (92.5 mg, y=43%). Unreacted starting material 3b was also recovered (49.3 mg, y=33%). $^1$H NMR (400 Hz, CDCl$_3$): δ 8.30 (d, J=8.0 Hz, 1H), 7.28 (dd, J$_1$=6.8 Hz, J$_2$=7.6 Hz, 1H), 7.25-7.20 (m, 2H), 7.07 (t, J=7.6 Hz, 1H), 6.80 (s, 1H), 6.17 (s, 1H), 4.36-4.28 (m, 1H), 3.89 (s, 3H), 3.78 (d, J=14.4 Hz, 1H), 3.46-3.34 (m, 3H), 2.90 (d, J=14.4 Hz, 1H), 2.73 (dd, J$_1$=16.4 Hz, J$_2$=2.8 Hz, 1H), 2.34 (s, 3H), 1.17 (s, 3H), 1.05 (s, 3H); $^{13}$C NMR (400 Hz, CDCl$_3$): δ 167.2, 149.0, 142.5, 142.2, 141.9, 129.9, 128.0, 125.3, 124.5, 124.1, 117.1, 112.0, 108.5, 64.8, 61.4, 58.1, 56.3, 53.4, 32.0, 26.3, 25.7, 25.4; MS (m/z). found 453.3 (M+Na)$^+$, 429.2 (M−H)$^−$. See FIG. 3.

Compound 3d:

To a stirred solution of IBD monomer (125 mg, 0.425 mmol) and 1,5-diiodopentane (0.63 mL, 4.25 mmol) in anhydrous dimethylformamide (3 mL) was added potassium carbonate (59 mg, 0.425 mmol) and the mixture was stirred at room temperature overnight. The reaction solution was diluted with dichloromethane, washed with brine and dried over anhydrous sodium sulfate. It was filtered and concentrated. The residue was purified by silica gel chromatography (hexanes/ethyl acetate) to give compound 3d as yellowish foam (94 mg, y=45%). $^1$H NMR (400 Hz, CDCl$_3$): δ 8.27 (d, J=8.0 Hz, 1H), 7.86 (d, J=4.8 Hz, 1H), 7.56 (s, 1H), 7.27 (dd, J$_1$=8.4 Hz, J$_2$=7.6 Hz, 2H), 7.10 (dd, J$_1$=7.6 Hz, J$_2$=7.2 Hz, 1H), 6.82 (s, 1H), 4.48 (dt, J$_1$=10.8 Hz, J$_2$=4.4 Hz, 1H), 4.15-4.07 (m, 2H), 3.96 (s, 3H), 3.70 (dd, J$_1$=16.8 Hz, J$_2$=10.8 Hz, 1H), 3.49 (dd, J$_1$=16.8 Hz, J$_2$=4.0 Hz, 1H), 3.22 (t, J=7.2 Hz, 2H), 1.96-1.87 (m, 4H), 1.64-1.57 (m, 2H); $^{13}$C NMR (400 Hz, CDCl$_3$): δ 164.0, 163.2, 151.4, 148.3, 142.2, 140.3, 129.6, 128.3, 124.9, 120.5, 117.0, 112.0, 110.6, 68.8, 56.4, 55.1, 33.3, 32.7, 28.0, 27.2, 6.6; MS (m/z). found 513.3 (M+Na)$^+$, 543.2 (M+3H$_2$O−H)$^−$. See FIG. 3.

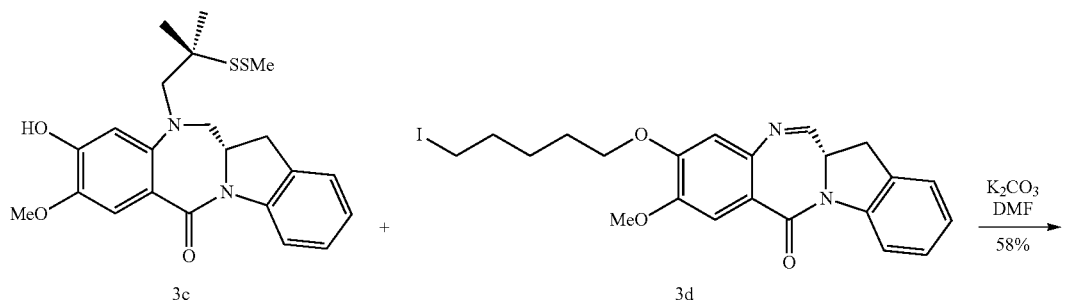

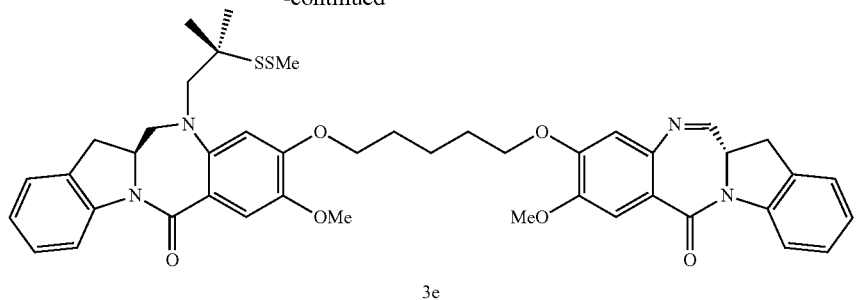

3e

Compound 3e:

To a stirred solution of the starting materials 3c (91 mg, 0.21 mmol) and 3d (94 mg, 0.19 mmol) in anhydrous dimethylformamide (1 mL) was added potassium carbonate (29 mg, 0.21 mmol) and the mixture was stirred at room temperature overnight. The reaction solution was diluted with dichloromethane, washed with brine and dried over anhydrous sodium sulfate. It was filtered, concentrated and the residue was purified by silica gel chromatography (hexanes/ethyl acetate) to give compound 3e as yellowish foam (89.1 mg, y=58%). $^1$H NMR (400 Hz, CDCl$_3$): δ 8.32-8.28 (m, 2H), 7.91 (bs, 1H), 7.57 (s, 1H), 7.36-7.21 (m, 5H), 7.15-7.05 (m, 2H), 6.85 (s, 1H), 6.74 (s, 1H), 4.53-4.48 (m, 1H), 4.37-4.31 (m, 1H), 4.21-4.03 (m, 4H), 3.98 (s, 3H), 3.88 (s, 3H), 3.86-3.70 (m, 2H), 3.55-3.35 (m, 4H), 2.93 (d, J=4.0 Hz, 1H), 2.73 (dd, J$_1$=16.4 Hz, J$_2$=2.4 Hz, 1H), 2.36 (s, 3H), 2.03-1.96 (m, 3H), 1.77-1.67 (m, 3H), 1.21 (s, 3H), 1.06 (s, 3H); MS (m/z). found 815.3 (M+Na)$^+$. See FIG. 3.

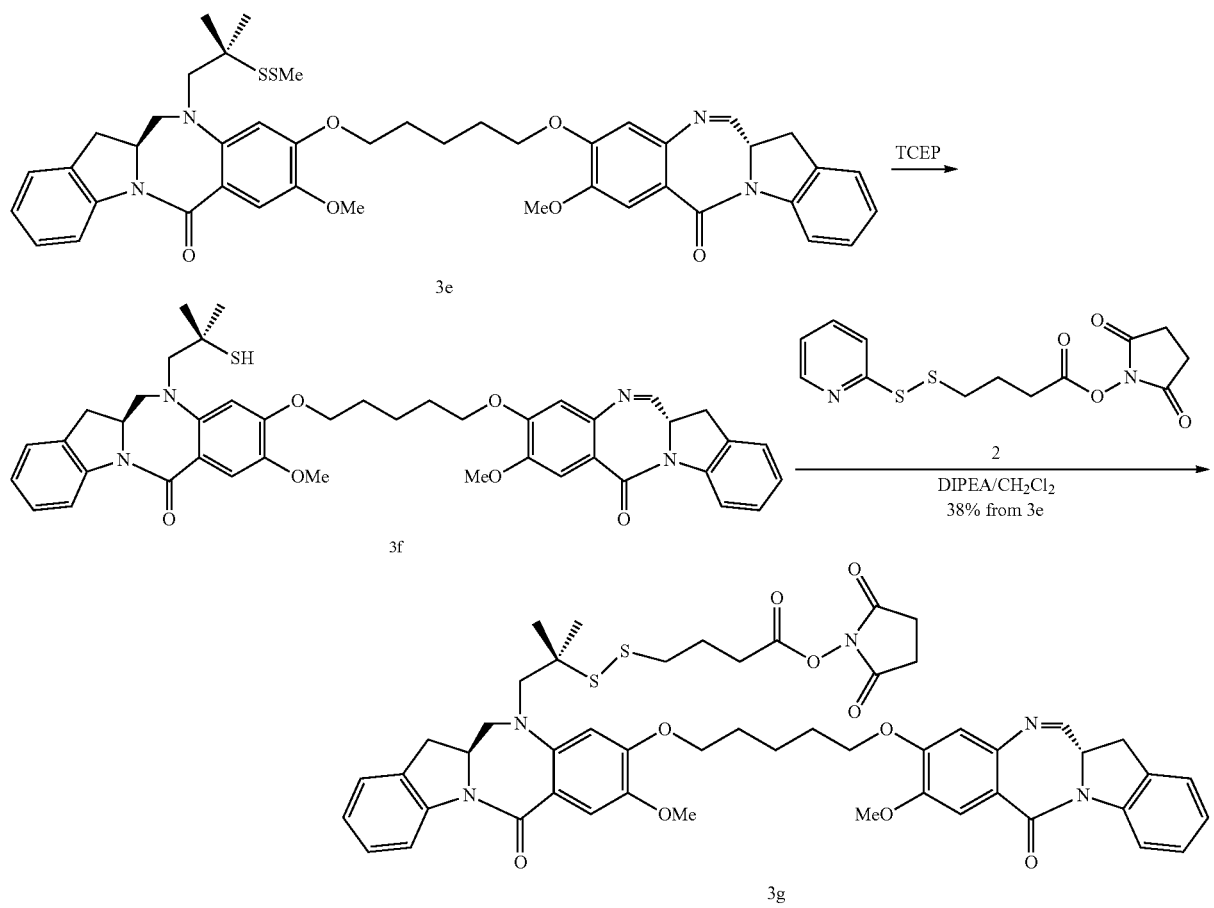

Compound 3g:

To a stirred solution of compound 3e (33.1 mg, 0.042 mmol) in acetonitrile (2 mL) and methanol (4 mL) was added freshly prepared TCEP solution (36 mg of TCEP HCl salt was neutralized with saturated sodium bicarbonate to pH ~6.5 then diluted with 0.4 mL of pH 6.5 phosphate buffer) at room temperature. The mixture was stirred at room temperature for 3 hours and then diluted with dichloromethane and deionized water, separated and the organic layer was washed with brine, dried over anhydrous sodium sulfate and filtered. The filtrate was concentrated and high vacuumed to give 31 mg of compound 3f as yellowish solid. It was dissolved in anhydrous dichloromethane (0.5 mL) SPDB NHS ester 2 (26 mg, 80% purity, 0.063 mmol) and diisopropylethylamine (11 μl, 0.063 mmol) were added subsequently. The mixture continued to be stirred at room temperature overnight, quenched with saturated ammonium chloride and diluted with dichloromethane, separated and washed with brine, dried over sodium sulfate, filtered and concentrated. The residue was purified by preparative reverse phase HPLC (C18 column, acetonitrile/water). The fractions containing product were combined, extracted with dichloromethane and concentrated to give compound 3g as yellowish solid (15.2 mg, y=38%). MS (m/z). found 984.3 (M+Na)$^+$, 1014.2 (M+3H$_2$O−H)$^−$. See FIG. 3.

Example 4

Compound 4b:

A stirred solution of compound 4a (111 mg, 0.108 mmol) in absolute ethanol (720 fit) and anhydrous dichloromethane (360 μL) was cooled to 0° C. in an ice bath. Sodium borohydride (0.817 mg, 0.022 mmol) in 50 uL absolute ethanol was added at 0° C. The reaction stirred at ambient temperature for two hours. The mixture was cooled to 0° C. in an ice bath, quenched with saturated ammonium chloride and extracted with dichloromethane. The organic extracts were washed with brine, dried over anhydrous sodium sulfate and filtered through Celite. The filtrate was concentrated under reduced pressure and the crude material was purified by RP-HPLC (C18 DI water/acetonitrile) to yield compound 4b (43 mg, 38%). $^1$H NMR (400 Hz, CDCl$_3$): δ8.26 (d, 1H, J=8.0 Hz), 8.18 (d, 1H, J=8.0 Hz), 7.77 (d, 1H, J=4.4 Hz), 7.51 (s, 1H), 7.41 (s, 2H), 7.17 (m, 6H), 7.03 (t, 1H, J=7.2 Hz), 6.96 (t, 1H, J=7.2 Hz), 6.76 (s, 1H), 6.04 (s, 1H), 5.13 (m, 4H), 4.38 (m, 2H), 3.90 (s, 3H), 3.81 (s, 3H), 3.79 (m, 2H), 3.63 (m, 1H), 3.51 (m, 8H), 3.43 (m, 6H), 3.25 (s, 3H), 2.73 (dd, 1H, J=3.6, 16.4 Hz), 2.22 (s, 3H), 2.04 (m, 2H), 1.81 (m, 2H), 1.18 (s, 6H); MS (m/z) found, 1051.9 (M+Na), 1069.9 (M+Na+H$_2$O). See FIG. 4.

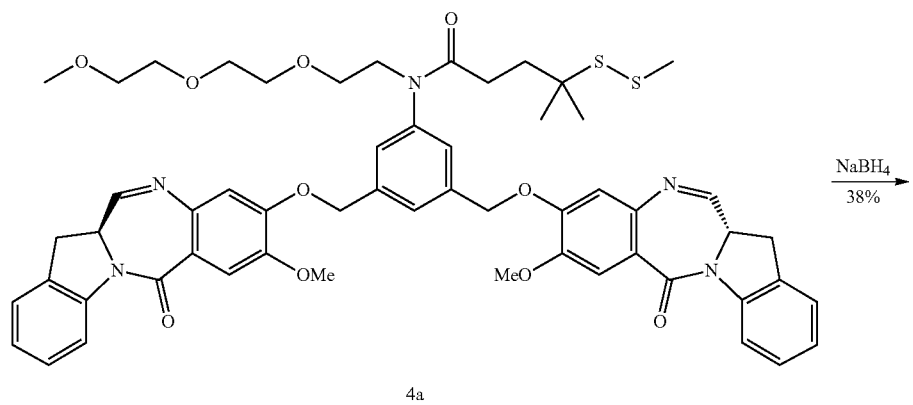

4a

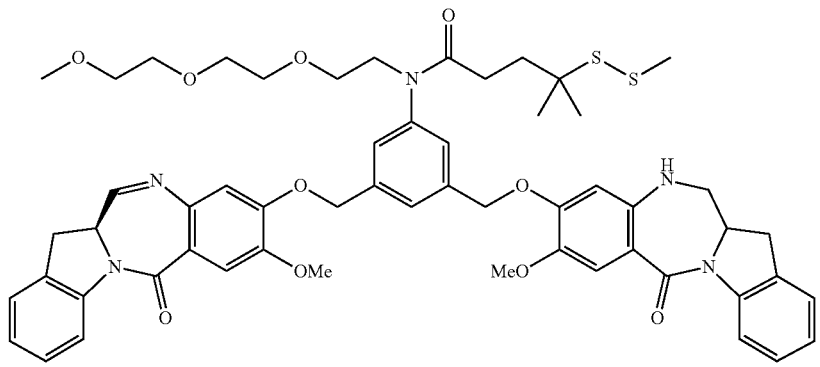

4b

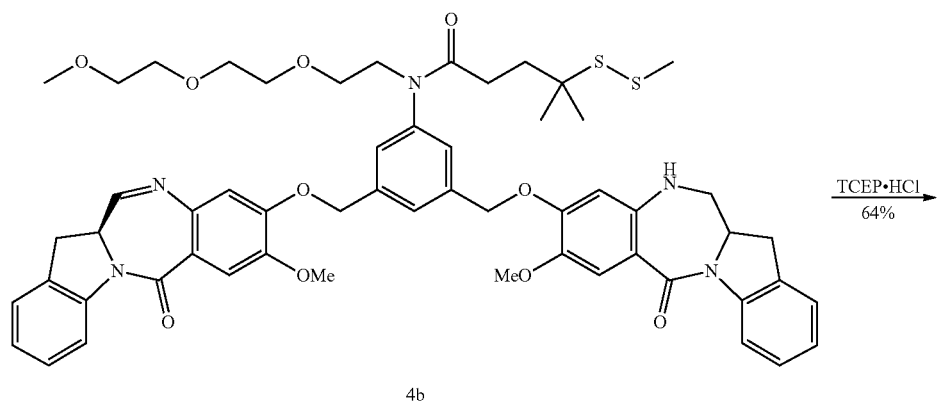

4b

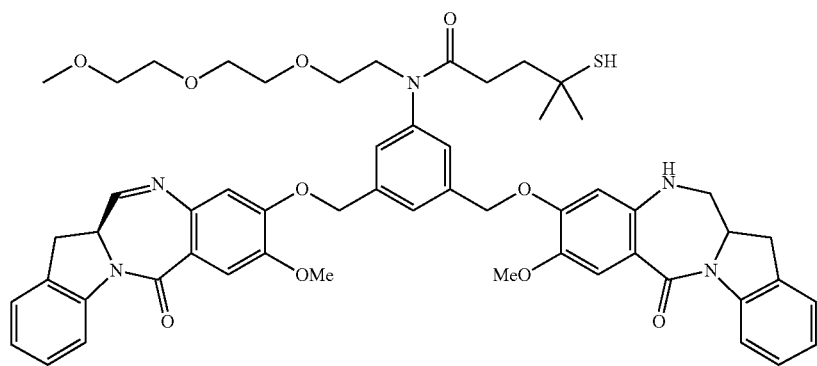

4c

Compound 4c:

To a stirred solution of compound 4b (40 mg, 0.039 mmol) in methanol (4.45 mL) and acetonitrile (2.225 mL) was added TCEP.HCl (39.0 mg, 0.136 mmol) in sodium phosphate buffer (0.89 mL, pH 6.5). The mixture stirred at ambient temperature for 18 hours. The mixture was diluted with dichloromethane and washed with water and brine. The organic extracts were dried over anhydrous sodium sulfate, filtered and concentrated. Purification by RP-hPLC (C18, DI water/acetonitrile) and extraction with dichloromethane yielded compound 4c (26.5 mg, 64%); MS (m/z) found, 1006.0 (M+Na). See FIG. 4.

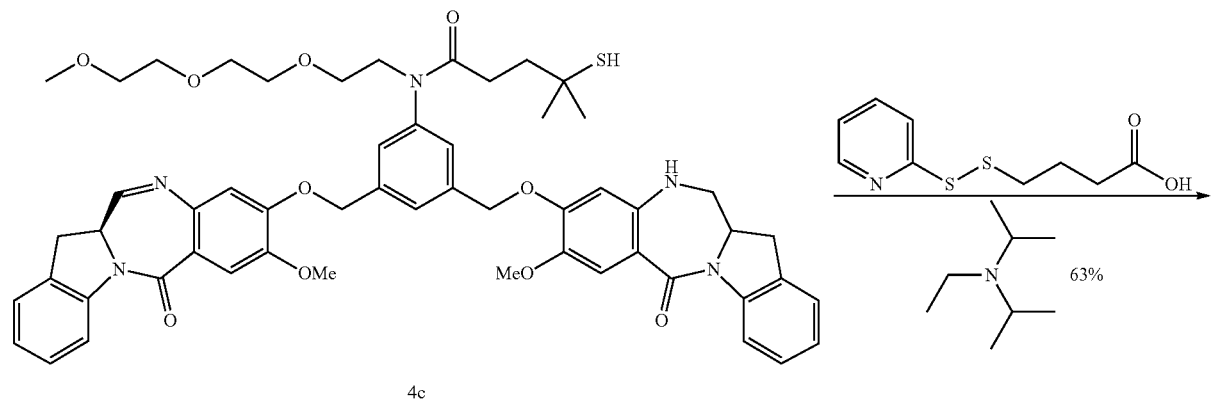

4c

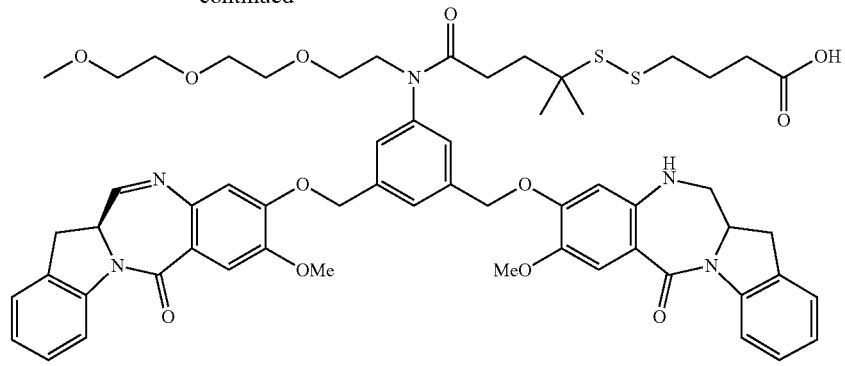

4d

Compound 4d:

To a stirred solution of compound 4c (24 mg, 0.024 mmol) in anhydrous dichloromethane (800 μL) was added PBA (11.18 mg, 0.049 mmol) and diisopropylethylamine (20.18 μL, 0.116 mmol). After stirring for 18 hours at ambient temperature the reaction was diluted with dichloromethane and quenched with saturated ammonium chloride. The layers were separated and the organic was washed with brine, dried over anhydrous sodium sulfate, filtered and concentrated under reduced pressure. Purification by PTLC (5% methanol/dichloromethane) yielded compound 4d (17 mg, 63%); MS (m/z) found, 1123.9 (M+Na) 1139.9 (M+K); 1099.8 (M−H) 117.9 (M−H+H$_2$O). See FIG. 4.

Compound 4e:

To a mixture of compound 4d (15 mg, 0.014 mmol) and N-hydroxy succinimide (4.70 mg, 0.041 mmol) in anhydrous dichloromethane (1.0 mL) was added EDC.HCl (7.83 mg, 0.041 mmol). After stirring 18 hours at ambient temperature the reaction was diluted with dichloromethane and quenched with saturated ammonium chloride. The mixture was washed with brine, dried over anhydrous sodium sulfate, filtered and concentrated under reduced pressure. The crude material was purified by RP-HPLC (C18, DI water/acetonitrile). Fractions containing product were pooled and extracted with dichloromethane, dried over anhydrous magnesium sulfate, filtered and concentrated to give compound 4e (13 mg, 80%); MS (m/z) found, 1220.8 (M+Na) 1238.8 (M+Na+H$_2$O), 1254.8 (M+K+H$_2$O). See FIG. 4.

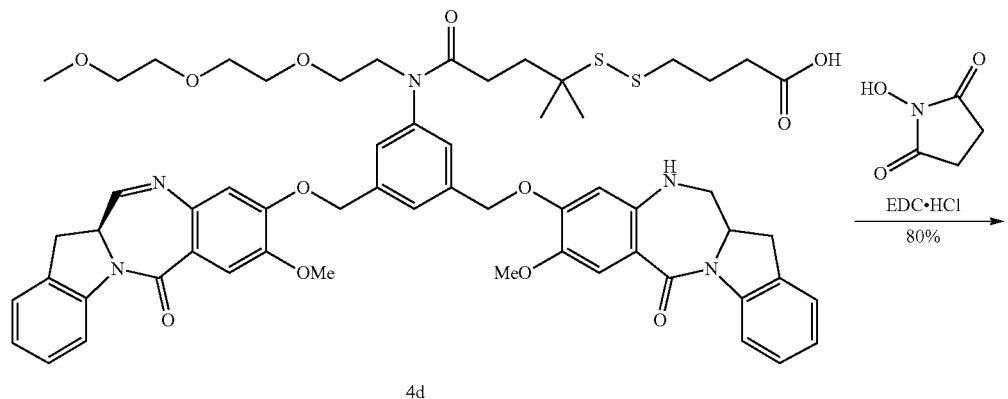

4d

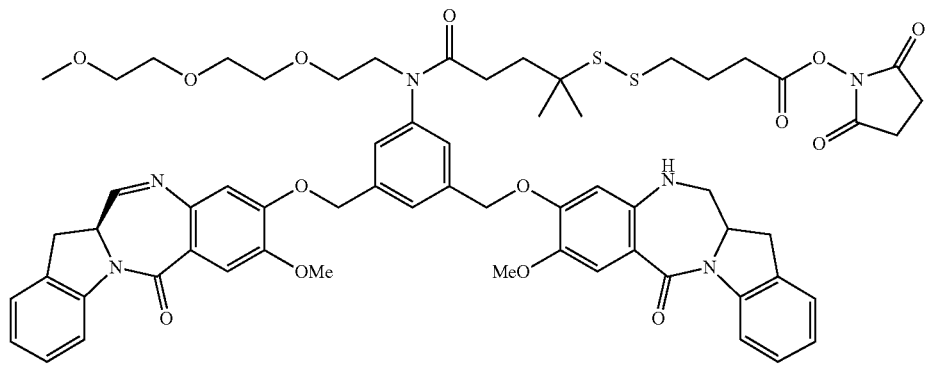

4e

Example 5

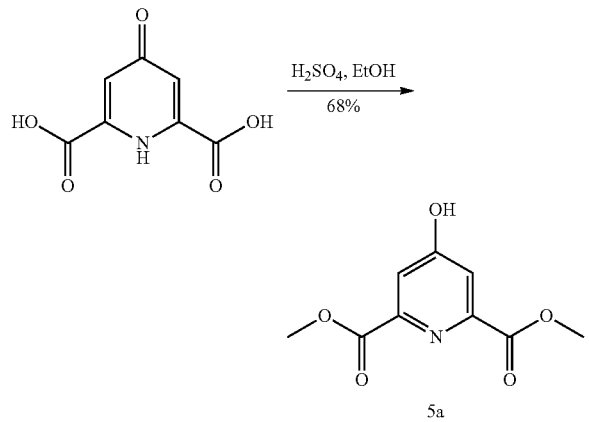

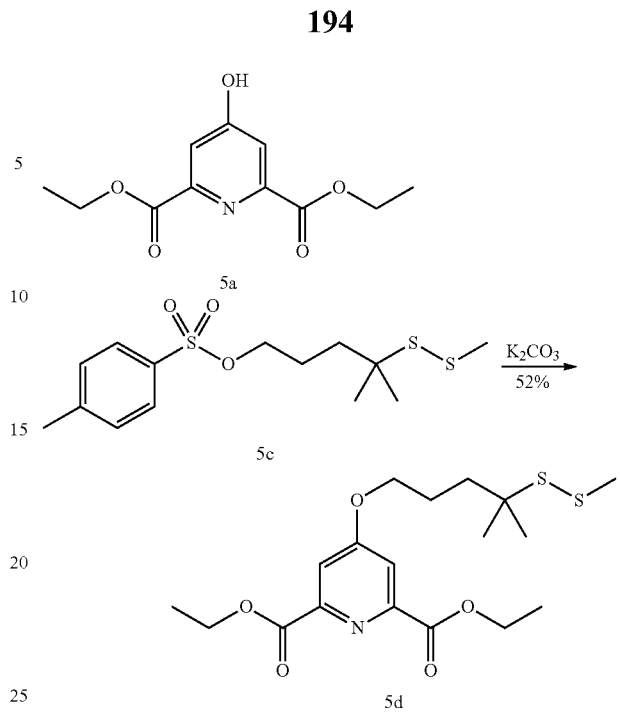

Compound 5a:

A mixture of chelidamic acid hydrate (3.0 g, 15.56 mmol) and sulfuric acid (0.6 mL, 11.26 mmol) in absolute ethanol (40 mL) was refluxed for 20 hours. The reaction was cooled to ambient temperature, neutralized with aqueous sodium carbonate, and then acidified with concentrated HCl. Water was added and the mixture was extracted with dichloromethane. The extracts were dried with anhydrous magnesium sulfate, filtered and concentrated. The crude material was purified by silica gel chromatography (5% methanol/dichloromethane) to yield diethyl 4-hydroxypyridine-2,6-dicarboxylate (5a) (2.5 g, 68%) as a white solid. See FIG. 5.

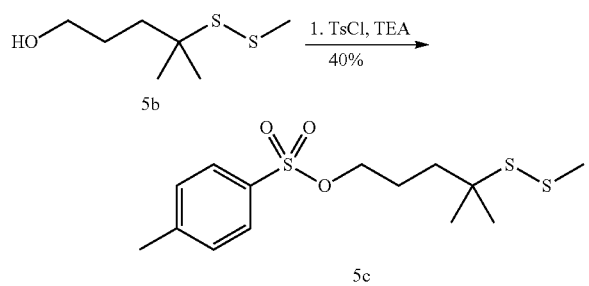

Compound 5c:

A solution of 4-methyl-4-(methyldisulfanyl)pentan-1-ol (5b) (2.0 g, 11.09 mmol) in anhydrous dichloromethane (55.5 mL) was cooled to 0° C. in an ice bath. Triethylamine (5.41 mL, 38.8 mmol) and toluene sulfonyl chloride (3.17 g, 16.64 mmol) were added at 0° C. The reaction stirred for three hours at ambient temperature. The mixture was extracted with ethyl acetate and washed with brine. The organic extracts were dried with anhydrous sodium sulfate, filtered and concentrated. Purification by silica gel chromatography (5% ethyl acetate/hexanes) resulted in 4-methyl-4-(methyldisulfanyl)pentyl 4-methylbenzenesulfonate (5c) (1.5g, 40%). 5b: $^1$H NMR (400 Hz, CDCl$_3$): δ3.42 (m, 2H), 2.19 (s, 3H), 1.77 (bs, 1H), 1.43 (m, 4H), 1.09 (s, 6H). 5c: $^1$H NMR (400 Hz, CDCl$_3$): δ7.66 (d, 2H, J=7.6 Hz), 7.22 (d, 2H, J=8.0 Hz), 3.90 (t, 2H, J=6.4 Hz), 2.32 (s, 3H), 2.23 (s, 3H), 1.60 (m, 2H), 1.44 (m, 2H), 1.11 (s, 6H). See FIG. 5.

Compound 5d:

To a stirred solution of 4-methyl-4-(methyldisulfanyl)pentyl 4-methylbenzenesulfonate (5c) (0.48 g, 1.435 mmol) and diethyl 4-hydroxypyridine-2,6-dicarboxylate (5a)(0.343 g, 1.435 mmol) in anhydrous dimethylformamide (6.5 mL) was added Potassium carbonate (0.297 g, 2.152 mmol). The reaction was stirred at 90° C. for 18 hours. Then allowed to cool to ambient temperature and quenched with saturated ammonium chloride. The mixture was extracted three times with ethyl acetate. The extracts were dried with anhydrous sodium sulfate, filtered and concentrated under reduced pressure. Purification by silica gel chromatography (30% hexanes/ethyl acetate) yielded diethyl 4-(4-methyl-4-(methyldisulfanyl)pentyloxy)pyridine-2,6-dicarboxylate (5d)(300 mg, 52%); $^1$H NMR (400 Hz, CDCl$_3$): δ 7.70 (s, 2H), 4.40 (q, 4H, J=7.2, 14.4 Hz), 4.07 (t, 2H, J=6. Hz), 2.35 (s, 3H), 1.86 (m, 2H), 1.70 (m, 2H), 1.38 (t, 6H, J=7.2 Hz), 1.27 (s, 6H); MS (m/z). found 424.1 (M+Na), 440.1 (M+K). See FIG. 5.

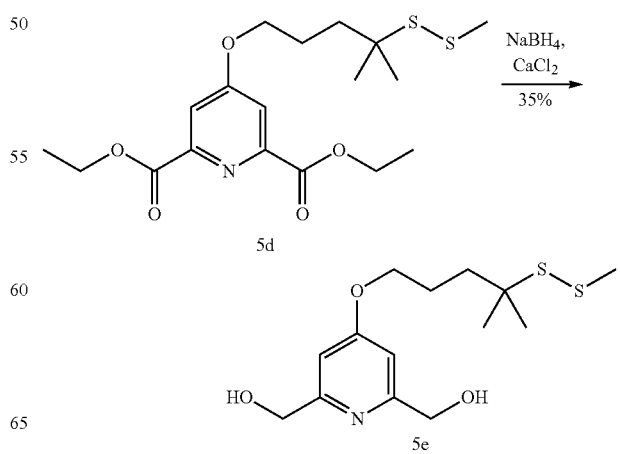

Compound 5e:

To a stirred solution of diethyl 4-(4-methyl-4-(methyldisulfanyl)pentyloxy)pyridine-2,6-dicarboxylate (5d) (270 mg, 0.672 mmol) in absolute ethanol (7.0 mL) was added calcium chloride (224 mg, 2.017 mmol) and sodium borohydride (76 mg, 2.017 mmol). The reaction was allowed to stir at ambient temperature for 90 minutes after which it was quenched with water and concentrated in vacuo to remove the ethanol. The mixture was then extracted twice with dichloromethane. The organic extracts were combined, washed with water, dried with anhydrous magnesium sulfate and filtered through celite. The filtrate was concentrated under reduced pressure and the crude material was purified by silica gel chromatography eluting with 10% methanol/dichloromethane to yield (4-(4-methyl-4-(methyldisulfanyl)pentyloxy)pyridine-2,6-diyl)dimethanol (5e)(75 mg, 35%); $^1$H NMR (400 Hz, CDCl$_3$): δ 6.63 (s, 2H), 4.60 (s, 4H), 3.95 (t, 2H, J=6.2 Hz), 3.54 (bs, 2H), 2.35 (s, 3H), 1.82 (m, 2H), 1.66 (m, 2H), 1.26 (s, 6H); MS (m/z). found 340.1 (M+Na). See FIG. 5.

0.402 mmol) were added. The mixture was stirred for 60 minutes at −5° C. The reaction was quenched with ice water and extracted with cold ethyl acetate. The organic extracts were washed with ice water, dried with anhydrous sodium sulfate, filtered and concentrated under reduced pressure to give the dimesylate. To a stirred mixture of the dimesylate intermediate (179 mg, 0.378 mmol) and IBD monomer (256 mg, 0.869 mmol) in anhydrous dimethylformamide (3.8 mL) was added potassium carbonate (261 mg, 1.890 mmol) and potassium iodide (31.4 mg, 0.189 mmol). The reaction was allowed to stir at ambient temperature for 18 hours. The mixture was quenched with water and extracted three times with dichloromethane. The organic extracts were dried with sodium sulfate, filtered and concentrated. The crude material was redissolved in acetonitrile and purified by RP-HPLC (C18, deionized water/acetonitrile). Fractions containing product were combined and extracted with dichloromethane, dried with anhydrous magnesium sulfate, filtered and concentrated under reduced pressure to yield compound 5f (65 mg, 20%); $^1$H NMR (400 Hz, CDCl$_3$): δ 8.20 (d, 2H, J=8.0

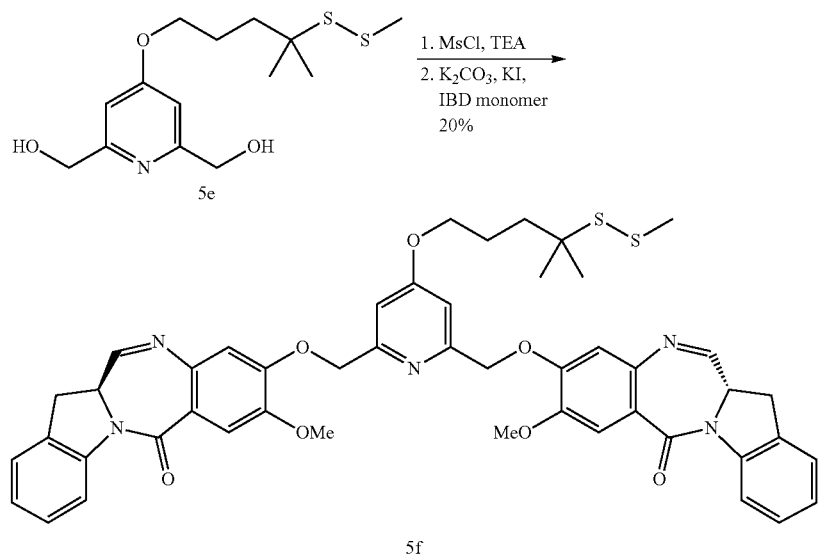

Compound 5f:

A stirred solution of (4-(4-methyl-4-(methyldisulfanyl)pentyloxy)pyridine-2,6-diyl)dimethanol (5e) (51 mg, 0.161 mmol) in anhydrous dichloromethane (1.6 mL) was cooled to −5° C. in an acetone/ice bath. Triethylamine (0.112 mL, 0.803 mmol) and methanesulfonyl chloride (0.031 mL, Hz), 7.78 (m, 2H), 7.53 (s, 2H), 7.20 (m, 4H), 7.04 (t, 2H, J=7.4 Hz), 6.91 (m, 2H), 6.80 (s, 2H), 5.22 (s, 4H), 4.40 (m, 2H), 3.94 (s, 6H), 3.93 (m, 2H), 3.63 (m, 2H), 3.42 (dd, 2H, J=Hz), 2.32 (s, 3H), 1.80 (m, 2H), 1.64 (m, 2H), 1.24 (s, 6H); MS (m/z). found 892.3 (M+Na) 910.3 (M+Na+H$_2$O) 928.3 (M+Na+2H$_2$O). See FIG. 5.

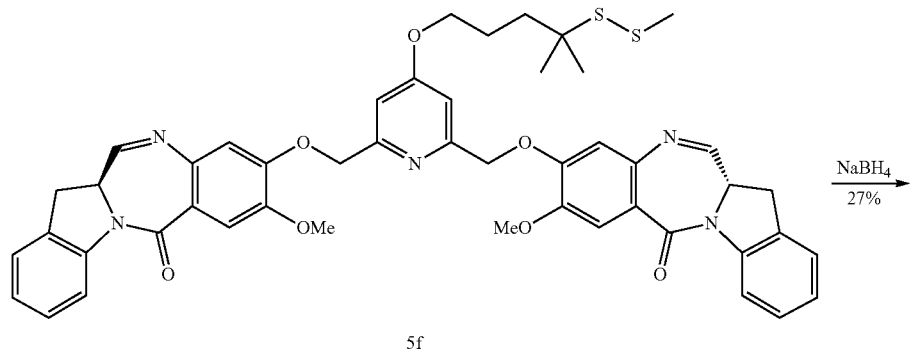

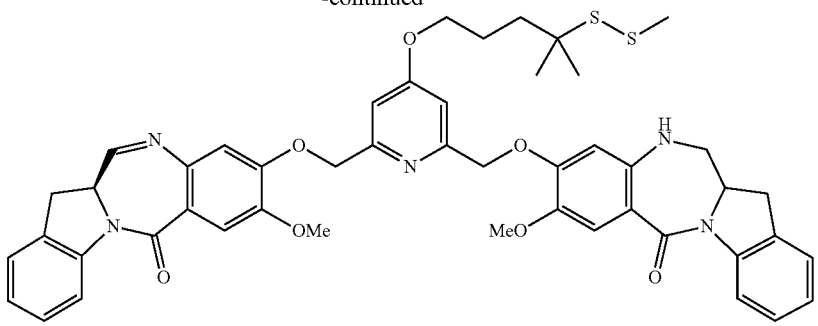

5g

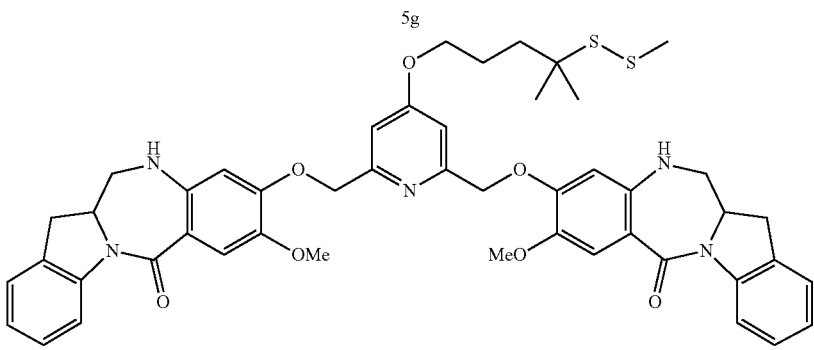

5h

Compound 5g and 5h:

A solution of compound 5f (74 mg, 0.085 mmol) in absolute ethanol (600 μL) and anhydrous dichloromethane (300 μL) was cooled 0° C. in an ice bath. Sodium borohydride (0.644 mg, 0.017 mmol) in 50 μL absolute ethanol was added at 0° C. The mixture was allowed to stir at ambient temperature for two hours and was then cooled to 0° C. The reaction was quenched with saturated ammonium chloride and extracted with dichloromethane. The organic extracts were washed with brine, dried over anhydrous sodium sulfate, filtered through Celite and concentrated under reduced pressure. The crude material was redissolved in dimethylformamide and purified by RP-HPLC (C18 deionized water/acetonitrile). Fractions containing compounds 5g and 5h were combined separately and extracted with dichloromethane, dried with anhydrous magnesium sulfate, filtered and concentrated to yield compound 5g (20 mg, 27%) and compound 5h. 5g: $^1$H NMR (400 Hz, CDCl$_3$): δ 8.25 (m, 1H), 8.18 (m, 1H), 7.77 (m, 1H), 7.51 (ss, 1H), 7.40 (ss, 1H), 7.18 (m, 4H), 7.08 (m, 1H), 7.03 (m, 1H), 6.92 (m, 2H), 6.86 (ss, 1H) 5.98/6.06 (ss, 1H), 5.24 (m, 4H), 4.40 (m, 1H), 4.30 (m, 1H), 3.94 (s, 3H), 3.92 (m, 2H), 3.84 (s, 3H), 3.62 (m, 1H), 3.37 (m, 4H), 2.65 (m or dd, 1H), 2.32 (ss, 3H), 1.77 (m, 2H), 1.64 (m, 2H), 1.24 (s, 6H). 5h: $^1$H NMR (400 Hz, CDCl$_3$): δ 8.24 (d, 2H, J=8.0 Hz), 7.39 (s, 2H), 7.14 (m, 4H), 6.97 (m, 2H), 6.93 (m, 2H), 6.15 (ss, 2H), 5.25 (s, 4H), 4.37 (m or t, 2H, J=9.8 Hz), 4.2 (bs, 2H), 3.94 (m, 2H), 3.83 (s, 6H), 3.40 (m, 6H), 2.72 (dd, 2H, J=Hz), 2.32 (s, 3H), 1.79 (m, 2H), 1.64 (m, 2H), 1.24 (s, 6H). See FIG. 5.

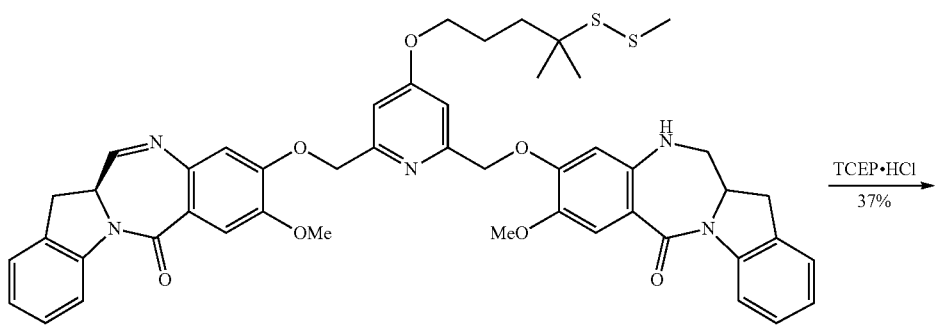

5g

TCEP·HCl
37%

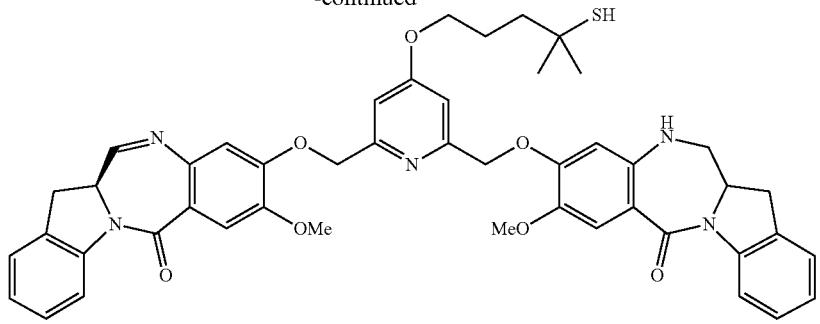

5i

Compound 5i:

To a stirred solution of compound 5g (20 mg, 0.023 mmol) in methanol (5.25 mL) and acetonitrile (1.750 mL) was added TCEP.HCl (19.72 mg, 0.069 mmol) in sodium phosphate buffer (0.7 mL, pH 6.5). The mixture was stirred for 3 hours at ambient temperature and then diluted with dichloromethane and water. The layers were separated and the organic was washed with brine. The crude product was purified by RP-HPLC (C18, deionized water/acetonitrile). Fractions containing product were combined, extracted with dichloromethane and evaporated to yield compound 5i (7 mg, 37%). MS (m/z). found 848.3 (M+Na) 866.3 (M+Na+ $H_2O$) 880.3 (M+Na+MeOH). See FIG. 5.

perature the reaction was quenched with saturated ammonium chloride solution and extracted with dichloromethane. The organic extracts were washed with brine, dried with anhydrous sodium sulfate, filtered and concentrated under reduced pressure. The crude material was purified by preparative RP-HPLC (C18, deionized water/acetonitrile). Fractions containing product were extracted with dichloromethane, filtered and evaporated to yield compound 5j (3 mg, 34%). MS (m/z). found 1063.3 (M+Na) 1081.3 (M+Na+ $H_2O$). See FIG. 5.

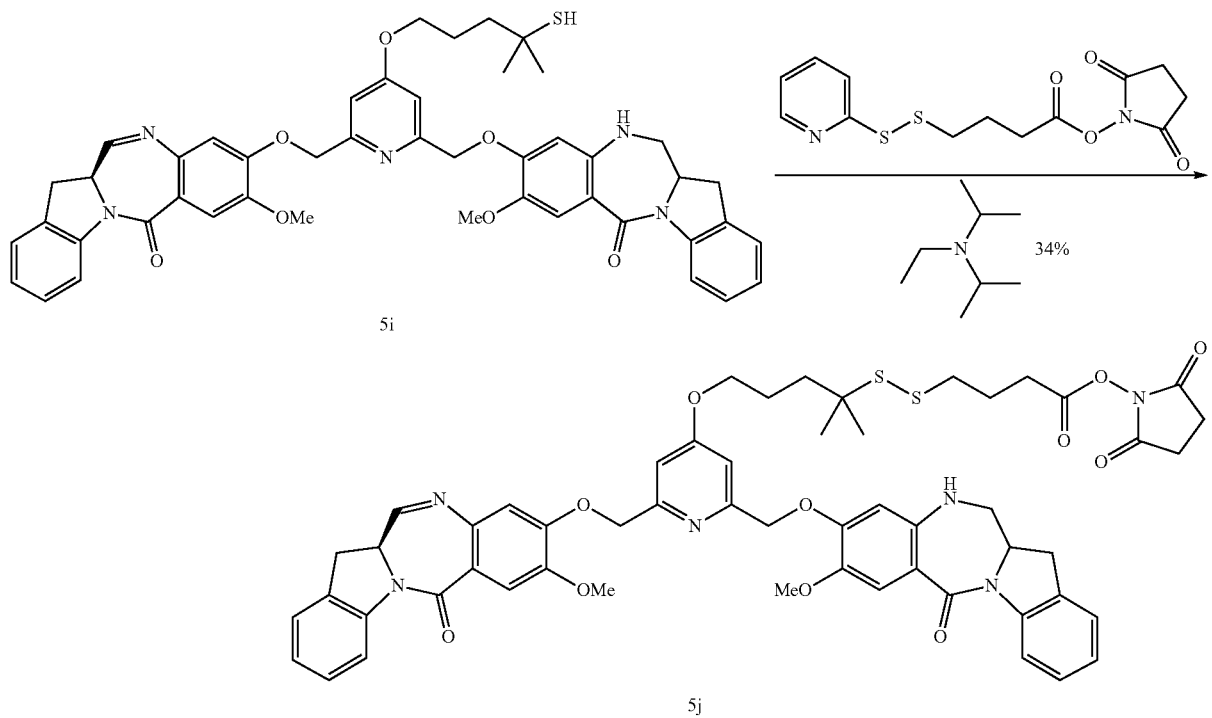

Compound 5j:

To a stirred solution of compound 5i (7 mg, 8.47 μmol) and 2,5-dioxopyrrolidin-1-yl 4-(pyridin-2-yldisulfanyl)butanoate (8.64 mg, 0.021 mmol) in anhydrous dichloromethane (113 μL) was added diisopropylethylamine (3.69 μL, 0.021 mmol). After stirring for 18 hours at ambient tem- Example 6

Preparation of Antibody-SPDB-Drug Conjugate

Compound 1g was pre-treated with 3 molar equivalents of sodium bisulfite (using a freshly prepared $NaHSO_3$ solution in water) in 96-98% DMA in water for 4-5 hrs at 25° C. For conjugation, the humanized antibody at 2 mg/mL was reacted with 5-7 molar equivalents of compound 1g (pre-treated with $NaHSO_3$) for 6 h at 25° C. in 85-90% PBS, pH 7.4, aqueous buffer, or 50 mM HEPES, pH 8.5, aqueous buffer, containing 10-15% N,N-dimethylacetamide (DMA) and then purified over a G25 gel filtration column in PBS, pH 7.4, to remove unreacted or hydrolyzed drug compound. The humanized antibody-SPDB-drug conjugates were dialyzed in 10 mM Histidine, 250 mM Glycine, 1% sucrose, pH 6.5 buffer. The Drug Antibody Ratio (DAR) of the conjugates were measured to be 2.2-2.9 by UV absorbance measurements at 280 and 320 nm and using the extinction coefficients of the drug and antibody at 280 nm (215,000 $M^{-1}$ $cm^{-1}$) and 320 nm (9137 $M^{-1}$ $cm^{-1}$). The percentage of monomer in the conjugates were determined as >90% by SEC (Size Exclusion Chromatography) using TSK-Gel G300SWXL column (7.8 mm×300 mm, 5 μm particle size). Based on the UV absorbance of the monomer peak in SEC it was also demonstrated that the monomer conjugate peaks had linked drug molecules. For free (unconjugated) drug assay, the conjugate was acetone extracted to remove protein, dried, and reconstituted in mobile phase and injected onto a VYDAC 208TP C8 reverse phase HPLC column (4.6×250 mm, 7 μm particle size) and compared to standards. The percentage of free drug compound in the conjugate was determined as <0.5% of conjugated drug compound. See FIG. 22.

Preparation of Humanized Ab-SPDB-2a Conjugate:

Humanized Ab at 8 mg/mL was derivatized with 4-6 molar equivalents of SPDB hetrobifunctional linker for 1.5 h at 25° C. in 95% PBS, PH 7.4, containing 5% DMA (v/v), and then purified over a G25 desalting column into citrate buffer (35 mM citrate buffer, pH 5.5, containing 2 mM EDTA, 150 mM NaCl) to remove unreacted linker. The LAR (Linker Antibody Ratio) were measured using UV absorbance at 280 and 343 nm without and with 50 mM dithiothreitol addition (to measure total antibody and dithiothreitol-released SPy) and were determined to be 2.7-4.1 LAR. The SPDB-modified antibody at 2 mg/mL was reacted with 2 molar equivalents of compound 2a (HCl salt) per linked SPDB for 20 h at ambient temperature in 85% citrate buffer, 15% DMA (v/v) and then purified over a G25 desalting column into PBS, pH 7.4 to remove unconjugated drug compound. The DAR of the final humanized Ab-SPDB-2a conjugate was measured by UV spectrophotometry at 280 and 350 nm and calculated to be ~1.7-2.1 DAR. The percentage of monomer and linked drug compound on the monomer in the conjugate was determined by HPLC using an SEC (size exclusion chromatography) column See FIG. 23.

Example 7

In Vitro Potency of Free Drugs and Conjugates

General Procedure Used: Samples of unconjugated free drug compounds or drug conjugates were added to 96-well flat bottomed tissue culture plates and titrated using serial dilutions to cover the desired molar range. Antigen positive ($Ag^+$) or Antigen negative ($Ag^-$) cells were added to the wells in specific cell densities in such a way that there were triplicate samples for each drug concentration for each corresponding cell line. The plates were then incubated at 37° C. in an atmosphere of 5% $CO_2$ for 4-5 days depending on the cell line. COLO 205 (1,000 cells/well), Namalwa (3,000 cells/well), HEL 92.1.7 (3,000 cells/well)—4 days; RH30(1,000 cells/well), HL60/QC (5,000 cells/well), Ramos (10,000 cells/well), KB (2,000 cells/well), BJAB (2,000 cells/well), NB4 (3,000 cells/well)—5 days, RPMI 8226 (8,000 cells/well)—6 days.

At the end of the incubation period cytotoxic potencies were then assessed using a WST-8 based cell viability assay and surviving cells were measured by developing with WST-8 (2-7 hours). The absorbance in each well was measured and the surviving fraction of cells at each concentration was plotted to reveal the cytotoxicity and/or antigen specificity (of the conjugates).

Using the general procedure described above, the cytotoxicity of the unconjugated free drug compounds was measured against seven cell lines: KB, a HeLa cell contaminant, HL60/QC, an acute myeloid leukemia cell line, Namalwa, a Burkitt lymphoma cell line, NB4, an acute promyelocytic leukemia cell line, HEL92.1.7, an erythroleukemia cell line, RPMI8226, a multiple myeloma cell line and BJAB, a B-cell leukemia cell line. The results, shown in FIG. 24 and Table 10 demonstrate the high potency of these compounds across a wide range of cell types. The potency and specificity of the antibody-drug conjugates were measured against antigen-expressing cells, with and without the additions of an excess amount of blocking unconjugated antibody to show specificity of the killing effect. The MY9-6-drug conjugate was extremely potent towards three different antigen-expressing cells: HL60/ATCC, HL60/QC and NB-4, despite the very low antigen expression in NB4 cells. The specific potency could be blocked by addition of excess unconjugated antibody, demonstrating that the cell killing effect is antigen-specific. Similarly, the huFOLR1-drug conjugate was effective in killing antigen-expressing KB cells in a specific manner. Results are illustrated in FIGS. 25 and 26.

TABLE 10

Potency of free drugs against various cell lines. The $IC_{50}$ values listed in the table are in the unit of nM.

|  | Namalwa | KB | HL60/QC | NB4 | HEL92.1.7 | RPMI8226 | BJAB |
|---|---|---|---|---|---|---|---|
| 1c | 0.056 | 0.16 | 0.023 |  |  |  |  |
| 1d | 0.069 | 0.18 | 0.032 |  |  |  |  |
| 1e | 2.4 | >3.0 | 0.67 |  |  |  |  |
| 27d |  | 0.23 | 0.05 | 0.039 | 0.14 | 0.07 | 0.04 |
| 27e |  | 0.39 | 0.09 | 0.13 | 0.2 | 0.24 | 0.12 |
| 27f |  | 4.4 | 1.7 | 1.1 | 1.8 | >3.0 | 1 |
| 29a | 0.002 | 0.004 | 0.001 | 0.0023 | 0.0031 | 0.011 | 0.001 |
| 29b | 0.003 | 0.007 | 0.006 | 0.007 | 0.007 | 0.005 | 0.003 |
| 29c | 0.013 | 0.057 | 0.03 | 0.023 | 0.027 | 0.16 | 0.015 |

Similar results have also been obtained using different cell lines and different conjugates of the invention, including: huMY9-6-SPDB-1f against HL60/QC (Ag+) cells, HL60/ATCC (Ag+) cells, and NB-4 (Ag+) cells (FIG. 25); huFOLR1-SPDB-1f against KB (Ag+) cells (FIG. 26); huMY9-6-SPDB-1f against antigen positive HL60/QC cells, HL60/ATCC cells, NB-4 cells, and HEL 92.1.7 cells (FIG. 29); huMy9-6-SPDB-1f, huMy9-6-sulfoSPDB-1f, and huMy9-6-BMPS-1f against HL60/QC (Ag+) cells (FIG. 34); chB38.1-SPDB-1f and chB38.1-sulfoSPDB-1f against COL0205 (Ag+) cells (FIG. 35); huMy9-6-SPDB-1f, huMy9-6-sulfoSPDB-1f, and huMy9-6-BMPS-1f against OCI-AML3 (Ag+) cells (FIG. 44). Also see FIG. 49 for the potency of the various conjugates against various cell lines, expressed as $IC_{50}$ values (nM). Note that in FIGS. 25, 29, 34, 35, and 44, conjugates were prepared in the presence of sodium bisulfite.

To compare in vitro potency measurements for the subject conjugates prepared with and without imine reactive reagent, such as sodium bisulfite, huMy9-6-BMPS-1f, huMy9-6-sulfo-SPDB-1f, and huMy9-6-Drug 2 were prepared with and without sodium bisulfite using the in situ sulfonation method (wherein the respective compounds of the invention was first mixed with sodium bisulfite and a bifunctional crosslinker bearing a reactive group, then the reaction mixture, without further purification, was reacted with the huMy9-6 monoclonal antibody as the cell-binding agent). $IC_{50}$s for the conjugates on HL60-QC cells are shown below. The data indicates that the inclusion of imine reactive group (such as sodium bisulfite) in the conjugate preparation step does not negatively impact the in vitro potency of the subject conjugates.

| Conjugate | NaHSO3 treatment | $IC_{50}$ (pM) | $IC_{50}$ (pM) huMy9-6 blocking |
|---|---|---|---|
| huMy9-BMPS-1f | − | 2 | 130 |
|  | + | 1.5 | 55 |
| huMy9-6-sulfo-SPDB-1f | − | 5.6 | 1200 |
|  | + | 7.1 | 610 |
| huMy9-6-Drug 2 | − | 16 | >3000 |
|  | + | 6.8 | >3000 |

It is apparent that pre-treatment of the drug compounds with sodium bisulfite (5 molar equivalents, 22 h, 4° C., 90:10 DMA: pH 5.5 water) prior to conjugation with huMy9-6 had no significant effect on the antigen dependent or antigen independent (antigen blocking with 1 μM unconjugated huMy9-6) in vitro potency of the conjugates.

Example 8

Binding of Antibody-Drug Conjugate is Similar to that of Unmodified Antibody

The binding of huMY9-6-drug conjugate was compared with that of the unmodified huMY9-6 antibody against antigen-expressing HL60/QC cells using flow cytometry. Briefly, the antigen-positive cells were incubated with conjugates or unmodified antibodies at 4° C., then with a secondary antibody-FITC conjugate at 4° C., fixed with formaldehyde (1% in PBS) and analyzed by flow cytometry. No significant difference was observed between the binding of the conjugate versus that of the unmodified antibody. An example is shown in FIG. 27, where a huMY9-6-drug conjugate bound to antigen-positive cells with a high affinity similar to that of the unmodified antibody.

Example 9

In Vivo Efficacy of huMY9-6-SPDB-1f Conjugate in HL60/QC Tumor Bearing Nude Mice In this study, the anti-tumor activity of huMY9-6-SPDB-1f was investigated in female nude mice bearing HL60/QC tumors, a human acute myeloid leukemia model. HL60/QC tumor cells, $2 \times 10^6$ cells/mouse were subcutaneously inoculated at a volume of 0.1 mL/mouse in the area over the right shoulder of female athymic nude mice, 5 weeks of age. Eight days after tumor cell inoculation mice were randomized into groups (n=6 per group) by tumor volume. Treatment was initiated the day of randomization, and groups included a control group dosed with PBS (200 μL/injection), or a single treatment at various doses (5 to 100 μg/kg) of huMY9-6-SPDB-1f (50 μg/kg if dose corresponded to 2.5 mg/kg antibody dose). All treatments were well tolerated with the mean body weight losses comparable to loss seen in PBS control mice. Mean tumor volume vs time is shown (FIGS. 28 and 36) with the data demonstrating a dose-dependent anti-tumor activity of the huMY9-6-SPDB-1f conjugate. The minimum effective dose was estimated to be 20 μg/kg, which is about 35-fold lower that the maximum tolerated dose.

Example 10

The tolerability of huFOLR-1 conjugates was investigated in female CD-1 mice. Animals were observed for seven days prior to study initiation and found to be free of disease or illness. The mice were administered a single i.v. injection of the conjugate and the animals were monitored daily for body weight loss, morbidity or mortality. Table 9 shows that for huFOLR1-drug1 the conjugate was tolerated at only the lowest dose tested of 50 μg/kg. In contrast, both mono-imine conjugates huFOLR1-Drug 2 and huFOLR1-SPDB-1f were found to be better tolerated with a maximum tolerated dose of <198 μg/kg and >560 μg/kg respectively.

TABLE 9
Tolerability comparison data for (A) huFOLR1-drug1, (B) huFOLR1-Drug 2, and (C) huFOLR1-SPDB-1f conjugates.
A)
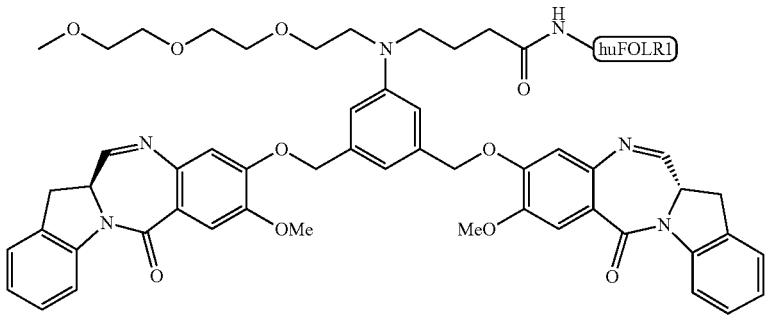
huFOLR1-drug1
MTD < 100 µg/kg
| Dose (µg/kg) | % Survival |
|---|---|
| 50 | 100 |
| 100 | 0 |
| 200 | 0 |
| 300 | 0 |
| 400 | 0 |
B)
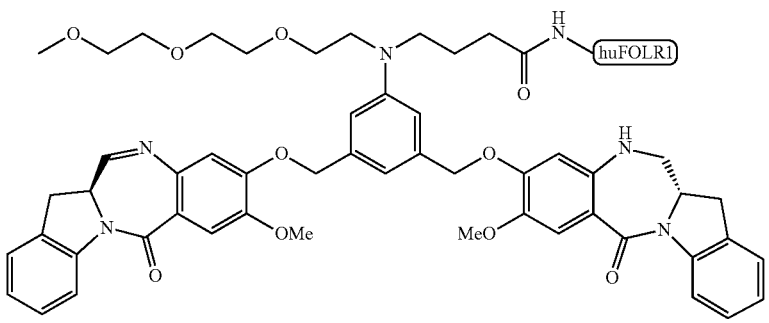
huFOLR1-drug2
MTD < 198 µg/kg
| Dose (µg/kg) | % Survival |
|---|---|
| 66 | 100 |
| 132 | 100 |
| 198 | 50 |
| 264 | 25 |
C)
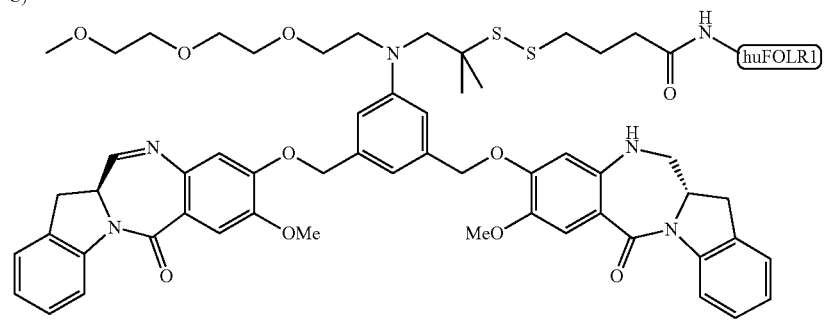
huFOLR1-SPDB-1f
MTD > 560 µg/kg TABLE 9-continued Tolerability comparison data for (A) huFOLR1-drug1, (B) huFOLR1-Drug 2, and (C) huFOLR1-SPDB-1f conjugates.

| Dose (μg/kg) | % Survival |
|---|---|
| 120 | 100 |
| 160 | 100 |
| 200 | 100 |
| 320 | 100 |
| 560 | 100 |

Example 11

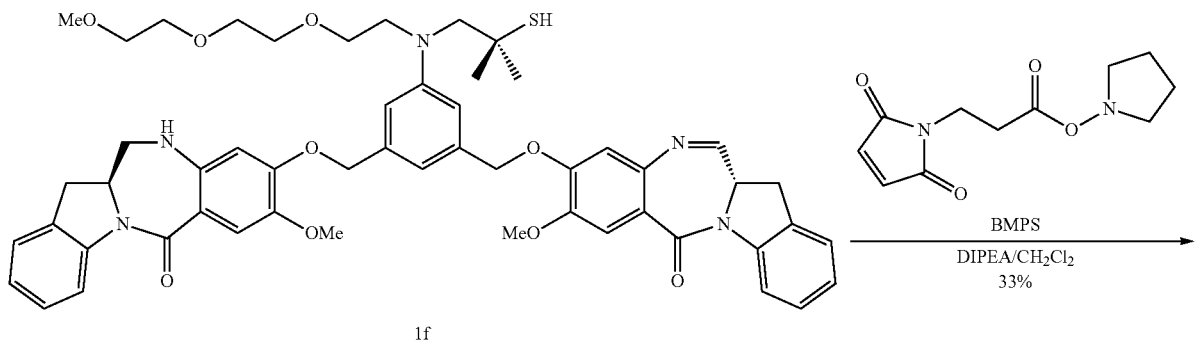

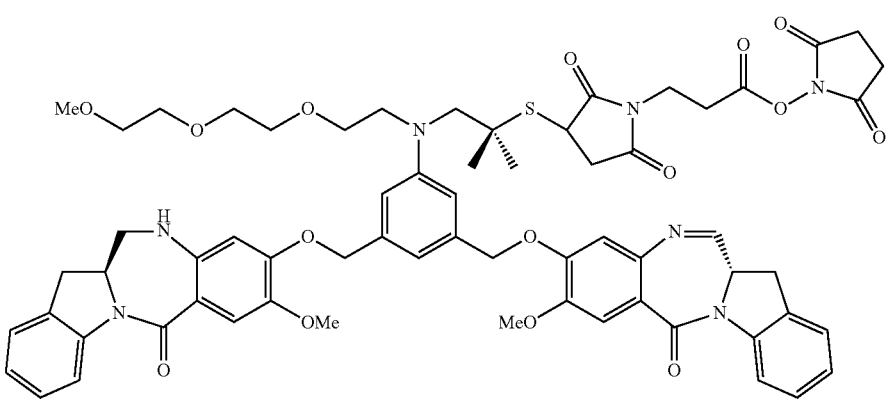

Compound 10:

To a stirred solution of 1f (18 mg, 0.019 mmol) and N-(β-maleimidopropyloxy)succinimide (BMPS) ester (9.2 mg, 0.034 mmol) in anhydrous dichloromethane (0.3 mL) was added anhydrous diisopropylethylamine (5 μL, 0.029 mmol). The mixture was stirred at room temperature for 27 hours, quenched with saturated ammonium chloride and diluted with dichloromethane. The organic layer was washed with brine, dried over anhydrous sodium sulfate, filtered and concentrated under reduced pressure. The residue was purified by preparative reverse phase HPLC (C18 column, $CH_3CN/H_2O$). The fractions containing product were combined, extracted with dichloromethane and evaporated to give compound 10 as a white solid (7.6 mg, y=33%). MS (m/z). found 1208.3 $(M+H)^+$. See FIG. 13.

Example 12

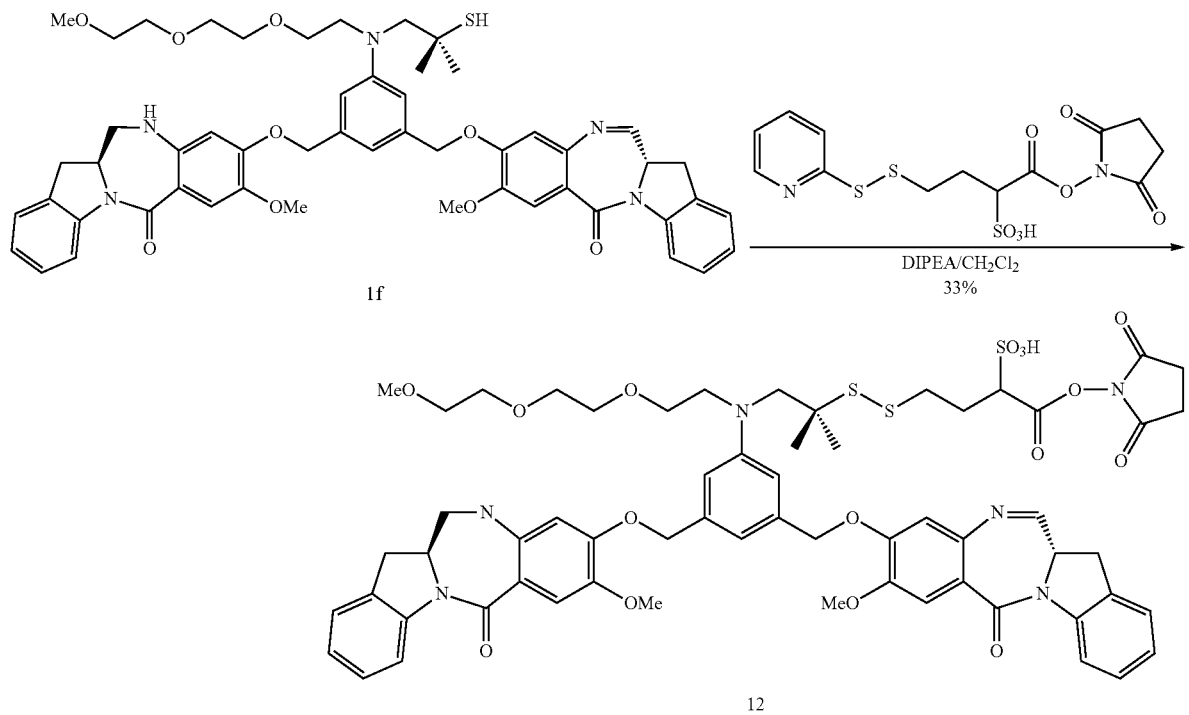

Compound 12:

To a stirred solution of 1f (16.5 mg, 0.018 mmol) and sulfo-SPDB (14.2 mg, 0.036 mmol) in anhydrous dichloromethane (0.3 mL) was added anhydrous diisopropylethylamine (9 μL, 0.054 mmol). The mixture was stirred at room temperature overnight and concentrated under reduced pressure. The residue was purified by preparative reverse phase HPLC (C18 column, $CH_3CN/H_2O$). The fractions containing product were combined, extracted with dichloromethane and evaporated to give 6.6 mg of compound 12 as yellowish foam. The aqueous layer was lyophilized to give another 0.5 mg of compound 12 as white solid. MS (m/z). found 1235.0 $(M-H)^-$. See FIG. 15.

Example 13

Preparation of Humanized Antibody-sulfoSPDB-1f Conjugate

A reaction containing 2.5 mg/mL huMy9-6 antibody and 10 molar equivalents of 10 (pretreated with 5-fold excess of sodium bisulfite in 90:10 DMA:water) in 50 mM HEPES (4-(2-hydroxyethyl)-1-piperazine ethanesulfonic acid) pH 8.5 buffer and 15% v/v DMA (N,N-dimethylacetamide) cosolvent was allowed to conjugate for 6 hours at 25° C. Post-reaction, the conjugate was purified and buffer exchanged into 250 mM Glycine, 10 mM Histidine, 1% sucrose, 0.01% Tween, 50 μM sodium bisulfite formulation buffer, using NAP desalting columns (Illustra Sephadex G-25 DNA Grade, GE Healthcare). Dialysis was performed in the same buffer for 4 hours at room temperature utilizing Slide-a-Lyzer dialysis cassettes (ThermoScientific 20,000 MWCO). The purified conjugate was found to have a DAR of 2.4 (by UV-Vis using molar extinction coefficients $\epsilon_{330\ nm}=15,484\ cm^{-1}M^{-1}$ and $\epsilon_{280\ nm}=30,115\ cm^{-1}M^{-1}$ for 1f, and $\epsilon_{280\ nm}=146,000\ cm^{-1}M^{-1}$ for My9-6 antibody), 96.7% monomer (by size exclusion chromatography), <1% unconjugated free drug compound (by acetone extraction/reverse-phase HPLC) and a final protein concentration of 1.4 mg/mL.

Figure 35B:
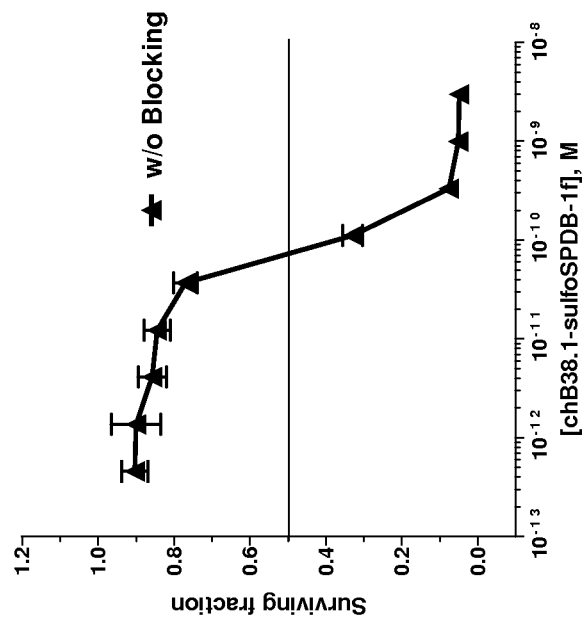
FIGS. 35A and 35B show in vitro cytotoxicity for chB38.1-SPDB-1f (A), and chB38.1-sulfoSPDB-1f (B) against COLO205 (Ag$^+$) cells. Note that in both experiments, sodium bisulfite was added to the conjugation reaction for making the conjugate.
Figure 35A:
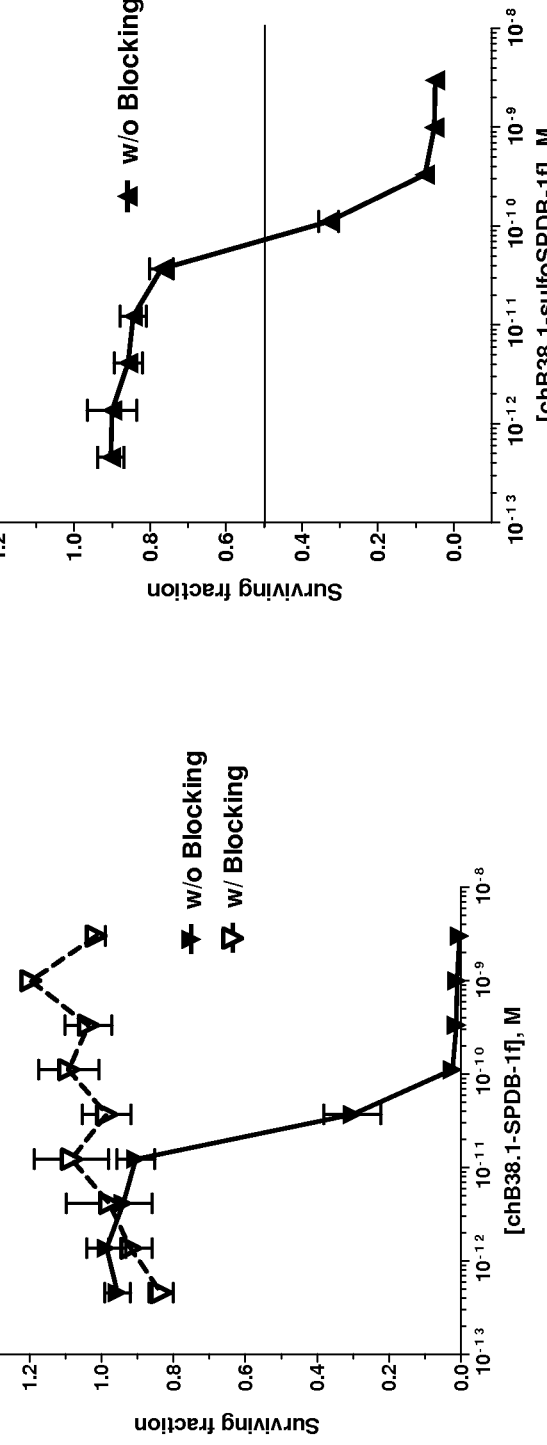
Figure 58:
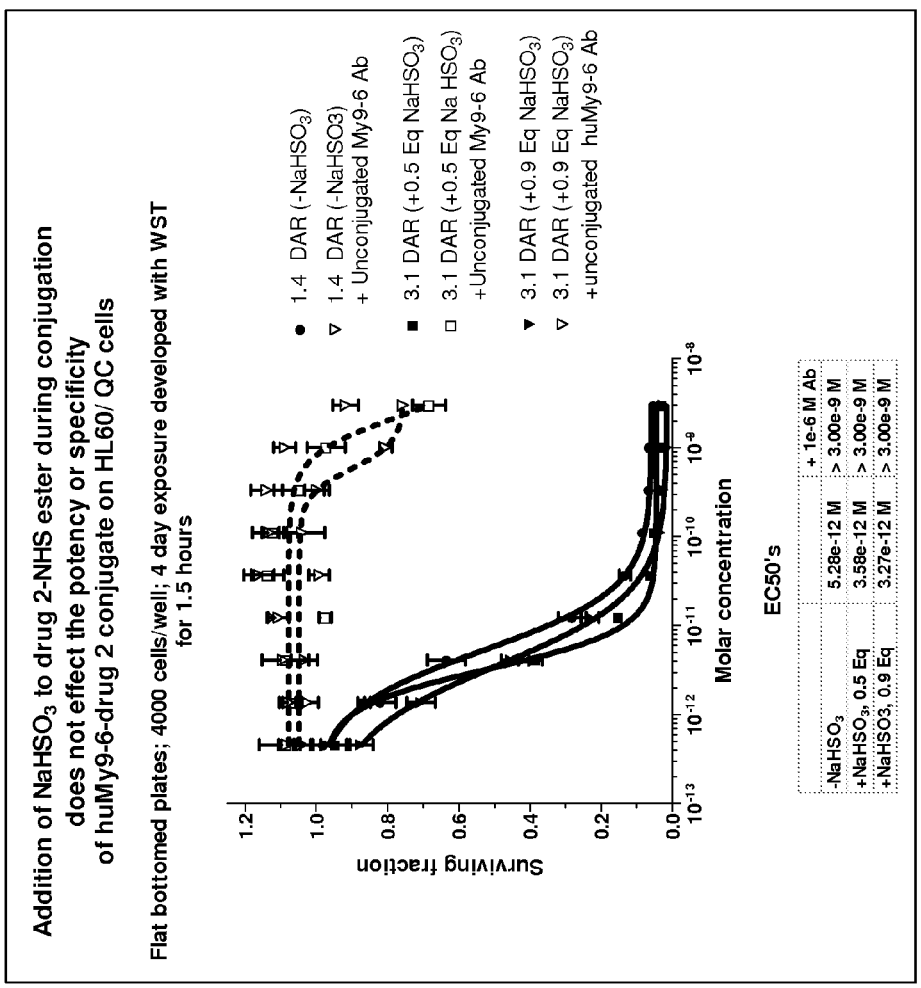
FIG. 58 shows similar in vitro cytotoxicity of HuMy9-6-Drug 2 (conjugates prepared without and with sodium bisulfite against CD33-antigen expressing HL60 cells.
Figure 59:
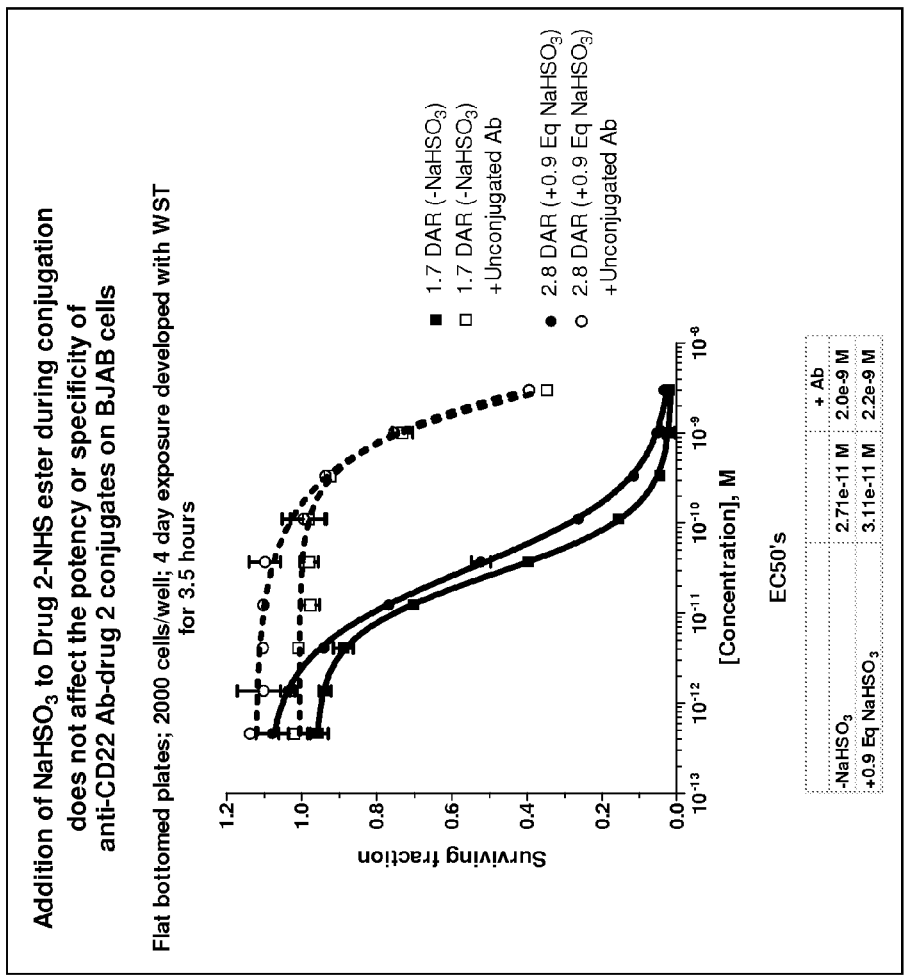
FIG. 59 shows similar in vitro cytotoxicity of anti-CD22 Ab-Drug 2 conjugates prepared without and with sodium bisulfite against CD22-antigen expressing BJAB cells.

In vitro potency of antibody-sulfoSPDB-1f conjugates were measured according to general procedure described in Example 7 and the data are shown in FIGS. 34 and 35. The antibody-sulfoSPDB-1f conjugates have comparable or higher potency than the antibody-SPDB-1f conjugates.

Use of covalent imine reactants, such as sodium bisulfite, improves Ab-compound conjugate specifications (e.g., % monomer and drug load). In one experiment, adduct formation was carried out with 5 molar equivalents of imine reactant over NHS-BMPS-1f in 90% DMSO/10% PBS pH 7.4 for 4 h at 25° C. The reaction mixture was then added to huMy9-6 antibody (4 molar equivalents IGN, 2 mg/ml, 10% v/v DMSO, 50 mM HEPES buffer, pH 8.5, 5 h, 25° C.). Conjugates made using sodium hydrosulfite, sodium bisulfite, or sodium metabisulfite had similar IGN/Ab ratios and % monomer, while conjugates made with no additive treatment led to very low drug incorporation. See table below.

| Reactant | IGN/Ab (UV) | % monomer (SEC) | % 1f on monomer |
|---|---|---|---|
| Sodium Hydrosulfite | 2.6 | 88 | 82 |
| Sodium Bisulfite | 2.6 | 88 | 83 |
| Sodium Metabisulfite | 2.7 | 88 | 82 |
| No additive | 0.1 | 98 | 94 |

Example 14

Preparation of Humanized Antibody-BMPS-1f Conjugate

A reaction containing 2.0 mg/mL huMy9-6 antibody and 5 molar equivalents of 12 (pretreated with 5-fold excess of sodium bisulfite in 90:10 DMA:water) in 50 mM HEPES (4-(2-hydroxyethyl)-1-piperazine ethanesulfonic acid) pH 8.5 buffer and 15% v/v DMA (N,N-dimethylacetamide) cosolvent was allowed to react for 6 hours at 25° C. Post-reaction, the conjugate was purified and buffer exchanged into 250 mM Glycine, 10 mM Histidine, 1% sucrose, 0.01% Tween, 50 µM sodium bisulfite formulation buffer, using NAP desalting columns (Illustra Sephadex G-25 DNA Grade, GE Healthcare). Dialysis was performed in the same buffer for 4 hours at room temperature utilizing Slide-a-Lyzer dialysis cassettes (ThermoScientific 20,000 MWCO). The purified conjugate was found to have a DAR of 2.8 (by UV-Vis using molar extinction coefficients $\epsilon_{330\ nm}$=15,484 cm$^{-1}$M$^{-1}$ and $\epsilon_{280\ nm}$=30,115 cm$^{-1}$M$^{-1}$ for 1f, and $\epsilon_{280\ nm}$=146,000 cm$^{-1}$M$^{-1}$ for My9-6 antibody), 91.7% monomer (by size exclusion chromatography), <1% unconjugated free drug compound (by acetone extraction/reverse-phase HPLC) and a final protein concentration of 1.2 mg/mL.

In vitro potency of antibody-BMPS-1f conjugates were measured according to general procedure described in Example 7 and the data are shown in FIGS. 34 and 35. The antibody-BMPS-1f conjugates have comparable potency to the antibody-SPDB-1f conjugates.

Example 15

In Vivo Efficacy of hu FOLR1-SPDB-1f Conjugate in KB Tumor Bearing Nude Mice In this study, the anti-tumor activity of hu FOLR1-SPDB-1f was investigated in female nude mice bearing KB tumors, a human cervical carcinoma model. KB, 1×10$^7$ cells/mouse were subcutaneously inoculated at a volume of 0.1 mL/mouse in the area over the right shoulder of female athymic nude mice, 6 weeks of age. Six days after tumor cell inoculation mice were randomized into groups (n=6 per group) by tumor volume. Treatment was initiated the day after randomization, and groups included a control group dosed with PBS (200 µL/injection), or a single treatment at various doses (20 to 200 µg/kg) of hu FOLR1-SPDB-1f (50 µg/kg linked drug dose corresponded to 2.8 mg/kg antibody dose). All treatments were well tolerated with no body weight loss seen in any of the test groups. Mean tumor volume vs time is shown (FIG. 37) with the data demonstrating a dose-dependent anti-tumor activity of the hu FOLR1-SPDB-1f conjugate. The minimum effective dose was estimated to be <50 µg/kg, which is about 14-fold lower than the maximum tolerated dose.

Similar in vivo results have also been obtained using other conjugates of the invention against various other cancer models, including huMy9-6-sulfo-SPDB-1f in MOLM-13 tumor bearing mice (FIG. 50); huMy9-6-sulfo-SPDB-1f in NB4 tumor bearing mice (FIG. 51); huMy9-6-BMPS-1f in HL60/QC tumor bearing mice (FIG. 52); huMy9-6-BMPS-1f in MOLM-13 tumor bearing mice (FIG. 53); huMy9-6-Drug 2 in HL60/QC tumor bearing mice (FIG. 56); and huMy9-6-Drug 2 in MOLM-13 tumor bearing mice (FIG. 57). Note that in FIGS. 53, 54, 56, and 57, conjugates were prepared in the presence of sodium bisulfite.

To compare in vivo efficacy of the subject conjugates prepared with or without an imine reactive group, huMy9-6-Drug 2 were formulated with or without 50 µM sodium bisulfite, and the conjugates were used to treat mice bearing HL60-QC tumor xenografts. The data below shows that conjugate formulated with or without 50 µM sodium bisulfite showed comparable T/C % at ~20 µg/kg drug dose, indicating that the inclusion of sodium bisulfite in the conjugate preparation step does not negatively impact the in vivo potency of the subject conjugate.

| NaHSO$_3$ | Minimum effective dose (µg/kg drug) | T/C % |
| --- | --- | --- |
| − | 18 | 20 |
| + | 19 | 16 |

Example 16

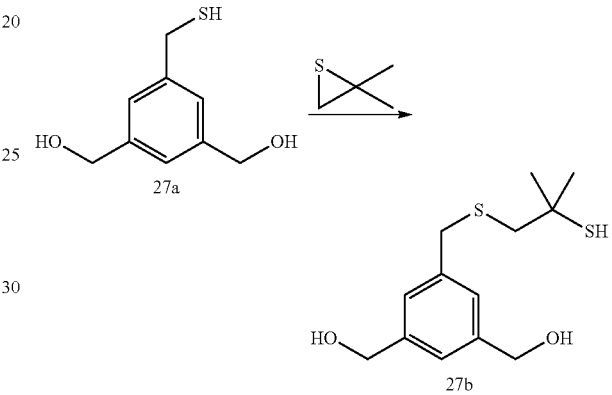

Compound 27b:
(5-((2-mercapto-2-methylpropylthio)methyl)-1,3-phenylene)dimethanol: (5-(mercaptomethyl)-1,3-phenylene)dimethanol (0.163 g, 0.885 mmol) was dissolved in methanol (3 mL) in a small vial and a stir bar was added. To this solution was added triethylamine (0.016 mL, 0.118 mmol) followed by 2,2-dimethylthiirane (0.058 mL, 0.590 mmol) and the resulting mixture was capped and stirred overnight (16 hrs) at room temperature. The reaction was then concentrated, redissolved in dichloromethane, loaded onto a silica ptlc plate (1000 micron) and the plate was developed using 10% methanol in dichloromethane. The band corresponding to the product was scraped, filtered with neat ethyl acetate, and concentrated to give (5-((2-mercapto-2-methylpropylthio)methyl)-1,3-phenylene)dimethanol (0.095 g, 0.349 mmol, 59.1% yield). $^1$H NMR (400 Hz, CDCl$_3$): δ 7.26 (s, 3H), 4.69 (s, 4H), 3.82 (s, 2H), 2.74 (s, 2H), 2.17 (s, 1H), 2.12 (br s, 2H), 1.43 (s, 6H); $^{13}$C NMR (400 Hz, CDCl$_3$): δ 141.6, 138.9, 126.7, 124.3, 65.0, 49.0, 45.4, 38.4, 31.5; MS (m/z), expected: 272.4. found 295.0 (M+Na). See FIG. 30.

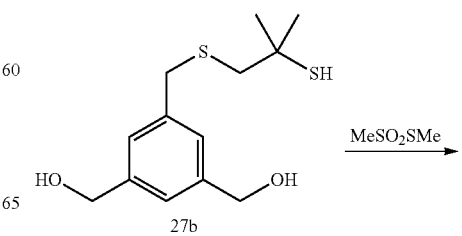

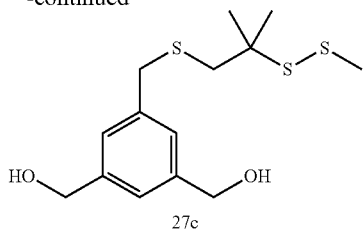

27c

Compound 27c:

(5-((2-methyl-2-(methyldisulfanyl)propylthio)methyl)-1,3-phenylene)dimethanol: (5-((2-mercapto-2-methylpropylthio)methyl)-1,3-phenylene)dimethanol (0.120 g, 0.440 mmol) was dissolved in ethanol (5 mL) and 1.0 M potassium phosphate buffer (pH 7) (5.00 mL) and cooled in an ice bath (a ppt formed but it was ignored). S-methyl methanesulfonothioate (0.083 mL, 0.881 mmol) was added and the mixture stirred overnight with gradual (over 30 minutes) warming to room temperature. The reaction was diluted with dichloromethane and the organic layer was removed, washed with water, dried over anhydrous sodium sulfate, and concentrated in vacuo. The residue was dissolved in dichloromethane and loaded onto a 500 micron ptlc plate and developed with 66% ethyl acetate in hexane. The band corresponding to the product was scraped, filtered using ethyl acetate, and concentrated to give (5-((2-methyl-2-(methyldisulfanyl)propylthio)methyl)-1,3-phenylene)dimethanol (0.091 g, 0.286 mmol, 64.9% yield). $^1$H NMR (400 Hz, CDCl$_3$): δ 7.27 (s, 3H), 4.71 (s, 4H), 3.78 (s, 2H), 2.77 (s, 2H), 2.41 (s, 3H), 1.94 (br s, 2H), 1.38 (s, 6H); $^{13}$C NMR (400 Hz, CDCl$_3$): δ 141.6, 139.0, 126.7, 124.2, 65.0, 51.8, 44.0, 38.2, 26.7, 25.3; MS (m/z), expected: 341.5. found 341.1 (M+Na). See FIG. 30.

added followed by the addition of methanesulfonyl chloride (50.7 μL, 0.653 mmol) at −5° C. The reaction was stirred at −5° C. for one hour after which it was diluted with cold ethyl acetate and ice was added. The mixture was transferred to a separatory funnel and extracted with cold ethyl acetate. The organic extracts were washed with ice water and then dried with anhydrous magnesium and sodium sulfate, filtered and concentrated under reduced pressure. The resulting (5-((2-methyl-2-(methyldisulfanyl)propylthio)methyl)-1,3-phenylene)bis(methylene)dimethanesulfonate was used without further purification.

IBD monomer (177 mg, 0.602 mmol) in anhydrous N,N-dimethylformamide (1.75 mL) was added to (5-((2-methyl-2-(methyldisulfanyl)propylthio)methyl)-1,3-phenylene)bis(methylene)dimethanesulfonate (119 mg, 0.251 mmol) at ambient temperature. Potassium carbonate (173 mg, 1.253 mmol) was added and the reaction was allowed to stir at ambient temperature for 20 hours. The reaction mixture was quenched with water and extracted with dichloromethane. The extracts were washed with brine and then dried with anhydrous sodium sulfate, filtered and concentrated on high vacuum. The crude product was purified by flash silica gel chromatography (neat DCM 4.2% MeOH/DCM). Fractions containing product were combined, concentrated and purified by semi-prep RP-HPLC (C18, A=DI water B=ACN, 20 mL/min) Fractions containing desired product were combined, extracted with dichloromethane, dried with anhydrous magnesium sulfate, filtered and concentrated to yield the desired product (46 mg, 21%). $^1$H NMR (400 Hz, CDCl$_3$): δ 8.19 (d, J=8.0 Hz, 2H), 7.77 (m, d, J=4.4 Hz, 2H), 7.50 (s, 2H), 7.34 (s, 1H), 7.31 (s, 2H), 7.19 (m, 4H), 7.03 (t, J=7.2, 7.6 Hz, 2H), 6.77 (s, 2H), 5.14

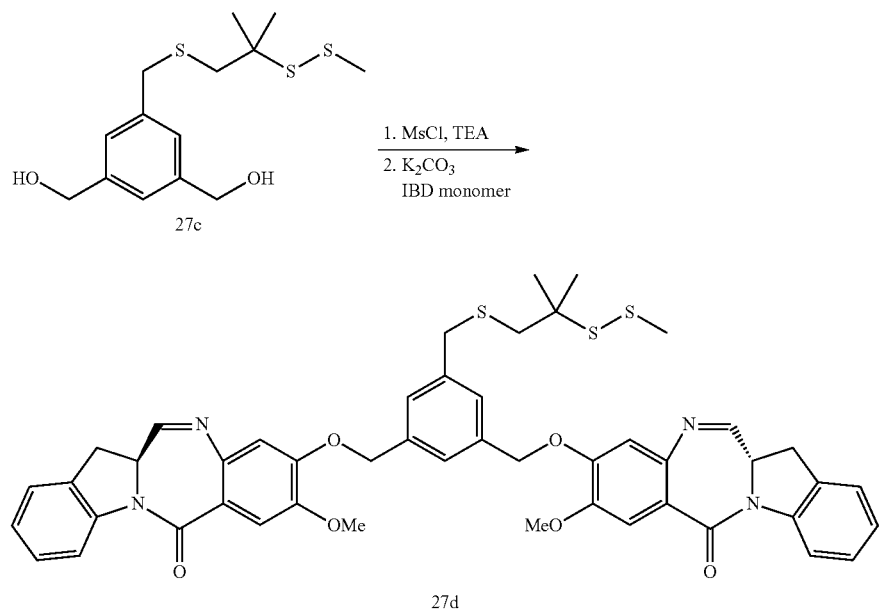 [SMILES: CSSC(C)(C)CSCc1cc(CO)cc(CO)c1 ; COc1cc2c(cc1OCc1cc(COc3cc4c(cc3OC)C(=O)N3c5ccccc5C[C@H]3C=N4)cc(CSCC(C)(C)SSC)c1)N=C[C@@H]1Cc3ccccc3N1C2=O]

27d

Compound 27d:

(5-((2-methyl-2-(methyldisulfanyl)propylthio)methyl)-1,3-phenylene)dimethanol (80 mg, 0.251 mmol) in anhydrous dichloromethane (1.75 mL) was cooled to −5° C. in a brine/ice bath. Triethylamine (105 μL, 0.753 mmol) was (m, 4H), 4.40 (m, 2H), 3.91 (s, 6H), 3.70 (m, 2H), 3.63 (m, 2H), 3.41 (m, 2H), 2.65 (s, 2H), 2.29 (s, 3H), 1.26 (s, 6H). MS (m/z), Calcd. 893.2 (M+Na)$^+$. found 893.2 (M+Na)$^+$, 911.2 (M+H$_2$O+Na)$^+$, 929.2 (M+2H$_2$O+Na)$^+$, 945.1 (M+2H$_2$O+K)$^+$. See FIG. 30.

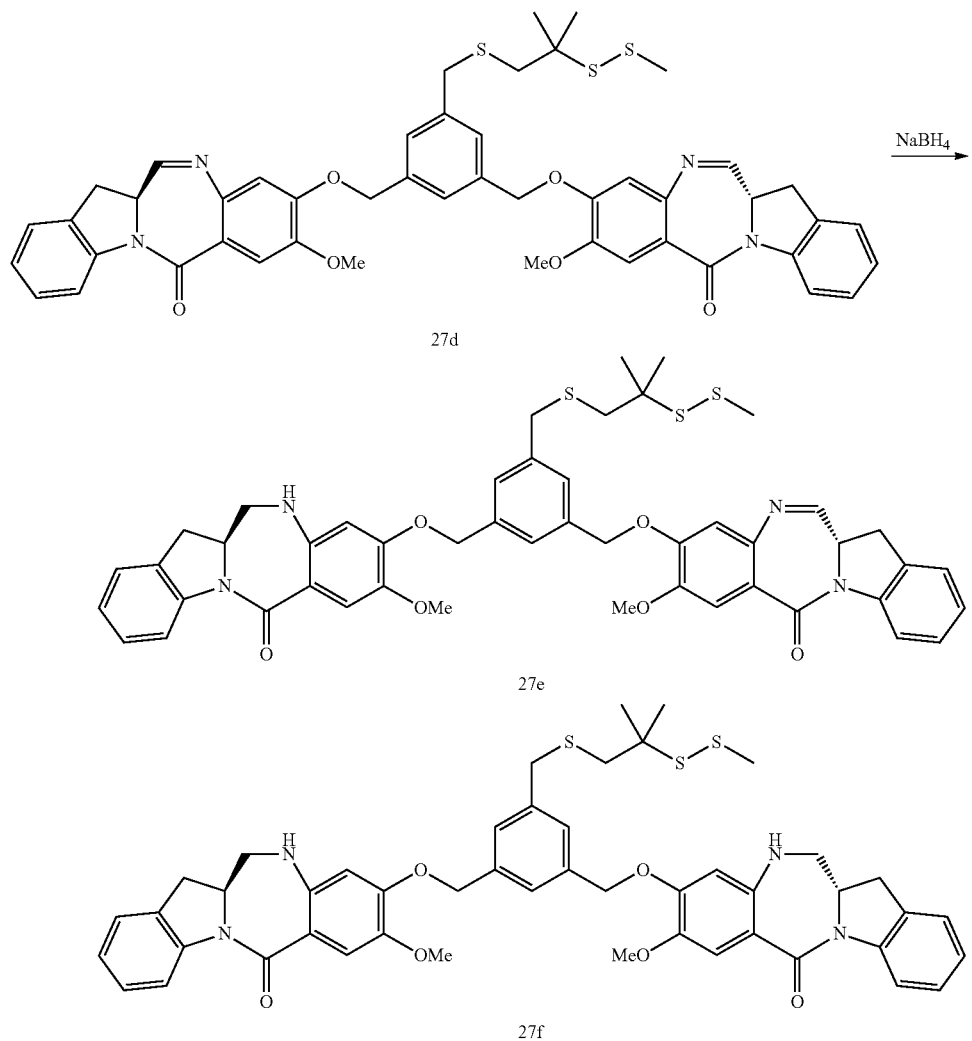

27d

27e

27f

Compound 27e and 27f:

To a cooled solution (0° C.) of 27d (50 mg, 0.057 mmol) in anhydrous dichloromethane (225 µL) and ethanol (450 µL) was added sodium borohydride (0.651 mg, 0.017 mmol). The reaction was stirred for five minutes at 0° C. and then at ambient temperature for 2.5 hrs. The reaction mixture was cooled to 0° C., quenched with saturated ammonium chloride, and extracted with dichloromethane. The organic extracts were washed with brine, dried over anhydrous sodium sulfate, filtered through Celite and concentrated. The crude material was purified by semi-prep RP-HPLC (C18, A=DI water B=ACN, 20 mL/min) Fractions containing desired product were combined, extracted with dichloromethane, dried with anhydrous magnesium sulfate, filtered and concentrated to yield the mono reduced amine 27e (11 mg, 22%) MS (m/z), Calcd. 895.3 (M+Na)+ found 895.2 (M+Na)+, 913.2 (M+H₂O+Na)+, 929.2 (M+H₂O+K)+ and the di-reduced amine 27f (5 mg, 10%) MS (m/z), Calcd. 897.3 (M+Na)+. found 897.3 (M+Na)+. See FIG. 30.

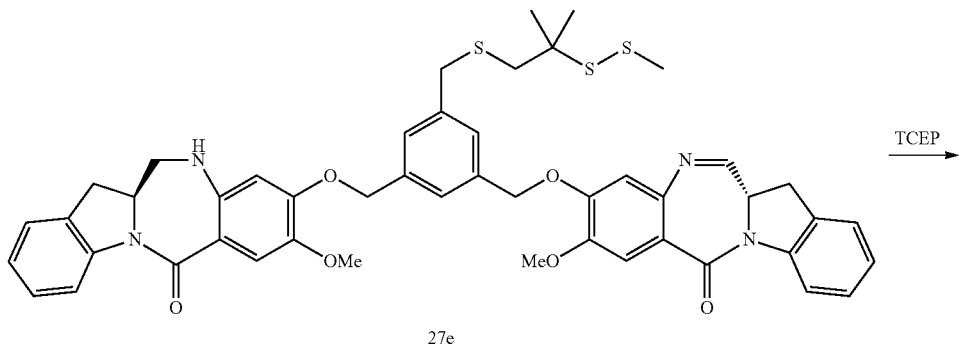

27e

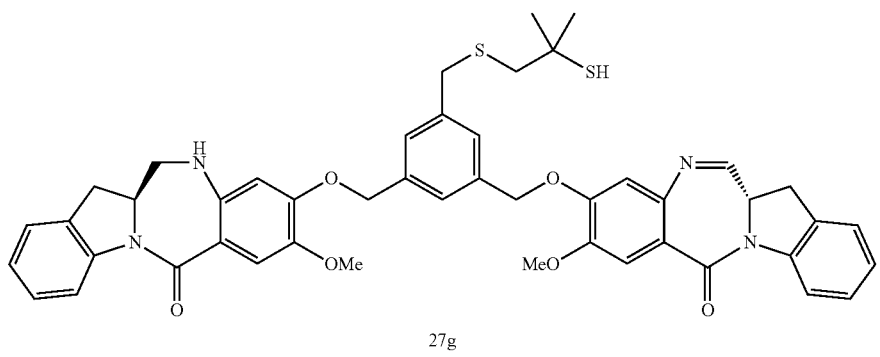

27g

Compound 27g:

To a stirred solution of 27e (10 mg, 0.011 mmol) in methanol (733 μL) and acetonitrile (880 μL) was added tris(2-Carboxyethyl) phosphine hydrochloride (9.85 mg, 0.034 mmol) in buffer 6.5 (147 μL). The mixture stirred at 3 hours at ambient temperature. The reaction was diluted with dichloromethane. Water was added and the layers were separated. The organic layer was washed with brine, dried with anhydrous sodium sulfate, filtered and concentrated under reduced pressure to give compound 27g (9 mg, 95%). MS (m/z), Calcd. 849.3 (M+Na)+. found 849.2 (M+Na)+, 867.2 (M+K)+. See FIG. 30.

Compound 27h:

To a stirred solution of 27g (9 mg, 10.88 μmol) and 2,5-dioxopyrrolidin-1-yl 4-(pyridin-2-yldisulfanyl)butanoate (9.3 mg, 0.023 mmol) in anhydrous dichloromethane (0.4 mL) was added anhydrous diisopropylethylamine (9 μl, 0.054 mmol) and the reaction was stirred at room temperature overnight. The mixture was quenched with saturated ammonium chloride solution and extracted with dichloromethane. The extracts were washed with brine, dried with anhydrous sodium sulfate and concentrated under reduced pressure. The residue was purified by preparative reverse phase HPLC (C18 column, $CH_3CN/H_2O$). The fractions containing product were combined, extracted with dichloromethane and evaporated to give compound 27h (5 mg, 44%). MS (m/z), Calcd. 1064.3 (M+Na)+. found 1064.1 (M+Na)+, 1082.1 (M+$H_2O$+Na)+, 1098.1 (M+$H_2O$+K)+. See FIG. 30.

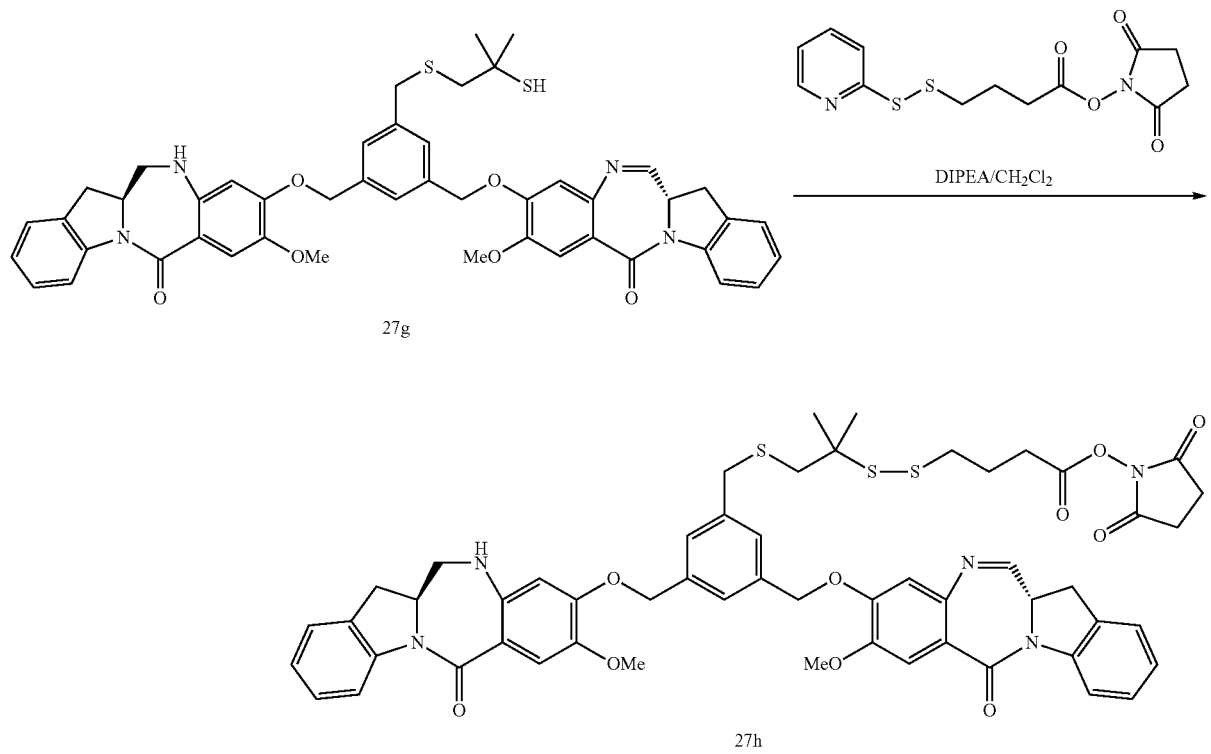 [SMILES: COc1cc2c(cc1OCc1cc(COc3cc4c(cc3OC)C(=O)N3c5ccccc5C[C@H]3CN4)cc(CSCC(C)(C)S)c1)N=C[C@@H]1Cc3ccccc3N1C2=O ; O=C(CCCSSc1ccccn1)ON1C(=O)CCC1=O ; COc1cc2c(cc1OCc1cc(COc3cc4c(cc3OC)C(=O)N3c5ccccc5C[C@H]3CN4)cc(CSCC(C)(C)SSCCCC(=O)ON3C(=O)CCC3=O)c1)N=C[C@@H]1Cc3ccccc3N1C2=O]

Example 17

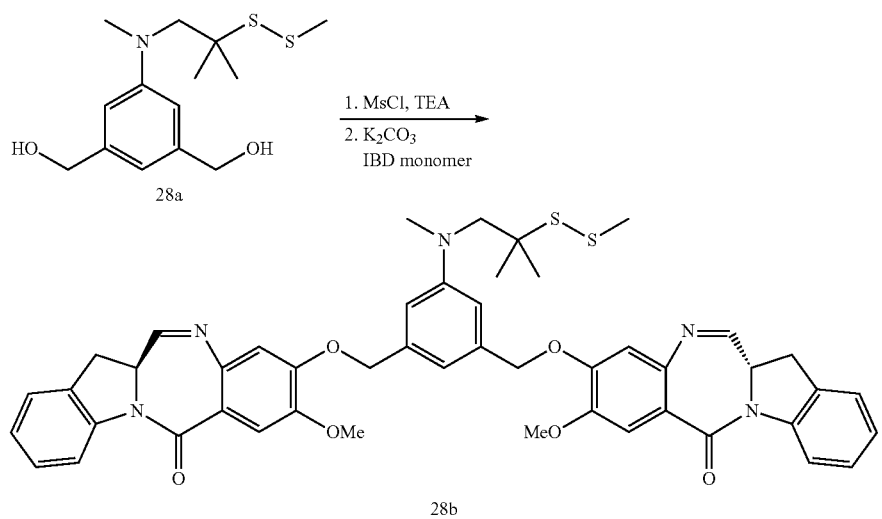

Compound 28b:

(5-(methyl(2-methyl-2-(methyldisulfanyl)propyl)amino)-1,3-phenylene)dimethanol (52 mg, 0.172 mmol) was dissolved in anhydrous dichloromethane (1.7 mL) and cooled to −5 in an acetone/ice bath. First, triethylamine (0.120 mL, 0.862 mmol) was added followed by methanesulfonyl chloride (0.040 mL, 0.517 mmol). The mixture was stirred in the bath for 1 hour. The reaction was then diluted with cold ethyl acetate and washed with cold water three times and then dried over anhydrous magnesium sulfate. The dimesylate was filtered, concentrated in vacuo, and placed under high vacuum until completely dry. The product was used as is directly in the next step.

IBD monomer (115 mg, 0.39 mmol) in anhydrous N,N-dimethylformamide (1.5 mL) was added to (5-(methyl(2-methyl-2-(methyldisulfanyl)propyl)amino)-1,3-phenylene)bis(methylene)dimethanesulfonate (72 mg, 0.156 mmol) at ambient temperature. Potassium carbonate (108 mg, 0.780 mmol) was added and the reaction was allowed to stir at ambient temperature for 20 hours. Water (10 mL) was added directly to the mixture with stirring resulting in the formation of a white precipitate. The mixture was filtered and the solids were washed with additional portions of water. The solid was then dissolved in dichloromethane, extracted with water, the organic layer was then dried over anhydrous sodium sulfate, filtered, and concentrated in vacuo to give compound 28b (104 mg, 78%) which was used in the next step without further treatment. MS (m/z). found 912.1 (M+2H$_2$O+Na). See FIG. 31.

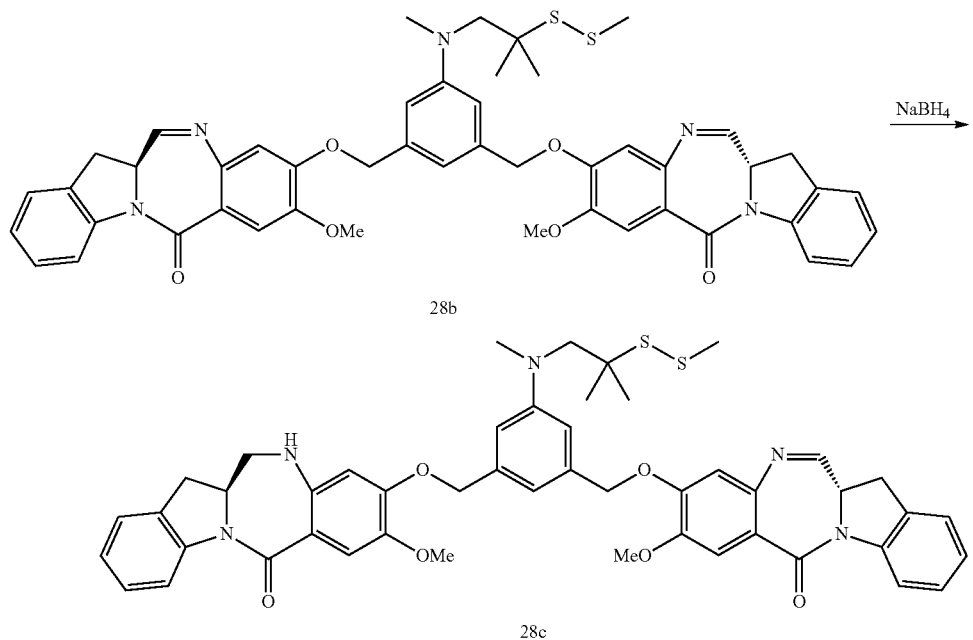

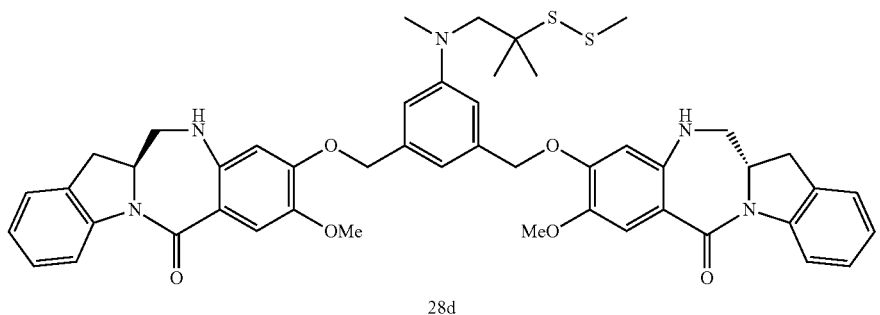

28d

Compound 28c and 28d:

Compound 28b (55 mg, 0.064 mmol) was dissolved in an anhydrous mixture of dichloromethane (0.4 mL) and ethanol (0.8 mL) and cooled to 0° C. in an ice bath. A sodium borohydride (0.731 mg, 0.019 mmol) solution dissolved in ethanol (100 μl) was then added and the mixture was stirred for 5 minutes and the ice bath was removed. The reaction was allowed to stir for 2 hours, quenched at low temperature by adding saturated ammonium chloride and dichloromethane, separated and the organic layer was washed with brine, dried over anhydrous sodium sulfate, filtered, and concentrated in vacuo. The residue was purified by semi-prep RP-HPLC (C18, A=DI water B=ACN, 20 mL/min) The fractions containing the desired products were extracted with dichloromethane and concentrated to give the mono-imine 28c (19 mg, 32%) MS (m/z), expected: 855.1. found: 896.2 (M+H$_2$O+Na) and the di-reduced amine 28d (22 mg, 38%) MS (m/z), expected: 857.1. found: 880.2 (M+Na)$^+$. See FIG. 31.

Example 18

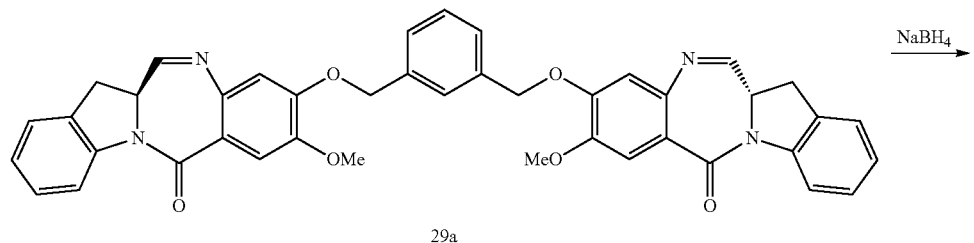

29a

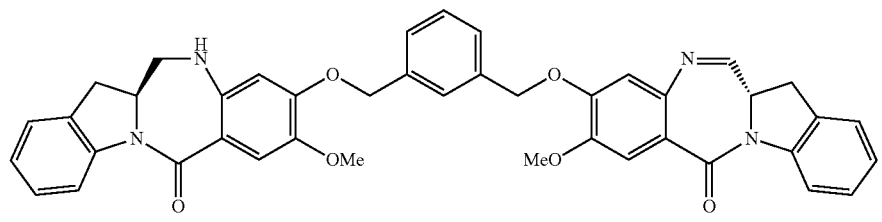

29b

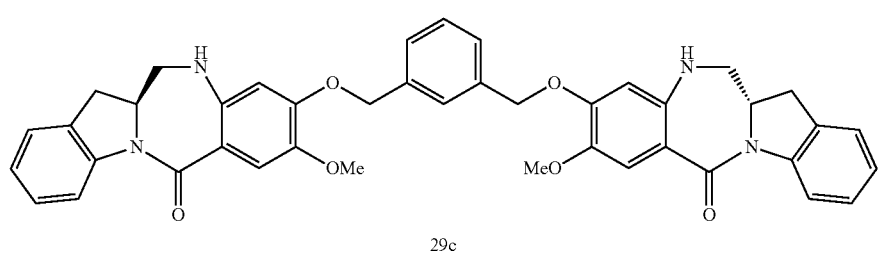

29c

Compound 29b and 29c:

Compound 29a (60 mg, 0.043 mmol) was dissolved in an anhydrous mixture of dichloromethane (0.25 mL) and ethanol (0.5 mL) and cooled to 0° C. in an ice bath. A sodium borohydride (0.493 mg, 0.013 mmol) solution dissolved in ethanol (50 µL) was then added and the mixture was stirred for 5 minutes and the ice bath was removed. The reaction was allowed to stir for 3 hours, quenched at low temperature by adding saturated ammonium chloride and dichloromethane, separated and the organic layer was washed with brine, dried over anhydrous sodium sulfate, filtered, and concentrated in vacuo. The residue was purified by semi-prep RP-HPLC (C18, A=DI water B=ACN, 20 mL/min) The fractions containing the desired products were extracted with dichloromethane and concentrated to give the mono-imine 29b (20 mg, 33%) MS (m/z), expected: 715.7. found: 715.2 (M+Na)$^+$, 733.2 (M+H$_2$O+Na)$^+$, 749.2 (M+H$_2$O+K)$^+$ and the di-reduced amine 29c (12 mg, 20%) MS (m/z), expected: 694.7. found: 717.2 (M+Na)$^+$. See FIG. 32.

Example 19

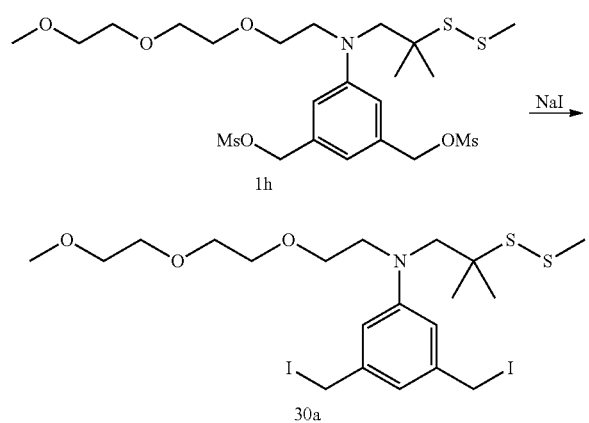

Compound 30a:

(5-((2-(2-(2-methoxyethoxy)ethoxy)ethyl)(2-methyl-2-(methyldisulfanyl)propyl)amino)-1,3-phenylene)bis(methylene)dimethanesulfonate (0.566 g, 0.960 mmol) was dissolved in acetone (30 mL) and a solution of sodium iodide (0.544 g, 3.63 mmol) dissolved in acetone (2 mL) was added with vigorous stirring. The reaction was monitored by tlc (50% ethyl acetate in hexane) and after 2 hours the reaction was filtered, concentrated in vacuo and dichloromethane was added to the residue. The solid salt left behind was filtered, the filtrate was concentrated and the resulting residue was purified on silica gel using a 3:5:2 mixture of ethyl acetate:hexane:dichloromethane to give 3,5-bis(iodomethyl)-N-(2-(2-(2-methoxyethoxy)ethoxy)ethyl)-N-(2-methyl-2-(methyldisulfanyl)propyl)aniline (0.505 g, 0.773 mmol, 74.5% yield) as a yellow oil. $^1$H NMR (400 Hz, CDCl$_3$): δ 6.75 (s, 2H), 6.73 (s, 1H), 4.38 (s, 4H), 3.63 (m, 14H), 3.40 (s, 3H), 2.50 (s, 3H), 1.38 (s, 6H); $^{13}$C NMR (400 Hz, CDCl$_3$): δ 148.7, 140.3, 117.3, 113.4, 71.9, 70.7, 70.6, 67.2, 59.8, 59.1, 53.5, 53.4, 51.8, 26.5, 25.6, 6.11; MS (m/z), Calcd 676.0 (M+Na)$^+$. found 675.8 (M+Na)$^+$. See FIG. 33.

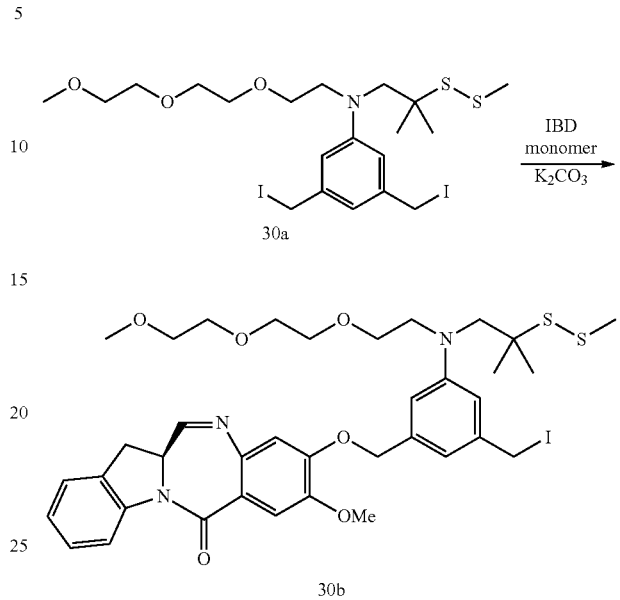

Compound 30b:

IBD Monomer (0.060 g, 0.204 mmol) was dissolved in acetone (4 ml) in a small vial, a stir bar was added, followed by 3,5-bis(iodomethyl)-N-(2-(2-(2-methoxyethoxy)ethoxy)ethyl)-N-(2-methyl-2-(methyldisulfanyl)propyl)aniline (0.167 g, 0.255 mmol) and potassium carbonate (0.070 g, 0.510 mmol). The vial was capped and stirred at room temperature overnight. The solids were filtered off and the filtrate was concentrated. The residue was dissolved in dichloromethane, extracted with water, and the organic layer was dried over anhydrous sodium sulfate, filtered, and concentrated in vacuo to give 108 mg of crude material. The crude material was purified on silica gel using 30% ethyl acetate to remove the di-iodo starting material followed by 10% methanol in dichloromethane to give the desired product 30b (21 mg, 0.026 mmol, 13%). MS (m/z), expected: 819.1. found: 858.0 (M+K)$^+$, 890.0 (M+CH$_3$OH+K)$^+$. See FIG. 33.

Compound 1d:

The reduced monomer 3b (4.16 mg, 0.014 mmol) was dissolved in acetone (2 ml) in a small vial, a stir bar was added, followed by 30b (10 mg, 0.012 mmol) and potassium carbonate (4.21 mg, 0.030 mmol). The vial was capped and stirred at room temperature overnight. The reaction was concentrated to remove the acetone and then redissolved in dichloromethane, extracted with water, dried over anhydrous sodium sulfate, filtered, and concenrated in vacuo. The residue was purified by reverse phase C18 HPLC to get 1d (2.1 mg, 2.125 µmol, 17.42% yield). MS (m/z). found 1010.4 (M+Na)$^+$, 1028.4 (M+H$_2$O+Na)$^+$. See FIG. 33.

Example 20

Synthesis of Compound 1

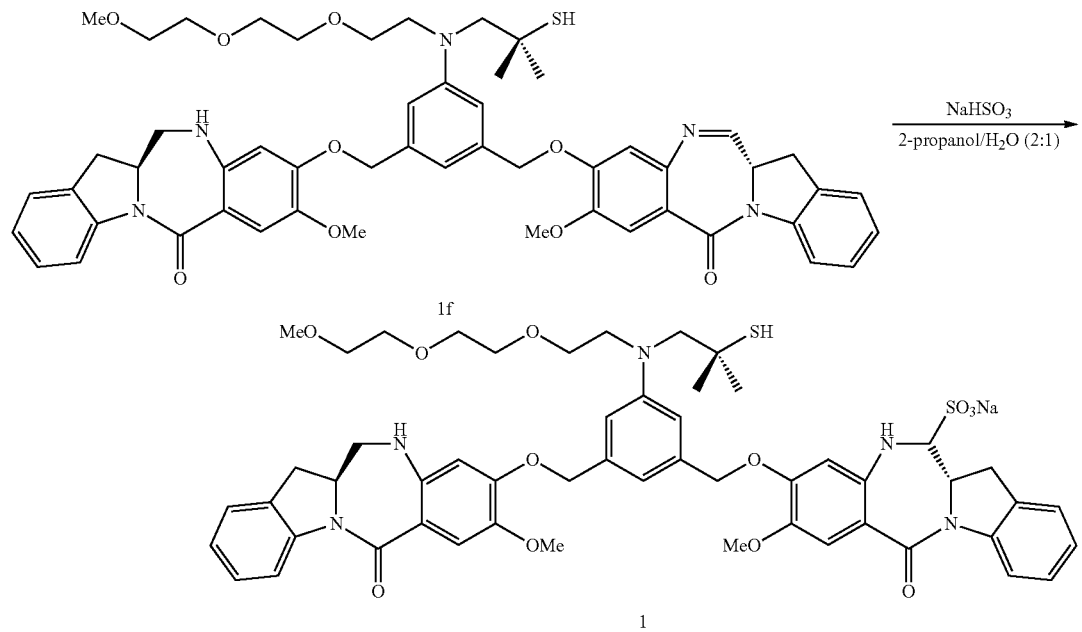

Compound 1:

To a stirred suspension of 1f (226 mg, 0.24 mmol) in IPA (20 mL) and deionized water (10 mL) was added sodium bisulphite (50 mg, 0.48 mmol). The mixture was stirred vigorously at rt for 2 hours. It was frozen with dry ice/aceton and lyophilized. The obtained white fluffy solid was dissolved in CH$_3$CN/H$_2$O and purified by reverse phase HPLC (C18 column, CH$_3$CN/H$_2$O). The fractions containing the desired product were combined and frozen with dry ice/acetone and lyophilized to give the desired compound 1 as white fluffy solid (179.6 mg, 5=71.6%). MS (m/z). found 1022.0 (M−H)$^−$. See FIG. 38.

Example 21

Synthesis of Compound 9c

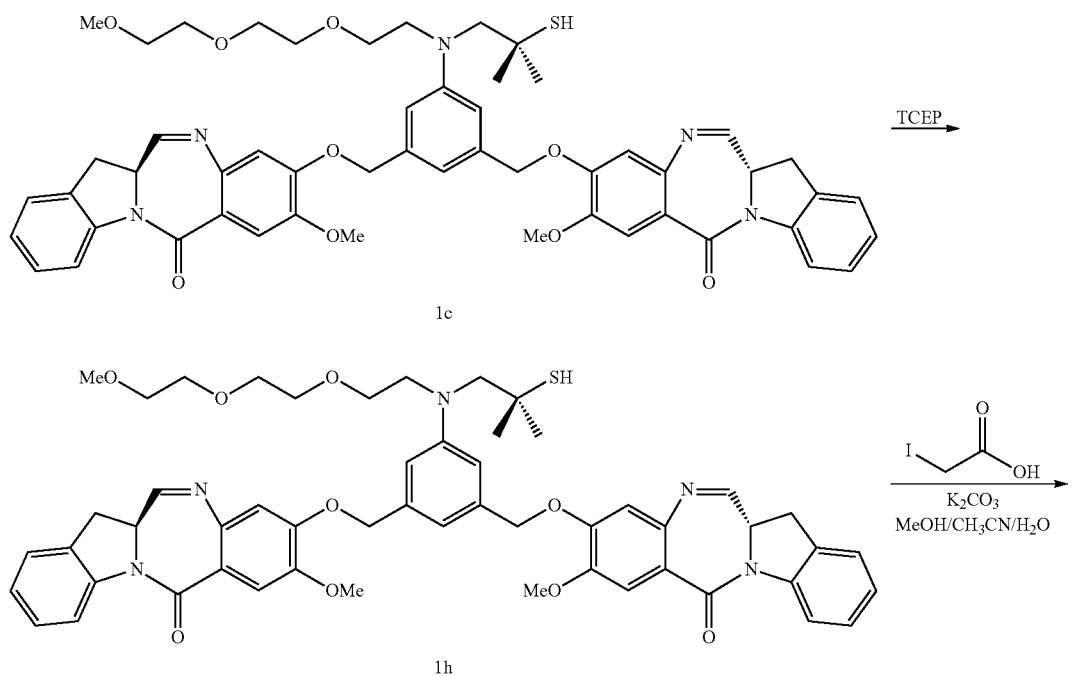

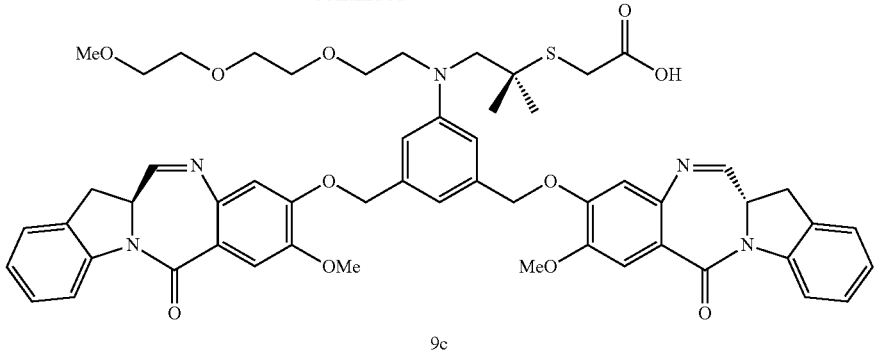

9c

Compound 9c:

To a stirred solution of 1c (60 mg, 0.061 mmol) in CH₃CN (3 mL) was added freshly prepared TCEP solution (49 mg, 0.17 mmol of TCEP HCl salt was neutralized with saturated sodium bicarbonate to pH ~6.5 then diluted with 0.5 mL of pH 6.5 phosphate buffer) at room temperature. MeOH (2.5 mL) was added and the mixture was stirred at room temperature for 3 hours. The reaction mixture was diluted with dichloromethane and deionized water, separated and the organic layer was washed with brine, dried over anhydrous Na₂SO₄ and filtered. The filtrate was stripped and high vacuumed to give 60 mg of 1h as light yellowish foam. MS (m/z). found 940.1 (M+H)⁺. It was dissolved in methanol (1.0 mL) and CH₃CN (1.4 mL) followed by addition of iodoacetic acid (24 mg, 0.13 mmol), deionized water (0.1 mL) and potassium carbonate (27 mg, 0.19 mmol). The mixture was stirred at rt overnight (monitored by LCMS). It was quenched with saturated ammonium chloride to make the solution acidic then diluted with dichloromethane, separated and washed with brine, dried over anhydrous Na₂SO₄, filtered and stripped to give compound 9c (57.8 mg, y=91%) which was directly used for next step without purification. MS (m/z). found 998.1 (M+H)⁺. See FIG. 12A.

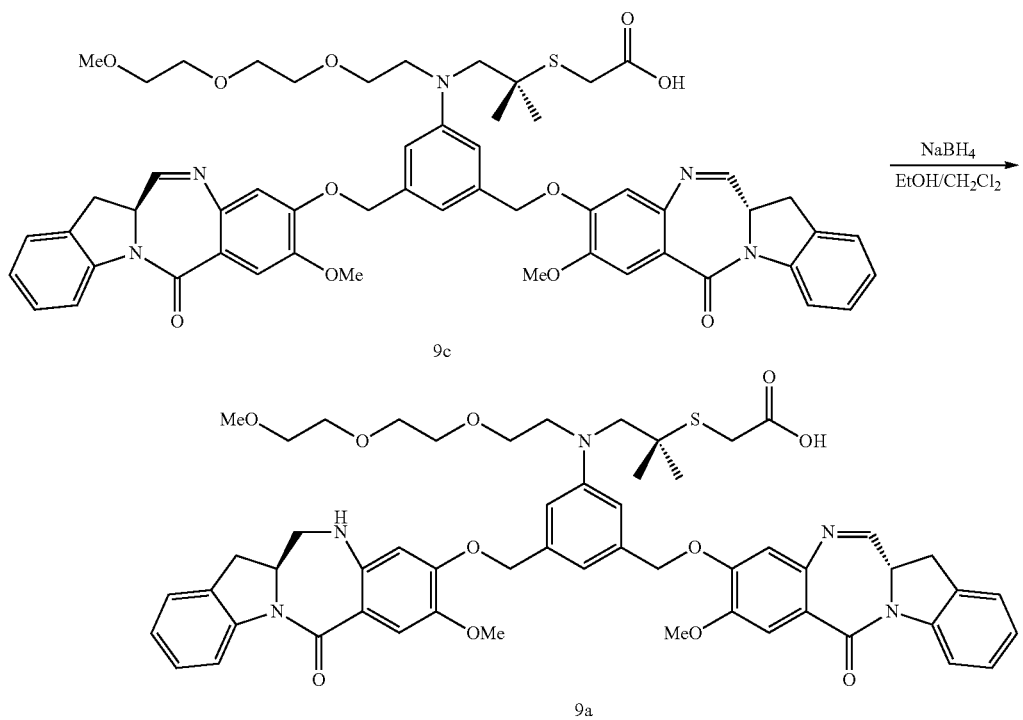

Compound 9a:

To a stirred solution of compound 9c (57.8 mg, 0.058 mmol) in anhydrous dichloromethane (0.2 mL) and absolute ethanol (0.6 mL) was added NaBH₄ (2.5 mg, 0.066 mmol) at 0° C. The ice bath was removed and the mixture was stirred at room temperature for 3 hours and then quenched with saturated ammonium chloride, diluted with dichloromethane, separated and the organic layer was washed with brine, dried over anhydrous Na₂SO₄ and filtered through celite and stripped. The residue was purified by reverse phase HPLC (C18 column, CH₃CN/H₂O). The product fractions were extracted with dichloromethane and stripped to give compound 9a (13.0 mg, y=22%). MS (m/z). found 1000.0 (M+H)⁺, 1015.9 (M+H₂O–H)⁻. See FIG. 12A.

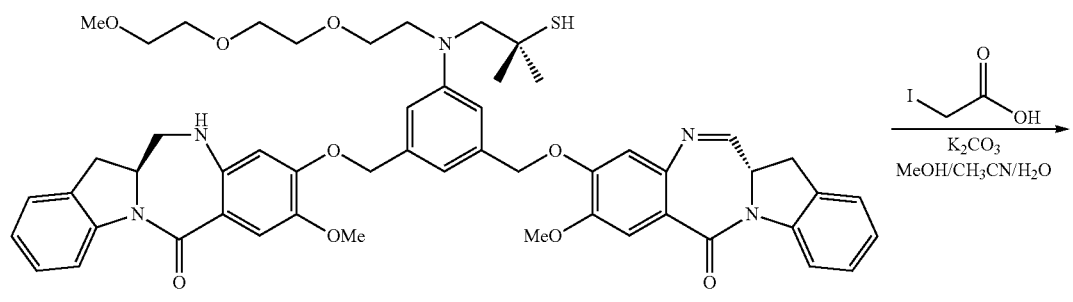

1f

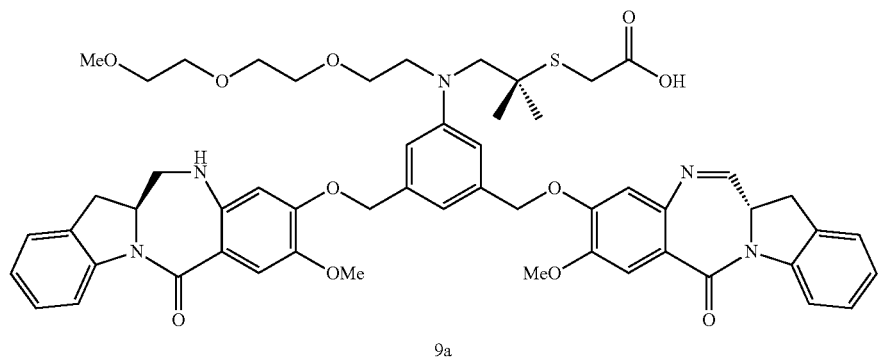

9a

Compound 9a:

To a solution of the free thiol 1f (45 mg, 0.048 mmol) and iodoacetic acid (18 mg, 0.096 mmol) in methanol (1.0 mL) and CH$_3$CN (1.4 mL) was added deionized water (0.1 mL) and potassium carbonate (20 mg, 0.14 mmol). The mixture was stirred at rt overnight (monitored by LCMS). It was quenched with saturated ammonium chloride to make the solution acidic then diluted with dichloromethane, separated and washed with brine, dried over anhydrous Na$_2$SO$_4$, filtered and stripped. The residue was purified by preparative reverse phase HPLC (C18, CH$_3$CN/H$_2$O). The pure product fractions (based on MS) were extracted with dichloromethane, stripped to give the desired acid 9a (18 mg, y=38%). MS (m/z). found 1000.1 (M+H)$^+$. See FIG. 12B.

Example 22

Synthesis of Compound 1d

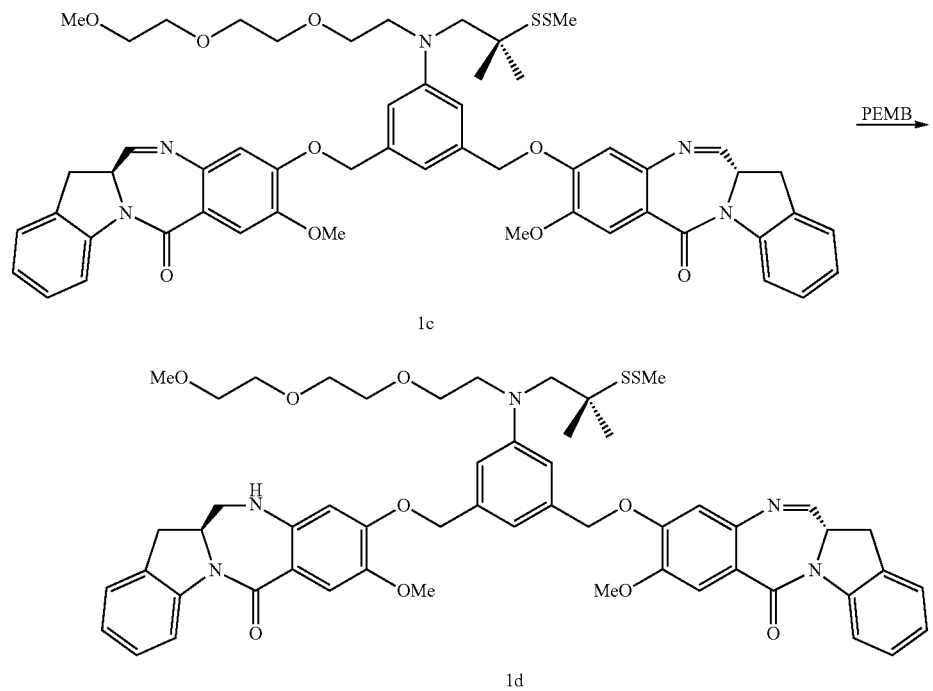

Compound 1d:

To a stirred solution of compound 1c (178 mg, 0.18 mmol) in anhydrous dichloromethane (1.2 mL) and absolute ethanol or anhydrous methanol (0.1 mL) was added 5-ethyl-2-methylpyridine borane (PEMB, 0.017 mL, 0.11 mmol) dropwise. The mixture was stirred at rt for 1 hour and quenched with 88% formic acid. It was basified with saturated NaHCO$_3$ and diluted with dichloromethane, separated and the organic layer was washed with brine, dried over anhydrous Na$_2$SO$_4$ and filtered through celite and stripped. The residue was dissolved in CH$_3$CN/H$_2$O/88% HCOOH (5:1:0.05) and purified by reverse phase HPLC (C18, CH$_3$CN/H$_2$O). The fractions that contained pure product were extracted with dichloromethane and stripped to give compound 1d (56 mg, y=31%). MS (m/z). found 988.1 (M+H)$^+$. See FIG. 39.

Compound 1d:

To a stirred solution of compound 1c (71 mg, 0.072 mmol) in anhydrous 1,2-dichloroethane (0.8 mL) was added sodium triacetoxyborohydride (14 mg, 0.65 mmol). The mixture was stirred at rt for 2 hours and quenched with saturated NaHCO$_3$ and diluted with dichloromethane, separated and the organic layer was washed with brine, dried over anhydrous Na$_2$SO$_4$ and filtered through celite and stripped. The residue was dissolved in CH$_3$CN/H$_2$O/88% HCOOH (5:1:0.05) and purified by reverse phase HPLC (C18, CH$_3$CN/H$_2$O). The fractions that contained pure product were extracted with dichlormethane and stripped to give compound 1d (17 mg, y=24%). MS (m/z). found 988.1 (M+H)$^+$. Unreacted starting material 1c was also recovered (24 mg, y=34%). See FIG. 40.

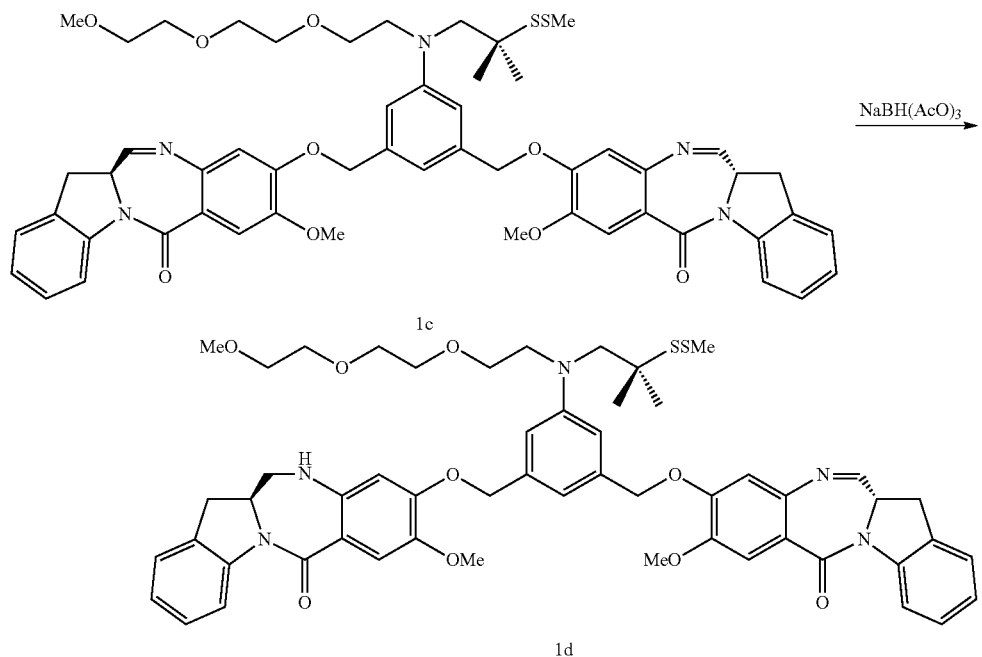

Example 23

Synthesis of Compound 31c

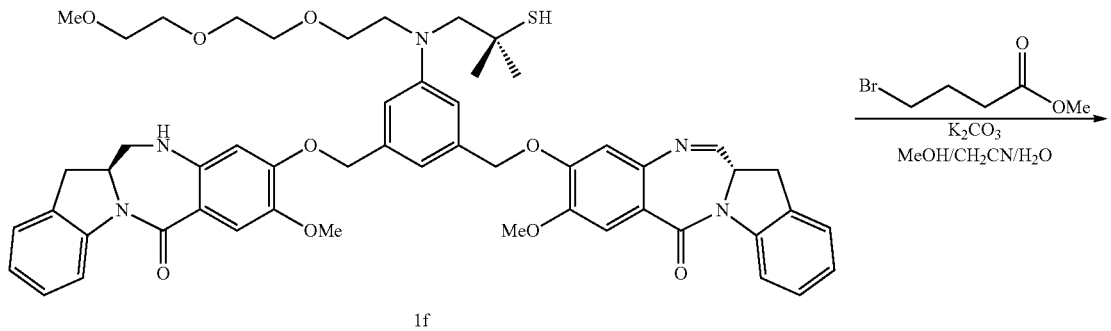

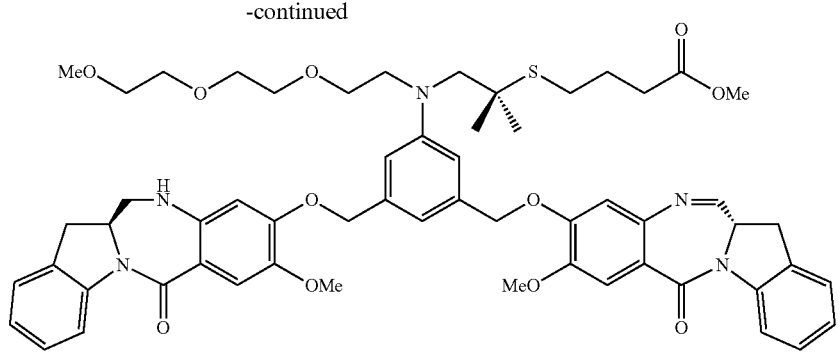

31a

Compound 31a:

To a solution of compound 1f (57.8 mg, 0.061 mmol) and methyl 4-bromobutyrate (22 mg, 0.12 mmol) in methanol (1.0 mL) and CH$_3$CN (1.0 mL) was added deionized water (0.1 mL) and potassium carbonate (17 mg, 0.12 mmol). The mixture was stirred at rt overnight then quenched with saturated ammonium chloride and diluted with dichloromethane, separated and washed with brine, dried over anhydrous Na$_2$SO$_4$, filtered and stripped. The residue was purified by preparative reverse phase HPLC (C18, CH$_3$CN/H$_2$O) to give the desired product 31a (14 mg, y=22%) as yellowish foam. MS (m/z). found 1042.1 (M+H)$^+$. See FIG. 41.

Compound 31b:

To a solution of the methyl ester 31a (14 mg, 0.013 mmol) in anhydrous 1,2-dichloroethane (1.5 mL) was added trimethyltin hydroxide (36 mg, 0.2 mmol). The mixture was stirred overnight in a 80° C. oil bath until starting material was completely consumed. It was cooled to room temperature, diluted with dichloromethane, washed with brine/drops 5% HCl and brine, dried and filtered. The filtrate was stripped and purified with silica gel chromatography (dichloromethane/MeOH) to give acid 31b as yellowish solid (10.2 mg, y=74%). MS (m/z). found 1028.2 (M+H)$^+$, 1044.1 (M+H$_2$O−H)$^−$. See FIG. 41.

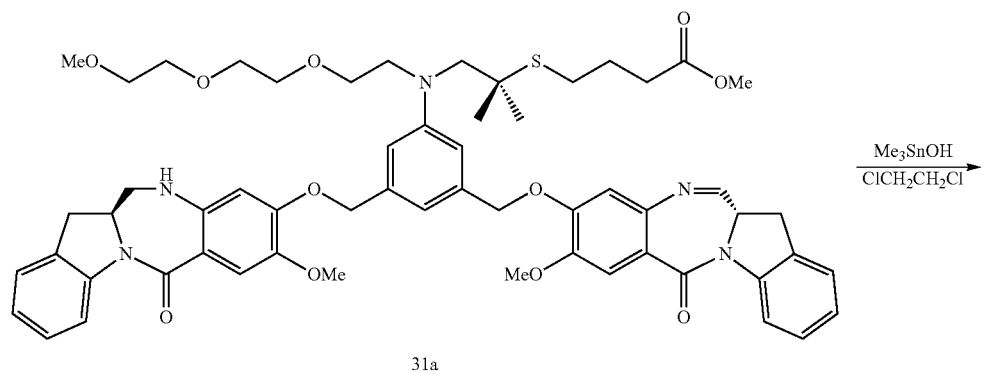

31a

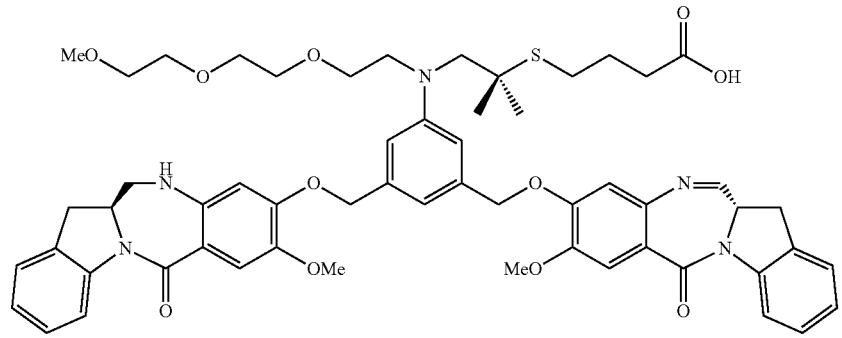

31b

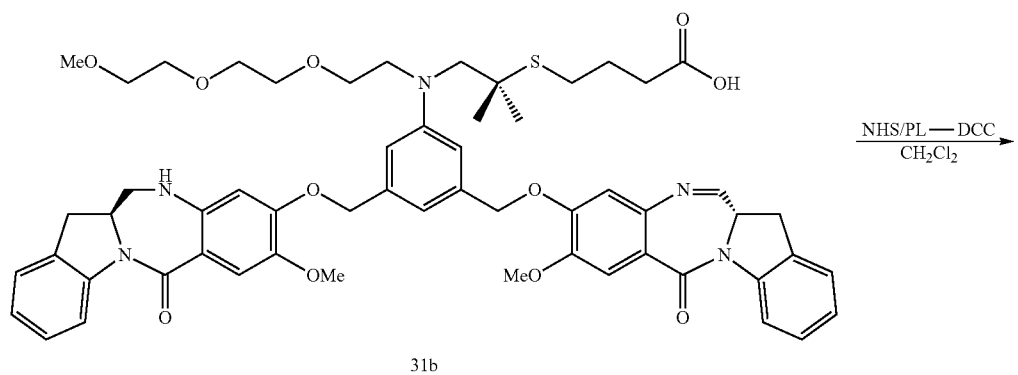

31b

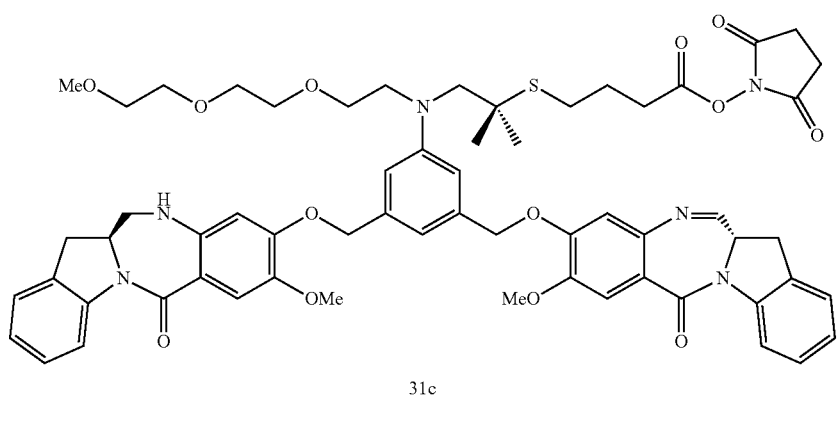

31c

Compound 31c:

To a solution of acid 31b (10.2 mg, 0.0099 mmol) in anhydrous dichloromethane (0.5 mL) was added N-hydoxysuccinimide (3.4 mg, 0.03 mmol) and PL-DCC (26 mg, 0.04 mmol, 1.55 mmol/g). The mixture was stirred at room temperature overnight and filtered to remove the resin. The resin was washed with dichloromethane then ethyl acetate. The filtrate was stripped and the residue was purified by reverse phase HPLC (C18, CH$_3$CN/H$_2$O). The fractions containing product were combined and lyophilized to give NHS ester 31c as white solid (3.6 mg, y=32%). MS (m/z). found 1125.1 (M+H)$^+$. See FIG. 41.

Example 24

Synthesis of Compound 32c

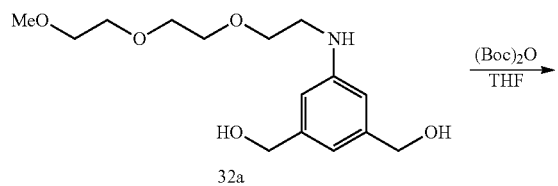

32a

-continued

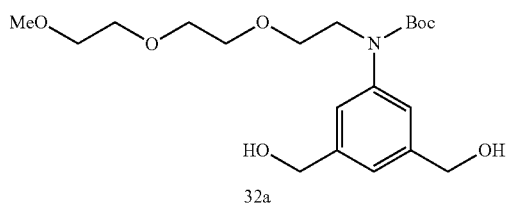

32a

Compound 32a:

To a stirred solution of the aniline 1a (339 mg, 1.1 mmol) in anhydrous tetrahydrofuran (4.0 mL) was added Boc anhydride (272 mg, 1.2 mmol). The mixture was continued to be stirred at room temperature for three days. The reaction mixture was concentrated under reduced pressure and the residue was purified by silica gel chromatography (CH$_2$Cl$_2$/MeOH) to give compound 32a (405 mg, y=90%) as colorless oil. $^1$H NMR (400 Hz, CDCl$_3$): δ 7.00 (s, 2H), 6.97 (s, 1H), 4.38 (s, 4H), 4.12 (s, 2h), 3.64 (t, J=5.6 Hz, 2H), 3.48-3.44 (m, 8H), 3.40-3.38 (m, 2H), 3.21 (s, 3H), 1.31 (s, 9H); $^{13}$C NMR (400 Hz, CDCl$_3$): δ 154.65, 142.3, 142.1, 124.1, 122.7, 80.2, 71.6, 70.3, 70.1, 69.9, 68.5, 63.9, 58.65, 49.4, 28.1. See FIG. 42.

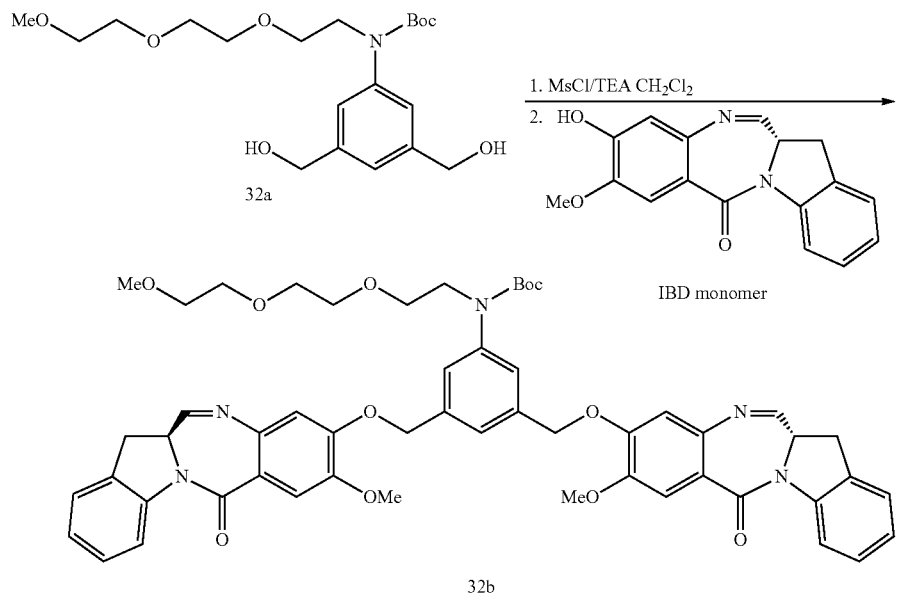

Compound 32b:

To a stirred solution of compound 32a (51 mg, 0.128 mmol) in anhydrous dichloromethane was added triethylamine (0.053 mL, 0.383 mmol) at −5~−10° C. Methansulfonyl chloride (0.026 mL, 0.332 mmol) was then added slowly in 15 minutes with a syringe. The mixture was stirred at −5-10° C. for 1 hours (TLC, DCM/MeOH 10:1). The reaction was quenched with ice/water, diluted with cold AcOEt, separated and the organic layer was washed with cold water, dried over anhydrous $Na_2SO_4/MgSO_4$, filtered and stripped. The residue was transferred into a small reaction flask with dichloromethane, stripped and high vacuumed. It was dissolved in anhydrous DMF (0.8 mL) followed by addition of IBD monomer (90 mg, 0.31 mmol) and potassium (53 mg, 0.38 mmol). The mixture was stirred at rt overnight. It was diluted with dichloromethane, washed with brine, dried over anhydrous sodium sulfate, filtered and stripped. The residue was purified by reverse phase HPLC (C18, $CH_3CN/H_2O$) to give compound 32b (56 mg, 46%) as yellowish solid. %). $^1$H NMR (400 Hz, $CDCl_3$): δ 8.29 (d, J=8.0 Hz, 2H), 7.87 (d, J=4.8 Hz, 2H), 7.60 (s, 2H), 7.38-7.36 (m, 3H), 7.33-7.27 (m, 4H), 7.13 (t, J=7.6 Hz, 2H), 6.88 (s, 2H), 5.21 (dd, $J_1$=20.0 Hz, $J_2$=12.4 Hz, 4H), 4.49 (dt, $J_1$=11.2 Hz, $J_2$=4.0 Hz, 2H), 3.99 (s, 6H), 3.83 (t, J=6.0 Hz, 2H), 3.76-3.48 (m, 14H), 3.35 (s, 3H), 1.43 (s, 9H); MS (m/z). found 992.2 $(M+H_2O+Na)^+$, 1010.2 $(M+2H_2O+Na)^+$. See FIG. 42.

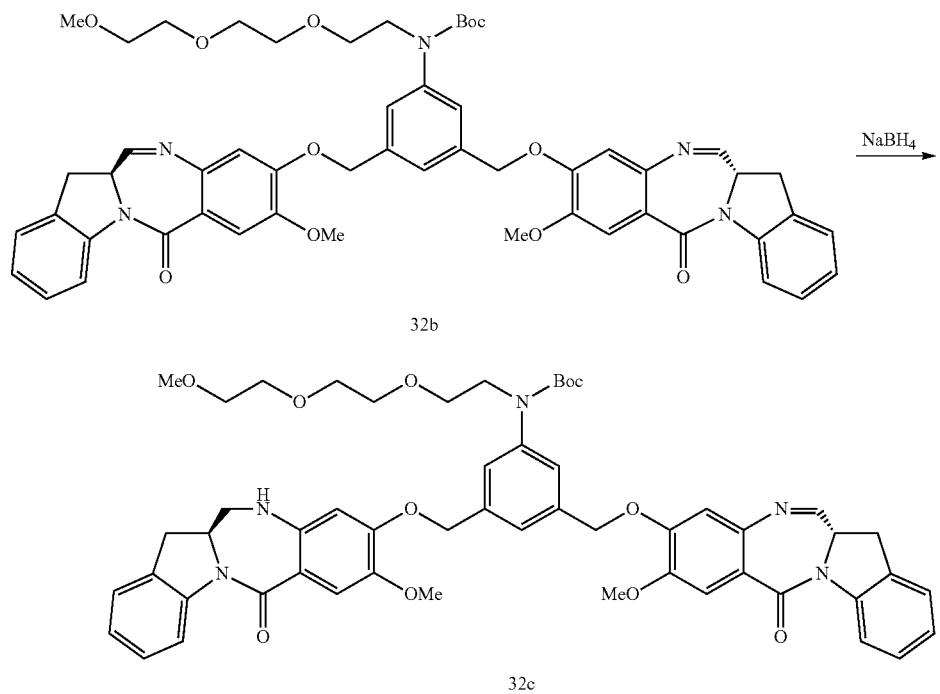

Compound 32c:

To a stirred solution of compound 32b (56 mg, 0.059 mmol) in anhydrous dichloromethane (0.3 mL) and absolute ethanol (0.9 mL) was added NaBH$_4$ (2.7 mg, 0.07 mmol) at 0° C. The ice bath was removed and the mixture was stirred at room temperature for 3 hours and then quenched with saturated ammonium chloride, diluted with dichloromethane, separated and the organic layer was washed with brine, dried over anhydrous Na$_2$SO$_4$ and filtered through celite and stripped. The residue was purified by reverse phase HPLC (C18 column, CH$_3$CN/H$_2$O). Recovered starting material 32b weighed 12 mg which was re-subjected to the reduction conditions and purified by reverse phase HPLC. All the fractions that contained pure product were extracted with dichloromethane and stripped to give compound 32c (20.7 mg, y=37%) as a light yellowish solid. MS (m/z). found 954.2 (M+H)$^+$. See FIG. 42.

Example 25

The tolerability of huMy9-6 conjugates was investigated in female CD-1 mice. Animals were observed for seven days prior to study initiation and found to be free of disease or illness. The mice were administered a single i.v. injection of the conjugate and the animals were monitored daily for body weight loss, morbidity or mortality. Table 10 shows that the huMy9-6-SPDB-1c di-imine disulfide containing conjugate was tolerated at a dose of less than 300 µg/kg. In contrast, the mono-imine disulfide conjugates huMy9-6-SPDB-1f and huMy9-6-sulfo-SPDB-1f were found to be better tolerated with a maximum tolerated dose of >729 µg/kg and <750 µg/kg respectively.

TABLE 10

Tolerability comparison data for (A) huMy9-6-SPDB-1c, (B) huMy9-6-SPDB-1f, (C) huMy9-6-sulfo-SPDB-1f, and (D) huMy9-6-BMPS-1f conjugates.

A)

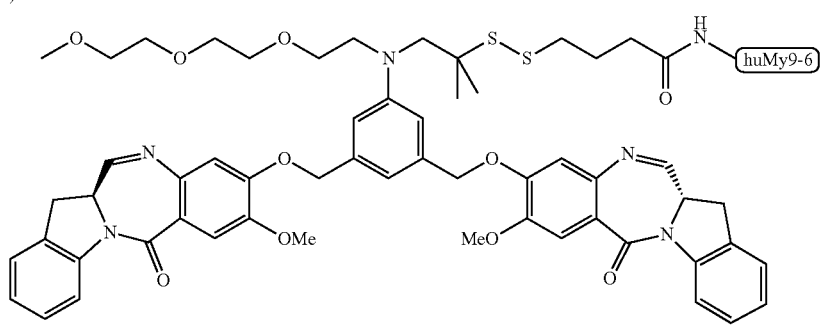

huMy9-6-SPDB-1c
MTD < 300 µg/kg

| Dose (µg/kg) | % Survival |
| --- | --- |
| 100 | 100 |
| 300 | 50 |
| 500 | 0 |
| 700 | 0 |

B)

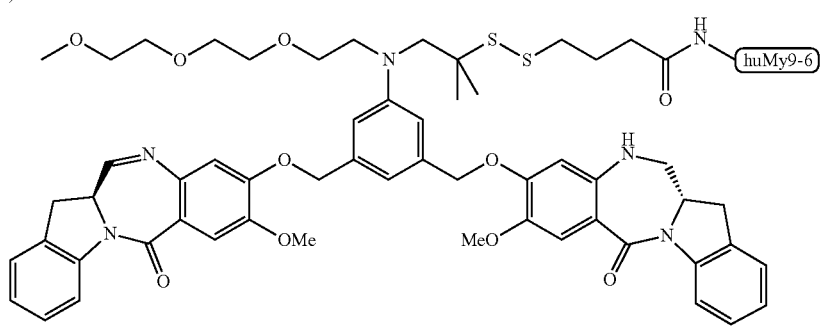

huMy9-6-SPDB-1f
MTD > 729 µg/kg

TABLE 10-continued
Tolerability comparison data for (A) huMy9-6-SPDB-1c, (B) huMy9-6-SPDB-1f, (C) huMy9-6-sulfo-SPDB-1f, and (D) huMy9-6-BMPS-1f conjugates.
| Dose (μg/kg) | % Survival |
|---|---|
| 405 | 100 |
| 567 | 100 |
| 729 | 100 |
C)
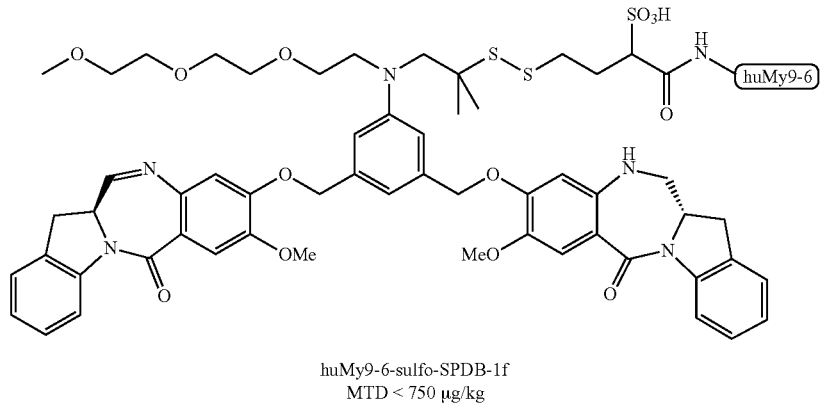 [SMILES: CNC(=O)C(CCSSC(C)(C)CN(CCOCCOCCOC)c1cc(COc2cc3c(cc2OC)C(=O)N2c4ccccc4C[C@H]2C=N3)cc(COc2cc3c(cc2OC)C(=O)N2c4ccccc4C[C@H]2CN3)c1)S(=O)(=O)O]
huMy9-6-sulfo-SPDB-1f
MTD < 750 μg/kg
| Dose (μg/kg) | % Survival |
|---|---|
| 450 | 100 |
| 600 | 100 |
| 750 | 88 |
| 900 | 50 |
D)
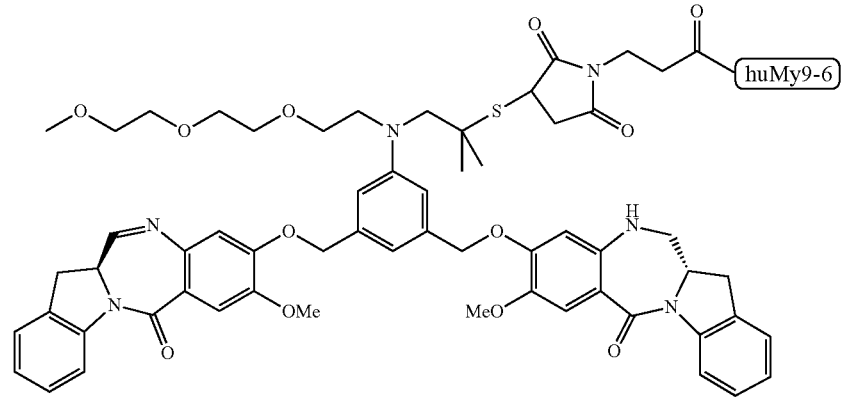
huMy9-6-BMPS-1f
MTD < 324 μg/kg
| Dose (μg/kg) | % Survival |
|---|---|
| 100 | 100 |
| 200 | 100 |
| 284 | 100 |
| 324 | 83 |
| 405 | 50 |

Example 26

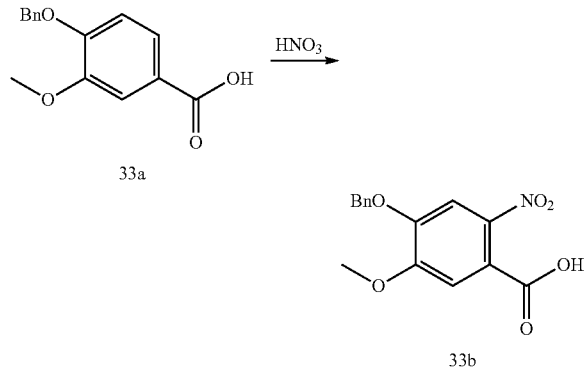

Compound 33b:

Compound 33a (20g, 77 mmol) was added as a thick suspension in anhydrous dichloromethane (100 mL) and was cooled to 0° C. Acetic acid (191 mL) was added, resulting in a clear solution which stirred at 0° C. until cool. Nitric acid (26 mL, 581 mmol) was added slowly dropwise through an addition funnel. The ice bath was removed and the solution continued to stir at room temperature. After 3 hours, the reaction was diluted with deionized water and extracted with dichloromethane. The organic layer was washed with brine, dried over anhydrous magnesium sulfate and the filtrate concentrated in vacuo. The crude residue was recrystallized using ethyl acetate and hexanes. The solid was filtered and washed with hexanes to give compound 33b as a yellow fluffy solid (13.8g, y=59%). $^1$H NMR (400 Hz, CDCl$_3$): δ 7.48-7.43 (m, 6H), 7.25 (s, 1H), 5.25 (s, 2H), 4.02 (s, 3H), MS (m/z): 326.1 (M+Na)$^+$. See FIG. 45.

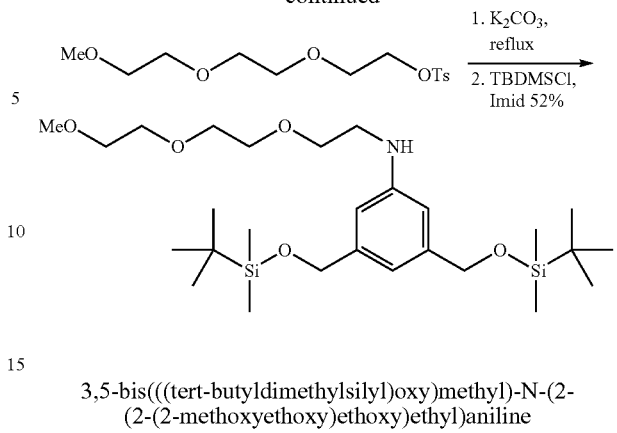

3,5-bis(((tert-butyldimethylsilyl)oxy)methyl)-N-(2-(2-(2-methoxyethoxy)ethoxy)ethyl)aniline A mixture of (5-amino-1,3-phenylene)dimethanol (11.78 g, 77 mmol), 2-(2-(2-methoxyethoxy)ethoxy)ethyl 4-methylbenzenesulfonate (15.3 g, 48.1 mmol), and potassium carbonate (13.28 g, 96 mmol) in DMF (96 ml) was refluxed for 20 hours. The reaction was cooled to ambient temperature and diluted with dichloromethane. The mixture was filtered through celite and concentrated in vacuo. The resulting orange oil was dissolved in dichloromethane (240 ml) and t-butyldimethylsilyl chloride (18.09 g, 120 mmol) and imidazole (9.80 g, 144 mmol) were added. The reaction was stirred at ambient temperature for 20 hours upon which it was diluted with dichloromethane and filtered through celite. Purification by silica gel chromatography (EtOAc/Hex) yielded 3,5-bis(((tert-butyldimethylsilyl)oxy)methyl)-N-(2-(2-(2-methoxyethoxy)ethoxy)ethyl)aniline (13g, 52%). $^1$H NMR (400 Hz, CDCl$_3$): δ6.52 (s, 1H), 6.40 (s, 2H), 4.56 (s, 4H), 3.60 (t, 2H, J=5.2 Hz), 3.56 (m, 6H), 3.46 (m, 2H), 3.29 (s, 3H), 3.20 (t, 2H, J=5.2 Hz), 0.84 (s, 18H), 0.00 (s, 12H). MS (m/z). found 550.1 (M+Na)$^+$. See FIG. 46.

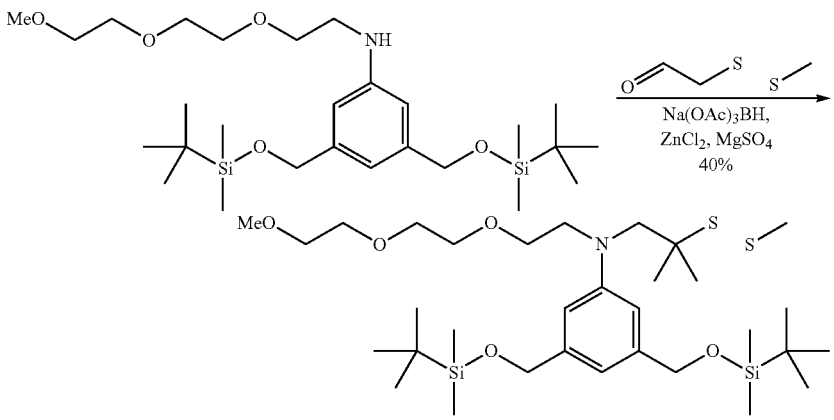

3,5-bis(((tert-butyldimethylsilyl)oxy)methyl)-N-(2-(2-(2-methoxyethoxy)ethoxy)ethyl)-N-(2-methyl-2-(methyldisulfanyl)propyl)aniline To a solution of 3,5-bis(((tert-butyldimethylsilyl)oxy)methyl)-N-(2-(2-(2-methoxyethoxy)ethoxy)ethyl)aniline (6.7 g, 12.69 mmol) in anhydrous 1,2-dichloroethane (50 ml) was added 2-(methyldithio)isobutyraldehyde (2.74 ml, 19.04 mmol), sodium triacetoxyborohydride (2.8g, 1 eq), zinc(II) chloride (0.865 g, 6.35 mmol) and magnesium sulfate (2.292 g, 19.04 mmol). The mixture was stirred for

Example 27

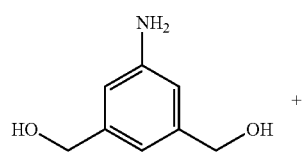

five hours at ambient temperature. Sodium triacetoxyborohydride (2.8g, 1 eq) was added. The reaction continued to stir at ambient temperature for 20 hours. The mixture was filtered through celite rinsing with dichloromethane and concentrated under reduced pressure then extracted with ethyl acetate and water. The organic extracts were washed with brine, dried over magnesium sulfate, filtered, concentrated and purified by combiflash (EtOAc/Hex) to give 3,5-bis(((tert-butyldimethylsilyl)oxy)methyl)-N-(2-(2-(2-methoxyethoxy)ethoxy)ethyl)-N-(2-methyl-2-(methyldisulfanyl)propyl)aniline (3.5g, 40%). $^1$H NMR (400 Hz, CDCl3): δ 6.73 (s, 2H), 6.59 (s, 1H), 4.56 (s, 4H), 3.65-3.51 (m, 14H), 3.30 (s, 3H), 2.38 (s, 3H), 1.28 (s, 6H), 0.84 (s, 18H), 0.00 (s, 12H). MS (m/z). found 684.2 (M+Na)$^+$. See FIG. 46.

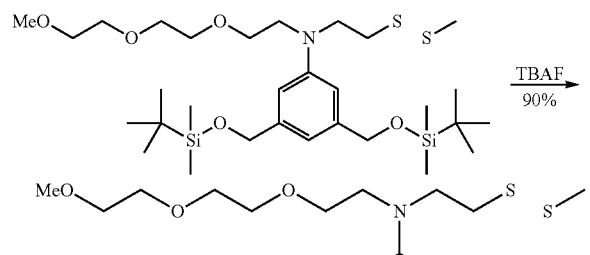

(5-((2-(2-(2-methoxyethoxy)ethoxy)ethyl)(2-methyl-2-(methyldisulfanyl)propyl)amino)-1,3-phenylene)dimethanol (1b)

Tetrabutylammonium fluoride (1M in THF) (10.57 ml, 10.57 mmol) was added dropwise to stirring solution of 3,5-bis(((tert-butyldimethylsilyl)oxy)methyl)-N-(2-(2-(2-methoxyethoxy)ethoxy)ethyl)-N-(2-methyl-2-(methyldisulfanyl)propyl)aniline (3.5 g, 5.29 mmol) in anhydrous THF (65 ml) at 0° C. in an ice bath. Following addition the mixture was stirred at ambient temperature for two hours. The mixture was quenched with saturated ammonium chloride and extracted with ethyl acetate. The extracts were washed with water and brine, dried with magnesium sulfate, filtered and concentrated under reduced pressure. Purification by silica gel chromatography (MeOH/DCM) yielded (5-((2-(2-(2-methoxyethoxy)ethoxy)ethyl)(2-methyl-2-(methyldisulfanyl)propyl)amino)-1,3-phenylene)dimethanol (2g, 87%). $^1$H NMR (400 Hz, CDCl3): δ 6.76 (s, 2H), 6.63 (s, 1H), 4.55 (s, 4H), 3.65-3.51 (m, 14H), 3.35 (s, 3H), 2.44 (s, 3H), 1.33 (s, 6H); 13C NMR (400 Hz, CDCl3): δ 149.0, 142.35, 114.0, 111.1, 71.98, 70.7, 70.6, 70.5, 67.6, 65.5, 59.75, 59.1, 53.9, 51.9, 26.6, 25.7, 20.75; MS (m/z). found 456.2 (M+Na)$^+$. See FIG. 46.

Example 28

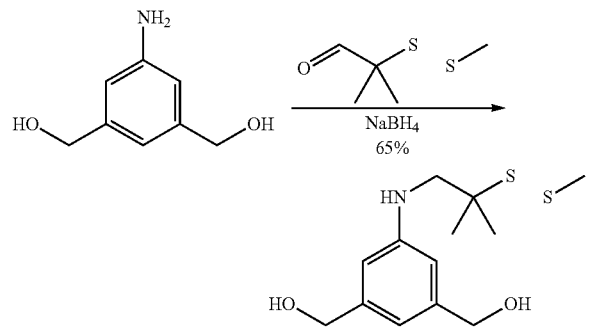

(5-(2-methyl-2-(methyldisulfanyl)propylamino)-1,3-phenylene)dimethanol (5-amino-1,3-phenylene)dimethanol (2.5 g, 16.32 mmol) and 2-(methyldithio)isobutyraldehyde (2.347 ml, 16.32 mmol) were stirred at ambient temperature in absolute ethanol (82 ml) until completely dissolved (3 hours). The mixture was cooled to 0° C. in an ice bath and sodium borohydride (0.741 g, 19.59 mmol) was added. The reaction was stirred for 1 hour at 0° C., and was then quenched slowly with cold 5% HCl solution. The mixture was diluted with dichloromethane and the pH was adjusted to pH=8 with saturated sodium bicarbonate solution then extracted with dichloromethane and then washed with brine. The organic extracts were dried over anhydrous sodium sulfate, filtered, and concentrated under reduced pressure. Purification by silica gel chromatography (MeOH/DCM) yielded (5-(2-methyl-2-(methyldisulfanyl)propylamino)-1,3-phenylene) dimethanol (3g, 65%) as a white solid. $^1$H NMR (400 Hz, CDCl$_3$): δ6.62 (s, 1H), 6.54 (s, 2H), 4.53 (s, 4H), 3.13 (s, 2H), 2.30 (s, 3H), 1.32 (s, 6H). See FIG. 47.

Example 29

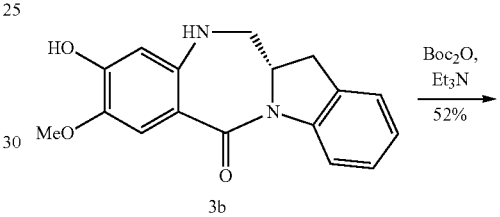

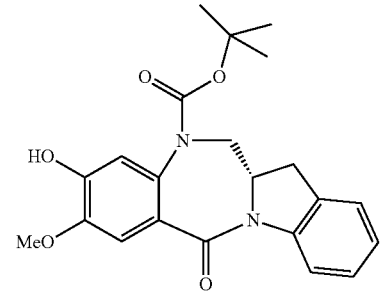

tert-butyl 9-hydroxy-8-methoxy-6-oxo-12a,13-dihydro-6H-benzo[5,6][1,4]diazepino[1,2-a]indole-11(12H)-carboxylate To a solution of 9-hydroxy-8-methoxy-11,12,12a,13-tetrahydro-6H-benzo[5,6][1,4]diazepino[1,2-a]indol-6-one 3b (0.3 g, 1.012 mmol) in methanol (5.06 ml) were added di-tert-butyl dicarbonate (0.265 g, 1.215 mmol), triethylamine (0.212 ml, 1.519 mmol) and DMAP (6.18 mg, 0.051 mmol). After 5 hours of stirring at ambient temperature the reaction mixture was concentrated in vacuo. The residue was redissolved in dichloromethane and filtered through celite. Purification by silica gel chromatography (20% EtOAc/DCM) yielded tert-butyl 9-hydroxy-8-methoxy-6-oxo-12a,13-dihydro-6H-benzo[5,6][1,4]diazepino[1,2-a]indole-11(12H)-carboxylate (0.21g, 52%) as a white solid. $^1$H NMR (400 Hz, CDCl$_3$): δ 8.25 (d, J=8.0 Hz, 1H), 7.44 (s, 1H), 7.18 (t, J=7.2 Hz, 1H), 7.11 (d, J=7.2 Hz, 1H), 6.98 (t, J=7.2 Hz, 1H), 6.39 (s, 1H), 4.37 (m, 1H), 3.75 (s, 3H), 3.42 (m, 3H), 2.74 (dd, J=3.6, 16.4 Hz, 1H), 1.47 (s, 9H). See FIG. 48.

Example 30

Preparation and Testing of huMy9-6-31c

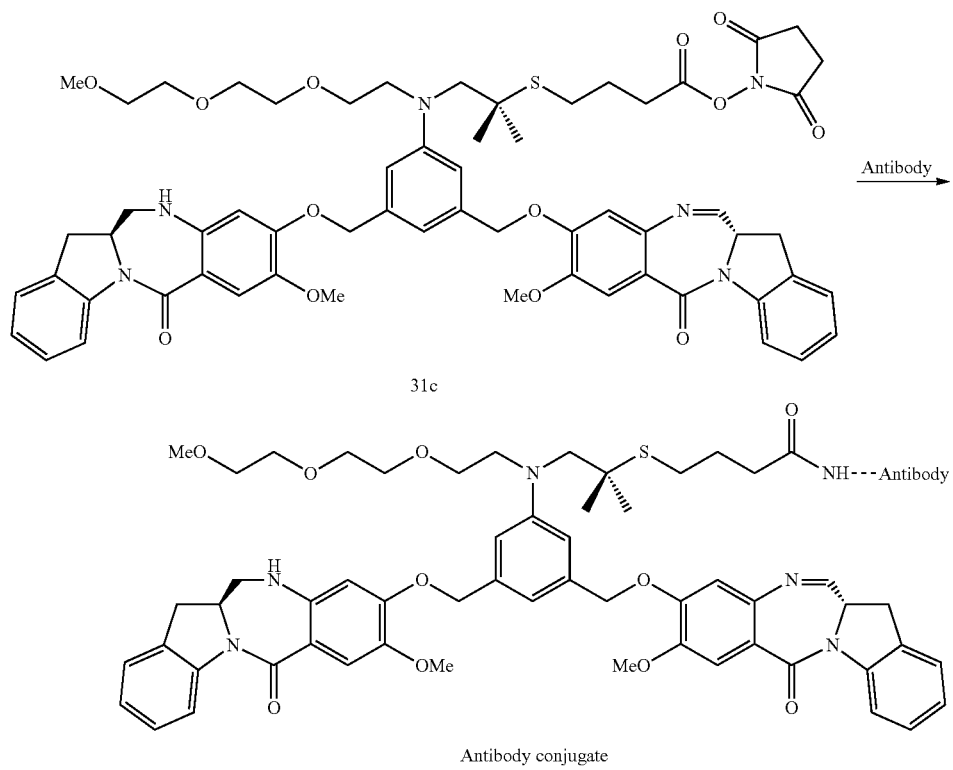

A reaction containing 2.0 mg/mL huMy9-6 antibody and 5 molar equivalents of compound 31c (pretreated with 5-fold excess of sodium bisulfite in 90:10 DMA:water) in 50 mM HEPES (4-(2-hydroxyethyl)-1-piperazine ethanesulfonic acid) pH 8.5 buffer and 10% v/v DMA (N,N-Dimethylacetamide) cosolvent was allowed to conjugate for 6 hours at 25° C. Post-reaction, the conjugate was purified and buffer exchanged into 250 mM Glycine, 10 mM Histidine, 1% sucrose, 0.01% Tween-20, 50 µM sodium bisulfite formulation buffer, pH 6.2, using NAP desalting columns (Illustra Sephadex G-25 DNA Grade, GE Healthcare). Dialysis was performed in the same buffer for 4 hours at room temperature utilizing Slide-a-Lyzer dialysis cassettes (ThermoScientific 20,000 MWCO).

The purified conjugate was found to have an average of 3.1 IGN molecules linked per antibody (by UV-Vis using molar extinction coefficients $\epsilon_{330\ nm}=15,484\ cm^{-1}M^{-1}$ and $\epsilon_{280\ nm}=30,115\ cm^{-1}M^{-1}$ for 1, and $\epsilon_{280\ nm}=207,000\ cm^{-1}M^{-1}$ for My9-6 antibody), 98% monomer (by size exclusion chromatography), <0.2% unconjugated drug (by dual-column reverse-phase HPLC analysis) and a final protein concentration of 0.4 mg/ml.

In vitro potency measurements for conjugates of huMy9-6 with 31c at two different drug loads were shown below. Both conjugates were highly potent towards antigen-positive HL60-QC cells, with $IC_{50}$ values between 1.3-1.8 pM. Antigen blocking with 1 µM unconjugated huMy9-6 significantly diminished the potency, demonstrating the antigen specificity of the cytotoxic effect.

| Conjugate huMy9-6-31c | $IC_{50}$ (pM) | $IC_{50}$ (pM) huMy9-6 blocking | Specificity window |
|---|---|---|---|
| 3.1 IGN/Ab | 1.8 | 940 | 522 |
| 3.9 IGN/Ab | 1.3 | 790 | 608 |

Example 31

In Vivo Efficacy of Various Conjugates in Tumor Bearing Nude Mice

In this study, the anti-tumor activity of several conjugates of the invention are investigated in immune-compromised mice (nude or SCID), preferably female nude mice, bearing various tumors. In some cases, in addition or as an alternative, nude rats may be employed. The conjugates to be tested include any one or more of the conjugates described herein. The various tumor cell lines that can be used for inoculating the nude mice included HL60/QC, MOLM-13, NB4, HEL92.1.7, OCI-AML3, KB, and/or any other cancer cell lines recognized in the art as a proper model for a disease indication (e.g., cancer). Some criteria that may be applied for the selection of tumor cell lines suitable for in vivo evaluation include: a) expression of the target antigen on the tumor cell, and, b) sensitivity of tumor cells to the unconjugated drug in vitro. For example, an in vitro cell line sensitivity screen, such as the 60-cell line screen described by the U.S. National Cancer Institute (see Voskoglou-Nomikos et al., 2003, Clinical Cancer Res. 9; 42227-4239, incorporated herein by reference) can be used as one of the guides to determine the types of cancers that may be suitable for treatment with the compounds of the invention. The potency of the various conjugates against the various tumor cell lines, as expressed by $IC_{50}$ values (nM), is measured accordingly.

The various tumor cell lines are inoculated to nude or SCID mice using substantially the same protocol as outlined in Example 15. For example, about $1 \times 10^6$-$5 \times 10^7$ tumor cells (typically $1 \times 10^7$) cells/mouse are subcutaneously inoculated at a volume of approximately 0.1-0.2 mL/mouse, in the area over the right shoulder of female athymic nude mice, 6 weeks of age. When the tumor has reached an average size of ~100 mm³ (typically 6 to 8 days after tumor cell inoculation), mice are randomized into groups (e.g., n=5-8 per group) by tumor volume. Treatment is initiated the day after randomization, and groups includes a control group dosed with the appropriate vehicle (200 μL/injection), or a single treatment at various doses (5 to 700 μg/kg) of the above referenced drug conjugates (50 μg/kg linked drug dose corresponded to about 2 mg/kg antibody dose). Multiple dosing schedules (for example treatment at day 1, 3, 5, or day 1, 4, 7) may also be employed.

Median and mean tumor volume vs time is measured, with the data demonstrating a dose-dependent anti-tumor activity of the subject conjugates. The minimum effective dose is then calculated and compared to the maximum tolerated dose.

Example 32

Preparation of huMy9-6-Sulfo-SPDB-1d Using the 4-nitroPy-Sulfo-SPDB Linker

A reaction containing 6 mg/mL huMy9-6 antibody and 5 molar equivalents of the highly reactive N-succinimidyl-4-(4-nitropyridyl-2-dithio)butanoate linker (20 mM stock in ethanol) was incubated for 3 h at 25° C. in 50 mM EPPS buffer at pH 8. Unreacted linker was removed using a NAP desalting column (Illustra Sephadex G-25 DNA Grade, GE Healthcare). The linker to antibody ratio (LAR) was determined to be about 2.3 based on antibody concentration and DTT-released nitropyridine-2-thione concentration by UV-Vis ($\epsilon_{394\ nm}$=14205 cm⁻¹M⁻¹ for 2-thio-4-nitropyridone).

Linker modified huMy9-6 was diluted to 2 mg/mL in 50 mM HEPES buffer at pH 8.5, 10% v/v DMA, and reacted with 2 molar equivalents of compound 1d per linker (5 mM stock in DMA; 4.6 equivalents per antibody) for 30 min at 25° C. Completion of disulfide exchange reaction was determined by monitoring absorbance increase at 394 nm by UV.

Post-reaction, the conjugate was purified and buffer exchanged into 250 mM glycine, 10 mM histidine, 1% sucrose, 0.01% Tween-20, 50 μM sodium bisulfite at pH 6.2 using a desalting column (G-25 Sephadex, fine grade, GE Healthcare).

Figure 60:
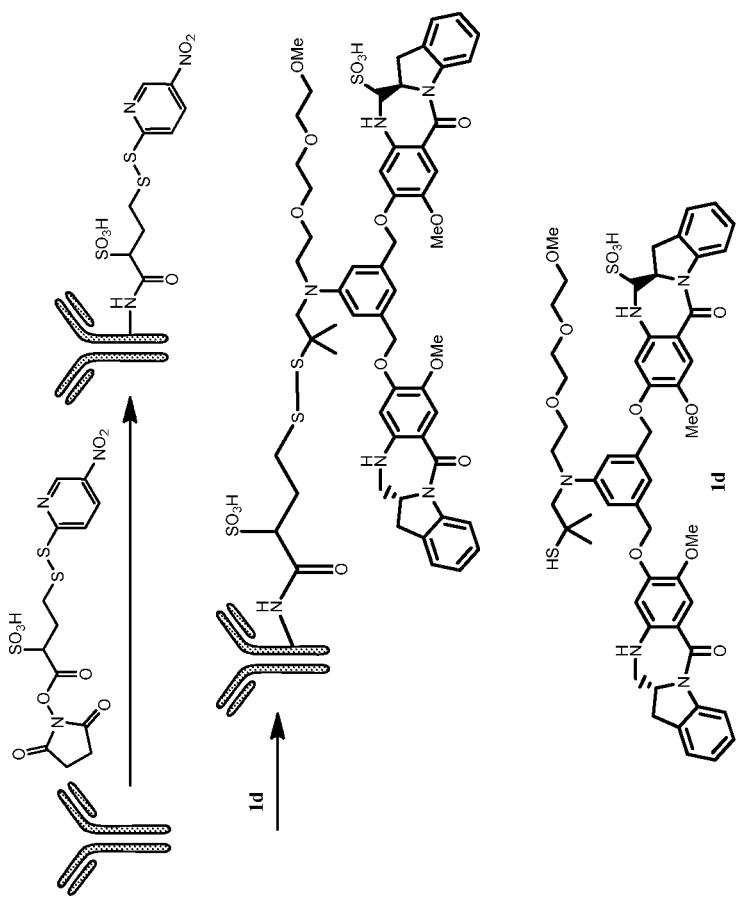
FIG. 60 shows the preparation of huMy9-6-sulfo-SPDB-1d using the highly reactive 4-nitroPy-sulfo-SPDB linker.

The purified conjugate was found to have an average of 2.1 molecules of 1d linked per antibody (by UV-Vis using molar extinction coefficients $\epsilon_{330\ nm}$=15,484 cm⁻¹M⁻¹ and $\epsilon_{280\ nm}$=30, 115 cm⁻¹M⁻¹ for 1d, and $\epsilon_{280\ nm}$=207,000 cm⁻¹M⁻¹ for huMy9-6), 98% monomer (by size exclusion chromatography), <1% unconjugated 1d (by acetone extraction/reverse-phase HPLC), a 70% protein yield, and a 32% overall 1d yield. See FIG. 60.

We claim:

1. A method of treating a cancer in a mammal comprising administering to said mammal a therapeutically effective amount of a conjugate comprising a cytotoxic compound and a cell binding agent (CBA), wherein the cytotoxic compound comprises a linking group which covalently links the cytotoxic compound to the CBA, and wherein said cytotoxic compound represented by the following structural formula:

(IA)

or a pharmaceutically acceptable salt thereof, wherein:
the double line = between N and C represents a single bond or a double bond, provided that when it is a double bond X is absent and Y is —H, or a linear or branched alkyl having 1 to 4 carbon atoms, and when it is a single bond, X is —H, the linking group, or an amine protecting moiety;

Y is a leaving group selected from —OR, —OCOR', —OCOOR', —OCONR'R", —NR'R", —NR'COR", —NR'NR'R", an optionally substituted 5- or 6-membered nitrogen-containing heterocycle, a guanidinum represented by —NR'(C=NH)NR'R", an amino acid, or a peptide represented by —NRCOP', wherein P' is an amino acid or a polypeptide containing between 2 to 20 amino acid units, —SR, —SOR', —SO$_2$M, —SO$_3$M, —OSO$_3$M, halogen, cyano and an azido;

M is —H or a cation;

R, for each occurrence, is independently selected from the group consisting of —H, an optionally substituted linear, branched or cyclic alkyl, alkenyl or alkynyl having from 1 to 10 carbon atoms, a polyethylene glycol unit —(CH$_2$CH$_2$O)$_n$—R$^c$, an optionally substituted aryl having 6 to 18 carbon atoms, an optionally substituted 5- to 18-membered heteroaryl ring containing one or more heteroatoms independently selected from nitrogen, oxygen, and sulfur, or an optionally substituted 3- to 18-membered heterocyclic ring containing 1 to 6 heteroatoms independently selected from O, S, N and P;

R' and R" are each independently selected from —H, —OH, —OR, —NHR, —NR$_2$, —COR, an optionally substituted linear, branched or cyclic alkyl, alkenyl or alkynyl having from 1 to 10 carbon atoms, a polyethylene glycol unit —(CH$_2$CH$_2$O)$_n$—R$^c$, and an optionally substituted 3-18-membered heterocyclic ring having 1 to 6 heteroatoms independently selected from O, S, N and P;

R$^c$ is —H or an optionally substituted linear or branched alkyl having 1 to 4 carbon atoms, or the linking group;

n is an integer from 1 to 24;

X' is selected from —H, an amine-protecting group, the linking group, an optionally substituted linear, branched or cyclic alkyl, alkenyl or alkynyl having from 1 to 10 carbon atoms, a polyethylene glycol unit —(CH$_2$CH$_2$O)$_n$—R$^c$, an optionally substituted aryl having 6 to 18 carbon atoms, an optionally substituted 5- to 18-membered heteroaryl ring containing one or more heteroatoms independently selected from nitrogen, oxygen, and sulfur, and an optionally substituted 3- to 18-membered heterocyclic ring containing 1 to 6 heteroatoms independently selected from O, S, N and P;

Y' is selected from —H, an oxo group, the linking group, an optionally substituted linear, branched or cyclic alkyl, alkenyl or alkynyl having from 1 to 10 carbon atoms, an optionally substituted 6- to 18-membered aryl, an optionally substituted 5- to 18-membered heteroaryl ring containing one or more heteroatoms independently selected from nitrogen, oxygen, and sulfur, an optionally substituted 3 to 18-membered heterocyclic ring having 1 to 6 heteroatoms;

R$_6$ is —H, —R, —OR, —SR, —NR'R", —NO$_2$, halogen or the linking group;

A and A' are the same or different, and are independently selected from —O—, oxo (—C(=O)—), —CRR'O—, —CRR'—, —S—, —CRR'S—, —N(R$_5$)— and —CRR'N(R$_5$)—, R$_5$ for each occurrence is independently —H or an optionally substituted linear or branched alkyl having 1 to 10 carbon atoms;

L', L", and L'" are the same or different, and are independently selected from —H, an optionally substituted linear, branched or cyclic alkyl, alkenyl or alkynyl having from 1 to 10 carbon atoms, a polyethylene glycol unit —(OCH$_2$CH$_2$)$_n$—R$^c$, halogen, guanidinium [—NH(C=NH)NH$_2$], —OR, —NR'R", —NO$_2$, —NR'COR", —SR, a sulfoxide represented by —SOR', a sulfone represented by —SO$_2$R', a sulfonate —SO$_3$M, a sulfate —OSO$_3$M, a sulfonamide represented by —SO$_2$NR'R", cyano, an azido, —COR', —OCOR', —OCONR'R" and the linking group, provided only one of L', L", and L'" is the linking group; and G is selected from —CH— or —N—, provided that the compound is not any one of the following compounds:

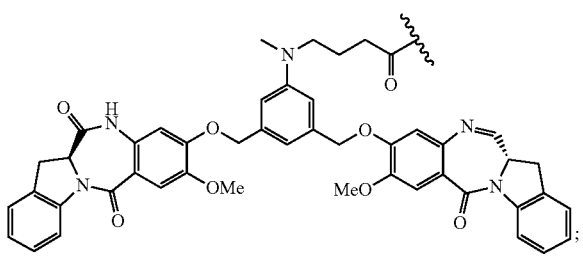

263
-continued

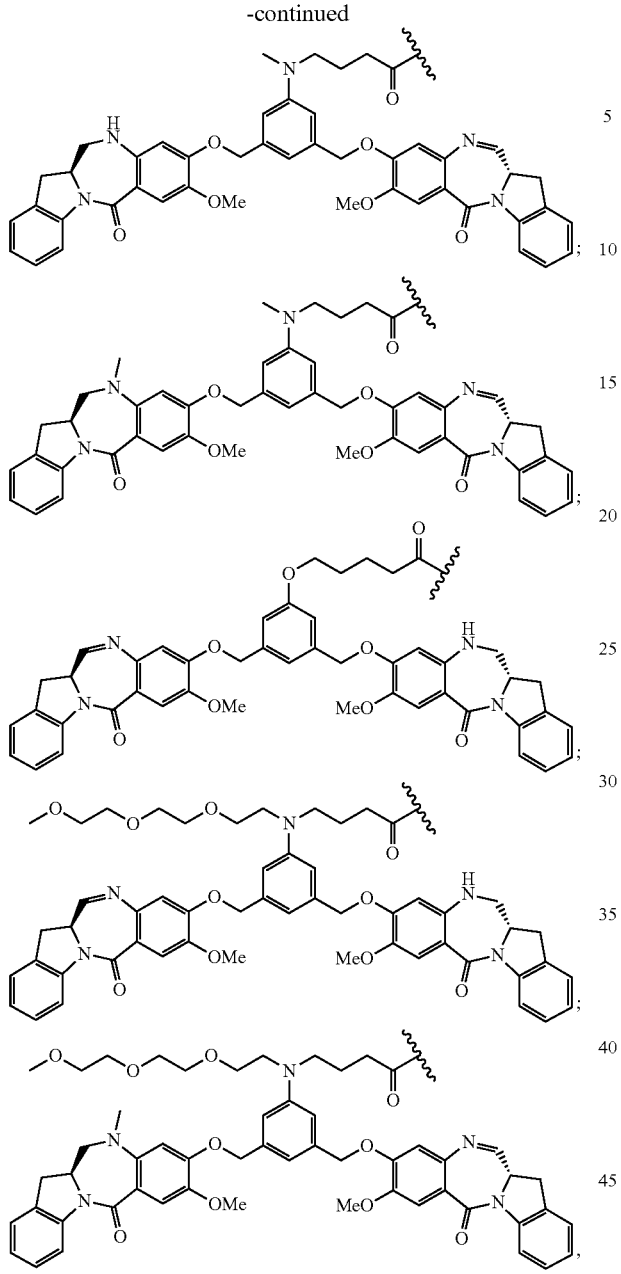

wherein the cancer is selected from the group consisting of leukemia, lymphoma, multiple myeloma, cervical cancer, non-small cell lung cancer, small-cell lung cancer, head and neck cancer and colon cancer; and
the optional substituent described above is a linear, branched or cyclic alkyl, alkenyl or alkynyl having from 1 to 10 carbon atoms, aryl, heteroaryl, heterocyclyl, halogen, —NH(C=NH)NH$_2$, —OR$^{100}$, NR$^{101}$R$^{102}$, —NO$_2$, —NR$^{101}$COR$^{102}$, —SR$^{100}$, —SOR$^{101}$, —SO$_2$R$^{101}$, —SO$_3$M, —OSO$_3$M, —SO$_2$NR$^{101}$R$^{102}$, cyano, an azido, —COR$^{101}$, —OCOR$^{101}$, —OCONR$^{101}$R$^{102}$ and a polyethylene glycol unit (—OCH$_2$CH$_2$)$_n$R$^{101}$ wherein M is H or a cation; R$^{100}$, R$^{101}$, R$^{102}$ and R$^{103}$ are each independently selected from the group consisting of H, linear, branched or cyclic alkyl, alkenyl or alkynyl having from 1 to 10 carbon atoms, a polyethylene glycol unit

264

(—OCH$_2$CH$_2$)$_n$—R$^{104}$, an aryl having from 6 to 10 carbon atoms, a heterocyclic ring having from 3 to 10 carbon atoms and a heteroaryl having 5 to 10 carbon atoms; n is an integer from 1 to 24, and R$^{104}$ is H or a linear or branched alkyl having 1 to 4 carbon atoms, wherein the alkyl, alkenyl, alkynyl, aryl, heteroaryl and heterocyclcyl in the groups represented by R$^{100}$, R$^{101}$, R$^{102}$, R$^{103}$ and R$^{104}$ are optionally substituted with one or more substituents independently selected from the group consisting of halogen, —OH, —CN, —NO$_2$ and unsubstituted linear or branched alkyl having 1 to 4 carbon atoms.

2. The method of claim 1, wherein L' is the linking group, and L'' and L''' are —H.

3. The method of claim 2, wherein A and A' are both —O—, R$_6$ is —OMe, and G is —CH—.

4. The method of claim 3, wherein L' is represented by the following formula:

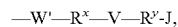

wherein:
W' and V are the same or different, and are each independently absent, or selected from —CR$^e$R$^{e'}$—, —O—, —O—C(=O)—, —C(=O)—O—, —S—, —SO—, —SO$_2$—, —CH$_2$—S—, —CH$_2$O—, —CH$_2$NR$^e$—, —O—(C=O)O—, —O—(C=O)N(R$^e$)—, —N(R$^e$)—, —N(R$^e$)—C(=O)—, —C(=O)—N(R$^e$)—, —N(R$^e$)—C(=O)O—, —N(C(=O)R$^e$)C(=O)—, —N(C(=O)R$^e$)—, —(O—CH$_2$—CH$_2$)$_n$—, —SS—, or —C(=O)—, or an amino acid, or a peptide having 2 to 8 amino acids;

R$^x$ and R$^y$ are the same or different, and are each independently absent or an optionally substituted linear, branched or cyclic alkyl, alkenyl, or alkynyl having 1 to 10 carbon atoms, an aryl bearing 6 to 10 carbon atoms or a 3- to 8-membered heterocyclic ring bearing 1 to 3 heteroatoms selected from O, N or S;

R$^e$ and R$^{e'}$ are the same or different, and are selected from —H, a linear, branched or cyclic alkyl, alkenyl, or alkynyl having 1 to 10 carbon atoms or —(CH$_2$—CH$_2$—O)$_n$—R$^k$, wherein R$^k$ is a —H, a linear, branched cyclic alkyl having 1 to 6 carbon atoms, optionally bearing a secondary amino (—NHR$^{101}$) or tertiary amino (—NR$^{101}$R$^{102}$) group or a 5- or 6-membered nitrogen containing heterocycle, such as piperidine or morpholine, wherein R$^{101}$ and R$^{102}$ are each independently a linear, branched, or cyclic alkyl, alkenyl or alkynyl having 1 to 10 carbon atoms; preferably, R$^{101}$ and R$^{102}$ are each independently a linear or branched alkyl having 1 to 6 carbon atoms;

n is an integer from 1 to 24; and

J is covalently linked to the CBA, and is selected from a succinimide, a acetamido, —S—, —SS—, —CH$_2$S—, —CH(Me)S—, —C(Me)$_2$S—, —NR$^{c1}$—, —CH$_2$NR$^{c1}$—, —NR$^{c1}$N—, and —C(=O)—, wherein R$^{c1}$ is —H or an optionally substituted linear or branched alkyl having 1 to 4 carbon atoms.

5. The method of claim 4, wherein:
W' is —O—, —N(R$^e$)— or —N(R$^e$)—C(=O)—;
R$^e$ is —H, -Me, or —(CH$_2$—CH$_2$—O)$_n$-Me;
n is an integer from 2 to 6;
R$^x$ is linear or branched alkyl bearing 1 to 6 carbon atoms;
V and R$^y$ are absent; and
J is —C(=O)—.

6. The method of claim 1, wherein the compound is represented by the following formula:

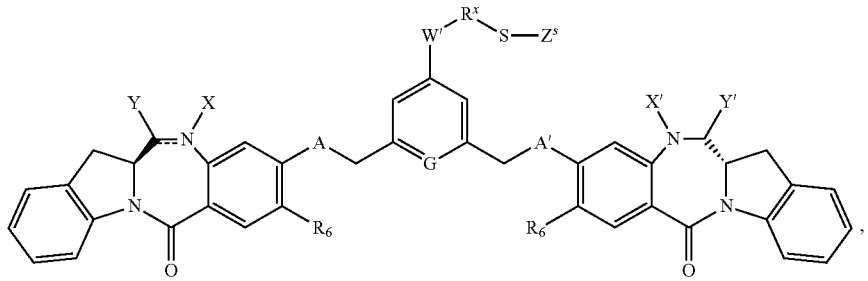

(XIII)

or a pharmaceutically acceptable salt thereof, wherein:

W' is absent, or selected from —O—, —N(R$^e$)—, —N(R$^e$)—C(=O)—, —N(C(=O)R$^e$)—, —S—, —CH$_2$—S—, or —CH$_2$NR$^e$—;

R$^x$ is absent or selected from a linear, branched or cyclic alkyl having 1 to 10 carbon atoms;

R$^e$ is —H, a linear, branched or cyclic alkyl, alkenyl or alkynyl having 1 to 10 carbon atoms or —(CH$_2$—CH$_2$—O)$_n$—R$^k$, wherein R$^k$ is a —H, a linear, branched cyclic alkyl having 1 to 6 carbon atoms, optionally bearing a secondary amino (—NHR$^{101}$) or tertiary amino (—NR$^{101}$R$^{102}$) group or a 5 or 6-membered nitrogen containing heterocycle, such as piperidine or morpholine, wherein R$^{101}$ and R$^{102}$ are each independently a linear, branched, or cyclic alkyl, alkenyl or alkynyl having 1 to 10 carbon atoms;

n is an integer from 2 to 6;

Z$^s$ is linked to the CBA, and is selected from:

a bond;

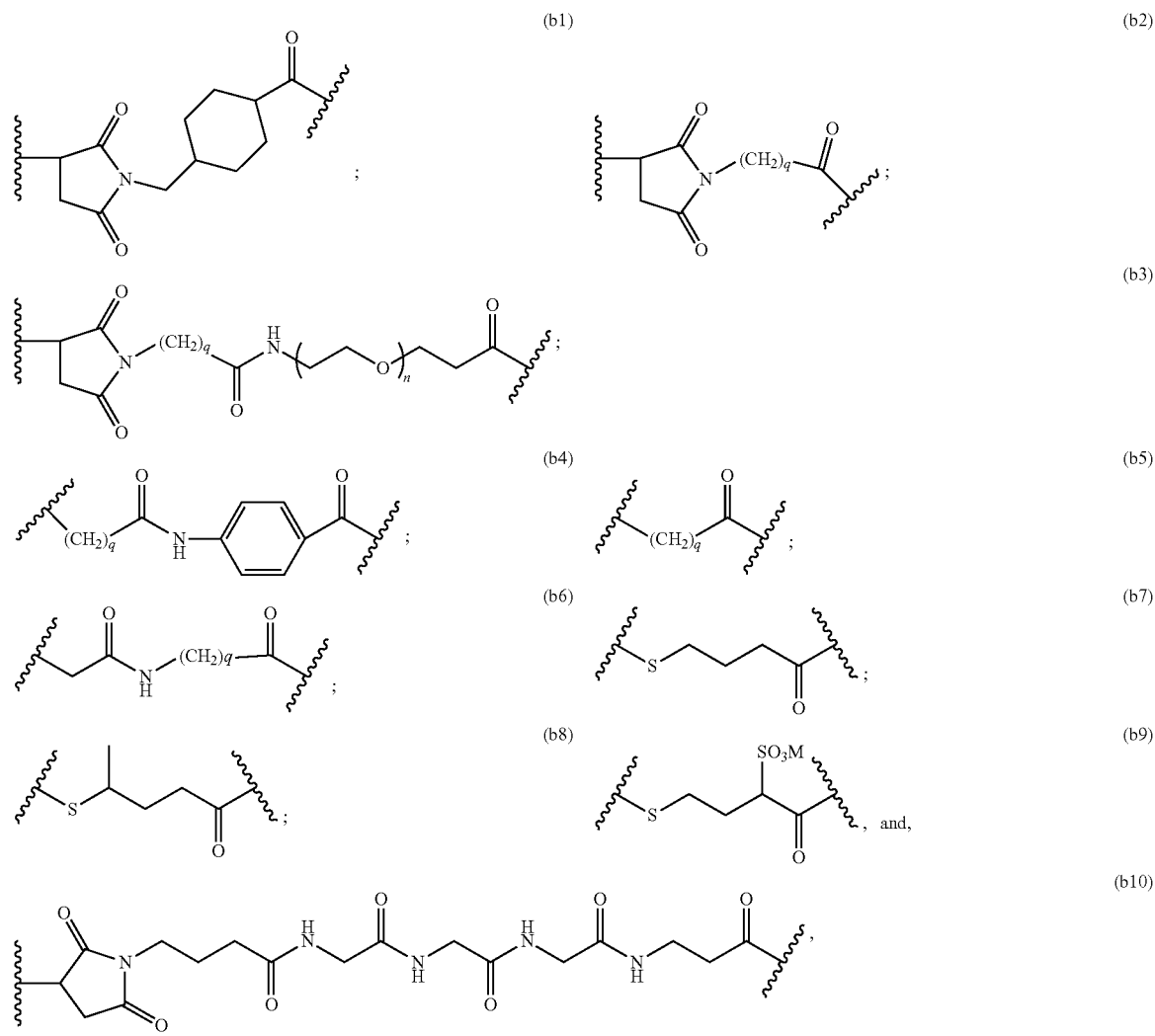

wherein:

q is an integer from 1 to 5; and,

M is —H or a cation, such as Na⁺ or K⁺.

7. The method of claim 6, wherein W' is —N(R$^e$)—.

8. The method of claim 7, wherein R$^e$ is —(CH$_2$—CH$_2$—O)$_n$—R$^k$, wherein R$^k$ is a —H, a linear, branched cyclic alkyl having 1 to 6 carbon atoms.

9. The method of claim 8, wherein R$^x$ is a linear or branched alkyl having 1 to 6 carbon atoms.

10. The method of claim 9, wherein R$^x$ is —(CH$_2$)$_p$—(CR$^f$R$^g$)—, wherein R$^f$ and R$^g$ are each independently selected from H or a linear or branched alkyl having 1 to 4 carbon atoms; and p is 0, 1, 2 or 3.

11. The method of claim 10, wherein R$^f$ and R$^g$ are the same or different, and are selected from H and Me; and p is 1.

12. The method of claim 6, wherein:

the double line ═ between N and C represents a single bond or a double bond, provided that when it is a double bond X is absent and Y is —H, and when it is a single bond, X is —H; Y is —OH or —SO$_3$M;

M is —H or a pharmaceutically acceptable cation;

X' and Y' are both —H;

A and A' are both —O—;

R$_6$ is —OMe; and

R$^x$ is a linear or branched alkyl having 1 to 6 carbon atoms.

13. The method of claim 1, wherein the conjugate is represented by the following formula:

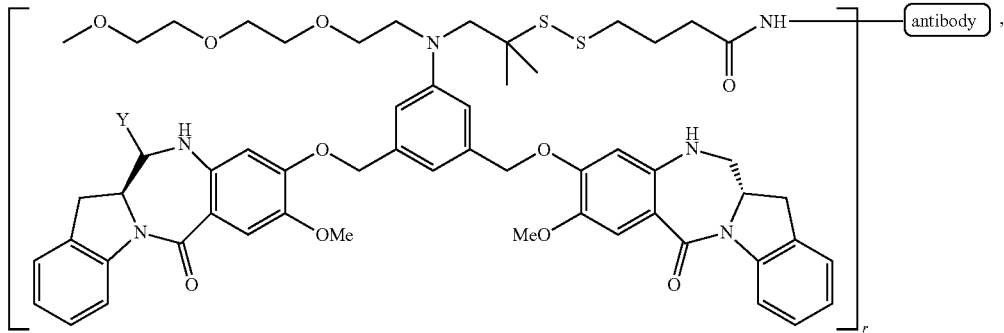

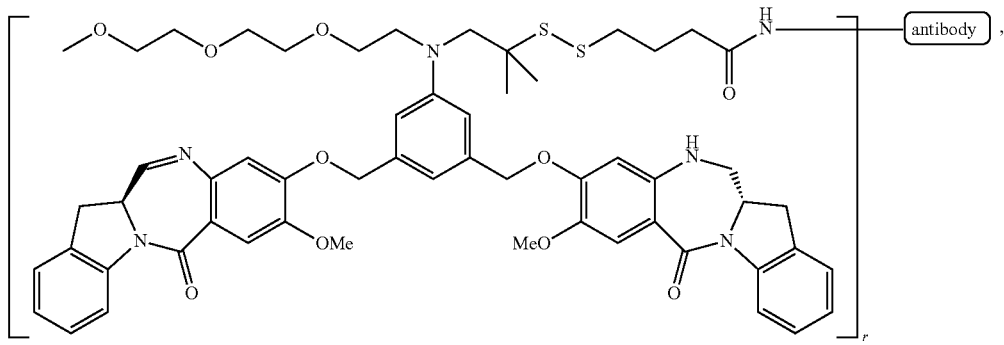

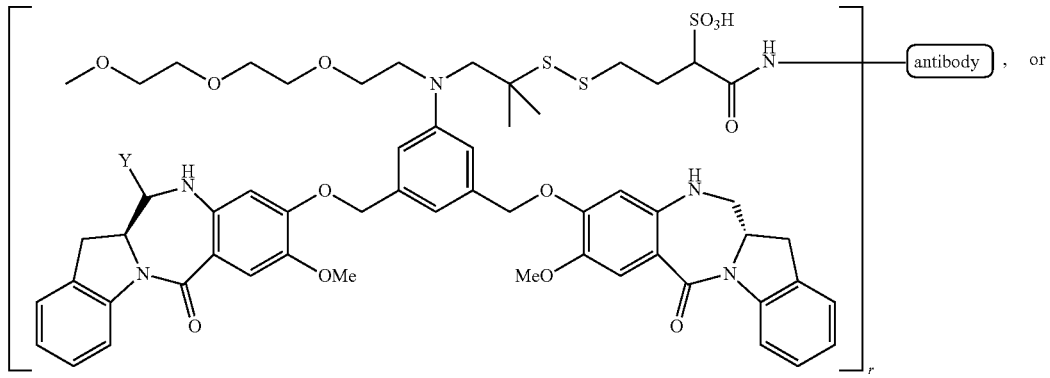

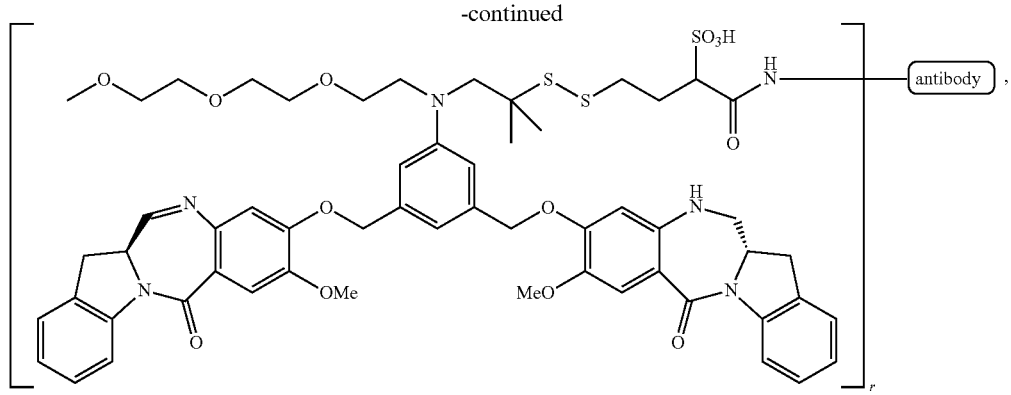

or a pharmaceutically acceptable salt thereof,
wherein r is an integer from 1 to 10, Y is —SO₃M, and M is —H or a pharmaceutically acceptable cation.

14. The method of claim 13, wherein the conjugate is represented by the following formula:

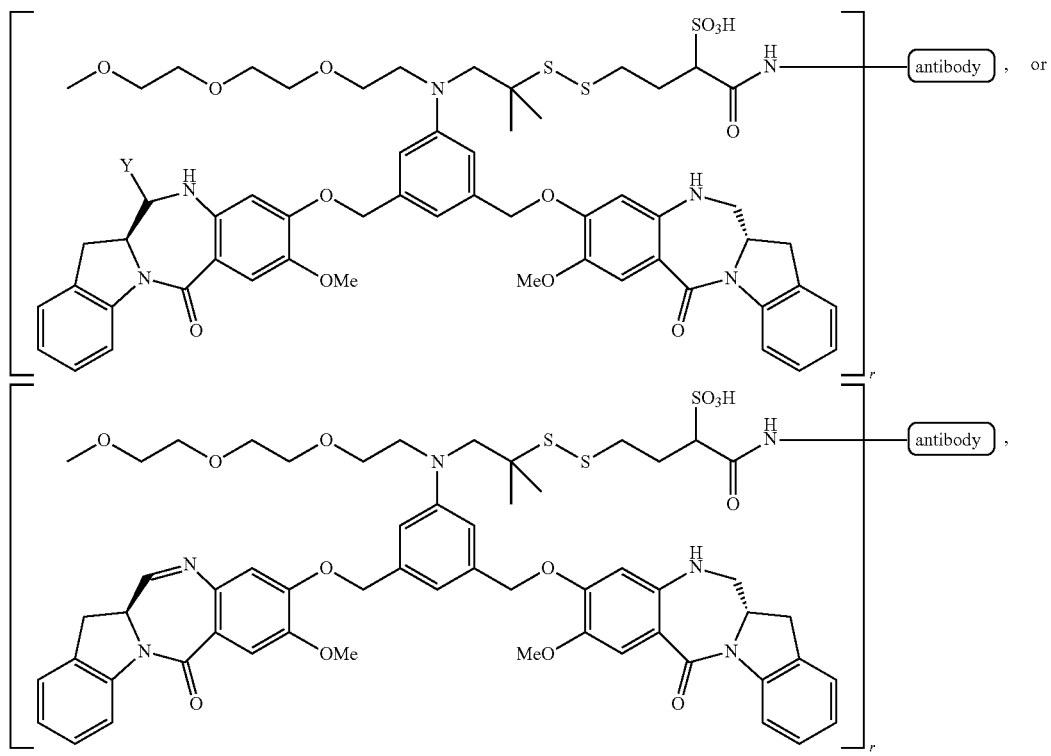

or a pharmaceutically acceptable salt thereof.

15. The method of claim 14, wherein M is —H, Na⁺ or K⁺.

16. The method of claim 14, wherein the antibody is huMy9-6.

17. The method of claim 1, wherein the conjugate comprises 1-10 cytotoxic compounds, each cytotoxic compound comprising the linking group linking the cytotoxic compound to the CBA, and each cytotoxic compound on the conjugate is the same.

18. The method of claim 1, wherein the cell-binding agent binds to target cells selected from tumor cells, virus infected cells, microorganism infected cells, parasite infected cells, autoimmune cells, activated cells, myeloid cells, activated T-cells, B cells, or melanocytes; cells expressing the CD4, CD6, CD19, CD20, CD22, CD30, CD33, CD37, CD38, CD40, CD44, CD56, EpCAM, CanAg, CALLA, or Her-2 antigens; Her-3 antigens; or cells expressing insulin growth factor receptor, epidermal growth factor receptor, and folate receptor.

19. The method of claim 1, wherein the cell-binding agent is an antibody, a single chain antibody, an antibody fragment that specifically binds to the target cell, a monoclonal antibody, a single chain monoclonal antibody, or a monoclonal antibody fragment that specifically binds to a target cell, a chimeric antibody, a chimeric antibody fragment that specifically binds to the target cell, a domain antibody, a domain antibody fragment that specifically binds to the target cell, a lymphokine, a hormone, a vitamin, a growth factor, a colony stimulating factor, or a nutrient-transport molecule.

20. The method of claim 1, wherein the antibody is a resurfaced antibody, a resurfaced single chain antibody, or a resurfaced antibody fragment.

21. The method of claim 1, wherein the antibody is a monoclonal antibody, a single chain monoclonal antibody, or a monoclonal antibody fragment thereof.

22. The method of claim 1, wherein the antibody is a humanized antibody, a humanized single chain antibody, or a humanized antibody fragment.

23. The method of claim 1, wherein the cancer is acute myelogenous leukemia (AML).

24. The method of claim 23, wherein the conjugate is represented by the following formula:

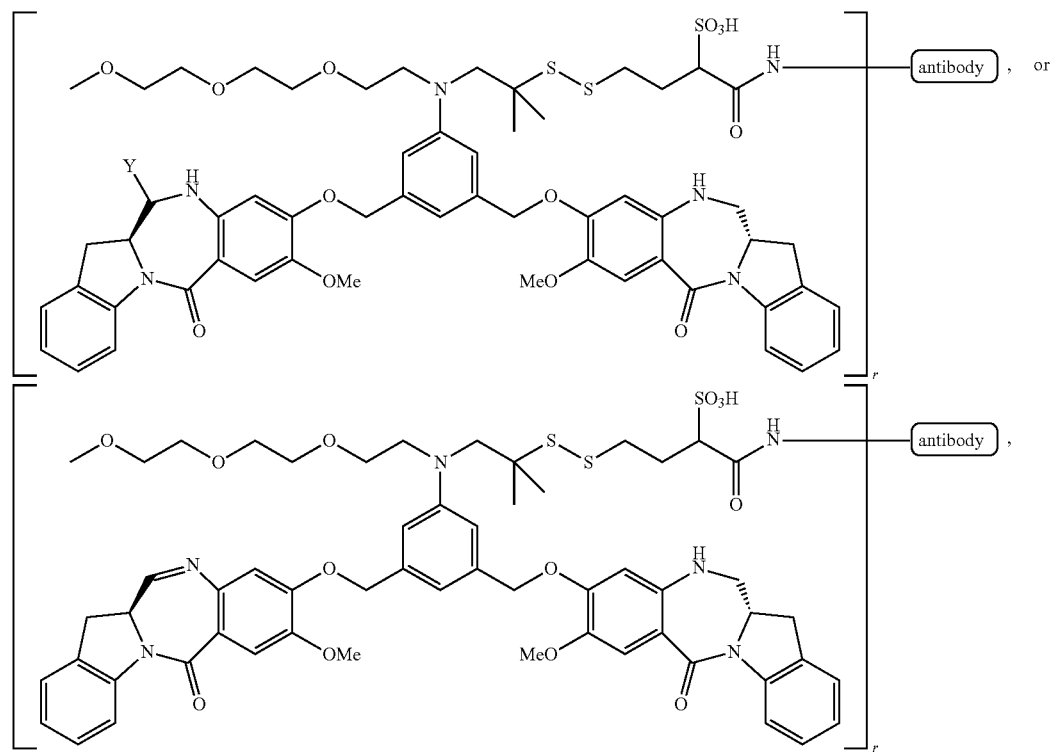

or a pharmaceutically acceptable salt thereof.

25. The method of claim 24, wherein the antibody is huMy9-6.

* * * * *